(12) United States Patent
Ho et al.

(10) Patent No.: US 10,301,389 B2
(45) Date of Patent: May 28, 2019

(54) ANTIGEN BINDING CONSTRUCTS TO CD3

(71) Applicant: ImaginAb, Inc., Inglewood, CA (US)

(72) Inventors: David T. Ho, Long Beach, CA (US); Tove Olafsen, Reseda, CA (US); Jason Romero, Los Angeles, CA (US); Christian P. Behrenbruch, Inglewood, CA (US)

(73) Assignee: IMAGINAB, INC., Inglewood, CA (US)

( * ) Notice: Subject to any disclaimer, the term of this patent is extended or adjusted under 35 U.S.C. 154(b) by 0 days.

(21) Appl. No.: 14/407,440

(22) PCT Filed: Jun. 13, 2013

(86) PCT No.: PCT/US2013/045719
§ 371 (c)(1),
(2) Date: Dec. 11, 2014

(87) PCT Pub. No.: WO2013/188693
PCT Pub. Date: Dec. 19, 2013

(65) Prior Publication Data
US 2015/0118252 A1 Apr. 30, 2015

Related U.S. Application Data

(60) Provisional application No. 61/660,594, filed on Jun. 15, 2012, provisional application No. 61/674,229, filed on Jul. 20, 2012, provisional application No. 61/776,673, filed on Mar. 11, 2013.

(51) Int. Cl.
| | | |
|---|---|---|
| C07K 16/28 | (2006.01) | |
| A61K 51/10 | (2006.01) | |
| G01N 33/569 | (2006.01) | |
| A61K 47/68 | (2017.01) | |
| A61K 39/00 | (2006.01) | |

(52) U.S. Cl.
CPC ...... *C07K 16/2809* (2013.01); *A61K 47/6849* (2017.08); *A61K 51/1027* (2013.01); *G01N 33/56966* (2013.01); *A61K 2039/505* (2013.01); *C07K 2317/24* (2013.01); *C07K 2317/526* (2013.01); *C07K 2317/53* (2013.01); *C07K 2317/565* (2013.01); *C07K 2317/622* (2013.01); *C07K 2317/626* (2013.01); *C07K 2317/64* (2013.01); *G01N 2333/7051* (2013.01)

(58) Field of Classification Search
None
See application file for complete search history.

(56) References Cited

U.S. PATENT DOCUMENTS 5,859,205 A * 1/1999 Adair .................. C07K 16/18
530/387.1
6,491,916 B1 * 12/2002 Bluestone et al. ......... 424/133.1

2005/0176028 A1 8/2005 Hofmeister et al.
2006/0002933 A1 1/2006 Bluestone et al.
2007/0081993 A1 * 4/2007 Kufer ................ C07K 16/2809
424/144.1
2009/0252748 A1 10/2009 Mi et al.
2011/0054151 A1 3/2011 Lazar et al.
2011/0268656 A1 11/2011 Ho et al.

FOREIGN PATENT DOCUMENTS

| WO | WO 9852975 A1 * 11/1998 | ......... C07K 16/2809 |
|---|---|---|
| WO | WO 2004/108158 | 12/2004 |
| WO | WO 2010042904 A2 * 4/2010 | |
| WO | WO 2012143524 A2 * 10/2012 | ....... A61K 47/48484 |

OTHER PUBLICATIONS

Martins et al. (Br J Radiol. Jan. 2008;81(961):25-9).*
Kjer-Nielsen et al. (PNAS, 2004, vol. 101, No. 20, 7675-7680).*
Janeway et al., Immunobiology, 5th Ed., Garland Science, pp. 94-105 (2001)).*
Vajdos et al. (J Mol Biol. Jul. 5, 2002;320(2):415-28).*
Lopes et al. (Rheumatology 2010;49:933-939).*
Li et al., Protein Engineering v.10 n.6 pp. 731-736, 1997.*
Hu et al., Cancer Research 56. 3055-3061, 1996.*
Olafsen et al. (Antibody Engineering vol. 2, "Generation of Single-Chain Fv Fragments and Multivalent Derivatives scFv-Fc and scFv-CH3 (Minibodies)," Chapter 6, Springer-Verlag Berlin Heidelberg, pp. 69-84, 2010.*
Keymeulen et al. (Blood. 2010;115:1145-1155).*
Eduardo Padlan, Mol Immunol. Feb. 1994;31(3):169-217 (Year: 1994).*
Goldsby et al., Immunology, 5th edition, 2002, pp. 79-83 (Year: 2002).*
Chaderjian et al., Biotechnol. Prog. 2005, 21, 550-553 (Year: 2005).*
International Search Report and Written Opinion dated Nov. 15, 2013 in International Application No. PCT/US2013/045719.
Supplementary Partial Search Report dated May 3, 2016 in European Application No. 13804247.8.
Extended European Search Report dated Aug. 29, 2016 in Application No. 13804247.8.
Office Action dated Aug. 29, 2017 in European Application No. 13804247.8.
Almagro, J. et al: Humanization of antibodies, Frontiers in Bioscience, vol. 13, pp. 1619-1633, (2008).
Asano R et al: Humanization of the bispecific epidermal growth factor receptor x CD3 diabody and its efficacy as a potential clinical reagent, Clinical Cancer Research, vol. 12, No. 13, pp. 4036-4042, (2006).

(Continued)

*Primary Examiner* — Zachary S Skelding
(74) *Attorney, Agent, or Firm* — Knobbe, Martens, Olson & Bear, LLP

(57) ABSTRACT

Antigen binding constructs that bind to CD3, for example antibodies, including antibody fragments (such as minibodies and cys-diabodies) that bind to CD3, are described herein. Methods of use are described herein.

9 Claims, 58 Drawing Sheets

Specification includes a Sequence Listing.

(56) References Cited

OTHER PUBLICATIONS

Le Gall F et al: Immunosuppressive properties of anti-CD3 single-chain Fv and diabody, Journal of Immunological Meth, vol. 285, No. 1, pp. 111-127, (2004).
Summons to Attend Oral Proceeding Pursuant to Rules 115(1) EPC dated Jul. 27, 2018 in European Patent Application No. 13804247.8.
Notice of Allowance dated Mar. 27, 2019 in U.S. Appl. No. 15/230,085.
Notice of Allowance dated Mar. 27, 2019 in U.S. Appl. No. 14/773,710.

* cited by examiner

```
Humanized VL:
muOKT3   QIVLTQSPAIMSASPGEKVTMTC SASSSVS--YMN WYQQKSGTSPKRWIY DTSKLAS GVPA
          *  ****                 *      *      *   *        *
Human    EIVLTQSPATLSLSPGERATLSLC RASQVSSYLA   WYQQKPGQAPRLLIY DASNRAT GIPA
          *                       *            *               *
huOKT3   EIVLTQSPATLSLSPGERATLSLC SASSSVS--YMN WYQQKPGQAPRLLIY DTSKLAS GVPA muOKT3   HFRGSGSGTSYSLTISGMEAEDAATYYC QQWSS--NPFT FGSGTKLEIN    SEQ ID NO: 1
          *                           *    *
Human    RFSGSGSGTDFTLTISSLEPEDFAVYYC QQRSNWPFFT  FGQGTKVEIK    SEQ ID NO: 2
          *                           *
huOKT3   HFRGSGSGTDYTLTISSLEPEDFAVYYC QQWSS--NPFT FGQGTKVEIK    SEQ ID NO: 3
```

FIG. 2A

```
Humanized VH:
muOKT3   QVQLQQSGAELARPGASVKMSCKAS GYTFTR YTMHWVKQRPGQGLEWIG YINPSRGYTN NY
          *                        *    *                    *
Human    QVQLVQSGAEVKKPGASVKVSCKAS GYTFTG YTMHWVRQAPGQGLEWMG WINPNSGGI  NY
          *                        *    *                    *
huOKT3   QVQLVQSGAEVKKPGASVKVSCKAS GYTFTR YTMHWVRQAPGQGLEWMG YINPSRGYTN NY muOKT3   NQKFKDKATLTTDKSSSTAYMQLSSLISEDSAVYYCAR YYDDHYCLDY WGQGTLLTVSS SEQ ID NO: 4
          *    *                               *
Human    AQKFQGRVTMTRDTSISTAYMELSRLRSDDTAVYYCAR ---DEYFQH-  WGQGTLVTVSS SEQ ID NO: 5
          *    *                               *
huOKT3   NQKFKDRVTMTIDTSISTAYMELSRLRSDDTAVYYCAR YYDDHYCLDY WGQSTLVTVSS SEQ ID NO: 6
```

FIG. 2B

FIG. 3A
Anti-CD3 VLVH Minibody (OKT3/Murine) Translated Sequence

```
tctagagccgccacc        SEQ ID NO: 118
XbaI Kozak
      1   M   E   T   D   T   L   L   L   W   V   L   L   L   W   V   P   G   S   T   G
      1   ATGGAAACCGACACTCTGCTGCTGTGGGTCCTGCTGCTGTGGGTGCCCGGATCAACTGGA
              Signal Peptide
     21   Q   I   V   L   T   Q   S   P   A   I   M   S   A   S   P   G   E   K   V   T
     61   CAGATCGTGCTGACTCAGTCTCCCGCTATCATGTCTGCCTCACCTGGCGAAAAAGTGACA
              V_L
     41   M   T   C   S   A   S   S   S   V   S   Y   M   N   W   Y   Q   Q   K   S   G
    121   ATGACCTGTTCCGCCTCTTCTTCCGTGTCTTACATGAATGGTACCAGCAGAAATCTGGG 61   T   S   P   K   R   W   I   Y   D   T   S   K   L   A   S   G   V   P   A   H
    181   ACTAGTCCTAAACGGTGGATCTACGATACTAGCAAACTGGCTTCTGGCGTGCCTGCTCAT 81   F   R   G   S   G   S   G   T   S   Y   S   L   T   I   S   G   M   E   A   E
    241   TTCCGTGGTTCTGGCTCTGGAACCTCTTACTCTCTGACCATCTCTGGCATGGAGGCCGAG 101   D   A   A   T   Y   Y   C   Q   Q   W   S   S   N   P   F   T   F   G   S   G
    301   GATGCCGCCACCTACTACTGCCAGCAGTGGAGTTCAAACCCTTTCACATTCGGCTCCGGC 121   T   K   L   E   I   N   G   S   T   S   G   G   G   S   G   G   G   S   G   G
    361   ACAAAACTGGAGATCAACGGCTCTACTAGTGGTGGAGGATCTGGTGGTGGATCTGGAGGG
                                    Linker
    141   G   G   S   S   Q   V   Q   L   Q   Q   S   G   A   E   L   A   R   P   G   A
    421   GGCGGATCATCTCAGGTCCAGCTGCAGCAGTCTGGTGCTGAACTGGCACGTCCTGGTGCC
                          V_H
    161   S   V   K   M   S   C   K   A   S   G   Y   T   F   T   R   Y   T   M   H   W
    481   TCCGTGAAAATGTCTTGTAAGGCCTCTGGTTACACCTTTACCCGGTACACTATGCATTGG 181   V   K   Q   R   P   G   Q   G   L   E   W   I   G   Y   I   N   P   S   R   G
    541   GTCAAACAGCGCCCTGGGCAGGGACTGGAATGGATTGGCTACATCAACCCTTCTCGTGGC 201   Y   T   N   Y   N   Q   K   F   K   D   K   A   T   L   T   T   D   K   S   S
    601   TACACAAACTACAATCAGAAATTCAAGGACAAGGCCACCCTGACAACCGACAAATCTTCT 221   S   T   A   Y   M   Q   L   S   S   L   T   S   E   D   S   A   V   Y   Y   C
    661   TCAACCGCCTACATGCAGCTGTCATCCCTGACCTCTGAGGATAGTGCTGTGTACTACTGT 241   A   R   Y   Y   D   D   H   Y   ▓   L   D   Y   W   G   Q   G   T   T   L   T
    721   GCTCGGTACTACGACGATCACTACTGTCTGGACTACTGGGGACAGGGAACAACACTGACT 261   V   S   S   E   P   K   S   C   D   K   T   H   T   C   P   P   C   G   G   G
    781   GTGTCCTCCGAACCCAAATCCTGTGACAAAACCCACACCTGTCCACCTTGTGGCGGTGGA
                      Hinge
    281   S   S   G   G   G   S   G   G   Q   P   R   E   P   Q   V   Y   T   L   P   P
    841   TCATCTGGCGGAGGGAGTGGAGGGCAGCCTAGGGAGCCTCAGGTCTACACACTGCCACCT
                                              CH3
    301   S   R   D   E   L   T   K   N   Q   V   S   L   T   C   L   V   K   G   F   Y
    901   TCTCGGGACGAACTGACAAAAAACCAGGTGTCCCTGACATGTCTGGTGAAGGGCTTCTAC 321   P   S   D   I   A   V   E   W   E   S   N   G   Q   P   E   N   N   Y   K   T
    961   CCTTCCGATATCGCTGTGGAGTGGGAGTCAAATGGCCAGCCCGAAAACAACTACAAAACC
```

FIG. 3B

```
341   T  P  P  V  L  D  S  D  G  S  F  F  L  Y  S  K  L  T  V  D
1021  ACCCCACCTGTGCTGGATTCGATGGCTCTTTCTTCCTGTACTCTAAACTGACCGTGGAT

361   K  S  R  W  Q  Q  G  N  V  F  S  C  S  V  M  H  E  A  L  H
1081  AAGAGTCGATGGCAGCAGGGAAACGTGTTCTCTTGCTCCGTGATGCACGAGGCCCTGCAT

381   N  H  Y  T  Q  K  S  L  S  L  S  P  G  K  -           SEQ ID NO: 7
1141  AATCATTACACCCAGAAATCACTGTCTCTGTCACCCGGCAAATGA           SEQ ID NO: 8
                                                    Stop
``` aagctt  SEQ ID NO: 119
HinDIII

FIG. 4A
Anti-CD3 VLVH Minibody (ABC1 Humanized OKT3) Translated Sequence

TCTAGAGCCGCCACC    SEQ ID NO: 120
XbaI

```
  1   M  E  T  D  T  L  L  L  W  V  L  L  L  W  V  P  G  S  T  G
  1   ATGGAAACCGACACTCTGCTGCTGTGGGTCCTGCTGCTGTGGGTGCCCGGATCAACTGGT
      Signal Peptide 21   D  I  Q  M  T  Q  S  P  S  S  L  S  A  S  V  G  D  R  V  T
 61   GACATCCAGATGACACAGTCTCCCTCTTCTCTGTCCGCCTCTGTGGGCGATCGAGTGACA
      V_L 41   I  T  C  S  A  S  S  S  V  S  Y  M  N  W  Y  Q  Q  T  P  G
121   ATCACCTGTAGCGCTTCATCCTCCGTGTCTTACATGAATTGGTACCAGCAGACCCCTGGC 61   K  A  P  K  R  W  I  Y  D  T  S  K  L  A  S  G  V  P  S  R
181   AAAGCTCCTAAACGATGGATCTACGACACCTCCAAACTGGCTTCCGGCGTGCCTTCACGA 81   F  S  G  S  G  S  G  T  D  Y  T  F  T  I  S  S  L  Q  P  E
241   TTTTCTGGTTCTGGTTCTGGGACCGACTACACCTTTACCATCTCATCACTGCAGCCTGAG 101   D  I  A  T  Y  Y  C  Q  Q  W  S  S  N  P  F  T  F  G  Q  G
301   GATATCGCCACATACTACTGTCAGCAGTGGTCTAGCAACCCTTTCACATTCGGGCAGGGC 121   T  K  L  Q  I  T  G  S  T  S  G  G  G  S  G  G  G  S  G  G
361   ACAAAACTGCAGATCACCGGCTCAACCTCTGGCGGTGGCTCTGGCGGCGGTAGTGGTGGT
                         Linker 141   G  G  S  S  Q  V  Q  L  V  Q  S  G  G  G  V  V  Q  P  G  R
421   GGTGGTTCTAGTCAGGTCCAGCTGGTCCAGTCTGGTGGAGGAGTGGTCCAGCCCGGGAGA
                     V_H 161   S  L  R  L  S  C  K  A  S  G  Y  T  F  T  R  Y  T  M  H  W
481   TCACTGAGGCTGTCCTGTAAGGCTAGTGGCTACACTTTTACACGGTACACCATGCATTGG 181   V  R  Q  A  P  G  K  G  L  E  W  I  G  Y  I  N  P  S  R  G
541   GTGAGGCAGGCACCTGGGAAAGGCCTGGAATGGATCGGATACATCAACCCTAGTAGGGGA 201   Y  T  N  Y  N  Q  K  V  K  D  R  F  T  I  S  R  D  N  S  K
601   TACACAAACTACAATCAGAAAGTCAAGGACCGGTTCACAATCTCTAGGGACAACTCTAAA 221   N  T  A  F  L  Q  M  D  S  L  R  P  E  D  T  G  V  Y  F  C
661   AACACCGCTTTTCTGCAGATGGACTCACTGAGGCCTGAGGACACTGGAGTGTACTTTTGT 241   A  R  Y  Y  D  D  H  Y  ▓  L  D  Y  W  G  Q  G  T  P  V  T
721   GCTCGGTACTACGATGATCATTACGCCCTGGATTACTGGGGACAGGGGACACCTGTCACT 261   V  S  S  E  P  K  S  C  D  K  T  H  T  C  P  P  C  G  G  G
781   GTCTCTTCCGAACCCAAATCTTGTGACAAAACCCACACATGCCCTCCATGTGGTGGCGGA
               Hinge 281   S  S  G  G  S  G  G  Q  P  R  E  P  Q  V  Y  T  L  P  P
841   TCCTCTGGTGGCGGTTCTGGGGGGCAGCCTAGGGAACCTCAGGTGTACACACTGCCACCT
                                CH3

301   S  R  D  E  L  T  K  N  Q  V  S  L  T  C  L  V  K  G  F  Y
901   TCTCGTGACGAACTGACCAAAAACCAGGTGTCACTGACCTGTCTGGTCAAGGGCTTTTAC

321   P  S  D  I  A  V  E  W  E  S  N  G  Q  P  E  N  N  Y  K  T
961   CCTTCCGACATTGCTGTGGAGTGGGAGTCAAATGGCCAGCCTGAAAACAACTACAAAACC
```

FIG. 4B

```
341  T  P  P  V  L  D  S  D  G  S  F  F  L  Y  S  K  L  T  V  D
1021 ACACCCCCGTCCTGGATTCCGATGGCTCTTTCTTCCTGTACTCTAAACTGACCGTCGAC

361  K  S  R  W  Q  Q  G  N  V  F  S  C  S  V  M  H  E  A  L  H
1081 AAATCTCGATGGCAGCAGGGAAACGTGTTCTCTTGTTCCGTCATGCACGAGGCTCTGCAC

381  N  H  Y  T  Q  K  S  L  S  L  S  P  G  K  -       SEQ ID NO: 9
1141 AATCACTACACACAGAAATCACTGAGCCTGAGCCCTGGAAAATGA     SEQ ID NO: 10
                                              Stop
```

AAGCTT   SEQ ID NO: 121
HinDIII

FIG. 5A
Anti-CD3 VLVH Minibody (ImaginAb Humanized OKT3) Translated Sequence

<u>TCTAGAGCCGCCACC</u>   SEQ ID NO: 122
Xbal

```
  1   M   E   T   D   T   L   L   L   W   V   L   L   L   W   V   P   G   S   T   G
  1   ATGGAAACCGACACTCTGCTGCTGTGGGTCCTGCTGCTGTGGGTGCCCGGATCAACTGGT
          Signal Peptide 21   D   I   Q   M   T   Q   S   P   S   S   L   S   A   S   V   G   D   R   V   T
 61   GACATCCAGATGACACAGTCTCCCTCTTTCTCTGTCCGCCTCTGTGGGCGATCGAGTGACA
          V_L 41   I   T   C   S   A   S   S   S   V   S   Y   M   N   W   Y   Q   Q   T   P   G
121   ATCACCTGTAGCGCTTCATCCTCCGTGTCTTACATGAATGGTACCAGCAGACCCCTGGC 61   K   A   P   K   R   W   I   Y   D   T   S   K   L   A   S   G   V   P   S   R
181   AAAGCTCCTAAACGATGGATCTACGACACCTCCAAACTGGCTTCCGGCGTGCCTTCACGA 81   F   S   G   S   G   S   G   T   D   Y   T   F   T   I   S   S   L   Q   P   E
241   TTTTCTGGTTCTGGTTCTGGGACCGACTACACCTTTACCATCTCATCACTGCAGCCTGAG 101   D   I   A   T   Y   Y   C   Q   Q   W   S   S   N   P   F   T   F   G   Q   G
301   GATATCGCCACATACTACTGTCAGCAGTGGTCTAGCAACCCTTTCACATTCGGGCAGGGC 121   T   K   L   Q   I   T   G   S   T   S   G   G   G   S   G   G   G   S   G   G
361   ACAAAACTGCAGATCACCGGCTCAACCTCTGGCGGTGGCTCTGGCGGCGGTAGTGGTGGT
                       Linker 141   G   G   S   S   Q   V   Q   L   V   Q   S   G   G   G   V   V   Q   P   G   R
421   GGTGGTTCTAGTCAGGTCCAGCTGGTCCAGTCTGGTGGAGGAGTGGTCCAGCCCGGGAGA
                       V_H 161   S   L   R   L   S   C   K   A   S   G   Y   T   F   T   R   Y   T   M   H   W
481   TCACTGAGGCTGTCCTGTAAGGCTAGTGGCTACACTTTTACACGGTACACCATGCATTGG 181   V   R   Q   A   P   G   K   G   L   E   W   I   G   Y   I   N   P   S   R   G
541   GTGAGGCAGGCACCTGGGAAAGGCCTGGAATGGATCGGATACATCAACCCTAGTAGGGGA 201   Y   T   N   Y   N   Q   K   V   K   D   R   F   T   I   S   R   D   N   S   K
601   TACACAAACTACAATCAGAAAGTCAAGGACCGGTTCACAATCTCTAGGGACAACTCTAAA 221   N   T   A   F   L   Q   M   D   S   L   R   P   E   D   T   G   V   Y   F   C
661   AACACCGCTTTTCTGCAGATGGACTCACTGAGGCCTGAGGACACTGGAGTGTACTTTTGT 241   A   R   Y   Y   D   D   H   Y   ▨   L   D   Y   W   G   Q   G   T   P   V   T
721   GCTCGGTACTACGATGATCATTACTGCCTGGATTACTGGGGACAGGGGACACCTGTCACT 261   V   S   S   E   P   K   S   C   D   K   T   H   T   C   P   P   C   G   G   G
781   GTCTCTTCCGAACCCAAATCTTGTGACAAAACCCACACATGCCCTCCATGTGGTGGCGGA
                   Hinge 281   S   S   G   G   G   S   G   G   Q   P   R   E   P   Q   V   Y   T   L   P   P
841   TCCTCTGGTGGCGGTTCTGGGGGGCAGCCTAGGGAACCTCAGGTGTACACACTGCCACCT
                                       CH3

301   S   R   D   E   L   T   K   N   Q   V   S   L   T   C   L   V   K   G   F   Y
901   TCTCGTGACGAACTGACCAAAAACCAGGTGTCACTGACCTGTCTGGTCAAGGGCTTTTAC
```

FIG. 5B

```
321   P   S   D   I   A   V   E   W   E   S   N   G   Q   P   E   N   N   Y   K   T
961   CCTTCCGACATTGCTGTGGAGTGGGAGTCAAATGGCCAGCCTGAAAACAACTACAAAACC

341   T   P   P   V   L   D   S   D   G   S   F   F   L   Y   S   K   L   T   V   D
1021  ACACCCCCCGTCCTGGATTCCGATGGCTCTTTCTTCCTGTACTCTAAACTGACCGTCGAC

361   K   S   R   W   Q   Q   G   N   V   F   S   C   S   V   M   H   E   A   L   H
1081  AAATCTCGATGGCAGCAGGGAAACGTGTTCTCTTGTTCCGTCATGCACGAGGCTCTGCAC

381   N   H   Y   T   Q   K   S   L   S   L   S   P   G   K   -    SEQ ID NO:11
1141  AATCACTACACACAGAAATCACTGAGCCTGAGCCCTGGAAAATGA  SEQ ID NO: 12
                                                   Stop
```

AAGCTT    SEQ ID NO: 123
HinDIII

Figure 6
Anti-CD3 VLVH Cys-Diabody (ImaginAb Humanized OKT3) Translated Sequence

<u>TCTAGA</u>GCCGCCACC   SEQ ID NO: 124
XbaI

```
  1   M  E  T  D  T  L  L  L  W  V  L  L  L  W  V  P  G  S  T  G
  1   ATGGAAACCGACACTCTGCTGCTGTGGGTCCTGCTGCTGTGGGTGCCGGATCAACTGGA
      Signal Peptide
 21   E  I  V  L  T  Q  S  P  A  T  L  S  L  S  P  G  E  R  A  T
 61   GAAATCGTGCTGACTCAGTCCCCTGCTACACTGTCTCTGTCACCTGGCGAACGAGCAACA
      V_L
 41   L  S  C  S  A  S  S  S  V  S  Y  M  N  W  Y  Q  Q  K  P  G
121   CTGTCCTGTTCTGCCTCTTCTTCTGTCTCATACATGAACTGGTACCAGCAGAAACCTGGA 61   Q  A  P  R  L  L  I  Y  D  T  S  K  L  A  S  G  V  P  A  H
181   CAGGCTCCTAGACTGCTGATCTACGACACCTCTAAACTGGCATCTGGCGTGCCCGCTCAT 81   F  R  G  S  G  S  G  T  D  F  T  L  T  I  S  S  L  E  P  E
241   TTCCGTGGCTCTGGATCTGGAACCGACTTTACCCTGACCATCTCTTCCCTGGAACCTGAG 101   D  F  A  V  Y  Y  C  Q  Q  W  S  S  N  P  F  T  F  G  Q  G
301   GATTTTGCCGTGTACTACTGCCAGCAGTGGTCTAGTAACCCTTTCACTTTTGGCCAGGGC 121   T  K  V  E  I  K  S  G  G  G  G  Q  V  Q  L  V  Q  S  G  A
361   ACTAAAGTGGAGATCAAATCCGGTGGTGGCGGACAGGTCCAGCTGGTCCAGAGTGGAGCT
                              Linker              V_H 141   E  V  K  K  P  G  A  S  V  K  V  S  C  K  A  S  G  Y  T  F
421   GAGGTGAAAAACCCGGCGCTTCCGTCAAAGTCTCCTGTAAGGCTAGCGGATACACATTC 161   T  R  Y  T  M  H  W  V  R  Q  A  P  G  Q  G  L  E  W  M  G
481   ACACGCTACACCATGCATTGGGTCCGGCAGGCTCCCGGACAGGGCCTGGAATGGATGGGA 181   Y  I  N  P  S  R  G  Y  T  N  Y  N  Q  K  F  K  D  R  V  T
541   TACATCAACCCTTCTCGGGGCTACACAAACTACAACCAGAAATTCAAGGATCGAGTGACC 201   M  T  T  D  T  S  I  S  T  A  Y  M  E  L  S  R  L  R  S  D
601   ATGACAACCGACACTAGCATCTCTACCGCCTACATGGAACTGAGCCGGCTGAGATCCGAT 221   D  T  A  V  Y  Y  C  A  R  Y  Y  D  D  H  Y  C  L  D  Y  W
661   GATACCGCTGTCTACTACTGTGCTCGGTACTACGATGATCATTACTGCCTGGATTACTGG 241   G  Q  G  T  L  V  T  V  S  S  G  G  C   SEQ ID NO: 13
721   GGGCAGGGCACACTGGTGACTGTGAGTTCCGGAGGATGT   SEQ ID NO: 14
```

<u>AAGCTT</u>   SEQ ID NO: 125
HinDIII

FIG. 9A
Anti-CD3 VHVL Minibody (OKT3/Murine) Translated Sequence

```
  1   M   E   T   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   M   D   W   V   W   T   L   L   F   L   L   S   V   T   A   G   V   H   S   Q
 61   ATGGATTGGGTGTGGACCTTGCTATTCCTGTTGTCAGTAACTGCAGGTGTCCACTCCCAG

41   V   Q   L   Q   Q   S   G   A   E   L   A   R   P   G   A   S   V   K   M   S
121   GTCCAGCTGCAGCAGTCTGGGGCTGAACTGGCAAGACCTGGGGCCTCAGTGAAGATGTCC

61   C   K   A   S   G   Y   T   F   T   R   Y   T   M   H   W   V   K   Q   R   P
181   TGCAAGGCTTCTGGCTACACCTTTACTAGGTACACGATGCACTGGGTAAAACAGAGGCCT

81   G   Q   G   L   E   W   I   G   Y   I   N   P   S   R   G   Y   T   N   Y   N
241   GGACAGGGTCTGGAATGGATTGGATACATTAATCCTAGCCGTGGTTATACTAATTACAAT

101   Q   K   F   K   D   K   A   T   L   T   T   D   K   S   S   S   T   A   Y   M
301   CAGAAGTTCAAGGACAAGGCCACATTGACTACAGACAAATCCTCCAGCACAGCCTACATG

121   Q   L   S   S   L   T   S   E   D   S   A   V   Y   Y   C   A   R   Y   Y   D
361   CAACTGAGCAGCCTGACATCTGAGGACTCTGCAGTCTATTACTGTGCAAGATATTATGAT

141   D   H   Y   C   L   D   Y   W   G   Q   G   T   T   L   T   V   S   S   G   S
421   GATCATTACTGCCTTGACTACTGGGGCCAAGGCACCACTCTCACAGTCTCCTCAGGCTCC

161   T   S   G   G   S   G   G   G   S   G   G   G   S   S   M   D   F   Q
481   ACATCCGGCGGAGGCTCTGGCGGTGGATCTGGCGGAGGCGGCTCATCCATGGATTTTCAA

181   V   Q   I   F   S   F   L   L   I   S   A   S   V   I   I   S   R   G   Q   I
541   GTGCAGATTTTCAGCTTCCTGCTAATCAGTGCCTCAGTCATAATATCCAGAGGACAAATT

201   V   L   T   Q   S   P   A   I   M   S   A   S   P   G   E   K   V   T   M   T
601   GTTCTCACCCAGTCTCCAGCAATCATGTCTGCATCTCCAGGGGAGAAGGTCACCATGACC

221   C   S   A   S   S   S   V   S   Y   M   N   W   Y   Q   Q   K   S   G   T   S
661   TGCAGTGCCAGCTCAAGTGTAAGTTACATGAACTGGTACCAGCAGAAGTCAGGCACCTCC

241   P   K   R   W   I   Y   D   T   S   K   L   A   S   G   V   P   A   H   F   R
721   CCCAAAAGATGGATTTATGACACATCCAAACTGGCTTCTGGAGTCCCTGCTCACTTCAGG

261   G   S   G   S   G   T   S   Y   S   L   T   I   S   G   M   E   A   E   D   A
781   GGCAGTGGGTCTGGGACCTCTTACTCTCTCACAATCAGCGGCATGGAGGCTGAAGATGCT

281   A   T   Y   Y   C   Q   Q   W   S   S   N   P   F   T   F   G   S   G   T   K
841   GCCACTTATTACTGCCAGCAGTGGAGTAGTAACCCATTCACGTTCGGCTCGGGGACAAAG

301   L   E   I   N   E   P   K   S   C   D   K   T   H   T   C   P   P   C   G   G
901   TTGGAAATAAACGAGCCTAAGTCCTGCGACAAGACCCACACCTGTCCCCCTTGCGGCGGA

321   G   S   S   G   G   G   S   G   G   Q   P   R   E   P   Q   V   Y   T   L   P
961   GGAAGCAGCGGAGGCGGATCCGGTGGCCAGCCTCGGGAGCCTCAGGTGTACACCCTGCCT

341   P   S   R   D   E   L   T   K   N   Q   V   S   L   T   C   L   V   K   G   F
1021  CCCTCCCGGGACGAGCTGACCAAGAACCAGGTGTCCCTGACCTGTCTGGTCAAGGGCTTC
```

FIG. 9B

```
 361    Y  P  S  D  I  A  V  E  W  E  S  N  G  Q  P  E  N  N  Y  K
1081    TACCCTTCCGATATCGCCGTGGAGTGGGAGTCCAACGGCCAGCCTGAGAACAACTACAAG

381    T  T  P  P  V  L  D  S  D  G  S  F  F  L  Y  S  K  L  T  V
1141    ACCACCCCTCCTGTGCTGGACTCCGACGGCTCCTTCTTCCTGTACTCCAAGCTCACAGTG

401    D  K  S  R  W  Q  Q  G  N  V  F  S  C  S  V  M  H  E  A  L
1201    GATAAGTCCCGGTGGCAGCAGGGCAACGTGTTCTCCTGCTCCGTGATGCACGAGGCCCTG

421    H  N  H  Y  T  Q  K  S  L  S  L  S  P  G  K  -     SEQ ID NO: 15
1261    CACAACCACTATACCCAGAAGTCCCTGTCCCTGTCTCCTGGCAAGTGA  SEQ ID NO: 16
```

Figure 10
Anti-CD3 VL-5-VH Cys-Diabody (OKT3/Murine) Translated Sequence

```
  1   M   E   T   D   T   L   L   L   W   V   L   L   L   W   V   P   G   S   T   G
  1   ATGGAAACCGACACCCTGCTGCTGTGGGTCCTGCTCCTCTGGGTGCCAGGCTCTACCGGC

21   Q   I   V   L   T   Q   S   P   A   I   M   S   A   S   P   G   E   K   V   T
 61   CAAATTGTTCTCACCCAGTCTCCAGCAATCATGTCTGCATCTCCAGGGGAGAAGGTCACC

41   M   T   C   S   A   S   S   S   V   S   Y   M   N   W   Y   Q   Q   K   S   G
121   ATGACCTGCAGTGCCAGCTCAAGTGTAAGTTACATGAACTGGTACCAGCAGAAGTCAGGC

61   T   S   P   K   R   W   I   Y   D   T   S   K   L   A   S   G   V   P   A   H
181   ACCTCCCCCAAAAGATGGATTTATGACACATCCAAACTGGCTTCTGGAGTCCCTGCTCAC

81   F   R   G   S   G   S   G   T   S   Y   S   L   T   I   S   G   M   E   A   E
241   TTCAGGGGCAGTGGGTCTGGGACCTCTTACTCTCTCACAATCAGCGGCATGGAGGCTGAA

101   D   A   A   T   Y   Y   C   Q   Q   W   S   S   N   P   F   T   F   G   S   G
301   GATGCTGCCACTTATTACTGCCAGCAGTGGAGTAGTAACCCATTCACGTTCGGCTCGGGG

121   T   K   L   E   I   N   S   G   G   G   G   Q   V   Q   L   Q   Q   S   G   A
361   ACAAAGTTGGAAATAAACTCTGGTGGAGGCGGGCAGGTCCAGCTGCAGCAGTCTGGGGCT

141   E   L   A   R   P   G   A   S   V   K   M   S   C   K   A   S   G   Y   T   F
421   GAACTGGCAAGACCTGGGGCCTCAGTGAAGATGTCCTGCAAGGCTTCTGGCTACACCTTT

161   T   R   Y   T   M   H   W   V   K   Q   R   P   G   Q   G   L   E   W   I   G
481   ACTAGGTACACGATGCACTGGGTAAAACAGAGGCCTGGACAGGGTCTGGAATGGATTGGA

181   Y   I   N   P   S   R   G   Y   T   N   Y   N   Q   K   F   K   D   K   A   T
541   TACATTAATCCTAGCCGTGGTTATACTAATTACAATCAGAAGTTCAAGGACAAGGCCACA

201   L   T   D   K   S   S   S   T   A   Y   M   Q   L   S   S   L   T   S   E
601   TTGACTACAGACAAATCCTCCAGCACAGCCTACATGCAACTGAGCAGCCTGACATCTGAG

221   D   S   A   V   Y   Y   C   A   R   Y   Y   D   D   H   Y   C   L   D   Y   W
661   GACTCTGCAGTCTATTACTGTGCAAGATATTATGATGATCATTACTGCCTTGACTACTGG

241   G   Q   G   T   T   L   T   V   S   S   G   G   C   -           SEQ ID NO: 17
721   GGCCAAGGCACCACTCTCACAGTCTCCTCAGGCGGATGCTGA         SEQ ID NO: 18
```

Figure 11
Anti-CD3 VH-5-VL Cys-Diabody (OKT3/Murine) Translated Sequence

```
  1   M  E  T  D  T  L  L  W  V  L  L  W  V  P  G  S  T  G
  1   ATGGAAACCGACACCCTGCTGCTGTGGGTGCTGCTGCTCTGGGTCCCAGGCTCCACCGGT

21   Q  V  Q  L  Q  Q  S  G  A  E  L  A  R  P  G  A  S  V  K  M
 61   CAGGTCCAGCTGCAGCAGTCTGGGGCTGAACTGGCAAGACCTGGGGCCTCAGTGAAGATG

41   S  C  K  A  S  G  Y  T  F  T  R  Y  T  M  H  W  V  K  Q  R
121   TCCTGCAAGGCTTCTGGCTACACCTTTACTAGGTACACGATGCACTGGGTAAAACAGAGG

61   P  G  Q  G  L  E  W  I  G  Y  I  N  P  S  R  G  Y  T  N  Y
181   CCTGGACAGGGTCTGGAATGGATTGGATACATTAATCCTAGCCGTGGTTATACTAATTAC

81   N  Q  K  F  K  D  K  A  T  L  T  T  D  K  S  S  S  T  A  Y
241   AATCAGAAGTTCAAGGACAAGGCCACATTGACTACAGACAAATCCTCCAGCACAGCCTAC

101   M  Q  L  S  S  L  T  S  E  D  S  A  V  Y  Y  C  A  R  Y  Y
301   ATGCAACTGAGCAGCCTGACATCTGAGGACTCTGCAGTCTATTACTGTGCAAGATATTAT

121   D  D  H  Y  C  L  D  Y  W  G  Q  G  T  T  L  T  V  S  S  S
361   GATGATCATTACTGCCTTGACTACTGGGGCCAAGGCACCACTCTCACAGTCTCCTCAAGT

141   G  G  G  Q  I  V  L  T  Q  S  P  A  I  M  S  A  S  P  G
421   GGTGGAGGAGGCCAAATTGTTCTCACCCAGTCTCCAGCAATCATGTCTGCATCTCCAGGG

161   E  K  V  T  M  T  C  S  A  S  S  S  V  S  Y  M  N  W  Y  Q
481   GAGAAGGTCACCATGACCTGCAGTGCCAGCTCAAGTGTAAGTTACATGAACTGGTACCAG

181   Q  K  S  G  T  S  P  K  R  W  I  Y  D  T  S  K  L  A  S  G
541   CAGAAGTCAGGCACCTCCCCCAAAAGATGGATTTATGACACATCCAAACTGGCTTCTGGA

201   V  P  A  H  F  R  G  S  G  S  G  T  S  Y  S  L  T  I  S  G
601   GTCCCTGCTCACTTCAGGGGCAGTGGGTCTGGGACCTCTTACTCTCTCACAATCAGCGGC

221   M  E  A  E  D  A  A  T  Y  Y  C  Q  Q  W  S  S  N  P  F  T
661   ATGGAGGCTGAAGATGCTGCCACTTATTACTGCCAGCAGTGGAGTAGTAACCCATTCACG

241   F  G  S  G  T  K  L  E  I  N  G  G  C      SEQ ID NO: 19
721   TTCGGCTCGGGGACAAAGTTGGAAATAAACGGCGGCTGC    SEQ ID NO: 20
```

Figure 12
Anti-CD3 VL-8-VH Cys-Diabody (OKT3/Murine) Translated Sequence

```
  1   M   E   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   Q   I   V   L   T   Q   S   P   A   I   M   S   A   S   P   G   E   K   V   T
 61   CAAATTGTTCTCACCCAGTCTCCAGCAATCATGTCTGCATCTCCAGGGGAGAAGGTCACC

41   M   T   C   S   A   S   S   S   V   S   Y   M   N   W   Y   Q   Q   K   S   G
121   ATGACCTGCAGTGCCAGCTCAAGTGTAAGTTACATGAACTGGTACCAGCAGAAGTCAGGC

61   T   S   P   K   R   W   I   Y   D   T   S   K   L   A   S   G   V   P   A   H
181   ACCTCCCCCAAAAGATGGATTTATGACACATCCAAACTGGCTTCTGGAGTCCCTGCTCAC

81   F   R   G   S   G   S   G   T   S   Y   S   L   T   I   S   G   M   E   A   E
241   TTCAGGGGCAGTGGGTCTGGGACCTCTTACTCTCTCACAATCAGCGGCATGGAGGCTGAA

101   D   A   A   T   Y   Y   C   Q   Q   W   S   S   N   P   F   T   F   G   S   G
301   GATGCTGCCACTTATTACTGCCAGCAGTGGAGTAGTAACCCATTCACGTTCGGCTCGGGG

121   T   K   L   E   I   N   G   G   G   S   G   G   G   G   Q   V   Q   L   Q   Q
361   ACAAAGTTGGAAATAAACGGCGGAGGCAGTGGCGGAGGCGGCCAGGTCCAGCTGCAGCAG

141   S   G   A   E   L   A   R   P   G   A   S   V   K   M   S   C   K   A   S   G
421   TCTGGGGCTGAACTGGCAAGACCTGGGGCCTCAGTGAAGATGTCCTGCAAGGCTTCTGGC

161   Y   T   F   T   R   Y   T   M   H   W   V   K   Q   R   P   G   Q   G   L   E
481   TACACCTTTACTAGGTACACGATGCACTGGGTAAAACAGAGGCCTGGACAGGGTCTGGAA

181   W   I   G   Y   I   N   P   S   R   G   Y   T   N   Y   N   Q   K   F   K   D
541   TGGATTGGATACATTAATCCTAGCCGTGGTTATACTAATTACAATCAGAAGTTCAAGGAC

201   K   A   T   L   T   T   D   K   S   S   S   T   A   Y   M   Q   L   S   S   L
601   AAGGCCACATTGACTACAGACAAATCCTCCAGCACAGCCTACATGCAACTGAGCAGCCTG

221   T   S   E   D   S   A   V   Y   Y   C   A   R   Y   Y   D   D   H   Y   C   L
661   ACATCTGAGGACTCTGCAGTCTATTACTGTGCAAGATATTATGATGATCATTACTGCCTT

241   D   Y   W   G   Q   G   T   L   T   V   S   S   G   G   C   SEQ ID NO: 21
721   GACTACTGGGGCCAAGGCACCACTCTCACAGTCTCCTCAGGCGGCTGC  SEQ ID NO: 22
```

Figure 13
Anti-CD3 VH-8-VL Cys-Diabody (OKT3/Murine) Translated Sequence

```
  1   M  E  T  D  T  L  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   Q  V  Q  L  Q  Q  S  G  A  E  L  A  R  P  G  A  S  V  K  M
 61   CAGGTCCAGCTGCAGCAGTCTGGGGCTGAACTGGCAAGACCTGGGGCCTCAGTGAAGATG

41   S  C  K  A  S  G  Y  T  F  T  R  Y  T  M  H  W  V  K  Q  R
121   TCCTGCAAGGCTTCTGGCTACACCTTTACTAGGTACACGATGCACTGGGTAAAACAGAGG

61   P  G  Q  G  L  E  W  I  G  Y  I  N  P  S  R  G  Y  T  N  Y
181   CCTGGACAGGGTCTGGAATGGATTGGATACATTAATCCTAGCCGTGGTTATACTAATTAC

81   N  Q  K  F  K  D  K  A  T  L  T  T  D  K  S  S  S  T  A  Y
241   AATCAGAAGTTCAAGGACAAGGCCACATTGACTACAGACAAATCCTCCAGCACAGCCTAC

101   M  Q  L  S  S  L  T  S  E  D  S  A  V  Y  Y  C  A  R  Y  Y
301   ATGCAACTGAGCAGCCTGACATCTGAGGACTCTGCAGTCTATTACTGTGCAAGATATTAT

121   D  D  H  Y  C  L  D  Y  W  G  Q  G  T  T  L  T  V  S  S  G
361   GATGATCATTACTGCCTTGACTACTGGGGCCAAGGCACCACTCTCACAGTCTCCTCAGGC

141   G  G  S  G  G  S  G  Q  I  V  L  T  Q  S  P  A  I  M  S  A
421   GGAGGGAGTGGCGGAGGTGGCCAAATTGTTCTCACCCAGTCTCCAGCAATCATGTCTGCA

161   S  P  G  E  K  V  T  M  T  C  S  A  S  S  S  V  S  Y  M  N
481   TCTCCAGGGGAGAAGGTCACCATGACCTGCAGTGCCAGCTCAAGTGTAAGTTACATGAAC

181   W  Y  Q  Q  K  S  G  T  S  P  K  R  W  I  Y  D  T  S  K  L
541   TGGTACCAGCAGAAGTCAGGCACCTCCCCCAAAAGATGGATTTATGACACATCCAAACTG

201   A  S  G  V  P  A  H  F  R  G  S  G  S  G  T  S  Y  S  L  T
601   GCTTCTGGAGTCCCTGCTCACTTCAGGGGCAGTGGGTCTGGGACCTCTTACTCTCTCACA

221   I  S  G  M  E  A  E  D  A  A  T  Y  Y  C  Q  Q  W  S  S  N
661   ATCAGCGGCATGGAGGCTGAAGATGCTGCCACTTATTACTGCCAGCAGTGGAGTAGTAAC

241   P  F  T  F  G  S  G  T  K  L  E  I  N  G  G  C      SEQ ID NO: 23
721   CCATTCACGTTCGGCTCGGGGACAAAGTTGGAAATAAACGGCGGCTGC    SEQ ID NO: 24
```

FIG. 14A
Anti-CD3 VHVL Minibody (ABC1) Translated Sequence

```
  1     M   E   T   D   T   L   L   L   W   V   L   L   L   W   V   P   G   S   T   G
  1    ATGGAAACCGACACCCTGCTGCTGTGGGTGCTGCTGCTCTGGGTCCCAGGCTCCACCGGT

21     Q   V   Q   L   V   Q   S   G   G   G   V   V   Q   P   G   R   S   L   R   L
 61    CAGGTCCAGCTGGTCCAGTCTGGTGGAGGAGTGGTCCAGCCCGGGAGATCACTGAGGCTG

41     S   C   K   A   S   G   Y   T   F   T   R   Y   T   M   H   W   V   R   Q   A
121    TCCTGTAAGGCTAGTGGCTACACTTTTACACGGTACACCATGCATTGGGTGAGGCAGGCA

61     P   G   K   G   L   E   W   I   G   Y   I   N   P   S   R   G   Y   T   N   Y
181    CCTGGGAAAGGCCTGGAATGGATCGGATACATCAACCCTAGTAGGGGATACACAAACTAC

81     N   Q   K   V   K   D   R   F   T   I   S   R   D   N   S   K   N   T   A   F
241    AATCAGAAAGTCAAGGACCGGTTCACAATCTCTAGGGACAACTCTAAAAACACCGCTTTT

101     L   Q   M   D   S   L   R   P   E   D   T   G   V   Y   F   C   A   R   Y   Y
301    CTGCAGATGGACTCACTGAGGCCTGAGGACACTGGAGTGTACTTTTGTGCTCGGTACTAC

121     D   D   H   Y   C   L   D   Y   W   G   Q   G   T   P   V   T   V   S   S   G
361    GATGATCATTACTGCCTGGATTACTGGGGACAGGGGACACCTGTCACTGTCTCTTCCGGC

141     S   T   S   G   G   G   S   G   G   G   S   G   G   G   S   S   D   I   Q
421    TCCACATCCGGCGGAGGCTCTGGCGGTGGATCTGGCGGAGGCGGCTCATCCGACATCCAG

161     M   T   Q   S   P   S   S   L   S   A   S   V   G   D   R   V   T   I   T   C
481    ATGACACAGTCTCCCTCTTCTCTGTCCGCCTCTGTGGGCGATCGAGTGACAATCACCTGT

181     S   A   S   S   S   V   S   Y   M   N   W   Y   Q   Q   T   P   G   K   A   P
541    AGCGCTTCATCCTCCGTGTCTTACATGAATTGGTACCAGCAGACCCCTGGCAAAGCTCCT

201     K   R   W   I   Y   D   T   S   K   L   A   S   G   V   P   S   R   F   S   G
601    AAACGATGGATCTACGACACCTCCAAACTGGCTTCCGGCGTGCCTTCACGATTTCTGGT

221     S   G   S   G   T   D   Y   T   F   T   I   S   S   L   Q   P   E   D   I   A
661    TCTGGTTCTGGGACCGACTACACCTTTACCATCTCATCACTGCAGCCTGAGGATATCGCC

241     T   Y   Y   C   Q   Q   W   S   S   N   P   F   T   F   G   Q   G   T   K   L
721    ACATACTACTGTCAGCAGTGGTCTAGCAACCCTTTCACATTCGGGCAGGGCACAAAACTG

261     Q   I   T   E   P   K   S   C   D   K   T   H   T   C   P   P   C   G   G
781    CAGATCACCGAGCCTAAGTCCTGCGACAAGACCCACACCTGTCCCCCTTGCGGCGGAGGA

281     S   S   G   G   S   G   G   Q   P   R   E   P   Q   V   Y   T   L   P   P
841    AGCAGCGGAGGCGGATCCGGTGGCCAGCCTCGGGAGCCTCAGGTGTACACCCTGCCTCCC

301     S   R   D   E   L   T   K   N   Q   V   S   L   T   C   L   V   K   G   F   Y
901    TCCCGGGACGAGCTGACCAAGAACCAGGTGTCCCTGACCTGTCTGGTCAAGGGCTTCTAC

321     P   S   D   I   A   V   E   W   E   S   N   G   Q   P   E   N   N   Y   K   T
961    CCTTCCGATATCGCCGTGGAGTGGGAGTCCAACGGCCAGCCTGAGAACAACTACAAGACC
```

FIG. 14B

```
 341    T  P  P  V  L  D  S  D  G  S  F  F  L  Y  S  K  L  T  V  D
1021   ACCCCTCCTGTGCTGGACTCCGACGGCTCCTTCTTCCTGTACTCCAAGCTCACAGTGGAT

361    K  S  R  W  Q  Q  G  N  V  F  S  C  S  V  M  H  E  A  L  H
1081   AAGTCCCGGTGGCAGCAGGGCAACGTGTTCTCCTGCTCCGTGATGCACGAGGCCCTGCAC

381    N  R  Y  T  Q  K  S  L  S  L  S  P  G  K  -     SEQ ID NO: 25
1141   AACCACTATACCCAGAAGTCCCTGTCCCTGCTCCTGGCAAGTGA      SEQ ID NO: 26
```

Figure 15
Anti-CD3 VL-5-VH Cys-Diabody (ABC1) Translated Sequence

```
  1    M  E  T  D  T  L  L  L  W  V  L  L  L  W  V  P  G  S  T  G
  1    ATGGAAACCGACACCCTGCTGCTGTGGGTGCTGCTGCTCTGGGTCCCAGGCTCCACCGGT

21    D  I  Q  M  T  Q  S  P  S  S  L  S  A  S  V  G  D  R  V  T
 61    GACATCCAGATGACACAGTCTCCCTCTTCTCTGTCCGCCTCTGTGGGCGATCGAGTGACA

41    I  T  C  S  A  S  S  S  V  S  Y  M  N  W  Y  Q  Q  T  P  G
121    ATCACCTGTAGCGCTTCATCCTCCGTGTCTTACATGAATTGGTACCAGCAGACCCCTGGC

61    K  A  P  K  R  W  I  Y  D  T  S  K  L  A  S  G  V  P  S  R
181    AAAGCTCCTAAACGATGGATCTACGACACCTCCAAACTGGCTTCCGGCGTGCCTTCACGA

81    F  S  G  S  G  S  G  T  D  Y  T  F  T  I  S  S  L  Q  P  E
241    TTTTCTGGTTCTGGTTCTGGGACCGACTACACCTTTACCATCTCATCACTGCAGCCTGAG

101    D  I  A  T  Y  Y  C  Q  Q  W  S  S  N  P  F  T  F  G  Q  G
301    GATATCGCCACATACTACTGTCAGCAGTGGTCTAGCAACCCTTTCACATTCGGGCAGGGC

121    T  K  L  Q  I  T  S  G  G  G  G  Q  V  Q  L  V  Q  S  G  G
361    ACAAAACTGCAGATCACCAGTGGTGGAGGAGGCCAGGTCCAGCTGGTCCAGTCTGGTGGA

141    G  V  V  Q  P  G  R  S  L  R  L  S  C  K  A  S  G  Y  T  F
421    GGAGTGGTCCAGCCCGGGAGATCACTGAGGCTGTCCTGTAAGGCTAGTGGCTACACTTTT

161    T  R  Y  T  M  H  W  V  R  Q  A  P  G  K  G  L  E  W  I  G
481    ACACGGTACACCATGCATTGGGTGAGGCAGGCACCTGGGAAAGGCCTGGAATGGATCGGA

181    Y  I  N  P  S  R  G  Y  T  N  Y  N  Q  K  V  K  D  R  F  T
541    TACATCAACCCTAGTAGGGGATACACAAACTACAATCAGAAAGTCAAGGACCGGTTCACA

201    I  S  R  D  N  S  K  N  T  A  F  L  Q  M  D  S  L  R  P  E
601    ATCTCTAGGGACAACTCTAAAAACACCGCTTTTCTGCAGATGGACTCACTGAGGCCTGAG

221    D  T  G  V  Y  F  C  A  R  Y  Y  D  D  H  Y  C  L  D  Y  W
661    GACACTGGAGTGTACTTTTGTGCTCGGTACTACGATGATCATTACTGCCTGGATTACTGG

241    G  Q  G  T  P  V  T  V  S  S  G  G  C     SEQ ID NO: 27
721    GGACAGGGGACACCTGTCACTGTCTCTTCCGGCGGCTGC     SEQ ID NO: 28
```

Figure 16
Anti-CD3 VH-5-VL Cys-Diabody (ABC1) Translated Sequence

```
  1   M  E  T  D  T  L  L  W  V  L  L  W  V  P  G  S  T  G
  1   ATGGAAACCGACACCCTGCTGCTGTGGGTGCTGCTGCTCTGGGTCCCAGGCTCCACCGGT

21   Q  V  Q  L  V  Q  S  G  G  G  V  V  Q  P  G  R  S  L  R  L
 61   CAGGTCCAGCTGGTCCAGTCTGGTGGAGGAGTGGTCCAGCCCGGGAGATCACTGAGGCTG

41   S  C  K  A  S  G  Y  T  F  T  R  Y  T  M  H  W  V  R  Q  A
121   TCCTGTAAGGCTAGTGGCTACACTTTTACACGGTACACCATGCATTGGGTGAGGCAGGCA

61   P  G  K  G  L  E  W  I  G  Y  I  N  P  S  R  G  Y  T  N  Y
181   CCTGGGAAAGGCCTGGAATGGATCGGATACATCAACCCTAGTAGGGGATACACAAACTAC

81   N  Q  K  V  K  D  R  F  T  I  S  R  D  N  S  K  N  T  A  F
241   AATCAGAAAGTCAAGGACCGGTTCACAATCTCTAGGGACAACTCTAAAAACACCGCTTTT

101   L  Q  M  D  S  L  R  P  E  D  T  G  V  Y  F  C  A  R  Y  Y
301   CTGCAGATGGACTCACTGAGGCCTGAGGACACTGGAGTGTACTTTTGTGCTCGGTACTAC

121   D  D  H  Y  C  L  D  Y  W  G  Q  G  T  P  V  T  V  S  S
361   GATGATCATTACTGCCTGGATTACTGGGGACAGGGGACACCTGTCACTGTCTCTTCCAGT

141   G  G  G  D  I  Q  M  T  Q  S  P  S  S  L  S  A  S  V  G
421   GGTGGAGGAGGCGACATCCAGATGACACAGTCTCCCTCTTCTCTGTCCGCCTCTGTGGGC

161   D  R  V  T  I  T  C  S  A  S  S  S  V  S  Y  M  N  W  Y  Q
481   GATCGAGTGACAATCACCTGTAGCGCTTCATCCTCCGTGTCTTACATGAATTGGTACCAG

181   Q  T  P  G  K  A  P  K  R  W  I  Y  D  T  S  K  L  A  S  G
541   CAGACCCCTGGCAAAGCTCCTAAACGATGGATCTACGACACCTCCAAACTGGCTTCCGGC

201   V  P  S  R  F  S  G  S  G  S  G  T  D  Y  T  F  T  I  S  S
601   GTGCCTTCACGATTTTCTGGTTCTGGTTCTGGGACCGACTACACCTTTACCATCTCATCA

221   L  Q  P  E  D  I  A  T  Y  Y  C  Q  Q  W  S  S  N  P  F  T
661   CTGCAGCCTGAGGATATCGCCACATACTACTGTCAGCAGTGGTCTAGCAACCCTTTCACA

241   F  G  Q  G  T  K  L  Q  I  T  G  G  C      SEQ ID NO: 29
721   TTCGGGCAGGGCACAAAACTGCAGATCACCGGCGGCTGC     SEQ ID NO: 30
```

Figure 17
Anti-CD3 VL-8-VH Cys-Diabody (ABC1) Translated Sequence

```
  1   M  E  T  D  T  L  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   D  I  Q  M  T  Q  S  P  S  S  L  S  A  S  V  G  D  R  V  T
 61   GACATCCAGATGACACAGTCTCCCTCTTCTCTGTCCGCCTCTGTGGGCGATCGAGTGACA

41   I  T  C  S  A  S  S  S  V  S  Y  M  N  W  Y  Q  Q  T  P  G
121   ATCACCTGTAGCGCTTCATCCTCCGTGTCTTACATGAATTGGTACCAGCAGACCCCTGGC

61   K  A  P  K  R  W  I  Y  D  T  S  K  L  A  S  G  V  P  S  R
181   AAAGCTCCTAAACGATGGATCTACGACACCTCCAAACTGGCTTCCGGCGTGCCTTCACGA

81   F  S  G  S  G  S  G  T  D  Y  T  F  T  I  S  S  L  Q  P  E
241   TTTTCTGGTTCTGGTTCTGGGACCGACTACACCTTTACCATCTCATCACTGCAGCCTGAG

101   D  I  A  T  Y  Y  C  Q  Q  W  S  S  N  P  F  T  F  G  Q  G
301   GATATCGCCACATACTACTGTCAGCAGTGGTCTAGCAACCCTTTCACATTCGGGCAGGGC

121   T  K  L  Q  I  T  G  G  G  S  G  G  G  G  Q  V  Q  L  V  Q
361   ACAAAACTGCAGATCACCGGCGGAGGAGTGGCGGAGGCGGCCAGGTCCAGCTGGTCCAG

141   S  G  G  G  V  V  Q  P  G  R  S  L  R  L  S  C  K  A  S  G
421   TCTGGTGGAGGAGTGGTCCAGCCCGGGAGATCACTGAGGCTGTCCTGTAAGGCTAGTGGC

161   Y  T  F  T  R  Y  T  M  H  W  V  R  Q  A  P  G  K  G  L  E
481   TACACTTTTACACGGTACACCATGCATTGGGTGAGGCAGGCACCTGGGAAAGGCCTGGAA

181   W  I  G  Y  I  N  P  S  R  G  Y  T  N  Y  N  Q  K  V  K  D
541   TGGATCGGATACATCAACCCTAGTAGGGGATACACAAACTACAATCAGAAAGTCAAGGAC

201   R  F  T  I  S  R  D  N  S  K  N  T  A  F  L  Q  M  D  S  L
601   CGGTTCACAATCTCTAGGGACAACTCTAAAAACACCGCTTTTCTGCAGATGGACTCACTG

221   R  P  E  D  T  G  V  Y  F  C  A  R  Y  Y  D  D  H  Y  C  L
661   AGGCCTGAGGACACTGGAGTGTACTTTTGTGCTCGGTACTACGATGATCATTACTGCCTG

241   D  Y  W  G  Q  G  T  P  V  T  V  S  S  G  G  C      SEQ ID NO: 31
721   GATTACTGGGGACAGGGGACACCTGTCACTGTCTCTTCCGGCGGCTGC    SEQ ID NO: 32
```

Figure 18
Anti-CD3 VH-8-VL Cys-Diabody (ABC1) Translated Sequence

```
  1   M  E  T  D  T  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   Q  V  Q  L  V  Q  S  G  G  S  V  V  Q  P  G  R  S  L  R  L
 61   CAGGTCCAGCTGGTCCAGTCTGGTGGAGGAGTGGTCCAGCCCGGGAGATCACTGAGGCTG

41   S  C  K  A  S  G  Y  T  F  T  R  Y  T  M  H  W  V  R  Q  A
121   TCCTGTAAGGCTAGTGGCTACACTTTTACACGGTACACCATGCATTGGGTGAGGCAGGCA

61   P  G  K  G  L  E  W  I  G  Y  I  N  P  S  R  G  Y  T  N  Y
181   CCTGGGAAAGGCCTGGAATGGATCGGATACATCAACCCTAGTAGGGGATACACAAACTAC

81   N  Q  K  V  K  D  R  F  T  I  S  R  D  N  S  K  N  T  A  F
241   AATCAGAAAGTCAAGGACCGGTTCACAATCTCTAGGGACAACTCTAAAAACACCGCTTTT

101   L  Q  M  D  S  L  R  P  E  D  T  G  V  Y  F  C  A  R  Y  Y
301   CTGCAGATGGACTCACTGAGGCCTGAGGACACTGGAGTGTACTTTTGTGCTCGGTACTAC

121   D  D  H  Y  C  L  D  Y  W  G  Q  G  T  P  V  T  V  S  S  G
361   GATGATCATTACTGCCTGGATTACTGGGGACAGGGGACACCTGTCACTGTCTCTTCCGGC

141   G  G  S  G  G  G  D  I  Q  M  T  Q  S  P  S  S  L  S  A
421   GGAGGGAGTGGCGGAGGCGGCGACATCCAGATGACACAGTCTCCCTCTTCTCTGTCCGCC

161   S  V  G  D  R  V  T  I  T  C  S  A  S  S  S  V  S  Y  M  N
481   TCTGTGGGCGATCGAGTGACAATCACCTGTAGCGCTTCATCCTCCGTGTCTTACATGAAT

181   W  Y  Q  Q  T  P  G  K  A  P  K  R  W  I  Y  D  T  S  K  L
541   TGGTACCAGCAGACCCCTGGCAAAGCTCCTAAACGATGGATCTACGACACCTCCAAACTG

201   A  S  G  V  P  S  R  F  S  G  S  G  S  G  T  D  Y  T  F  T
601   GCTTCCGGCGTGCCTTCACGATTTTCTGGTTCTGGTTCTGGGACCGACTACACCTTTACC

221   I  S  S  L  Q  P  E  D  I  A  T  Y  Y  C  Q  Q  W  S  S  N
661   ATCTCATCACTGCAGCCTGAGGATATCGCCACATACTACTGTCAGCAGTGGTCTAGCAAC

241   P  F  T  F  G  Q  G  T  K  L  Q  I  T  G  G  C    SEQ ID NO: 33
721   CCTTTCACATTCGGGCAGGGCACAAAACTGCAGATCACCGGCGGCTGC  SEQ ID NO: 34
```

FIG. 19A
Anti-CD3 VHVL Minibody (ImaginAb Humanized OKT3) Translated Sequence

```
  1   M   E   T   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   Q   V   Q   L   V   Q   S   G   A   E   V   K   K   P   G   A   S   V   K   V
 61   CAGGTCCAGCTGGTCCAGAGTGGAGCTGAGGTGAAAAAACCCGGCGCTTCCGTCAAAGTC

41   S   C   K   A   S   G   Y   T   F   T   R   Y   T   M   H   W   V   R   Q   A
121   TCCTGTAAGGCTAGCGGATACACCTTTACTCGTACACCATGCATTGGGTCCGGCAGGCT

61   P   G   Q   G   L   E   W   M   G   Y   I   N   P   S   R   G   Y   T   N   Y
181   CCCGGACAGGGCCTGGAATGGATGGGATACATCAACCCTTCTCGGGCTACACAAACTAC

81   N   Q   K   F   K   D   R   V   T   M   T   I   D   T   S   I   S   T   A   Y
241   AATCAGAAATTCAAGGATCGAGTGACCATGACAACCGACACTTCAATCTCTACCGCTTAC

101   M   E   L   S   R   L   R   S   D   D   T   A   V   Y   Y   C   A   R   Y   Y
301   ATGGAACTGTCTCGGCTGAGGAGTGACGATACCGCTGTCTACTACTGTGCTCGGTACTAC

121   D   D   H   Y   C   L   D   Y   W   G   Q   G   T   L   V   T   V   S   S   G
361   GACGACCATTACTGCCTGGATTACTGGGGCAGGGCACACTGGTGACTGTGTCTAGCGGC

141   S   T   S   G   G   G   S   G   G   G   S   G   G   G   S   E   I   V
421   TCCACATCCGGTGGAGGCTCTGGCGGTGGATCTGGCGGAGGTGGCTCATCCGAAATCGTG

161   L   T   Q   S   P   A   T   L   S   L   S   P   G   E   R   A   T   L   S   C
481   CTGACTCAGTCCCTGCTACACTGTCTCTGTCACCTGGCGAACGAGCAACACTGTCCTGT

181   S   A   S   S   S   V   S   Y   M   N   W   Y   Q   Q   K   P   G   Q   A   P
541   TCTGCCTCTTCTTCTGTCTCATACATGAACTGGTACCAGCAGAAACCTGGACAGGCTCCT

201   R   L   L   I   Y   D   T   S   K   L   A   S   G   V   P   A   H   F   R   G
601   AGACTGCTGATCTACGACACCTCTAAACTGGCATCTGGCGTGCCCGCTCATTTCCGTGGC

221   S   G   S   G   T   D   F   T   L   T   I   S   S   L   E   P   E   D   F   A
661   TCTGGATCTGGAACCGACTTTACTCTGACCATCTCTTCCCTGGAACTGAGGATTTTGCC

241   V   Y   Y   C   Q   Q   W   S   S   N   P   F   T   F   G   Q   G   T   K   V
721   GTGTACTACTGCCAGCAGTGGTCTAGTAACCCTTTCACTTTTGGCCAGGGCACTAAAGTG

261   E   I   K   E   P   K   S   C   D   K   T   H   T   C   P   P   C   G   G   G
781   GAGATCAAGGAGCCTAAGTCCTGCGACAAGACCCACACTTGTCCCCCTTGCGGTGGAGGA

281   S   S   G   G   S   G   G   Q   P   R   E   P   Q   V   Y   T   L   P   P
841   AGCAGCGGAGGCGGATCCGGTGGCCAGCCTCGGGAGCCTCAGGTGTACACCCTGCCTCCT

301   S   R   D   E   L   T   K   N   Q   V   S   L   T   C   L   V   K   G   F   Y
901   TCCCGGACGAGCTGACCAAGAACCAGGTCCCTGACTTGTCTGGTCAAGGGCTTCTAC

321   P   S   D   I   A   V   E   W   E   S   N   G   Q   P   E   N   N   Y   K   T
961   CCTTCCGATATCGCCGTGGAGTGGGAGTCCAACGGCCAGCCTGAGAACAACTACAAGACC

341   T   P   P   V   L   D   S   D   G   S   F   F   L   Y   S   K   L   T   V   D
1021  ACCCCTCCTGTGCTGGACTCCGACGGCTCCTTCTTCCTGTACTCAAGCTCACAGTGGAT
```

FIG. 19B

```
 361    K  S  R  W  Q  Q  G  N  V  F  S  C  S  V  M  H  E  A  L  H
1081    AAGTCCCGGTGGCAGCAGGGCAACGTGTTCTCCTGCTCCGTGATGCACGAGGCCCTGCAC

381    N  H  Y  T  Q  K  S  L  S  L  S  P  G  K  -     SEQ ID NO: 35
1141    AACCACTATACCCAGAAGTCCCTGTCCCTGTCTCCTGGCAAGTGA     SEQ ID NO: 36
```

Figure 20
Anti-CD3 VL-5-VH Cys-Diabody (ImaginAb Humanized OKT3) Translated Sequence

```
  1   M   E   T   D   T   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   E   I   V   L   T   Q   S   P   A   T   L   S   L   S   P   G   E   R   A   T
 61   GAAATCGTGCTGACTCAGTCCCCTGCTACACTGTCTCTGTCACCTGGCGAACGAGCAACA

41   L   S   C   S   A   S   S   S   V   S   Y   M   N   W   Y   Q   Q   K   P   G
121   CTGTCCTGTTCTGCCTCTTCTTCTGTCTCATACATGAACTGGTACCAGCAGAAACCTGGA

61   Q   A   P   R   L   L   I   Y   D   T   S   K   L   A   S   G   V   P   A   H
181   CAGGCTCCTAGACTGCTGATCTACGACACCTCTAAACTGGCATCTGGCGTGCCCGCTCAT

81   F   R   G   S   G   S   G   T   D   F   T   L   T   I   S   S   L   E   P   E
241   TTTCGTGGCTCTGGATCTGGAACCGACTTTACCCTGACCATCTCTTCCCTGGAACCTGAG

101   D   F   A   V   Y   Y   C   Q   Q   W   S   S   N   P   F   T   F   G   Q   G
301   GATTTTGCCGTGTACTACTGCCAGCAGTGGTCTAGTAACCCTTTCACTTTTGGCCAGGGC

121   T   K   V   E   I   K   S   G   G   G   G   Q   V   Q   L   V   Q   S   G   A
361   ACTAAAGTGGAGATCAAGAGTGGTGGAGGAGGCCAGGTCCAGCTGGTCCAGAGTGGAGCT

141   E   V   K   K   P   G   A   S   V   K   V   S   C   K   A   S   G   Y   T   F
421   GAGGTGAAAAAACCCGGCGCTTCCGTCAAAGTCTCCTGTAAGGCTAGCGGATACACCTTT

161   T   R   Y   T   M   H   W   V   R   Q   A   P   G   Q   G   L   E   W   M   G
481   ACTCGCTACACCATGCATTGGGTCCGGCAGGCTCCCGGACAGGGCCTGGAATGGATGGGA

181   Y   I   N   P   S   R   G   Y   T   N   Y   N   Q   K   F   K   D   R   V   T
541   TACATCAACCCTTCTCGGGGCTACACAAACTACAATCAGAAATTCAAGGATCGAGTGACC

201   M   T   T   D   T   S   I   S   T   A   Y   M   E   L   S   R   L   R   S   D
601   ATGACAACCGACACTTCAATCTCTACCGCTTACATGGAACTGTCTCGGCTGAGGAGTGAC

221   D   T   A   V   Y   Y   C   A   R   Y   Y   D   D   H   Y   C   L   D   Y   W
661   GATACCGCTGTCTACTACTGTGCTCGGTACTACGACGACCATTACTGCCTGGATTACTGG

241   G   Q   G   T   L   V   T   V   S   S   G   G   C      SEQ ID NO: 37
721   GGGCAGGGCACACTGGTGACTGTGTCTAGCGGCGGCTGC    SEQ ID NO: 38
```

Figure 21
Anti-CD3 VH-5-VL Cys-Diabody (ImaginAb Humanized OKT3) Translated Sequence

```
  1   M  E  T  D  T  L  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   Q  V  Q  L  V  Q  S  G  A  E  V  K  K  P  G  A  S  V  K  V
 61   CAGGTCCAGCTGGTCCAGAGTGGAGCTGAGGTGAAAAAACCCGGCGCTTCCGTCAAAGTC

41   S  C  K  A  S  G  Y  T  F  T  R  Y  T  M  H  W  V  R  Q  A
121   TCCTGTAAGGCTAGCGGATACACCTTTACTCGCTACACCATGCATTGGGTCCGGCAGGCT

61   P  G  Q  G  L  E  W  M  G  Y  I  N  P  S  R  G  Y  T  N  Y
181   CCCGGACAGGGCCTGGAATGGATGGGATACATCAACCCTTCTCGGGGCTACACAAACTAC

81   N  Q  K  F  K  D  R  V  T  M  T  T  D  T  S  I  S  T  A  Y
241   AATCAGAAATTCAAGGATCGAGTGACCATGACAACCGACACTTCAATCTCTACCGCTTAC

101   M  E  L  S  R  L  R  S  D  D  T  A  V  Y  Y  C  A  R  Y  Y
301   ATGGAACTGTCTCGGCTGAGGAGTGACGATACCGCTGTCTACTACTGTGCTCGGTACTAC

121   D  D  H  Y  C  L  D  Y  W  G  Q  G  T  L  V  T  V  S  S  S
361   GACGACCATTACTGCCTGGATTACTGGGGCAGGGCACACTGGTGACTGTGTCTAGCAGT

141   G  G  G  G  E  I  V  L  T  Q  S  P  A  T  L  S  L  S  P  G
421   GGTGGAGGAGGCGAAATCGTGCTGACTCAGTCCCCTGCTACACTGTCTCTGTCACCTGGC

161   E  R  A  T  L  S  C  S  A  S  S  S  V  S  Y  M  N  W  Y  Q
481   GAACGAGCAACACTGTCCTGTTCTGCCTCTTCTTCTGTCTCATACATGAACTGGTACCAG

181   Q  K  P  G  Q  A  P  R  L  L  I  Y  D  T  S  K  L  A  S  G
541   CAGAAACCTGGACAGGCTCCTAGACTGCTGATCTACGACACCTCTAAACTGGCATCTGGC

201   V  P  A  R  F  R  G  S  G  S  G  T  D  F  T  L  T  I  S  S
601   GTGCCCGCTCGATTTTCGTGGCTCTGGATCCGGAACCGACTTTACCCTGACCATCTCTTCC

221   L  E  P  E  D  F  A  V  Y  Y  C  Q  Q  W  S  S  N  P  F  T
661   CTGGAACCTGAGGATTTTGCCGTGTACTACTGCCAGCAGTGGTCTAGTAACCCTTTCACT

241   F  G  Q  G  T  K  V  E  I  K  G  G  C                        SEQ ID NO: 39
721   TTTGGCCAGGGCACTAAAGTGGAGATCAAGGGCGGCTGC                       SEQ ID NO: 40
```

Figure 22
Anti-CD3 VL-8-VH Cys-Diabody (ImaginAb Humanized OKT3) Translated Sequence

```
  1   M  E  T  D  T  L  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   E  I  V  L  T  Q  S  P  A  T  L  S  L  S  P  G  E  R  A  T
 61   GAAATCGTGCTGACTCAGTCCCCTGCTACACTGTCTCTGTCACCTGGCGAACGAGCAACA

41   L  S  C  S  A  S  S  S  V  S  Y  M  N  W  Y  Q  Q  K  P  G
121   CTGTCCTGTTCTGCCTCTTCTTCTGTCTCATACATGAACTGGTACCAGCAGAAACCTGGA

61   Q  A  P  R  L  L  I  Y  D  T  S  K  L  A  S  G  V  P  A  H
181   CAGGCTCCTAGACTGCTGATCTACGACACCTCTAAACTGGCATCTGGCGTGCCCGCTCAT

81   F  R  G  S  G  S  G  T  D  F  T  L  T  I  S  S  L  E  P  E
241   TTTCGTGGCTCTGGATCTGGAACCGACTTTACCCTGACCATCTCTTCCCTGGAACCTGAG

101   D  F  A  V  Y  Y  C  Q  Q  W  S  S  N  P  F  T  F  G  Q  G
301   GATTTTGCCGTGTACTACTGCCAGCAGTGGTCTAGTAACCCTTTCACTTTTGGCCAGGGC

121   T  K  V  E  I  K  G  G  G  S  G  G  G  G  Q  V  Q  L  V  Q
361   ACTAAAGTGGAGATCAAGGGCGGAGGGAGTGGCGGAGGCGGCCAGGTCCAGCTGGTCCAG

141   S  G  A  E  V  K  K  P  G  A  S  V  K  V  S  C  K  A  S  G
421   AGTGGAGCTGAGGTGAAAAAACCCGGCGCTTCCGTCAAAGTCTCCTGTAAGGCTAGCGGA

161   Y  T  F  T  R  Y  T  M  H  W  V  R  Q  A  P  G  Q  G  L  E
481   TACACCTTTACTCGCTACACCATGCATTGGGTCCGGCAGGCTCCCGGACAGGGCCTGGAA

181   W  M  G  Y  I  N  P  S  R  G  Y  T  N  Y  N  Q  K  F  K  D
541   TGGATGGGATACATCAACCCTTCTCGGGGCTACACAAACTACAATCAGAAATTCAAGGAT

201   R  V  T  M  T  T  D  T  S  I  S  T  A  Y  M  E  L  S  R  L
601   CGAGTGACCATGACAACCGACACTTCAATCTCTACCGCTTACATGGAACTGTCTCGGCTG

221   R  S  D  D  T  A  V  Y  Y  C  A  R  Y  Y  D  D  H  Y  C  L
661   AGGAGTGACGATACCGCTGTCTACTACTGTGCTCGGTACTACGACGACCATTACTGCCTG

241   D  Y  W  G  Q  G  T  L  V  T  V  S  S  G  G  C                SEQ ID NO: 41
721   GATTACTGGGGCAGGGCACTGGTGACTGTGTCTAGCGGCGGCTGC                   SEQ ID NO: 42
```

Figure 23
Anti-CD3 VH-8-VL Cys-Diabody (ImaginAb Humanized OKT3) Translated Sequence

```
  1   M   E   T   D   T   L   L   W   V   L   L   W   V   P   G   S   T   G
  1   ATGGAAACCGACACCCTGCTGCTGTGGGTGCTGCTGCTCTGGGTCCCAGGCTCCACCGGT

21   Q   V   Q   L   V   Q   S   G   A   E   V   K   K   P   G   A   S   V   K   V
 61   CAGGTCCAGCTGGTCCAGAGTGGAGCTGAGGTGAAAAAACCCGGCGCTTCCGTCAAAGTC

41   S   C   K   A   S   G   Y   T   F   T   R   Y   T   M   H   W   V   R   Q   A
121   TCCTGTAAGGCTAGCGGATACACCTTTACTCGCTACACCATGCATTGGGTCCGGCAGGCT

61   P   G   Q   G   L   E   W   M   G   Y   I   N   P   S   R   G   Y   T   N   Y
181   CCCGGACAGGGCCTGGAATGGATGGGATACATCAACCCTTCTCGGGGCTACACAAACTAC

81   N   Q   K   F   K   D   R   V   T   M   T   T   D   T   S   I   S   T   A   Y
241   AATCAGAAATTCAAGGATCGAGTGACCATGACAACCGACACTTCAATCTCTACCGCTTAC

101   M   E   L   S   R   L   R   S   D   D   T   A   V   Y   Y   C   A   R   Y   Y
301   ATGGAACTGTCTCGGCTGAGGAGTGACGATACCGCTGTCTACTACTGTGCTCGGTACTAC

121   D   D   H   Y   C   L   D   Y   W   G   Q   G   T   L   V   T   V   S   S   G
361   GACGACCATTACTGCCTGGATTACTGGGGGCAGGGCACACTGGTGACTGTGTCTAGCGGC

141   G   S   G   G   G   E   I   V   L   T   Q   S   P   A   T   L   S   L
421   GGAGGGAGTGGCGGAGGCGGCGAAATCGTGCTGACTCAGTCCCCTGCTACACTGTCTCTG

161   S   P   G   E   R   A   T   L   S   C   S   A   S   S   S   V   S   Y   M   N
481   TCACCTGGCGAACGAGCAACACTGTCCTGTTCTGCCTCTTCTTCTGTCTCATACATGAAC

181   W   Y   Q   Q   K   P   G   Q   A   P   R   L   L   I   Y   D   T   S   K   L
541   TGGTACCAGCAGAAACCTGGACAGGCTCCTAGACTGCTGATCTACGACACCTCTAAACTG

201   A   S   G   V   P   A   R   F   R   G   S   G   S   G   T   D   F   T   L   T
601   GCATCTGGCGTGCCCGCTCATTTCGTGGCTCTGGATCTGGAACCGACTTTACCCTGACC

221   I   S   S   L   E   P   E   D   F   A   V   Y   Y   C   Q   Q   W   S   S   N
661   ATCTCTTCCCTGGAACCTGAGGATTTTGCCGTGTACTACTGCCAGCAGTGGTCTAGTAAC

241   P   F   T   F   G   Q   G   T   K   V   E   I   K   G   G   C         SEQ ID NO: 43
721   CCTTTCACTTTTGGCCAGGGCACTAAAGTGGAGATCAAGGGCGGCTGC        SEQ ID NO: 44
```

FIG. 24A
Anti-CD3 VLVH Minibody (ABC2) Translated Sequence

```
   1  M  E  T  D  T  L  L  L  W  V  L  L  L  W  V  P  G  S  T  G
   1  ATGGAAACCGACACCCTGCTGCTGTGGGTGCTGCTGCTCTGGGTCCCAGGCTCCACCGGT

21  D  I  Q  L  T  Q  P  N  S  V  S  T  S  L  G  S  T  V  K  L
  61  GACATCCAGCTGACTCAGCCCAACTCTGTGTCTACGTCTCTAGGAAGCACAGTCAAGCTG

41  S  C  T  L  S  S  G  N  I  E  N  N  Y  V  H  W  Y  Q  L  Y
 121  TCTTGCACACTCAGCTCTGGTAACATAGAAAACAACTATGTGCACTGGTACCAGCTATAT

61  E  G  R  S  P  T  T  M  I  Y  D  D  D  K  R  P  D  G  V  P
 181  GAGGGAAGATCTCCCACCACTATGATTTATGATGATGATAAGAGACCGGATGGTGTCCCT

81  D  R  F  S  G  S  I  D  R  S  S  N  S  A  F  L  T  I  R  N
 241  GACAGGTTCTCTGGCTCCATTGACAGGTCTTCCAACTCAGCCTTCCTGACAATCCATAAT

101  V  A  I  E  D  E  A  I  Y  F  C  R  S  Y  V  S  S  F  N  V
 301  GTGGCAATTGAAGATGAAGCTATCTACTTCTGTCATTCTTATGTTAGTAGTTTTAATGTT

121  F  G  G  G  T  K  L  T  V  L  G  S  T  S  G  G  G  S  G  G
 361  TTCGGCGGTGGAACAAAGCTCACTGTCCTTGGCTCCACATCCGGCGGAGGCTCTGGCGGT

141  G  S  G  G  G  S  S  D  I  Q  L  T  Q  P  N  S  V  S  T
 421  GGATCTGGCGGAGGCGGCTCATCCGACATCCAGCTGACTCAGCCCAACTCTGTGTCTACG

161  S  L  G  S  T  V  K  L  S  C  T  L  S  S  G  N  I  E  N  N
 481  TCTCTAGGAAGCACAGTCAAGCTGTCTTGCACACTCAGCTCTGGTAACATAGAAAACAAC

181  Y  V  H  W  Y  Q  L  Y  E  G  R  S  P  T  T  M  I  Y  D  D
 541  TATGTGCACTGGTACCAGCTATATGAGGGAAGATCTCCCACCACTATGATTTATGATGAT

201  D  K  R  P  D  G  V  P  D  R  F  S  G  S  I  D  R  S  S  N
 601  GATAAGAGACCGGATGGTGTCCCTGACAGGTTCTCTGGCTCCATTGACAGGTCTTCCAAC

221  S  A  F  L  T  I  H  N  V  A  I  E  D  E  A  I  Y  F  C  H
 661  TCAGCCTTCCTGACAATCCATAATGTGGCAATTGAAGATGAAGCTATCTACTTCTGTCAT

241  S  Y  V  S  S  F  N  V  F  G  G  G  T  K  L  T  V  L  E  P
 721  TCTTATGTTAGTAGTTTTAATGTTTTCGGCGGTGGAACAAAGCTCACTGTCCTTGAGCCT

261  K  S  C  D  K  T  H  T  C  P  P  C  G  G  G  S  S  G  G  G
 781  AAGTCCTGCGACAAGACCCACACCTGTCCCCCTTGCGGCGGAGGAAGCAGCGGAGGCGGA

281  S  G  G  Q  P  R  E  P  Q  V  Y  T  L  P  P  S  R  D  E  L
 841  TCCGGTGGCCAGCCTCGGGAGCCTCAGGTGTACACCCTGCCTCCCTCCCGGGACGAGCTG

301  T  K  N  Q  V  S  L  T  C  L  V  K  G  F  Y  P  S  D  I  A
 901  ACCAAGAACCAGGTGTCCCTGACCTGTCTGGTCAAGGGCTTCTACCCTTCCGATATCGCC

321  V  E  W  E  S  N  G  Q  P  E  N  N  Y  K  T  T  P  P  V  L
 961  GTGGAGTGGGAGTCCAACGGCCAGCCTGAGAACAACTACAAGACCACCCCTCCTGTGCTG

341  D  S  D  G  S  F  F  L  Y  S  K  L  T  V  D  K  S  R  W  Q
1021  GACTCCGACGGCTCCTTCTTCCTGTACTCCAAGCTCACAGTGGATAAGTCCCGGTGGCAG
```

FIG. 24B

```
 361    Q  G  N  V  F  S  C  S  V  M  H  E  A  L  H  N  H  Y  T  Q
1081    CAGGGCAACGTGTTCTCCTGCTCCGTGATGCACGAGGCCCTGCACAACCACTATACCCAG

381    K  S  L  S  L  S  P  G  K  -   SEQ ID NO: 45
1141    AAGTCCCTGTCCCTGTCTCCTGGCAAGTGA   SEQ ID NO: 46
```

FIG. 25A
Anti-CD3 VHVL Minibody (ABC2) Translated Sequence

```
  1    M   E   T   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21    D   I   Q   L   T   Q   P   N   S   V   S   T   S   L   G   S   T   V   K   L
 61   GACATCCAGCTGACTCAGCCCAACTCTGTGTCTACGTCTCTAGGAAGCACAGTCAAGCTG

41    S   C   T   L   S   S   G   N   I   E   N   N   Y   V   H   W   Y   Q   L   Y
121   TCTTGCACACTCAGCTCTGGTAACATAGAAAACAACTATGTGCACTGGTACCAGCTATAT

61    E   G   R   S   P   T   T   M   I   Y   D   D   D   K   R   P   D   G   V   P
181   GAGGGAAGATCTCCCACCACTATGATTTATGATGATGATAAGAGACCGGATGGTGTCCCT

81    D   R   F   S   G   S   I   D   R   S   S   N   S   A   F   L   T   I   H   N
241   GACAGGTTCTCTGGCTCCATTGACAGGTCTTCCAACTCAGCCTTCCTGACAATCCATAAT

101    V   A   I   E   D   E   A   I   Y   F   C   H   S   Y   V   S   S   F   N   V
301   GTGGCAATTGAAGATGAAGCTATCTACTTCTGTCATTCTTATGTTAGTAGTTTTAATGTT

121    F   G   G   G   T   K   L   T   V   L   G   S   T   S   G   G   G   S   G   G
361   TTCGGCGGTGGAACAAAGCTCACTGTCCTTGGCTCCACATCCGGCGGAGGCTCTGGCGGT

141    G   S   G   G   G   G   S   S   D   I   Q   L   T   Q   P   N   S   V   S   T
421   GGATCGGCGGAGGCGGCTCATCCGACATCCAGCTGACTCAGCCCAACTCTGTGTCTACG

161    S   L   G   S   T   V   K   L   S   C   T   L   S   S   G   N   I   E   N   N
481   TCTCTAGGAAGCACAGTCAAGCTGTCTTGCACACTCAGCTCTGGTAACATAGAAAACAAC

181    Y   V   H   W   Y   Q   L   Y   E   G   R   S   P   T   T   M   I   Y   D   D
541   TATGTGCACTGGTACCAGCTATATGAGGGAAGATCTCCCACCACTATGATTTATGATGAT

201    D   K   R   P   D   G   V   P   D   R   F   S   G   S   I   D   R   S   S   N
601   GATAAGAGACCGGATGGTGTCCCTGACAGGTTCTCTGGCTCCATTGACAGGTCTTCCAAC

221    S   A   F   L   T   I   H   N   V   A   I   E   D   E   A   I   Y   F   C   H
661   TCAGCCTTCCTGACAATCCATAATGTGGCAATTGAAGATGAAGCTATCTACTTCTGTCAT

241    S   Y   V   S   S   F   N   V   F   G   G   G   T   K   L   T   V   L   E   P
721   TCTTATGTTAGTAGTTTTAATGTTTTCGGCGGTGGAACAAAGCTCACTGTCCTTGAGCCT

261    K   S   C   D   K   T   H   T   C   P   P   C   G   G   G   S   G   G   G
781   AAGTCCTGCGACAAGACCCACACCTGTCCCCCTTGCGGCGGAGGAAGCAGCGGAGGCGGA

281    S   G   G   Q   P   R   E   P   Q   V   Y   T   L   P   P   S   R   D   E   L
841   TCCGGTGGCCAGCCTCGGGAGCCTCAGGTGTACACCCTGCCTCCCTCCCGGGACGAGCTG

301    T   K   N   Q   V   S   L   T   C   L   V   K   G   F   Y   P   S   D   I   A
901   ACCAAGAACCAGGTGTCCCTGACCTGTCTGGTCAAGGGCTTCTACCCTTCCGATATCGCC

321    V   E   W   E   S   N   G   Q   P   E   N   N   Y   K   T   T   P   P   V   L
961   GTGGAGTGGGAGTCCAACGGCCAGCCTGAGAACAACTACAAGACCACCCCTCCTGTGCTG

341    D   S   D   G   S   F   F   L   Y   S   K   L   T   V   D   K   S   R   W   Q
1021  GACTCCGACGGCTCCTTCTTCCTGTACTCCAAGCTCACAGTGGATAAGTCCCGGTGGCAG
```

FIG. 25B

```
361   Q  G  N  V  F  S  C  S  V  M  H  E  A  L  H  N  H  Y  T  Q
1081  CAGGGCAACGTGTTCTCCTGCTCCGTGATGCACGAGGCCCTGCACAACCACTATACCCAG

381   K  S  L  S  L  S  P  G  K  -      SEQ ID NO: 47
1141  AAGTCCCTGTCCCTGTCTCCTGGCAAGTGA    SEQ ID NO: 48
```

Figure 26
Anti-CD3 VL-5-VH Cys-Diabody (ABC2) Translated Sequence

```
  1    M   E   T   D   T   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21    D   I   Q   L   T   Q   P   N   S   V   S   T   S   L   G   S   T   V   K   L
 61   GACATCCAGCTGACTCAGCCCAACTCTGTGTCTACGTCTCTAGGAAGCACAGTCAAGCTG

41    S   C   T   L   S   S   G   N   I   E   N   N   Y   V   H   W   Y   Q   L   Y
121   TCTTGCACACTCAGCTCTGGTAACATAGAAAACAACTATGTGCACTGGTACCAGCTATAT

61    E   G   R   S   P   T   T   M   I   Y   D   D   D   K   R   P   D   G   V   P
181   GAGGGAAGATCTCCCACCACTATGATTTATGATGATGATAAGAGACCGGATGGTGTCCCT

81    D   R   F   S   G   S   I   D   R   S   S   N   S   A   F   L   T   I   H   N
241   GACAGGTTCTCTGGCTCCATTGACAGGTCTTCCAACTCAGCCTTCCTGACAATCCATAAT

101    V   A   I   E   D   E   A   I   Y   F   C   H   S   Y   V   S   S   F   N   V
301   GTGGCAATTGAAGATGAAGCTATCTACTTCTGTCATTCTTATGTTAGTAGTTTTAATGTT

121    F   G   G   G   T   K   L   T   V   L   S   G   G   G   G   D   I   Q   L   T
361   TTCGGCGGTGGAACAAAGCTCACTGTCCTTAGTGGTGGAGGAGGCGACATCCAGCTGACT

141    Q   P   N   S   V   S   T   S   L   G   S   T   V   K   L   S   C   T   L   S
421   CAGCCCAACTCTGTGTCTACGTCTCTAGGAAGCACAGTCAAGCTGTCTTGCACACTCAGC

161    S   G   N   I   E   N   N   Y   V   H   W   Y   Q   L   Y   E   G   R   S   P
481   TCTGGTAACATAGAAAACAACTATGTGCACTGGTACCAGCTATATGAGGGAAGATCTCCC

181    T   T   M   I   Y   D   D   D   K   R   P   D   G   V   P   D   R   F   S   G
541   ACCACTATGATTTATGATGATGATAAGAGACCGGATGGTGTCCCTGACAGGTTCTCTGGC

201    S   I   D   R   S   S   N   S   A   F   L   T   I   R   N   V   A   I   E   D
601   TCCATTGACAGGTCTTCCAACTCAGCCTTCCTGACAATCCATAATGTGGCAATTGAAGAT

221    E   A   I   Y   F   C   H   S   Y   V   S   S   F   N   V   F   G   G   G   T
661   GAAGCTATCTACTTCTGTCATTCTTATGTTAGTAGTTTTAATGTTTTCGGCGGTGGAACA

241    K   L   T   V   L   G   G   C        SEQ ID NO: 49
721   AAGCTCACTGTCCTTGGCGGCTGC              SEQ ID NO: 50
```

Figure 27
Anti-CD3 VH-5-VL Cys-Diabody (ABC2) Translated Sequence

```
  1   M   E   T   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   D   I   Q   L   T   Q   P   N   S   V   S   T   S   L   G   S   T   V   K   L
 61   GACATCCAGCTGACTCAGCCCAACTCTGTGTCTACGTCTCTAGGAAGCACAGTCAAGCTG

41   S   C   T   L   S   S   G   N   I   E   N   N   Y   V   H   W   Y   Q   L   Y
121   TCTTGCACACTCAGCTCTGGTAACATAGAAAACAACTATGTGCACTGGTACCAGCTATAT

61   E   G   R   S   P   T   T   M   I   Y   D   D   D   K   R   P   D   G   V   P
181   GAGGGAAGATCTCCCACCACTATGATTTATGATGATGATAAGAGACCGGATGGTGTCCCT

81   D   R   F   S   G   S   I   D   R   S   S   N   S   A   F   L   T   I   H   N
241   GACAGGTTCTCTGGCTCCATTGACAGGTCTTCCAACTCAGCCTTCCTGACAATCCATAAT

101   V   A   I   E   D   E   A   I   Y   F   C   H   S   Y   V   S   S   F   N   V
301   GTGGCAATTGAAGATGAAGCTATCTACTTCTGTCATTCTTATGTTAGTAGTTTTAATGTT

121   F   G   G   G   T   K   L   T   V   L   S   G   G   G   G   D   I   Q   L   T
361   TTCGGCGGTGGAACAAAGCTCACTGTCCTTAGTGGTGGAGGAGGCGACATCCAGCTGACT

141   Q   P   N   S   V   S   T   S   L   G   S   T   V   K   L   S   C   T   L   S
421   CAGCCCAACTCTGTGTCTACGTCTCTAGGAAGCACAGTCAAGCTGTCTTGCACACTCAGC

161   S   G   N   I   E   N   N   Y   V   H   W   Y   Q   L   Y   E   G   R   S   P
481   TCTGGTAACATAGAAAACAACTATGTGCACTGGTACCAGCTATATGAGGGAAGATCTCCC

181   T   T   M   I   Y   D   D   D   K   R   P   D   G   V   P   D   R   F   S   G
541   ACCACTATGATTTATGATGATGATAAGAGACCGGATGGTGTCCCTGACAGGTTCTCTGGC

201   S   I   D   R   S   S   N   S   A   F   L   T   I   H   N   V   A   I   E   D
601   TCCATTGACAGGTCTTCCAACTCAGCCTTCCTGACAATCCATAATGTGGCAATTGAAGAT

221   E   A   I   Y   F   C   H   S   Y   V   S   S   F   N   V   F   G   G   G   T
661   GAAGCTATCTACTTCTGTCATTCTTATGTTAGTAGTTTTAATGTTTTCGGCGGTGGAACA

241   K   L   T   V   L   G   G   C                SEQ ID NO: 51
721   AAGCTCACTGTCCTTGGCGGCTGC                      SEQ ID NO: 52
```

Figure 28
Anti-CD3 VL-8-VH Cys-Diabody (ABC2) Translated Sequence

```
  1   M   E   T   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   D   I   Q   L   T   Q   P   N   S   V   S   T   S   L   G   S   T   V   K   L
 61   GACATCCAGCTGACTCAGCCCAACTCTGTGTCTACGTCTCTAGGAAGCACAGTCAAGCTG

41   S   C   T   L   S   S   G   N   I   E   N   N   Y   V   H   W   Y   Q   L   Y
121   TCTTGCACACTCAGCTCTGGTAACATAGAAAACAACTATGTGCACTGGTACCAGCTATAT

61   E   G   R   S   P   T   T   M   I   Y   D   D   D   K   R   P   D   G   V   P
181   GAGGGAAGATCTCCCACCACTATGATTTATGATGATGATAAGAGACCGGATGGTGTCCCT

81   D   R   F   S   G   S   I   D   R   S   S   N   S   A   F   L   T   I   H   N
241   GACAGGTTCTCTGGCTCCATTGACAGGTCTTCCAACTCAGCCTTCCTGACAATCCATAAT

101   V   A   I   E   D   E   A   I   Y   F   C   H   S   Y   V   S   S   F   N   V
301   GTGGCAATTGAAGATGAAGCTATCTACTTCTGTCATTCTTATGTTAGTAGTTTTAATGTT

121   F   G   G   G   T   K   L   T   V   L   G   G   G   S   G   G   G   G   D   I
361   TTCGGCGGTGGAACAAAGCTCACTGTCCTTGGCGGAGGGAGTGGCGGAGGCGGCGACATC

141   Q   L   T   Q   P   N   S   V   S   T   S   L   G   S   T   V   K   L   S   C
421   CAGCTGACTCAGCCCAACTCTGTGTCTACGTCTCTAGGAAGCACAGTCAAGCTGTCTTGC

161   T   L   S   S   G   N   I   E   N   N   Y   V   H   W   Y   Q   L   Y   E   G
481   ACACTCAGCTCTGGTAACATAGAAAACAACTATGTGCACTGGTACCAGCTATATGAGGGA

181   R   S   P   T   T   M   I   Y   D   D   D   K   R   P   D   G   V   P   D   R
541   AGATCTCCCACCACTATGATTTATGATGATGATAAGAGACCGGATGGTGTCCCTGACAGG

201   F   S   G   S   I   D   R   S   S   N   S   A   F   L   T   I   H   N   V   A
601   TTCTCTGGCTCCATTGACAGGTCTTCCAACTCAGCCTTCCTGACAATCCATAATGTGGCA

221   I   E   D   E   A   I   Y   F   C   H   S   Y   V   S   S   F   N   V   F   G
661   ATTGAAGATGAAGCTATCTACTTCTGTCATTCTTATGTTAGTAGTTTTAATGTTTTCGGC

241   G   G   T   K   L   T   V   L   G   G   C       SEQ ID NO: 53
721   GGTGGAACAAAGCTCACTGTCCTTGGCGGCTGC    SEQ ID NO: 54
```

Figure 29
Anti-CD3 VH-8-VL Cys-Diabody (ABC2) Translated Sequence

```
  1   M  E  T  D  T  L  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   D  I  Q  L  T  Q  P  N  S  V  S  T  S  L  G  S  T  V  K  L
 61   GACATCCAGCTGACTCAGCCCAACTCTGTGTCTACGTCTCTAGGAAGCACAGTCAAGCTG

41   S  C  T  L  S  S  G  N  I  E  N  N  Y  V  H  W  Y  Q  L  Y
121   TCTTGCACACTCAGCTCTGGTAACATAGAAAACAACTATGTGCACTGGTACCAGCTATAT

61   E  G  R  S  P  T  T  M  I  Y  D  D  D  K  R  P  D  G  V  P
181   GAGGGAAGATCTCCCACCACTATGATTTATGATGATGATAAGAGACCGGATGGTGTCCCT

81   D  R  F  S  G  S  I  D  R  S  S  N  S  A  F  L  T  I  H  N
241   GACAGGTTCTCTGGCTCCATTGACAGGTCTTCCAACTCAGCCTTCCTGACAATCCATAAT

101   V  A  I  E  D  E  A  I  Y  F  C  H  S  Y  V  S  S  F  N  V
301   GTGGCAATTGAAGATGAAGCTATCTACTTCTGTCATTCTTATGTTAGTAGTTTTAATGTT

121   F  G  G  G  T  K  L  T  V  L  G  G  S  G  G  G  G  D  I
361   TTCGGCGGTGGAACAAAGCTCACTGTCCTTGGCGGAGGGAGTGGCGGAGGCGGCGACATC

141   Q  L  T  Q  P  N  S  V  S  T  S  L  G  S  T  V  K  L  S  C
421   CAGCTGACTCAGCCCAACTCTGTGTCTACGTCTCTAGGAAGCACAGTCAAGCTGTCTTGC

161   T  L  S  S  G  N  I  E  N  N  Y  V  H  W  Y  Q  L  Y  E  G
481   ACACTCAGCTCTGGTAACATAGAAAACAACTATGTGCACTGGTACCAGCTATATGAGGGA

181   R  S  P  T  T  M  I  Y  D  D  D  K  R  P  D  G  V  P  D  R
541   AGATCTCCCACCACTATGATTTATGATGATGATAAGAGACCGGATGGTGTCCCTGACAGG

201   F  S  G  S  I  D  R  S  S  N  S  A  F  L  T  I  H  N  V  A
601   TTCTCTGGCTCCATTGACAGGTCTTCCAACTCAGCCTTCCTGACAATCCATAATGTGGCA

221   I  E  D  E  A  I  Y  F  C  H  S  Y  V  S  S  F  N  V  F  G
661   ATTGAAGATGAAGCTATCTACTTCTGTCATTCTTATGTTAGTAGTTTTAATGTTTTCGGC

241   G  G  T  K  L  T  V  L  G  G  C        SEQ ID NO: 55
721   GGTGGAACAAAGCTCACTGTCCTTGGCGGCTGC        SEQ ID NO: 56
```

FIG. 30A
Anti-CD3 VLVH Minibody (ABC3) Translated Sequence

```
  1   M   E   T   D   T   L   L   L   W   V   L   L   L   W   V   P   G   S   T   G
  1   ATGGAAACCGACACCCTGCTGCTGTGGGTGCTGCTGCTCTGGGTCCCAGGCTCCACCGGT

21   E   I   V   L   T   Q   S   P   A   T   L   S   L   S   P   G   E   R   A   T
 61   GAAATTGTGCTGACCCAGAGCCCGGCGACCCTGAGCCTGAGCCCGGGCGAACGTGCGACC

41   L   S   C   R   A   S   Q   S   V   S   S   Y   L   A   W   Y   Q   Q   K   P
121   CTGAGCTGCCGCGCGAGCCAGAGCGTGAGCAGCTATCTGGCGTGGTATCAGCAGAAACCG

61   G   Q   A   P   R   L   L   I   Y   D   A   S   N   R   A   T   G   I   P   A
181   GGCCAGGCGCCGCGCCTGCTGATTTATGATGCGAGCAACCGCGCGACCGGCATTCCGGCG

81   R   F   S   G   S   G   S   G   T   D   F   T   L   T   I   S   S   L   E   P
241   CGCTTTAGCGGCAGCGGCAGCGGCACCGATTTTACCCTGACCATTAGCAGCCTGGAACCG

101   E   D   F   A   V   Y   Y   C   Q   Q   R   S   N   W   P   P   L   T   F   G
301   GAAGATTTTGCGGTGTATTATTGCCAGCAGCGCAGCAACTGGCCGCCGCTGACCTTTGGC

121   G   G   T   K   V   E   I   K   G   S   T   S   G   G   G   S   G   G   G   S
361   GGCGGCACCAAAGTGGAAATTAAAGGCTCCACATCCGGCGGAGGCTCTGGCGGTGGATCT

141   G   G   G   G   S   S   Q   V   Q   L   V   E   S   G   G   G   V   V   Q   P
421   GGCGGAGGCGGCTCATCCCAGGTGCAGCTGGTGGAAAGCGGCGGCGGCGTGGTGCAGCCG

161   G   R   S   L   R   L   S   C   A   A   S   G   F   K   F   S   G   Y   G   M
481   GGCCGCAGCCTGCGCCTGAGCTGCGCGGCGAGCGGCTTTAAATTTAGCGGCTATGGCATG

181   H   W   V   R   Q   A   P   G   K   G   L   E   W   V   A   V   I   W   Y   D
541   CATTGGGTGCGCCAGGCGCCGGGCAAAGGCCTGGAATGGGTGGCGGTGATTTGGTATGAT

201   G   S   K   K   Y   Y   V   D   S   V   K   G   R   F   T   I   S   R   D   N
601   GGCAGCAAAAAATATTATGTGGATAGCGTGAAAGGCCGCTTTACCATTAGCCGCGATAAC

221   S   K   N   T   L   Y   L   Q   M   N   S   L   R   A   E   D   T   A   V   Y
661   AGCAAAAACACCCTGTATCTGCAGATGAACAGCCTGCGCGCGGAAGATACCGCGGTGTAT

241   Y   C   A   R   Q   M   G   Y   W   R   F   D   L   W   G   R   G   T   L   V
721   TATTGCGCGCGCCAGATGGGCTATTGGCATTTGATCTGTGGGGCCGCGGCACCCTGGTG

261   T   V   S   S   E   P   K   S   C   D   K   T   H   T   C   P   P   C   G   G
781   ACCGTGAGCAGCGAGCCTAAGTCCTGCGACAAGACTCACACCTGTCCCCCTTGCGGCGGA

281   G   S   S   G   G   G   S   G   G   Q   P   R   E   P   Q   V   Y   T   L   P
841   GGAAGCAGCGGAGGCGGATCCGGTGGCCAGCCTCGGGAGCCTCAGGTGTACACCCTGCCT

301   P   S   R   D   E   L   T   K   N   Q   V   S   L   T   C   L   V   K   G   F
901   CCCTCCCGGGACGAGCTGACCAAGAACCAGGTGTCCCTGACCTGCCTGGTCAAGGGCTTC

321   Y   P   S   D   I   A   V   E   W   E   S   N   G   Q   P   E   N   N   Y   K
961   TACCCTTCCGATATCGCCGTGGAGTGGGAGTCCAATGGCCAGCCTGAGAACAACTACAAG

341   T   T   P   P   V   L   D   S   D   G   S   F   F   L   Y   S   K   L   T   V
1021  ACCACCCCTCCTGTGCTGGACTCCGACGGCTCCTTCTTCCTGTACTCCAAGCTCACAGTG
```

FIG. 30B

```
361    D   K   S   R   W   Q   Q   G   N   V   F   S   C   S   V   M   H   E   A   L
1081   GATAAGTCCCGGTGGCAGCAGGGCAACGTGTTCTCCTGCTCCGTGATGCACGAGGCCCTG

381    H   N   R   Y   T   Q   K   S   L   S   L   S   P   G   K   -      SEQ ID NO: 57
1141   CACAACCACTATACCCAGAAGTCCCTGTCCCTGTCCTGGCAAGTGA                SEQ ID NO: 58
```

FIG. 31A
Anti-CD3 VHVL Minibody (ABC3) Translated Sequence

```
  1    M   E   T   D   T   L   L   L   W   V   L   L   L   W   V   P   G   S   T   G
  1    ATGGAAACCGACACCCTGCTGCTGTGGGTGCTGCTGCTCTGGGTCCCAGGCTCCACCGGT

21    Q   V   Q   L   V   E   S   G   G   G   V   V   Q   P   G   R   S   L   R   L
 61    CAGGTGCAGCTGGTGGAAAGCGGCGGCGGCGTGGTGCAGCCGGGCCGCAGCCTGCGCCTG

41    S   C   A   A   S   G   F   K   F   S   G   Y   G   M   H   W   V   R   Q   A
101    AGCTGCGCGGCGAGCGGCTTTAAATTTAGCGGCTATGGCATGCATTGGGTGCGCCAGGCG

61    P   G   K   G   L   E   W   V   A   V   I   W   Y   D   G   S   K   Y   Y
181    CCGGGCAAAGGCCTGGAATGGGTGGCGGTGATTTGGTATGATGGCAGCAAAAAATATTAT

81    V   D   S   V   K   G   R   F   I   I   S   R   D   N   S   K   N   T   L   Y
241    GTGGATAGCGTGAAAGGCCGCTTTACCATTAGCCGCGATAACAGCAAAAACACCCTGTAT

101    L   Q   M   N   S   L   R   A   E   D   T   A   V   Y   Y   C   A   R   Q   M
301    CTGCAGATGAACAGCCTGCGCGCGGAAGATACCGCGGTGTATTATTGCGCGCGCCAGATG

121    G   Y   W   H   F   D   L   W   G   R   G   T   L   V   T   V   S   S   G   S
361    GGCTATTGGCATTTTGATCTGTGGGGCCGCGGCACCCTGGTGACCGTGAGCAGCGGCTCC

141    T   S   G   G   S   G   G   G   S   G   G   G   S   E   I   V   L
421    ACATCCGGCGGAGGCTCTGGCGGTGGATCTGGCGGAGGCGGCTCATCCGAAATTGTGCTG

161    T   Q   S   P   A   T   L   S   L   S   P   G   E   R   A   T   L   S   C   R
481    ACCCAGAGCCCGGCGACCCTGAGCCTGAGCCCGGGCGAACGCGCGACCCTGAGCTGCCGC

181    A   S   Q   S   V   S   S   Y   L   A   W   Y   Q   Q   K   P   G   Q   A   P
541    GCGAGCCAGAGCGTGAGCAGCTATCTGGCGTGGTATCAGCAGAAACCGGGCCAGGCGCCG

201    R   L   L   I   Y   D   A   S   N   R   A   T   G   I   P   A   R   F   S   G
601    CGCCTGCTGATTTATGATGCGAGCAACCGCGCGACCGGCATTCCGGCGCGCTTTAGCGGC

221    S   G   S   G   T   D   F   T   L   T   I   S   S   L   E   P   E   D   F   A
661    AGCGGCAGCGGCACCGATTTTACCCTGACCATTAGCAGCCTGGAACCGGAAGATTTTGCG

241    V   Y   Y   C   Q   Q   R   S   N   W   P   P   L   T   F   G   G   G   T   K
721    GTGTATTATTGCCAGCAGCGCAGCAACTGGCCGCCGCTGACCTTTGGCGGCGGCACCAAA

261    V   E   I   K   E   P   K   S   C   D   K   T   H   T   C   P   P   C   G   G
781    GTGGAAATTAAAGAGCCTAAGTCCTGCGACAAGACCCACACCTGTCCCCCTTGCGGCGGA

281    G   S   S   G   G   S   G   G   Q   P   R   E   P   Q   V   Y   T   L   P
841    GGAAGCAGCGGAGGCGGATCCGGTGGCCAGCCTCGGGAGCCTCAGGTGTACACCCTGCCT

301    P   S   R   D   E   L   T   K   N   Q   V   S   L   T   C   L   V   K   G   F
901    CCCTCCCGGGACGAGCTGACCAAGAACCAGGTGTCCCTGACCTGTCTGGTCAAGGGCTTC

321    Y   P   S   D   I   A   V   E   W   E   S   N   G   Q   P   E   N   N   Y   K
961    TACCCTTCCGATATCGCCGTGGAGTGGGAGTCCAACGGCCAGCCTGAGAACAACTACAAG

341    T   T   P   P   V   L   D   S   D   G   S   F   F   L   Y   S   K   L   T   V
1021   ACCACCCCTCCTGTGCTGGACTCCGACGGCTCCTTCTTCCTGTACTCCAAGCTCACAGTG
```

FIG. 31B

```
361    D  K  S  R  W  Q  Q  G  N  V  F  S  C  S  V  M  H  E  A  L
1081   GATAAGTCCCGGTGGCAGCAGGGCAACGTGTTCTCCTGCTCCGTGATGCACGAGGCCCTG

381    H  N  H  Y  T  Q  K  S  L  S  L  S  P  G  K  -              SEQ ID NO: 59
1141   CACAACCACTATACCCAGAAGTCCCTGTCCCTGTCCCTGGCAAGTGA              SEQ ID NO: 60
```

Figure 32- Anti-CD3 VL-5-VH Cys-Diabody (ABC3) Translated Sequence

```
  1  M  E  T  D  T  L  L  L  W  V  L  L  L  W  V  P  G  S  T  G
  1  ATGGAAACCGACACCCTGCTGCTGTGGGTGCTGCTGCTCTGGGTCCCAGGCTCCACCGGT

21  E  I  V  L  T  Q  S  P  A  T  L  S  L  S  P  G  E  R  A  T
 61  GAAATTGTGCTGACCCAGAGCCCGGCGACCCTGAGCCTGAGCCCGGGCGAACGCGCGACC

41  L  S  C  R  A  S  Q  S  V  S  S  Y  L  A  W  Y  Q  Q  K  P
121  CTGAGCTGCCGCGCGAGCCAGAGCGTGAGCAGCTATCTGGCGTGGTATCAGCAGAAACCG

61  G  Q  A  P  R  L  L  I  Y  D  A  S  N  K  A  T  G  I  P  A
181  GGCCAGGCGCCGCGCCTGCTGATTTATGATGCGAGCAACCGCGCGACCGGCATTCCGGCG

81  R  F  S  G  S  G  S  G  T  D  F  T  L  T  I  S  S  L  E  P
241  CGCTTTAGCGGCAGCGGCAGCGGCACCGATTTTACCCTGACCATTAGCAGCCTGGAACCG

101  E  D  F  A  V  Y  Y  C  Q  Q  R  S  N  W  P  P  L  T  F  G
301  GAAGATTTTGCGGTGTATTATTGCCAGCAGCGCAGCAACTGGCCGCCGCTGACCTTTGGC

121  G  G  T  K  V  E  I  K  S  G  G  G  G  Q  V  Q  L  V  E  S
361  GGCGGCACCAAAGTGGAAATTAAAAGTGGTGGAGGAGGCCAGGTGCAGCTGGTGGAAAGC

141  G  G  G  V  V  Q  P  G  R  S  L  R  L  S  C  A  A  S  G  F
421  GGCGGCGGCGTGGTGCAGCCGGGCCGCAGCCTGCGCCTGAGCTGCGCGGCGAGCGGCTTT

161  K  F  S  G  Y  G  M  H  W  V  R  Q  A  P  G  K  G  L  E  W
481  AAATTTAGCGGCTATGGCATGCATTGGGTGCGTCAGGCGCCGGGCAAAGGCCTGGAATGG

181  V  A  V  I  W  Y  D  G  S  K  K  Y  Y  V  D  S  V  K  G  R
541  GTGGCGGTGATTTGGTATGATGGCAGCAAAAAATATTATGTGGATAGCGTGAAAGGCCGC

201  F  T  I  S  R  D  N  S  K  N  T  L  Y  L  Q  M  N  S  L  R
601  TTTACCATTAGCCGCGATAACAGCAAAAACACCCTGTATCTGCAGATGAACAGCCTGCGC

221  A  E  D  T  A  V  Y  Y  C  A  R  Q  M  G  Y  W  H  F  D  L
661  GCGGAAGATACCGCGGTGTATTATTGCGCGCGCCAGATGGGCTATTGGCATTTTGATCTG

241  W  G  R  G  T  L  V  T  V  S  S  G  G  C      SEQ ID NO: 61
721  TGGGGCCGCGGCACCCTGGTGACCGTGAGCAGCGGCGGCTGC    SEQ ID NO: 62
```

Figure 33- Anti-CD3 VH-5-VL Cys-Diabody (ABC3) Translated Sequence

```
  1   M  E  T  D  T  L  L  L  W  V  L  L  L  W  V  P  G  S  T  G
  1   ATGGAAACCGACACCCTGCTGCTGTGGGTGCTGCTGCTCTGGGTCCCAGGCTCCACCGGT

21   Q  V  Q  L  V  E  S  G  G  G  V  V  Q  P  G  R  S  L  R  L
 61   CAGGTGCAGCTGGTGGAAAGCGGCGGCGGCGTGGTCCAGCCGGGCCGCAGCCTGCGCCTG

41   S  C  A  A  S  G  F  K  F  S  G  Y  G  M  H  W  V  R  Q  A
121   AGCTGCGCGGCGAGCGGCTTTAAATTTAGCGGCTATGGCATGCATTGGGTGCGCCAGGCG

61   P  G  K  G  L  E  W  V  A  V  I  W  Y  D  G  S  K  K  Y  Y
181   CCGGGCAAAGGCCTGGAATGGGTGGCGGTGATTTGGTATGATGGCAGCAAAAAATATTAT

81   V  D  S  V  K  G  R  F  T  I  S  R  D  N  S  K  N  T  L  Y
241   GTGGATAGCGTGAAAGGCCGCTTTACCATTAGCCGCGATAACAGCAAAAACACCCTGTAT

101   L  Q  M  N  S  L  R  A  E  D  T  A  V  Y  Y  C  A  R  Q  M
301   CTGCAGATGAACAGCCTGCGCGCGGAAGATACCGCGGTGTATTATTGCGCGCGCCAGATG

121   G  Y  W  R  F  D  L  W  G  R  G  T  L  V  T  V  S  S  S  G
361   GGCTATTGGCGTTTTGATCTGTGGGGCCGCGGCACCCTGGTGACCGTGAGCAGCAGTGGT

141   G  G  E  I  V  L  T  Q  S  P  A  T  L  S  L  S  P  G  E
421   GGAGGAGGCGAAATTGTGCTGACCCAGAGCCCGGCGACCCTGAGCCTGAGCCCGGGCGAA

161   R  A  T  L  S  C  R  A  S  Q  S  V  S  S  Y  L  A  W  Y  Q
481   CGCGCGACCCTGAGCTGCCGCGCGAGCCAGAGCGTGAGCAGCTATCTGGCGTGGTATCAG

181   Q  K  P  G  Q  A  P  R  L  L  I  Y  D  A  S  N  R  A  T  G
541   CAGAAACCGGGCCAGGCGCCGCGCCTGCTGATTTATGATGCGAGCAACCGCGCGACCGGC

201   I  P  A  R  F  S  G  S  G  S  G  T  D  F  T  L  T  I  S  S
601   ATTCCGGCGCGCTTTAGCGGCAGCGGCAGCGGCACCGATTTTACCCTGACCATTAGCAGC

221   L  E  P  E  D  F  A  V  Y  Y  C  Q  Q  R  S  N  W  P  P  L
661   CTGGAACCGGAAGATTTTGCGGTGTATTATTGCCAGCAGCGCAGCAACTGGCCGCCGCTG

241   T  F  G  G  G  T  K  V  E  I  K  G  G  C       SEQ ID NO: 63
721   ACCTTTGGCGGCGGCACCAAAGTGGAAATTAAAGGCGGCTGC      SEQ ID NO: 64
```

Figure 34
Anti-CD3 VL-8-VH Cys-Diabody (ABC3) Translated Sequence

```
  1  M  E  T  D  T  L  L  L  W  V  L  L  L  W  V  F  G  S  T  G
  1  ATGGAAACCGACACCCTGCTGCTGTGGGTGCTGCTGCTCTGGGTCCAGGCTCCACCGGT

21  E  I  V  L  T  Q  S  P  A  T  L  S  L  S  P  G  E  R  A  T
 61  GAAATTGTGCTGACCCAGAGCCCGGCGACCCTGAGCCTGAGCCCGGGCGAACGCGCGACC

41  L  S  C  R  A  S  Q  S  V  S  S  Y  L  A  W  Y  Q  Q  R  P
121  CTGAGCTGCCGCGCGAGCCAGAGCGTGAGCAGCTATCTGGCGTGGTATCAGCAGAAACCG

61  G  Q  A  P  R  L  L  I  Y  D  A  S  N  R  A  T  G  I  P  A
181  GGCCAGGCGCCGCGCCTGCTGATTTATGATGCGAGCAACCGCGCGACCGGCATTCCGGCG

81  R  F  S  G  S  G  S  G  T  D  F  T  L  T  I  S  S  L  E  P
241  CGCTTTAGCGGCAGCGGCAGCGGCACCGATTTTACCCTGACCATTAGCAGCCTGGAACCG

101  E  D  F  A  V  Y  Y  C  Q  Q  R  S  N  W  P  P  L  T  F  G
301  GAAGATTTTGCGGTGTATTATTGCCAGCAGCGCAGCAACTGGCCGCCGCTGACCTTTGGC

121  G  G  T  K  V  E  I  K  G  G  S  G  G  G  Q  V  Q  L
361  GGCGGCACCAAAGTGGAAATTAAAGGCGGAGGGAGTGGCGGAGGCGGCCAGGTGCAGCTG

141  V  E  S  G  G  G  V  V  Q  P  G  R  S  L  R  L  S  C  A  A
421  GTGGAAAGCGGCGGCGGCGTGGTGCAGCCGGGCCGCAGCCTGCGCCTGAGCTGCGCGGCG

161  S  G  F  K  F  S  G  Y  G  M  H  W  V  R  Q  A  P  G  K  G
481  AGCGGCTTTAAATTTAGCGGCTATGGCATGCATTGGGTGCGCCAGGCGCCGGGCAAAGGC

181  L  E  W  V  A  V  I  W  Y  D  G  S  K  K  Y  Y  V  D  S  V
541  CTGGAATGGGTGGCGGTGATTTGGTATGATGGCAGCAAAAAATATTATGTGGATAGCGTG

201  K  G  R  F  T  I  S  R  D  N  S  K  N  T  L  Y  L  Q  M  N
601  AAAGGCCGCTTTACCATTAGCCGCGATAACAGCAAAAACACCCTGTATCTGCAGATGAAC

221  S  L  R  A  E  D  T  A  V  Y  Y  C  A  R  Q  M  G  Y  W  H
661  AGCCTGCGCGCGGAAGATACCGCGGTGTATTATTGCGCGCGCCAGATGGGCTATTGGCAT

241  F  D  L  W  G  R  G  T  L  V  T  V  S  S  G  G  C    SEQ ID NO: 65
721  TTTGATCTGTGGGGCCGCGGCACCCTGGTGACCGTGAGCAGCGGCGGCTGC  SEQ ID NO: 66
```

Figure 35
Anti-CD3 VH-8-VL Cys-Diabody (ABC3) Translated Sequence

```
  1    M  E  T  D  T  L  L  L  W  V  L  L  L  W  V  P  G  S  T  G
  1    ATGGAAACCGACACCCTGCTGCTGTGGGTGCTGCTGCTCTGGGTCCCAGGCTCCACCGGT

21    Q  V  Q  L  V  E  S  G  G  G  V  V  Q  P  G  R  S  L  R  L
 61    CAGGTGCAGCTGGTGGAAAGCGGCGGCGGCGTGGTGCAGCCGGGTCGCAGCCTGCGCCTG

41    S  C  A  A  S  G  F  K  F  S  G  Y  G  M  R  W  V  R  Q  A
121    AGCTGCGCGGCGAGCGGCTTTAAATTTAGCGGCTATGGCATGCATTGGGTGCGCCAGGCG

61    P  G  K  G  L  E  W  V  A  V  I  W  Y  D  G  S  K  K  Y  Y
181    CCGGGCAAAGGCCTGGAATGGGTGGCGGTGATTTGGTATGATGGCAGCAAAAAATATTAT

81    V  D  S  V  K  G  R  F  T  I  S  R  D  N  S  K  N  T  L  Y
241    GTGGATAGCGTGAAAGGCCGCTTTACCATTAGCCGCGATAACAGCAAAAACACCCTGTAT

101    L  Q  M  N  S  L  R  A  E  D  T  A  V  Y  Y  C  A  R  Q  M
301    CTGCAGATGAACAGCCTGCGCGCGGAAGATACCGCGGTGTATTATTGCGCGCGCCAGATG

121    G  Y  W  H  F  D  L  W  G  R  G  T  L  V  T  V  S  S  G  G
361    GGCTATTGGCATTTTGATCTGTGGGGCCGCGGCACCCTGGTGACCGTGAGCAGCGGCGGA

141    G  S  G  G  G  G  E  I  V  L  T  Q  S  P  A  T  L  S  L  S
421    GGGAGTGGCGGAGGCGGCGAAATTGTGCTGACCCAGAGCCCGGCGACCCTGAGCCTGAGC

161    P  G  E  R  A  T  L  S  C  R  A  S  Q  S  V  S  S  Y  L  A
481    CCGGGCGAACGCGCGACCCTGAGCTGCCGCGCGAGCCAGAGCGTGAGCAGCTATCTGGCG

181    W  Y  Q  Q  K  P  G  Q  A  P  R  L  L  I  Y  D  A  S  N  R
541    TGGTATCAGCAGAAACCGGGCCAGGCGCCGCGCCTGCTGATTTATGATGCGAGCAACCGC

201    A  T  G  I  P  A  R  F  S  G  S  G  S  G  T  D  F  T  L  T
601    GCGACCGGCATTCCGGCGCGCTTTAGCGGCAGCGGCAGCGGCACCGATTTTACCCTGACC

221    I  S  S  L  E  P  E  D  F  A  V  Y  Y  C  Q  Q  R  S  N  W
661    ATTAGCAGCCTGGAACCGGAAGATTTTGCGGTGTATTATTGCCAGCAGCGCAGCAACTGG

241    P  P  L  T  F  G  G  G  T  K  V  E  I  K  G  G  C           SEQ ID NO: 67
721    CCGCCGCTGACCTTTGGCGGCGGCACCAAAGTGGAAATTAAAGGCGGCTGC           SEQ ID NO: 68
```

FIG. 36a muVL (murine OKT3)

caaattgttctcacccagtctccagcaatcatgtctgcatctccaggggagaaggtcacc
Q I V L T Q S P A I M S A S P G E K V T
atgacctgc agtgcaagtgtaagttacatgaac tggtaccagcagaagtca
M T C  S A S S V S Y M N  W Y Q Q K S
ggcacctcccccaaaagatggatttat gacacatccaaactggcttct ggagtccctgct
G T S P K R W I Y  D T S K L A S  G V P A
cacttcagggcagtgggtctgggacctcttactctctcacaatcagcagcatggaggct
H F R G S G S G T S Y S L T I S G M E A
gaagatgctgccacttattactgc cagcagtggagtagtaaccattacg ttcggctcg
E D A A T Y Y C  Q Q W S S N P F T  F G S
gggacaaagttggaaataaaac     SEQ ID NO: 114
G T K L E I N            SEQ ID NO: 70

FIG. 36b huVL_vA (ABC1)

gacatccagatgacccagtctccttcctctgtctctgcatctgtaggagacagagtcaca
D I Q M T Q S P S S L S A S V G D R V T
atcacatgt tctgttctagctgtctgtcttacatgaac tggtaccagcagacacct
I T C  S V L A V C L H E  W Y Q Q T P
ggaaaggctcctaagcggtggatctac gacacatctaagctcgcttct ggagtcccttct
G K A P K R W I Y  D T S K L A S  G V P S
agattctctgctctggtctgggacagacagactacactctcaccatctctctccaacct
R F S G S G S G T D Y T F T I S S L Q P
gaggacatcgctacatactactgc caacagtggtctagcaatccttcaca ttcggacag
E D I A T Y Y C  Q Q W S S N P F T  F G Q
gggaaaaagctggaaatcaga    SEQ ID NO: 71
G T K L Q I T          SEQ ID NO: 72

FIG. 36c huVL_vB (humanized OKT3)

```
gaaattgtgttgacacagtccccagccaccctgtctttgtctccaggggaaagagccacc
 E  I  V  L  T  Q  S  P  A  T  L  S  L  S  P  G  E  R  A  T
ctctcctgc agtgccagctcaagtgtaagtacatgaac tggtaccagcagaaacct
 L  S  C  |A  S  S  S  V  S  Y  M  N| W  Y  Q  Q  K  P
ggccaggctcccaggctcctcatctat gacacatccaaactggcttct ggagtccctgct
 G  Q  A  P  R  L  L  I  Y |D  T  S  K  L  A  S| G  V  P  A
cactcagggcagtggatctgggacagacttcactctcaccatcagcagcctagagcct
 H  F  R  G  S  G  S  G  T  D  F  T  L  T  I  S  S  L  E  P
gaagattttgcagtttattactgt cagcagtggagtagtaaccattacg ttcggccaa
 E  D  F  A  V  Y  Y  C |Q  Q  W  S  S  N  P  F  T| F  G  Q
Gggaccaaggtggaaatcaaa  SEQ ID NO: 73
 G  T  K  V  E  I  K   SEQ ID NO: 74
```

FIG. 36d muVH (murine OKT3)

```
caggtccagctgcagcagtctggggctgaactggcaagacctggggcctcagtgaagatg
 Q  V  Q  L  Q  Q  S  G  A  E  L  A  R  P  G  A  S  V  K  M
tcctgcaaggcttct ggctacaccttcact agg tacacgatgcactgggtaaaacagagg
 S  C  K  A  S |G  Y  T  F  T  R| Y  T  M  H  W  V  K  Q  R
cctggacagggtctggaatggatt gga tacattaatcctagccgtggttatact aattac
 P  G  Q  G  L  E  W  I  G |Y  I  N  P  S  R  G  Y  T| N  Y
aatcagaagttcaaggacaaggccacattgactactgacaaatcctccagcacagcctac
 N  Q  K  F  K  D  K  A  T  L  T  T  D  K  S  S  S  T  A  Y
atgcaactgagcagcctgacatctgaggactctgcagtctattactgtgcaaga tattat
 M  Q  L  S  S  L  T  S  E  D  S  A  V  Y  Y  C  A  R |Y  Y
gatgatcattactgccttgactac tggggccaaggcaccactctcacagtctcctca  SEQ ID NO: 75
 D  D  H  Y  C  L  D  Y| W  G  Q  G  T  T  L  T  V  S  S   SEQ ID NO: 76
```

FIG. 36e muVH_C105S
caggtccagctgcagcagtctgggctgactggcagacctggggctctagtgaagatg
 Q  V  Q  L  Q  Q  S  G  A  E  L  A  R  P  G  A  S  V  K  M
tcctgcaaggcttct ggctacacctttactagg tacacgatgcactgggtaaaacagagg
 S  C  K  A  S  G  Y  T  F  T  R  Y  T  M  H  W  V  K  Q  R
cctggacaaggtctggaatggattgga tacattaatcctagccgtggttatact aattac
 P  G  Q  G  L  E  W  I  G  Y  I  N  P  S  R  G  Y  T  N  Y
aatcagaagttcaaggacaaggccacattgactacagacacatcctccagcacagcctac
 N  Q  K  F  K  D  K  A  T  L  T  T  D  K  S  S  S  T  A  Y
atgcaactgagcagcctgacatctgaggactctgcagtctattactgtgcaaga tattat
 M  Q  L  S  S  L  T  S  E  D  S  A  V  Y  Y  C  A  R  Y  Y
gatgatcattactactgactac tggggccaaggcaccactctcacagtctcctca SEQ ID NO: 77
 D  D  H  Y  Y  D  Y  W  G  Q  G  T  T  L  T  V  S  S    SEQ ID NO:78

FIG. 36f huVH_vA
caggttcagctggtggagtctggaggaggagtcgtccagcctgaaggtcctgagactg
 Q  V  Q  L  V  Q  S  G  G  G  V  V  Q  P  G  R  S  L  R  L
tcttgtaaggcttct ggatacacct tcactaga tacacaatgcactgggttcagcaggct
 S  C  K  A  S  G  Y  T  F  T  R  Y  T  M  H  W  V  R  Q  A
cctggaaaggggact cgagtggattgga tacattaatcctagcagagttatact aactac
 P  G  K  G  L  E  W  I  G  Y  I  N  P  S  R  G  Y  T  N  Y
aatcagaagttgaaggacagattcacagaattctaagaataccagcctc
 N  Q  K  V  K  D  R  F  T  I  S  R  D  N  S  K  N  T  A  F
ctgcagatggactcactgagacctgaggatacaggagtctattttgtgctaga tattac
 L  Q  M  D  S  L  R  P  E  D  T  G  V  Y  F  C  A  R  Y  Y
gatgaccactactgtgactac tgggccaaggtaccccggtcaccgtgagctca SEQ ID NO: 79
 D  D  H  Y  Y  D  Y  W  G  Q  G  T  P  V  T  V  S  S    SEQ ID NO: 80

FIG. 36g huVH_vA_C105S

```
caggttcagtcagtggtgcagtctggaggaggagtcgtccagcctgaaggtccctgagactg
 Q  V  Q  L  V  Q  S  G  G  G  V  V  Q  P  G  R  S  L  R  L
tcttgtaaggcttct ggatacacctt cactaga tacacaatgcactgggtcagacaggct
 S  C  K  A  S  G  Y  T  F  T  R  Y  T  M  H  W  V  R  Q  A
cctggaaaggactcgagtggatggga tacattaatcctagcagaggttatactaactac
 P  G  K  G  L  E  W  M  G  Y  I  N  P  S  R  G  Y  T  N  Y
aatcagaaggtgaaggacagattcaccatctctagagacaattctaagaatacagcctc
 N  Q  K  V  K  D  R  F  T  I  S  R  D  N  S  K  N  T  A  F
ctgcagatggactcactgagacctgaggagtctatttttgtgctagatattac  SEQ ID NO:81
 L  Q  M  D  S  L  R  P  E  D  T  G  V  Y  F  C  A  R  Y  Y
gatgaccactactgactggtaccccaaggtcaccgtctcctca  SEQ ID NO: 82
 D  D  H  Y  S  L  D  Y  W  G  Q  G  T  L  V  T  V  S  S
```

FIG. 36h huVH_vB (humanized OKT3)

```
caggtgcagctggtgcagtctggggctgaggtgaagaagcctggggcctcagtgaaggtc
 Q  V  Q  L  V  Q  S  G  A  E  V  K  K  P  G  A  S  V  K  V
tcctgcaaggcttct ggatacaccttcaccagg tacacgatgcactgggtgcgacaggcc
 S  C  K  A  S  G  Y  T  F  T  R  Y  T  M  H  W  V  R  Q  A
cctggacaagggcttgagtgatggga tacattaatcctagccgtggttatactaactac
 P  G  Q  G  L  E  W  M  G  Y  I  N  P  S  R  G  Y  T  N  Y
aatcagaaggtcaagggcagggtcaccatgaccagagacacgtccatcagcacagcctac
 N  Q  K  V  K  G  R  V  T  M  T  D  T  S  I  S  T  A  Y
atggagctgagcaggctgagatctgacgacacggccgtgtattactgtgcgaga tattat  SEQ ID NO:83
 M  E  L  S  R  L  R  S  D  D  T  A  V  Y  Y  C  A  R  Y  Y
gatgatcattactgactggtaccccaaggtcaccgtctcctca  SEQ ID NO:84
 D  D  H  Y  S  L  D  Y  W  G  Q  G  T  L  V  T  V  S  S
```

FIG. 36i huVH_vB_C105S

```
caggtgcagctggtggagtctgggggctgaggtgaagaagcctggggcctcagtgaaggtc
 Q  V  Q  L  V  Q  S  G  A  E  V  K  K  P  G  A  S  V  K  V
tcctgcaaggcttct ggatacaccttcaccagg tacacgatggtgactggtgcgacaggcc
 S  C  K  A  S  G  Y  T  F  T  R   Y  T  M  E  W  V  R  Q  A
cctggacaagggcttgagtggatgga tacattaatcctagccgtggttatactaattac aattac
 P  G  Q  G  L  E  W  M  G  Y  I  N  P  S  R  G  Y  T  N  Y
aatcagaagttcaaggacagggtcacgatgaccacagacacgtccatcagcacagcctac
 N  Q  K  F  K  D  R  V  T  M  T  T  D  T  S  I  S  T  A  Y
atggagctgagcaggctgagatctgaggacacggccgtgtattactgtgcgagaga tattat SEQ ID NO:85
 M  E  L  S  R  L  R  S  D  D  T  A  V  Y  Y  C  A  R  Y  Y
gatgattactcacttgactac tggggccagggcaccctggtcaccgtctcctca SEQ ID NO:86
 D  D  Y  S  L  D  Y  W  G  Q  G  T  L  V  T  V  S  S
```

FIG. 37A)

Leader sequence:

Atggaaacgacaacctgtgctgtggtgctgctgctctggtcccaggctccaccggt SEQ ID NO: 87
M  E  T  D  T  L  L  W  V  L  L  L  W  V  P  G  S  T  G  SEQ ID NO: 88

Five aa linker:

Agtggtggaggaggc SEQ ID NO: 89
S  G  G  G  G    SEQ ID NO: 90

Eight aa linker:

Ggcggaggaggatggtggcggaggcygc SEQ ID NO: 91
G  G  G  G  S  G  G  G  G    SEQ ID NO: 92

Cysteine tail:

Ggcggctgc SEQ ID NO: 93
G  G  C    SEQ ID NO: 94

FIG. 37B)

Leader sequence:
Atggaaccgacaccctgctgctgtggtgctgctcttggtgctgctgttggtcccaggtgctccaccggt    SEQ ID NO: 95
 M  E  T  D  T  L  L  L  W  V  L  L  L  W  V  P  G  S  T  G              SEQ ID NO: 96

Eighteen aa linker:
Ggctccacatccggcggaggctctggcggtggatctggcggaggcggctcatcc    SEQ ID NO: 97
 G  S  T  S  G  G  G  S  G  G  G  S  G  G  G  S  S        SEQ ID NO: 98

IgG1 hinge/linker-CH3 domain:
gagcctaagtcctgcgacaagacccacacctgtcccccctgcccgcygaggagcagcggc
 E  P  K  S  C  D  K  T  H  T  C  P  P  C  P  G  G  S  G
ggcggatccggtggccagcctcggagcctcaggtgtacaccctgcctccctcccggac
 G  G  S  G  Q  P  R  E  P  Q  V  Y  T  L  P  P  S  R  D
gagctgaccaagaaccaggtgtccctgacctgtctggtcaaggcttctactacccttccgat
 E  L  T  K  N  Q  V  S  L  T  C  L  V  K  G  F  Y  P  S  D
atcgccgtggagtgggagtccaacggccagcctgagaacaactacaagaccacccctcct
 I  A  V  E  W  E  S  N  G  Q  P  E  N  N  Y  K  T  T  P  P
gtgctggactccgacggctcccttcttctactccaagctcacagtggataagtccgg
 V  L  D  S  D  G  S  F  F  L  Y  S  K  L  T  V  D  K  S  R
tggcagcaggcaacgtgttctcctgctccgtgatgcacgaggcccctgcacaaccactat
 W  Q  Q  G  N  V  F  S  C  S  V  M  H  E  A  L  H  N  H  Y
Acccagaagtccctgtcctgtggcaag    SEQ ID NO: 99
 T  Q  K  S  L  S  L  S  P  G  K    SEQ ID NO: 100

FIG. 37C)

| | | | |
|---|---|---|---|
| IgG1 | EPKSCDKTHT | CPPCP | APELLGGP | SEQ ID NO: 101 |
| IgG1v1 | EPKSCDKTHT | CPPCP | GGGSGGGSG | SEQ ID NO: 102 |
| IgG2 | ERK | CCVECPPCP | APPVA-GP | SEQ ID NO: 103 |
| IgG3 | ELKTPLGDTTHT | CPRCP(EPKSCDTPPPCPRCP)x3 | APELLGGP | SEQ ID NO: 104 |
| IgG3v1 | ELKTPLGDTTHT | CPRCP | APELLGGP | SEQ ID NO: 105 |
| IgG3v2 | EPKSCDTPPP | CPRCP | APELLGGP | SEQ ID NO: 106 |
| IgG4 | ESKYGPP | CPSCP | APEFLGGP | SEQ ID NO: 107 |
| IgG4v1 | ESKYGPP | CPPCP | APEFLGGP | SEQ ID NO: 108 |

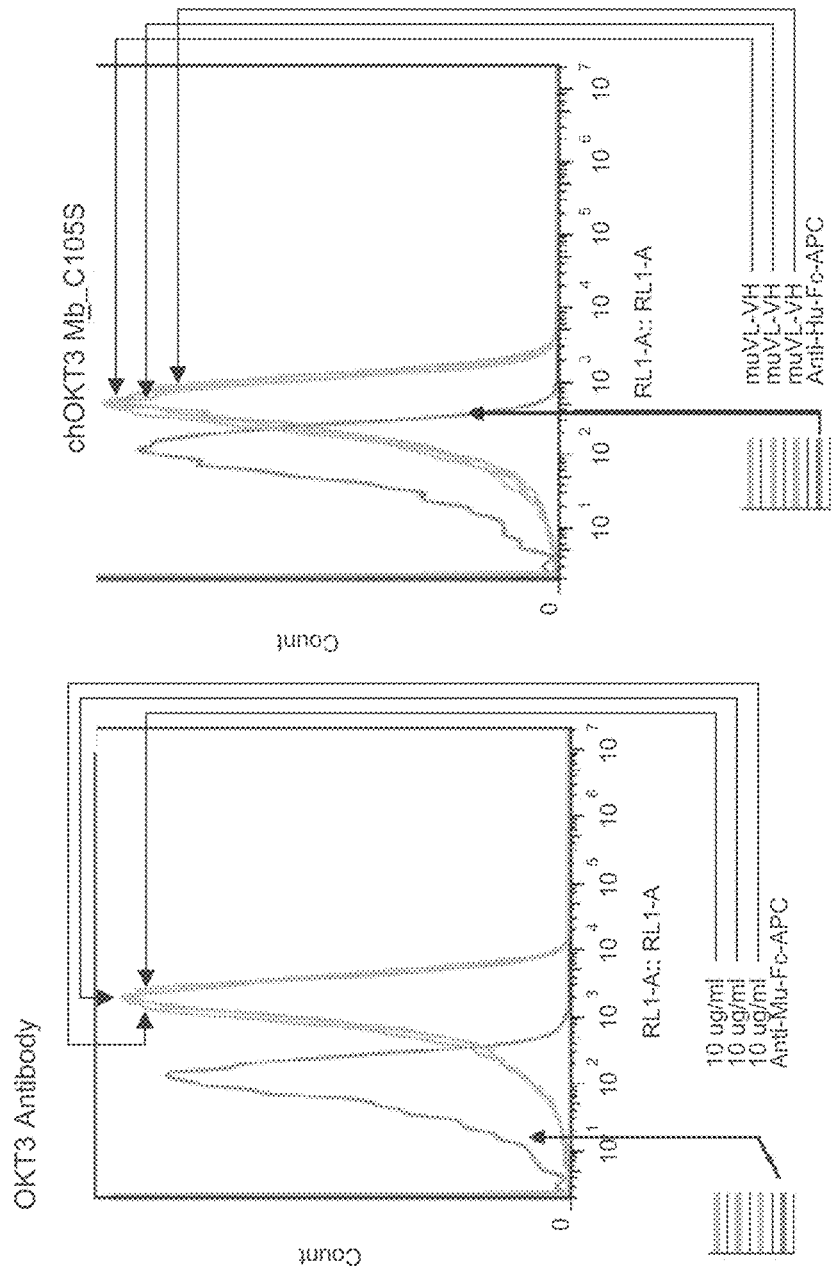

huMb Version B_C105S huMb_Version A_C105S

FIG. 40

Signal Peptide

MQSSTHWRVL GLCLLSVGVW GQ         SEQ ID NO: 109

CD3e

DGNEEMGG ITQTPYKVSI SGTTVILTCP QYPGSEILWQ HNDKNIGGDE DDKNIGSDED HLSLKEFSEL EQSGYYVCYP
RGSKPEDANF YLYLRARVCE NCMEMDVMSV ATIVIVDICI TGGLLLLVYY WSKNRKAKAK PVTRGAGAGG KQRGQNKERP
PPVPNPDYEP IRKGQRDLYS GLNQRRI     SEQ ID NO: 110

ANTIGEN BINDING CONSTRUCTS TO CD3

CROSS-REFERENCE TO RELATED APPLICATIONS

The present application is the U.S. national phase entry under 35 U.S.C. § 371 of PCT/US2013/045719, filed Jun. 13, 2013, which claims the benefit of U.S. Provisional Application No. 61/660,594, filed Jun. 15, 2012, U.S. Provisional Application No. 61/674,229, filed Jul. 20, 2012, and U.S. Provisional Application No. 61/776,673, filed Mar. 11, 2013, the entireties of each of which is hereby incorporated by referenced in its entirety.

REFERENCE TO SEQUENCE LISTING

The present application is being filed along with a Sequence Listing in electronic format. The Sequence Listing is provided as a file entitled SeqLisIGNAB015WO.txt, created and last saved on May 31, 2013, which is 151,318 bytes in size. The information in the electronic format of the Sequence Listing is incorporated herein by reference in its entirety.

FIELD

Embodiments described herein relate generally to antigen binding constructs, such as antibodies, including antibody fragments, that bind to CD3, (such as minibodies, cys-diabodies, and scFv), as well as methods for their use.

BACKGROUND

CD3 (cluster of differentiation 3) was discovered concurrently with the monoclonal antibody OKT3. Initially, OKT3 was found to bind to all mature, peripheral T cells, and later the CD3 epsilon subunit as part of the TCR-CD3 complex was determined to be the cell surface antigen bound by OKT3. ("Monoclonal antibodies defining distinctive human T cell surface antigens" Kung et al. 1979) OKT3 was subsequently tested as an immunosuppressant for transplant rejection with the initial trial studying acute kidney allograft rejection ("Treatment of acute renal allograft rejection with OKT3 monoclonal antibody" Cosimi et al. 1981).

SUMMARY

In some embodiments, an antigen binding construct is provided. The antigen binding construct comprises a HCDR1 of the HCDR1 in SEQ ID NO: 6 or 86, a HCDR2 of the HCDR2 in SEQ ID NO: 6 or 86, a HCDR3 of the HCDR3 in SEQ ID NO: 6 or 86, a LCDR1 of the LCDR1 in SEQ ID NO: 3, a LCDR2 of the LCDR2 in SEQ ID NO: 3, and a LCDR3 of the LCDR3 in SEQ ID NO: 3.

In some embodiments, a humanized cys-diabody that binds to CD3 is provided. The humanized cys-diabody comprises a polypeptide that comprises a single-chain variable fragment (scFv) comprising a variable heavy ($V_H$) domain linked to a variable light ($V_L$); and a C-terminal Cysteine.

In some embodiments, a humanized minibody that binds to CD3 is provided. The humanized minibody comprises a polypeptide that comprises a single-chain variable fragment (scFv) that binds to CD3, the scFv comprising a variable heavy ($V_H$) domain linked a variable light ($V_L$) domain; a hinge-extension domain comprising a human IgG1 hinge region; and a human IgG $C_H3$ sequence.

In some embodiments a nucleic acid encoding an antibody as provided herein is provided.

In some embodiments, a cell line producing an antibody as provided herein is provided.

In some embodiments, a kit comprising an antigen binding construct as provided herein and a detectable marker is provided.

In some embodiments, a method of detecting the presence or absence of a CD3 is provided. The method can include applying an antigen binding construct to a sample; and detecting a binding or an absence of binding of the antigen binding construct thereof to CD3.

In some embodiments, a method of targeting a therapeutic agent to a CD3 is provided. The method can include administering to a subject an antigen binding construct as provided herein, wherein the antigen binding construct is conjugated to a therapeutic agent.

In some embodiments, a method of neutralizing a T cell in a subject in need thereof is provided. The method can include administering to the subject an antigen binding construct as provided herein.

BRIEF DESCRIPTION OF THE DRAWINGS

FIGS. 2A and 2B depict sequences showing the humanization of OKT3 variable light (FIG. 2A) and heavy (FIG. 2B) regions. The shaded and bolded cysteine in HCDR3 indicates the cysteine that was modified to a serine for some of the present embodiments. In some embodiments, HCDR3 (YYDDHYCLDY) (SEQ ID NO: 69) can be swapped with YYDDHYSLDY (SEQ ID NO: 69) (HCDR3 is YYDDHY (C/S)LDY (SEQ ID NO: 69)). Mouse sequences were compared with human variable light and heavy germline genes in FIGS. 2A and 2B. The murine OKT3 variable amino acid sequences (muOKT3) aligned with the human acceptor variable sequences (Human) are shown. The humanized/CDR grafted sequences (murine OKT3 CDRs within the human framework) are shown below (huOKT3, referred to as huVL_vB (panel A) and huVH_vB (panel B)). The CDRs are boxed using Chothia definition and the asterisks indicate residues that differ between the murine and the human framework.

FIGS. 3A and 3B depict some embodiments of a minibody to CD3 ($V_LV_H$ orientation, murine)

FIGS. 4A and 4B depict some embodiments of a minibody to CD3 ($V_LV_H$ orientation—ABC1).

FIGS. 5A and 5B depict some embodiments of a minibody to CD3 ($V_LV_H$ orientation, humanized).

FIG. 6 depicts some embodiments of a cys-diabody to CD3 (humanized).

FIGS. 9A and 9B provide some embodiments of a CD3 minibody.

FIG. 10 provides some embodiments of a CD3 cys-diabody.

FIG. 11 provides some embodiments of a CD3 cys-diabody.

FIG. 12 provides some embodiments of a CD3 cys-diabody.

FIG. 13 provides some embodiments of a CD3 cys-diabody.

FIGS. 14A and 14B provide some embodiments of a CD3 minibody.

FIG. 15 provides some embodiments of a CD3 cys-diabody.

FIG. 16 provides some embodiments of a CD3 cys-diabody.

FIG. 17 provides some embodiments of a CD3 cys-diabody.

FIG. 18 provides some embodiments of a CD3 cys-diabody.

FIGS. 19A and 19B provide some embodiments of a CD3 minibody.

FIG. 20 provides some embodiments of a CD3 cys-diabody.

FIG. 21 provides some embodiments of a CD3 cys-diabody.

FIG. 22 provides some embodiments of a CD3 cys-diabody.

FIG. 23 provides some embodiments of a CD3 cys-diabody.

FIGS. 24A and 24B provide some embodiments of a CD3 minibody.

FIGS. 25A and 25B provide some embodiments of a CD3 minibody.

FIG. 26 provides some embodiments of a CD3 cys-diabody.

FIG. 27 provides some embodiments of a CD3 cys-diabody.

FIG. 28 provides some embodiments of a CD3 cys-diabody.

FIG. 29 provides some embodiments of a CD3 cys-diabody.

FIGS. 30A and 30B provide some embodiments of a CD3 minibody.

FIGS. 31A and 31B provide some embodiments of a CD3 minibody.

FIG. 32 provides some embodiments of a CD3 cys-diabody.

FIG. 33 provides some embodiments of a CD3 cys-diabody.

FIG. 34 provides some embodiments of a CD3 cys-diabody.

FIG. 35 provides some embodiments of a CD3 cys-diabody.

FIG. 36a-36i depicts anti-CD3 variable light ($V_L$; a, b, c) and variable heavy ($V_H$; d, e, f, g, h, i) sequences. The DNA with the translated amino acid sequences is shown. The $V_H$ residue at position 105 is underlined. CDRs are boxed using Chothia definition.

FIG. 37A-C depict various embodiments regarding additional sequences that can be included in antigen binding constructs provided herein. FIG. 37A provides additional components used for generating cys-diabodies and FIG. 37B provides additional components for minibodies. FIG. 37C provides amino acid sequences of IgG hinge regions and variants thereof.

FIG. 39A-39D are flow cytometry analysis of anti-CD3 minibody variants.

FIG. 40 depicts the sequence of human CD3 Epsilon (amino acid sequence). Residues shaded have been identified as the epitope for OKT3.

DETAILED DESCRIPTION

Figure 1:
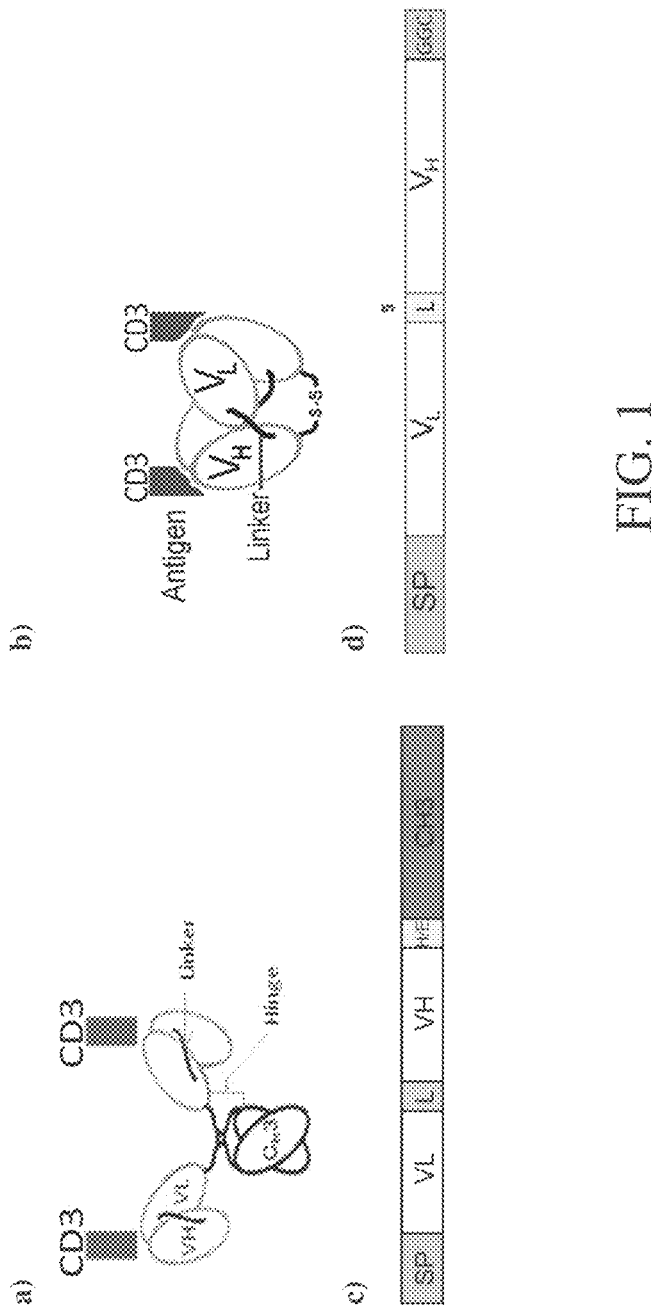
FIG. 1A is a depiction of the anti-CD3 minibody in the $V_HV_L$ orientation. The minibody forms a covalently bound homodimer that can bind two antigens (for example, CD3).
FIG. 1B is a depiction of the anti-CD3 cys-diabody in the $V_LV_H$ orientation. The shortened linker forces cross-pairing of two scFv and enables binding to two antigens, and the formation of a covalent bond between the two terminal cysteines.
FIG. 1C is a depiction of the assembled cDNA gene expression construct for anti-CD3 minibody in $V_LV_H$ orientation.
FIG. 1D is a depiction of the assembled cDNA gene expression construct for the anti-CD3 cys-diabody in $V_LV_H$ orientation. Abbreviations: SP=signal peptide, $V_H$=variable heavy domain, $V_L$=variable light domain, $C_H3$=third constant domain, L=linker, H/E=hinge/extension, GGC=glycine, glycine, cysteine.
FIG. 1E is a flow chart depicting some embodiments of methods provided herein.

Described herein are antigen binding constructs, including antibodies and fragments thereof, such as cys-diabodies and minibodies, that bind to a target molecule, CD3. Such antigen binding constructs can be useful for detecting the presence, localization, and/or quantities of the target molecule (CD3 and/or CD3+ cells). Such antigen binding constructs can also be useful for modulating the biologic activity associated with CD3 expression on immune cells and for targeting therapeutic agents to cells that express the CD3 protein. In some embodiments, methods are provided for detecting the presence or absence of the target molecule (or "target") using antigen binding constructs (including antibodies, and constructs such as cys-diabodies and/or minibodies). In some embodiments, methods are provided for using the antigen binding constructs for therapeutic purposes.

To date, there are no commercial imaging agents targeting CD3. Initial proof-of-concept preclinical imaging has been performed with a humanized anti-CD3 antibody, Visilizumab which was not derived from OKT3 ("Radiolabeled humanized anti-CD3 monoclonal antibody Visilizumab for imaging human T-lymphocytes" Malviya et al. 2009). Imaging of CD3+ T-cells is useful for anti-CD3 therapy since the treatment is effective if the organ of interested has been entirely infiltrated with CD3+ T-cells. A potential CD3 imaging agent would allow for the selection of the patient and also a way to monitor treatment. Imaging with a full-length antibody typically requires a longer time post-injection for optimal imaging than with the fragments provided herein.

Definitions And Various Embodiments

The term "treating" or "treatment" of a condition may refer to preventing the condition, slowing the onset and/or rate of development of the condition, reducing the risk of developing the condition, preventing and/or delaying the development of symptoms associated with the condition, reducing or ending symptoms associated with the condition, generating a complete or partial regression of the condition, or some combination thereof. The term "prevent" does not require the absolute prohibition of the disorder or disease.

A "therapeutically effective amount" or a "therapeutically effective dose" is an amount that produces a desired therapeutic effect in a subject, such as preventing, treating a target condition, delaying the onset of the disorder and/or symptoms, and/or alleviating symptoms associated with the condition. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and/or the route of administration. One skilled in the clinical and pharmacological arts will be able to determine a therapeutically effective amount through routine experimentation, for example by monitoring a subject's response to administration of a compound and adjusting the dosage accordingly, given the present disclosure. For additional guidance, see Remington: The Science and Practice of Pharmacy 21$^{st}$ Edition, Univ. of Sciences in Philadelphia (USIP), Lippincott Williams & Wilkins, Philadelphia, Pa., 2005.

The term "antigen binding construct" includes all varieties of antibodies, including binding fragments thereof. Further included are constructs that include 1, 2, 3, 4, 5, and/or 6 CDRs. In some embodiments, these CDRs can be distributed between their appropriate framework regions in a traditional antibody. In some embodiments, the CDRs can be contained within a heavy and/or light chain variable region. In some embodiments, the CDRs can be within a heavy chain and/or a light chain. In some embodiments, the CDRs can be within a single peptide chain. In some embodiments, the CDRs can be within two or more peptides that are covalently linked together. In some embodiments, they can be covalently linked together by a disulfide bond. In some embodiments, they can be linked via a linking molecule or moiety. In some embodiments, the antigen binding proteins are non-covalent, such as a diabody and a monovalent scFv. Unless otherwise denoted herein, the antigen binding constructs described herein bind to the noted target molecule. The term "target" or "target molecule" denotes the CD3 protein. Examples of CD3 proteins are known in the art, and include, for example the CD3 protein of SEQ ID NO: 110, in FIG. 40. In some embodiments, any of the antigen binding constructs (including minibodies and/or diabodies) provided herein can have their CDRs and/or heavy and/or light chain variable regions provided in a monovalent form (scFv). Such embodiments can be useful for imaging and can be associated with a detectable marker. In some embodiments, any of the antigen binding constructs (including minibodies and/or diabodies) provided herein can have their CDRs and/or heavy and/or light chain variable regions to provide for bi-specific targeting and/or heavy and/or light chain variable regions to provide for bi-specific targeting. Such targeting can link two different antigen expressing cells with one being an immune effector cell expressing CD3 and the other a target cell (ie tumor cell) that will be selectively killed resulting in disease amelioration. In some embodiments, even though the constructs are bivalent, they can also function as monovalent contructs (for example, they can bind only one epitope at a time).

The term "antibody" includes, but is not limited to, genetically engineered or otherwise modified forms of immunoglobulins, such as intrabodies, chimeric antibodies, fully human antibodies, humanized antibodies, antibody fragments, and heteroconjugate antibodies (for example, bispecific antibodies, scFv, diabodies, triabodies, tetrabodies, etc.). The term "antibody" includes cys-diabodies and minibodies. Thus, each and every embodiment provided herein in regard to "antibodies" is also envisioned as cys-diabody and/or minibody embodiments, unless explicitly denoted otherwise. The term "antibody" includes a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. In some embodiments, a full length antibody can be composed of two identical pairs of polypeptide chains, each pair having one "light" and one "heavy" chain (connected through a disulfide bond. The recognized immunoglobulin genes include the kappa, lambda, alpha, gamma, delta, epsilon, and mu constant region genes, as well as the myriad immunoglobulin variable region genes. For full length chains, the light chains are classified as either kappa or lambda. For full length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. As used in this application, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (for example, F(ab')$_2$) with the same binding specificity. In some embodiments, the antibody binds specifically to a desired target.

"Complementarity-determining domains" or "complementarity-determining regions ("CDRs") interchangeably refer to the hypervariable regions of VL and VH. The CDRs are the target protein-binding site of the antibody chains that harbors specificity for such target protein. In some embodiments, there are three CDRs (CDR1-3, numbered sequentially from the N-terminus) in each VL and/or VH, constituting about 15-20% of the variable domains. The CDRs are structurally complementary to the epitope of the target protein and are thus directly responsible for the binding specificity. The remaining stretches of the VL or VH, the so-called framework regions (FRs), exhibit less variation in amino acid sequence (Kuby, Immunology, 4th ed., Chapter 4. W.H. Freeman & Co., New York, 2000).

The positions of the CDRs and framework regions can be determined using various well known definitions in the art, for example, Kabat (Wu, T. T., E. A. Kabat. 1970. An analysis of the sequences of the variable regions of Bence Jones proteins and myeloma light chains and their implications for antibody complementarity. J. Exp. Med. 132: 211-250; Kabat, E. A., Wu, T. T., Perry, H., Gottesman, K., and Foeller, C. (1991) Sequences of Proteins of Immunological Interest, 5th ed., NIH Publication No. 91-3242, Bethesda, Md.), Chothia Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)), ImMunoGeneTics database (IMGT) (on the worldwide web at imgt.org/) Giudicelli, V., Duroux, P., Ginestoux, C., Folch, G., Jabado-Michaloud, J., Chaume, D. and Lefranc, M.-P. IMGT/LIGM-DB, the IMGT® comprehensive database of immunoglobulin and T cell receptor nucleotide sequences Nucl. Acids Res., 34, D781-D784 (2006), PMID: 16381979; Lefranc, M.-P., Pommié, C., Ruiz, M., Giudicelli, V., Foulquier, E., Truong, L., Thouvenin-Contet, V. and Lefranc, G., IMGT unique numbering for immunoglobulin and T cell receptor variable domains and Ig superfamily V-like domains Dev. Comp. Immunol., 27, 55-77 (2003). PMID: 12477501; Brochet, X., Lefranc, M.-P. and Giudicelli, V. IMGT/V-QUEST: the highly customized and integrated system for IG and TR standardized V-J and V-D-J sequence analysis Nucl. Acids Res, 36, W503-508 (2008); AbM (Martin et al., Proc. Natl. Acad. Sci. USA, 86:9268-9272 (1989); the contact definition (MacCallum et al., J. Mol. Biol., 262:732-745 (1996)), and/or the automatic modeling and analysis tool Honegger A, Plückthun A. (world wide web at bioc dot uzh dot ch/antibody/Numbering/index dot html).

The term "binding specificity determinant" or "BSD" interchangeably refer to the minimum contiguous or non-contiguous amino acid sequence within a complementarity determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody. In some embodiments, CDR3 of the heavy chain variable region is sufficient for the antigen binding construct specificity.

An "antibody variable light chain" or an "antibody variable heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody variable light chains and/or antibody variable heavy chains may, from time to time, be collectively referred to as "antibody chains." These terms encompass antibody chains containing mutations that do not disrupt the basic structure of $V_L$ or $V_H$, as one skilled in the art will readily recognize. In some embodiments, full length heavy and/or light chains are contemplated. In some embodiments, only the variable region of the heavy and/or light chains are contemplated as being present.

Antibodies can exist as intact immunoglobulins or as a number of fragments produced by digestion with various peptidases. Thus, for example, pepsin digests an antibody below the disulfide linkages in the hinge region to produce F(ab)'$_2$, a dimer of Fab' which itself is a light chain ($V_L$-$C_L$) joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is a Fab with part of the hinge region. (Paul, Fundamental Immunology 3d ed. (1993). While various antibody fragments are defined in terms of the digestion of an intact antibody, one of skill will appreciate that such fragments may be synthesized de novo either chemically or by using recombinant DNA methodology. Thus, the term "antibody," as used herein, also includes antibody fragments either produced by the modification of whole antibodies, or those synthesized de novo using recombinant DNA methodologies (for example, single chain Fv) or those identified using phage display libraries (see, for example, McCafferty et al., Nature 348:552-554 (1990)).

For preparation of monoclonal or polyclonal antibodies, any technique known in the art can be used (see, for example, Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985; Advances in the production of human monoclonal antibodies Shixia Wang, Antibody Technology Journal 2011:1 1-4; J Cell Biochem. 2005 Oct. 1; 96(2):305-13; Recombinant polyclonal antibodies for cancer therapy; Sharon J, Liebman M A, Williams B R; and Drug Discov Today. 2006 Jul., 11(13-14):655-60, Recombinant polyclonal antibodies: the next generation of antibody therapeutics?, Haurum J S). Techniques for the production of single chain antibodies (U.S. Pat. No. 4,946,778) can be adapted to produce antibodies to polypeptides of this invention. Also, transgenic mice, or other organisms such as other mammals, may be used to express fully human monoclonal antibodies. Alternatively, phage display technology can be used to identify high affinity binders to selected antigens (see, for example, McCafferty et al., supra; Marks et al., Biotechnology, 10:779-783, (1992)).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. In some embodiments, the terms "donor" and "acceptor" sequences can be employed. Humanization can be essentially performed following the method of Winter and co-workers (see, for example, Jones et al., Nature 321:522-525 (1986); Riechmann et al., Nature 332:323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some complementarity determining region ("CDR") residues and possibly some framework ("FR") residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, for example, an enzyme, toxin, hormone, growth factor, and drug; or (b) the variable region, or a portion thereof, is altered, replaced or exchanged with a variable region having a different or altered antigen specificity.

Antibodies further include one or more immunoglobulin chains that are chemically conjugated to, or expressed as, fusion proteins with other proteins. It also includes bispecific antibodies. A bispecific or bifunctional antibody is an artificial hybrid antibody having two different heavy/light chain pairs and two different binding sites that recognize different epitopes on the same antigen or two completely different antigens. The two antigens can be present on the same cell to enhance selectivity or may be expressed on different cells in which case the bispecific serves as a bridge between two antigen expressing cells. Other antigen-binding fragments or antibody portions of the invention include bivalent scFv (diabody), where the antibody molecule recognizes two different epitopes, single binding domains (sdAb or nanobodies), and minibodies.

The term "antibody fragment" includes, but is not limited to one or more antigen binding fragments of antibodies alone or in combination with other molecules, including, but not limited to Fab', F(ab')$_2$, Fab, Fv, rIgG (reduced IgG), scFv fragments, single domain fragments (nanobodies), peptibodies, minibodies, diabodies, and cys-diabodies. The term "scFv" refers to a single chain Fv ("fragment variable") antibody in which the variable domains of the heavy chain and of the light chain of a traditional two chain antibody have been joined to form one chain.

A pharmaceutically acceptable carrier may be a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier is "pharmaceutically acceptable" in that it is be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits. The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (for example, topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the antigen binding construct can be delivered intraoperatively as a local administration during an intervention or resection.

The term "CD3 dependent disorder" includes rheumatoid arthritis, multiple sclerosis, type 1 diabetes, lupus erythematosus, inflammatory bowel disease, diabetes, organ transplant rejection, autoimmune diseases, allergies and other disorders where T and/or Natural Killer (NK) cells play a role in the pathology.

A minibody is an antibody format that has a smaller molecular weight than the full-length antibody while maintaining the bivalent binding property against an antigen. Because of its smaller size, the minibody has a faster clearance from the system and enhanced penetration when targeting tumor tissue. With the ability for strong targeting combined with rapid clearance, the minibody is advantageous for diagnostic imaging and delivery of cytotoxic/radioactive payloads for which prolonged circulation times may result in adverse patient dosing or dosimetry. Due to differences in PK and the absence of a constant region that binds Fc gamma receptors, minibodies can ligate and stimulate immune responses in a more controlled manner resulting in fewer or decreased unwanted biologic effects such as the induction of a life threatening cytokine storm. Minibodies directed to CD3 are expected to promote immune tolerance.

The phrase "specifically (or selectively) bind," when used in the context of describing the interaction between an antigen, for example, a protein, to an antibody or antibody-derived binding agent, refers to a binding reaction that is determinative of the presence of the antigen in a heterogeneous population of proteins and other biologics, for example, in a biological sample, for example, a blood, serum, plasma or tissue sample. Thus, under designated immunoassay conditions, in some embodiments, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, for example, Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M, or $10^{-13}$ M.

The term "isolated," when applied to a nucleic acid or protein, denotes that the nucleic acid or protein is essentially free of other cellular components with which it is associated in the natural state. In some embodiments, it can be in either a dry or aqueous solution. Purity and homogeneity can be determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. In some embodiments, this can denote that the nucleic acid or protein is at least 85% pure, more preferably at least 95% pure, and most preferably at least 99% pure of molecules that are present under in vivo conditions.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (for example, degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine. Amino acid analogs refer to compounds that have the same basic chemical structure as a naturally occurring amino acid, for example, an alpha-carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, for example, Creighton, Proteins (1984)).

"Percentage of sequence identity" can be determined by comparing two optimally aligned sequences over a comparison window, wherein the portion of the polynucleotide sequence in the comparison window may comprise additions or deletions (i.e., gaps) as compared to the reference sequence (for example, a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (for example, 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. Some embodiments provided herein provide polypeptides or polynucleotides that are substantially identical to the polypeptides or polynucleotides, respectively, exemplified herein (for example, any one or more of the variable regions exemplified in any one of FIGS. 2A, 2B, 3A, 3B, 4A, 4B, 5A, 5B, and 6 and 9A, 9B, 10-13, 14A, 14B, 15-18, 19A, 19B, 20-23, 24A, 24B, 25A, 25B, 26-29, 30A, 30B, 31A, 31B, and 32-35; any one or more of the CDRs exemplified in any one of FIGS. 2A, 2B, 3A, 3B, 4A, 4B, 5A, 5B, and 6 and 9A, 9B, 10-13, 14A, 14B, 15-18, 19A, 19B, 20-23, 24A, 24B, 25A, 25B, 26-29, 30A, 30B, 31A, 31B, and 32-35; any one or more of the FRs exemplified in any one of FIGS. 2A, 2B, 3A, 3B, 4A, 4B, 5A, 5B, and 6 and 9A, 9B, 10-13, 14A, 14B, 15-18, 19A, 19B, 20-23, 24A, 24B, 25A, 25B, 26-29, 30A, 30B, 31A, 31B, and 32-35; and any one or more of the nucleic acid sequences exemplified in any one of FIGS. 3A, 3B, 4A, 4B, 5A, 5B, and 6 and 9A, 9B, 10-13, 14A, 14B, 15-18, 19A, 19B, 20-23, 24A, 24B, 25A, 25B, 26-29, 30A, 30B, 31A, 31B, and 32-35). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, for example, amino acid sequences of 20 or fewer amino acids, in some embodiments, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, for example, Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, for example, Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, in some embodiments, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "subject," "patient," and "individual" interchangeably refer to an entity that is being examined and/or treated. This can include, for example, a mammal, for example, a human or a non-human primate mammal. The mammal can also be a laboratory mammal, for example, mouse, rat, rabbit, hamster. In some embodiments, the mammal can be an agricultural mammal (for example, equine, ovine, bovine, porcine, camelid) or domestic mammal (for example, canine, feline).

The term "therapeutically acceptable amount" or "therapeutically effective dose" interchangeably refer to an amount sufficient to effect the desired result. In some embodiments, a therapeutically acceptable amount does not induce or cause undesirable side effects. A therapeutically acceptable amount can be determined by first administering a low dose, and then incrementally increasing that dose until the desired effect is achieved.

The term "co-administer" refers to the administration of two active agents in the blood of an individual or in a sample to be tested. Active agents that are co-administered can be concurrently or sequentially delivered.

Antigen Binding Constructs (Including Antibodies and Binding Fragments)

Antigen binding constructs that bind to the target are described herein. An antigen binding construct is a molecule that includes one or more portions of an immunoglobulin or immunoglobulin-related molecule that specifically binds to, or is immunologically reactive with the target molecule.

Anti-CD3 antibody fragments, such as minibodies and cys-diabody fragments are provided in some embodiments. The antibody fragments can be used, for example, for imaging and for treating a variety of disorders involving the immune system. Schematic representations of exemplary minibody and cys-diabody fragments are illustrated in FIGS. 1A-1D.

In some embodiments, an antigen binding construct includes a heavy chain CDR1 (HCDR1) of the HCDR 1 in SEQ ID NOs: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a heavy chain CDR2 (HCDR2) of the HCDR2 in SEQ ID NOs: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a heavy chain CDR3 (HCDR3) of the HCDR3 in SEQ ID NOs: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a light chain CDR1 (LCDR1) of the LCDR1 in SEQ ID NOs: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a light chain CDR2 (LCDR2) of the LCDR2 in SEQ ID NOs: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; and/or a light chain CDR3 (LCDR3) of the LCDR3 in SEQ ID NOs: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67. These constructs can be in any of the forms provided herein, including diabodies, cys-diabodies, minibodies, scFv, etc. In some embodiments, the antigen binding construct includes 6, 5, 4, 3, 2, or 1, the above CDRs (some embodiments of the CDRs are indicated in FIGS. 2A and 2B). In some embodiments, the antigen binding construct includes HCDR3. In some embodiments, the antigen binding construct binds specifically to the target molecule. In some embodiments, the antigen binding construct competes for binding with one or more of the antibodies having the herein provided CDRs. In some embodiments, the antigen binding construct includes at least the 3 heavy chain CDRs noted herein. In some embodiments, the antigen binding construct includes heavy chain CDR3. In some embodiments, the antigen binding construct further includes any one of the heavy chain CDR2 sequences provided herein.

In some embodiments, the antigen binding construct is human or humanized. In some embodiments, the antigen binding construct includes at least one human framework region, or a framework region with at least about 80% sequence identity, for example at least about 80%, 85%, 90%, 93%, 95%, 97%, or 99% identity to a human framework region. In some embodiments the antigen binding construct includes a heavy chain FR1 (HFR1) of the HFR1 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a heavy chain FR2 (HFR2) of the HFR2 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a heavy chain FR3 (HFR3) of the HFR3 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a heavy chain FR4 (HFR4) of the HFR4 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a light chain FR1 (LFR1) of the LFR1 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a light chain FR2 (LFR2) of the LFR2 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; a light chain FR3 (LFR3) of the LFR3 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67; and a light chain FR4 (LFR4) of the LFR4 in SEQ ID NO: 4, 6, 7, 9, 11, 15, 25, 35, 45, 47, 57, 59, 13, 17, 19, 21, 23, 27, 29, 31, 33, 37, 39, 41, 43, 49, 51, 53, 55, 61, 63, 65, or 67. In some embodiments, the antigen binding construct includes 8, 7, 6, 5, 4, 3, 2, or 1 of the listed FRs.

In some embodiments, the antigen binding construct includes a detectable marker. In some embodiments, the antigen binding construct includes a therapeutic agent.

In some embodiments, the antigen binding construct is bivalent. Bivalent antigen binding construct can include at least a first antigen binding domain, for example a first scFv, and at least a second antigen binding domain, for example a second scFv. In some embodiments, a bivalent antigen binding construct is a multimer that includes at least two monomers, for example at least 2, 3, 4, 5, 6, 7, or 8 monomers, each of which has an antigen binding domain. In some embodiments, the antigen binding construct is a minibody. In some embodiments, the antigen binding construct is a diabody, including, for example, a cys-diabody. The minibody and/or the cys-diabody can include any of the CDR and heavy chain variable region and/or light chain variable region embodiments provided herein (for example, the CDR sequences provided in FIGS. 2A and 2B. In some embodiments, the antigen binding construct is a monovalent scFv. In some embodiments, a monovalent scFv is provided that includes the HCDR1 in the HCDR1 of FIG. 2A, the HCDR2 in the HCDR2 of FIG. 2A, the HCDR3 in the HCDR3 of FIG. 2A, the LCDR1 in the LCDR1 of FIG. 2B, the LCDR2 in the LCDR2 of FIG. 2B, and the LCDR31 in the LCDR3 of FIG. 2B. In some embodiments, the monovalent scFv includes the heavy chain variable region of the heavy chain variable region in FIG. 2A. In some embodiments, the monovalent scFv includes the light chain variable region of the light chain variable region in FIG. 2B. In some embodiments, the monovalent scFv includes the heavy chain variable region of the heavy chain variable region in FIG. 2A and the light chain variable region of the light chain variable region in FIG. 2B. In some embodiments, the antigen binding construct is arranged as outlined in the table below:

TABLE 0.1

| 1<br>Name | 2<br>Leader | 3<br>Region 1 | 4<br>Linker | 5<br>Region 2 | 6<br>Remainder |
|---|---|---|---|---|---|
| chOKT3 Mb_C105S | Leader | muV$_L$ SEQ ID NO: 70 | 18aa Linker | muV$_H$ SEQ ID NO: 76 | IgG1 hinge/linker-CH3 domain |
| huMb_Version A_C105S | Leader | huV$_L$_vA SEQ ID NO: 72 | 18aa Linker | huV$_H$_vA_C105S SEQ ID NO: 82 | IgG1 hinge/linker-CH3 domain |
| huMb Version B_C105S | Leader | huV$_L$_vB SEQ ID NO: 74 | 18aa Linker | huV$_H$_vB_C105S SEQ ID NO: 86 | IgG1 hinge/linker-CH3 domain |
| chOKT3 Mb | Leader | muV$_L$ SEQ ID NO : 70 | 18aa Linker | muV$_H$ SEQ ID NO: 76 | IgG1 hinge/linker-CH3 domain |

TABLE 0.1-continued

| 1 Name | 2 Leader | 3 Region 1 | 4 Linker | 5 Region 2 | 6 Remainder |
|---|---|---|---|---|---|
| huMb_Version A | Leader | huV$_L$_vA SEQ ID NO: 72 | 18aa Linker | huV$_H$_vA SEQ ID NO: 80 | IgG1 hinge/linker-CH3 domain |
| huMb Version B | Leader | huV$_L$_vB SEQ ID NO: 74 | 18aa Linker | huV$_H$_vB SEQ ID NO: 84 | IgG1 hinge/linker-CH3 domain |

Thus, in some embodiments, the construct can include any of the constructs on a single row in Table 0.1. In some embodiments, the minibody constructs can include any combination in Table 0.1. In some embodiments, for example, the first item in the first row, column 2 can be combined with the first row, column 3 to the first row column 4, to the first row column 5, to the first row, column 6. In some embodiments, column 3 and column 6 can be swapped with one another. In some embodiments, for example, the first item in the first row, column 2 can be combined with the first row, column 3 to the second row column 4, to the second row column 5, to the second row, column 6. Thus, the table represents all possible combinations, both within a single row and across various rows (and with columns swapped).

In some embodiments, the antigen binding construct is bispecific. Bispecific constructs can include at least a first binding domain, for example an scFv that binds specifically to a first epitope, and at least a second binding domain, for example an scFv that binds specifically to a second epitope. Thus, bispecific antigen binding constructs can bind to two epitopes. In some embodiments, the first epitope and the second epitope are part of the same antigen, and the bispecific antigen binding construct can thus bind to two epitopes of the same antigen. In some embodiments, the first epitope is part of a first antigen, and the second epitope is part of a second antigen, and the bispecific antigen binding construct can thus bind to two different antigens. In some embodiments, the antigen binding construct binds to two epitopes simultaneously. In some embodiments, the two epitopes can be either on the same cell or on separate cells. In some embodiments, the two epitopes can be on the same antigen.

In some embodiments, the antigen binding construct has a heavy chain variable region of the heavy chain variable region in SEQ ID NO 6 or 86. In some embodiments, the antigen binding construct has a heavy chain variable region that includes a sequence with at least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 6 or 86. In some embodiments, the antigen binding construct has a light chain variable region that includes SEQ ID NO: 3. In some embodiments, the antigen binding construct has a light chain variable region that includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 3. In some embodiments, the antigen binding construct is a human antigen binding construct and has a heavy chain variable region, a light chain variable region, or a heavy and light chain that is at least as identical as at least the heavy and/or light chain variable sequences noted above.

Some embodiments provided herein include an antigen binding construct that competes for binding to the target molecule with one or more antigen binding constructs provided herein. In some embodiments, the competing antigen binding construct binds to the same epitope on the target molecule as the reference antigen binding construct. In some embodiments, the reference antigen binding construct binds to a first epitope of the target molecule, and the competing antigen binding construct binds to a second epitope of the target molecule, but interferes with binding of the reference antigen binding construct to the target molecule, for example by sterically blocking binding of the reference antigen binding construct, or by inducing a conformational change in the target molecule. In some embodiments, the first epitope overlaps with the second epitope.

In some embodiments, the minibody and cys-diabody formats have advantageous pharmacokinetic characteristics for diagnostic imaging and certain therapeutic applications while maintaining the high binding affinity and specificity of a parental antibody. Compared to imaging with the full-length parental antibody, the pharmacokinetics are more desirable for these fragments in that they are able to target the antigen and then rapidly clear the system for rapid high-contrast imaging. In some embodiments, the shorter serum half-lives for the minibody and the cys-diabody allow for optimal imaging ranging over a long period of time from approximately 4-72 hours post injection for the minibody and 2-48 hours post-injection for the cys-diabody. This can allow for same day imaging, which can provide a significant advantage in the clinic with respect to patient care management.

In addition, the cys-diabody antibody format features the C-terminus cysteine tail. These two sulfhydryl groups (following mild reduction) provide a strategy for site-specific conjugation of functional moieties such as radiolabels that need not interfere with the cys-diabody's binding activity.

In some embodiments, the CD3 antibody fragments can comprise one, two, or three of the variable light region CDRs and/or one, two, or three of the variable heavy region CDRs from an anti-CD3 antibody. For example, an antibody fragment may contain one, two or three of the variable region CDRs and/or one, two, or three of the variable heavy region CDRs of muOKT3. In some embodiments an antibody fragment may contain one or more CDRs from the variable heavy or light regions of ABC1. In some embodiments, an antibody fragment comprises one or more CDR regions from the variable heavy or light regions of a humanized anti-CD3 antibody, such as the humanized OKT3 described herein. The sequences of several exemplary antibody fragments are provided herein.

Diabodies that Bind to the Target Molecule

In some embodiments, the antigen binding construct can be a diabody. The diabody can include a first polypeptide chain which includes a heavy (V$_H$) chain variable domain connected to a light chain variable domain (V$_L$) on the first polypeptide chain. In some embodiments, the light and heavy variable chain domains can be connected by a linker. The linker can be of the appropriate length to reduce the likelihood of pairing between the two domains on the first polypeptide chain and a second polypeptide chain comprising a light chain variable domain ($V_L$) linked to a heavy chain variable domain $V_H$ on the second polypeptide chain connected by a linker that is too short to allow significant pairing between the two domains on the second polypeptide chain.

In some embodiments, the appropriate length of the linker encourages chain pairing between the complementary domains of the first and the second polypeptide chains and can promote the assembly of a dimeric molecule with two functional antigen binding sites. Thus, in some embodiments, the diabody is bivalent. In some embodiments, the diabody can be a cysteine linked diabody (a cys-Db). A schematic of a cys-Db binding to two antigen sites is illustrated in FIG. 1B.

In some embodiments, the linker can be a peptide. In some embodiments, the linker can be any suitable length that promotes such assembly, for example, between 1 and 20 amino acids, such as 5 and 10 amino acids in length. As described further herein, some cys-diabodies can include a peptide linker that is 5 to 8 amino acids in length. In some embodiments, the linker need not be made from, or exclusively from amino acids, and can include, for example, modified amino acids (see, for example, Increased Resistance of Peptides to Serum Proteases by Modification of their Amino Groups, Rossella Galati, Alessandra Verdina, Giuliana Falasca, and Alberto Chersi, (2003) Z. Naturforsch, 58c, 558-561). In some embodiments, the linker can be 1, 2, 3, 4, 5, 6, 7, 8, 9, 10, 11, 12, 13, 14, 15, 16, 17, 18, 19, or 20 amino acids in length. In some embodiments, the linker can be from 2 to 30 angstroms in length, for example 2.5 to 27 angstroms.

In some embodiments, the antigen binding construct includes a humanized cys-diabody. The humanized cys-diabody can include a single-chain variable fragment (scFv) that includes a variable heavy ($V_H$) domain linked to a variable light ($V_L$) domain, and a C-terminal Cysteine. In some embodiments, the humanized cys-diabody is a homodimer. In some embodiments, the humanized diabody is a heterodimer. In some embodiments, individual monomers are provided that each have a cysteine terminal residue.

In some embodiments, the scFv of the humanized cys-diabody has a $V_H$-$V_L$ orientation or a $V_L$-$V_H$ orientation. As used herein, a $V_H$-$V_L$ (which may also be referred to herein as "$V_H V_L$") orientation means that the variable heavy domain ($V_H$) of the scFv is upstream from the variable light domain ($V_L$) and a $V_L V_H$ orientation means that the $V_L$ domain of the scFv is upstream from the $V_H$ domain. As used herein, "upstream" means toward the N-terminus of an amino acid or toward the 5' end of a nucleotide sequence.

The antibody variable regions can be linked together by a linker as described herein. In some embodiments, the linker is a GlySer linker as described herein. In some embodiments, the linker can be as shown below:

GSTSGGGSGGGSGGGGS - SEQ ID NO: 111

GSTSGSGKPGSSEGSTKG - SEQ ID NO: 112

GGGGSGGGGSGGGGS - SEQ ID NO: 113

In some embodiments, the cys-diabody includes a detectable marker.

In some embodiments, the cys-diabody includes a pair of monomers. Each monomer can include a polypeptide. In some embodiments, the polypeptides of the monomers are identical (for example, cys-diabody can be a homodimer). In some embodiments, the polypeptides of the monomers are different (for example, the cys-diabody can be a heterodimer).

In some embodiments, the polypeptide of the monomer includes SEQ ID NO: 13 (See FIG. 6). In some embodiments, the polypeptide of the monomer includes a sequence with least about 80% identity, for example at least about 80%, 85%, 86%, 87%, 88%, 89%, 90%, 91%, 92%, 93%, 94%, 95%, 96%, 97%, 98%, or 99% identity to SEQ ID NO: 13 (cys-diabody ($V_L$-5-$V_H$)).

In some embodiments, the polypeptide of the monomer includes SEQ ID NO: 17 (See FIG. 10). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, or 99% identity to SEQ ID NO: 17 (cys-diabody ($V_L$-5-$V_H$), murine).

In some embodiments, the polypeptide of the monomer includes SEQ ID NO: 19 ($V_H$-5-$V_L$)] (See FIG. 11). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 19.

In some embodiments, the polypeptide of the monomer includes SEQ ID NO: 21 (murine OKT3 cys-diabody ($V_L$-8-$V_H$)] (See FIG. 12). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 21.

In some embodiments, the polypeptide of the monomer includes SEQ ID NO: 23 (murine OKT3 cys-diabody ($V_H$-8-$V_L$)] (See FIG. 13). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 23.

In some embodiments, the polypeptide of the monomer includes SEQ ID NO: 27 (ABC1 ("antigen binding construct1") cys-diabody ($V_L$-5-$V_H$)] (See FIG. 15). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 27.

In some embodiments, the polypeptide of the monomer includes SEQ ID NO: 29 (ABC1 cys-diabody ($V_H$-5-$V_L$)] (See FIG. 16). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 29.

In some embodiments, the polypeptide of the monomer includes SEQ ID NO: 31 (ABC1 cys-diabody ($V_L$-8-$V_H$)] (See FIG. 17). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 31.

In some embodiments, the polypeptide of the monomer includes SEQ ID NO: 33 (ABC1 cys-diabody ($V_H$-8-$V_L$)] (See FIG. 18). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 33.

In some embodiments, the polypeptide of the monomer includes SEQ ID NO: 37 (humanized OKT3 cys-diabody ($V_L$-5-$V_H$)] (See FIG. 20). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 37.

In some embodiments, the polypeptide of the monomer includes SEQ ID NO: 39 (humanized OKT3 cys-diabody ($V_H$-5-$V_L$)] (See FIG. 21). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 39.

In some embodiments, the polypeptide of the monomer includes SEQ ID NO: 41 (humanized OKT3 cys-diabody ($V_L$-8-$V_H$)] (See FIG. 22). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 41.

In some embodiments, the polypeptide of the monomer includes SEQ ID NO: 43 (humanized OKT3 cys-diabody ($V_H$-8-$V_L$)] (See FIG. 23). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 43.

In some embodiments, the polypeptide of the monomer includes SEQ ID NO: 49 (ABC2 cys-diabody ($V_L$-5-$V_H$)] (See FIG. 26). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 49.

In some embodiments, the polypeptide of the monomer includes SEQ ID NO: 51 (ABC2 cys-diabody ($V_H$-5-$V_L$)] (See FIG. 27). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 51.

In some embodiments, the polypeptide of the monomer includes SEQ ID NO: 53 (ABC2 cys-diabody ($V_L$-8-$V_H$)] (See FIG. 28). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 53.

In some embodiments, the polypeptide of the monomer includes SEQ ID NO: 55 (ABC2 cys-diabody ($V_H$-8-$V_L$)] (See FIG. 29). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 55.

In some embodiments, the polypeptide of the monomer includes SEQ ID NO: 61 (ABC3 cys-diabody ($V_L$-5-$V_H$)] (See FIG. 32). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 61.

In some embodiments, the polypeptide of the monomer includes SEQ ID NO: 63 (ABC3 cys-diabody ($V_H$-5-$V_L$)] (See FIG. 33). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 63.

In some embodiments, the polypeptide of the monomer includes SEQ ID NO: 65 (ABC3 cys-diabody ($V_L$-8-$V_H$)] (See FIG. 34). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 65.

In some embodiments, the polypeptide of the monomer includes SEQ ID NO: 67 (ABC3 cys-diabody ($V_H$-8-$V_L$)] (See FIG. 35). In some embodiments, the polypeptide of the monomer includes a sequence with least about 80% identity, for example at least about 80%, 85%, 86%, 87%, 88%, 89%, 90%, 91%, 92%, 93, 94, 95%, 96%, 97%, 98%, 99%, or 100% identity to SEQ ID NO: 67.

In some embodiments, the cysteines are cross-linked with one another. In some embodiments, the cysteines are reduced, and thus, these tail forming cysteines do not form a disulfide bond with one another. In some embodiments, one or more of the "tail forming" cysteines form a covalent bond with one or more detectable marker, such as a fluorescent probe.

As will be appreciated by those of skill in the art, while the present disclosure generally references "cys-diabodies" alternative arrangements can be employed to achieve the same or similar ends. In some embodiments, any covalently modifiable moiety can be employed in place of one or more of the cysteines. For example, this can include a GlySer linker, a GlyLeu linker, and/or an insert cysteine after a short tag. In some embodiments, the connection can be established via a coiled coil or a leucine zipper. In some embodiments, the "tail" itself can include functional groups on its end so that it can selectively bind to a desired residue and/or location at the ends of each of the polypetides, in place of the disulfide bond itself. In some embodiments, rather than the tail providing space between the two polypeptide chains, the covalently modifiable moieties can be attached directly to the end of the heavy or light chain polypeptide, but the two covalently modifiable moieties can be connected by a linker.

In some embodiments, a chimeric cys-diabody that binds to the target molecule is provided. In some embodiments, the chimeric cys-diabody includes a monomer in the VL-VH format, and includes the sequence of SEQ ID NO: 13, 17, 21, 27, 31, 37, 41, 49, 53, 61, or 65, or a sequence having at least about 80% identity thereto, for example at least about 80%, 85%, 90%, 95%, 96%, 97%, 98%, or 99%% identity thereto. In some embodiments, the chimeric cys-diabody includes a monomer in the $V_H$-$V_L$ format, and includes the sequence of SEQ ID NO: 19, 23, 29, 33, 39, 43, 51, 55, 63, or 67, or a sequence having at least about 80% identity thereto, for example at least about 80%, 85%, 90%, 95%, 96%, 97%, 98%, or 99%% identity thereto.

In some embodiments, the cys-diabody includes one or more of the CDRs provided in the CDRs in FIGS. 2A, 2B, and/or 36A-36I. In some embodiments, the cys-diabody includes the sequence YYDDHY(C/S)LDY (SEQ ID NO: 69) as HCDR3, while the remaining heavy, light, or heavy and light chain variable regions can be at least about 80% identical to the heavy, light, or light and heavy variable regions within SEQ ID NO: 3 and SEQ ID NO: 6, for example at least about 80%, 85%, 86%, 87%, 88%, 89%, 90%, 91%, 92%, 93, 94, 95%, 96%, 97%, 98%, 99%, or 100% identity to SEQ ID NO: 6. In some embodiments, the cys-diabody includes the sequence YYDDHY(C/S)LDY (SEQ ID NO: 69) as HCDR3, while the remaining 1, 2, 3, 4, 5, or 6 CDRs can include one or more of the CDRs of the CDRs shown in FIGS. 2A, 2B, and/or 36A-36I. In some embodiments, the remaining CDRs can be different from those shown in FIGS. 2A, 2B, and/or 36A-36I.

In some embodiments, any of the constructs provided herein (including those arrangements noted as cys-diabody embodiments, can be provided as a scFv embodiment. In such embodiments, the construct can still include the cysteine on the tail, but simply not be cross-linked. In other embodiments, the construct need not have the cysteine in a tail or the tail at all.

Linker and/or Tail Options

In some embodiments, for individual antigen binding constructs, the heavy and light chain variable domains can associate in different ways. For this reason, the use of different linker lengths allows for conformational flexibility and range-of-motion to ensure formation of the disulfide bonds.

In some embodiments, the two linker lengths can be somewhere between (and including) about 1 to 50 amino acids, for example, 2 to 15, 2 to 14, 3 to 13, 4 to 10, or 5 amino acids to 8 amino acids. In some embodiments, each linker within a pair for a diabody can be the same length. In some embodiments, each linker within the pair can be a different length. In some embodiments, any combination of linker length pairs can be used, as long as they allow and/or promote the desired combinations. In some embodiments, a modified amino acid can be used.

FIGS. 6, 10-13, 15-18, 20-23, 26-29, 32-35 provide Cys-Db variants, $V_H5V_L$, $V_H8$ $V_L$, $V_L5V_H$, and VL8VH. Producing and testing the expression and binding of all four variants allows for identification of a desired format for protein production for each new Cys-Db. Evaluating the set of variants can help to make certain that a high-quality, stable protein is produced where the disulfide bridge is available. Therefore, engineering a Cys-Db can involve using two distinct linker lengths, not one—as in the minibody, as well as both orientations of the variable regions, $V_H/V_L$ and $V_L/V_H$.

In some embodiments, the linker is a GlySer linker. The GlySer linker can be a polypeptide that is rich in Gly and/or Ser residues. In some embodiments, at least about 40% of the amino acid residues of the GlySer linker are Gly, Ser, or a combination of Gly and Ser, for example at least about 40%, 50%, 60%, 70%, 80%, or 90%. In some embodiments, the GlySer linker is at least about 2 amino acids long, for example at least about 3, 4, 5, 6, 7, 8, 9, 10, 11, 12, 13, 14, 15, 16, 17, 18, 19, 20, 25, 30, 35, or 40 amino acids long. In some embodiments, the linker includes at least one of SEQ ID NO: 11, 112, and 113.

In some embodiments, a cysteine is added at the C-terminus of the diabody. This cysteine can allow the diabody complex to form covalent cysteine bonds and provides the option for available sulfur residues for site-specific conjugation of functional moieties such as radiolabels. In some embodiments, a terminal end of the antibody itself is altered so as to contain a cysteine. In some embodiments, a tail sequence, for example (Gly-Gly-Cys) is added at the C-terminus. In some embodiments, the cysteine tail sequence allows two monomers of a cys-diabody to form disulfide bonds with each other. In some embodiments, the cysteine tail sequence allows a cys-diabody to form disulfide linkages with a detectable moiety such as a detectable marker and/or therapeutic agent. The sulfhydryl groups of the cysteine tail can undergo mild reduction prior to site-specific conjugation of a desired functional moiety, for example a detectable marker and/or therapeutic agent. In some embodiments, the tail is at least about 1 amino acid long, for example at least about 1, 2, 3, 4, 5, 6, 7, 8, 9, 10, 11, 12, 13, 14, 15, 16, 17, 18, 19, 20, 25, 30, 35, or 40 amino acids long. In some embodiments, the tail includes at least one of GGCGGC (SEQ ID NO: 115), GGCGC (SEQ ID NO: 116), and GGCC (SEQ ID NO: 117). In some embodiments, the tail is 3 to 8 amino acids in length. In some embodiments, the tail can and/or include a coiled coil and/or a leucine zipper. As noted above, in some embodiments, the cysteine is located at the c-terminus; however, this does not require that the cysteine be located as the last c-terminal amino acid. Instead, this denotes that the cysteine can be part of any of the residues that are located in the c-terminus of the protein.

In some embodiments, the linking option between the two c-terminuses can be achieved by a cysteine, for direct and/or indirect, cross-linking.

Minibodies that Bind to the Target Molecule

A "minibody" as described herein includes a homodimer, wherein each monomer is a single-chain variable fragment (scFv) linked to a human IgG1 $C_H3$ domain by a linker, such as a hinge sequence. In some embodiments, the hinge sequence is a human IgG1 hinge sequence.

In some embodiments, the hinge sequence is an artificial hinge sequence. In some embodiments, the hinge sequence can be an IgG hinge from any one or more of the four classes. The artificial hinge sequence may include a portion of a human IgG1 hinge and a GlySer linker sequence.

In some embodiments, the artificial hinge sequence includes approximately the first 14 or 15 residues of the human IgG1 hinge followed by a linker sequence. In some embodiments, the linker can be any of those provided herein. In some embodiments, the linker can be a GlySer linker sequence that is 6, 7, 8, 9 or 10 amino acids in length. In some embodiments, the artificial hinge sequence includes approximately the first 15 residues of the IgG1 hinge followed by a GlySer linker sequence that is about 10 amino acids in length. In some embodiments, association between the $C_H3$ domains causes the minibody to exist as a stable dimer.

In some embodiments, the minibody scFv sequence can include CDR and/or FR, and or variable region sequences that are similar and/or the same to a diabody sequence described herein (for Example, as found in FIGS. 2A and/or 2B). In some embodiments, the minibody scFv has a sequence (CDR, CDRs, full set of 6 CDRS, heavy chain variable region, light chain variable region, heavy and light chain variable regions, etc) that is at identical to a scFv of a cys-diabody described herein.

In some embodiments, the minibody has a sequence that is at least about 80% identical to a sequence in SEQ ID NO: 7, 9, 11, 15, 25, 35, 45, 47, 57, 59, 84, or 86 for example at least about 80%, 85%, 86%, 87%, 88%, 89%, 90%, 91%, 92%, 93, 94, 95%, 96%, 97%, 98%, or 99% identity.

In some embodiments, the minibody has a variable chain region (heavy, light or heavy and light chain variable region) that is at least about 80% identical to a sequence in SEQ ID NO: 7, 9, 11, 15, 25, 35, 45, 47, 57, 59, 84, or 86 for example at least about 80%, 85%, 86%, 87%, 88%, 89%, 90%, 91%, 92%, 93, 94, 95%, 96%, 97%, 98%, or 99% identity.

The scFv can have a $V_HV_L$ or a $V_LV_H$ orientation. In some embodiments, the $V_H$ and $V_L$ are linked to each other by an amino acid linker sequence. The amino acid linker can be a linker as described herein. In some embodiments, the linker is Gly-Ser-rich and approximately 15-20 amino acids in length. In another embodiment, the linker is Gly-Ser rich and is 18 amino acids in length. In some embodiments, the linker length varies between (and including) about 1 to 50 amino acids, for example, 2 to 30, 3 to 20, 4 to 15, or 5 amino acids to 8 amino acids. In some embodiments, the minibody scFv has a sequence that is at least about 80% identical to a scFv of a cys-diabody described herein, for example at least about 80%, 85%, 86%, 87%, 88%, 89%, 90%, 91%, 92%, 93, 94, 95%, 96%, 97%, 98%, or 99% identity. The scFv can have a $V_H V_L$ or a $V_L V_H$ orientation.

In some embodiments, each monomer of the minibody includes the following elements, from N-terminus to C-terminus: (a) an scFv sequence that includes a $V_H$ domain linked to a $V_L$ domain and that binds to the target molecule, (b) a hinge-extension domain comprising a human IgG1 hinge region, and (c) a human IgG $C_H 3$ sequence. In some embodiments, each monomer of the minibody includes an IgG2, an IgG3, or an IgG4 $C_H 3$. In some embodiments, the minibody is encoded by a nucleic acid can be expressed by a cell, a cell line or other suitable expression system as described herein. Thus, a signal sequence can be fused to the N-terminus of the scFv to enable secretion of the minibody when expressed in the cell or cell line.

In some embodiments, a chimeric minibody that binds to the target molecule is provided. In some embodiments, the chimeric minibody includes a monomer in the $V_L$-$V_H$ format, and includes the sequence of SEQ ID NO: 7, 9, 11, 45, or 57, or a sequence having at least about 80% identity thereto, for example at least about 80%, 85%, 90%, 95%, 96%, 97%, 98%, or 99%% identity thereto. In some embodiments, the chimeric minibody includes a monomer in the $V_H$-$V_L$ format, and includes the sequence of SEQ ID NO: 15, 25, 35, 47, or 59, or a sequence having at least about 80% identity thereto, for example at least about 80%, 85%, 90%, 95%, 96%, 97%, 98%, or 99%% identity thereto. In some embodiments, the minibody comprises one or more of the CDRs outlined in FIG. 2A, 2B, or 36A-36I. In some embodiments, the minibody comprises one or more of the variable regions in FIG. 2A, 2B, or 36A-36I.

In some embodiments, the minibody includes the heavy chain variable region as outlined in FIG. 2B. In some embodiments, the minibody includes the light chain variable region as outlined in FIG. 2A.

In some embodiments, the minibody includes one or more of the CDRs provided in the CDRs in. FIG. 2A, 2B, or 36A-36I. In some embodiments, the minibody includes the sequence YYDDHY(C/S)LDY (SEQ ID NO: 69) as HCDR3, while the remaining heavy, light, or heavy and light chain variable regions can be at least about 80% identical to the heavy, light, or light and heavy variable regions within SEQ ID NO: 3 and SEQ ID NO: 6 (or SEQ ID NO: 86), for example at least about 80%, 85%, 86%, 87%, 88%, 89%, 90%, 91%, 92%, 93, 94, 95%, 96%, 97%, 98%, 99%, or 100% identity to SEQ ID NO: 6 (or SEQ ID NO: 86). In some embodiments, the minibody includes the sequence YYDDHY(C/S)LDY (SEQ ID NO: 69) as HCDR3, while the remaining 1, 2, 3, 4, 5, or 6 CDRs can include one or more of the CDRs of the CDRs shown in FIGS. 2A, 2B, and/or 36A-36I. In some embodiments, the remaining CDRs can be different from those shown in FIGS. 2A, 2B, and/or 36A-36I.

In some embodiments, the minibody and/or cys-diabody and/or antibody and/or scFv (for example, the antigen binding construct) includes one or more of the residues in the humanized sequence shown in FIGS. 2A and/or 2B that is denoted with an asterisk. In some embodiments, while one or more of the residues marked with an asterisk in FIG. 2A or 2B is present; the remaining sequence can be varied. For example, the sequence can have 80, 81, 82, 83, 84, 85, 86, 87, 88, 89, 90, 91, 92, 93, 94, 95, 96, 97, 98, 99 percent or greater identity to the remaining sections of the sequence. In some embodiments, the human and/or humanized antigen binding construct will include one or more of the asterisked residues in FIGS. 2A and/or 2B, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75. In some embodiments, the antigen binding construct includes one or more of the highlighted residues in FIGS. 2A and/or 2B. In some embodiments, the antigen binding construct includes one or more of the highlighted residues in FIGS. 2A and/or 2B as well as the boxed CDR sections, whereas other residues are allowed to vary.

Alternatively, and/or in addition to, the antigen binding construct can include one or more of the asterisked residues in FIGS. 2A and/or 2B, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75. In some embodiments, the CDR residues are maintained and the residues with the asterisk are maintained, but one or more of the other residues are allowed to vary. In some embodiments, the light chain variable region includes the 3 CDRs from SEQ ID NO: 3 and the tyrosine shaded in FIG. 2A. In some embodiments, the heavy chain variable region includes the 3 CDRs from SEQ ID NO: 6 and/or 86 and the threonine shaded in FIG. 2B. In some embodiments, the light chain variable region includes the 3 CDRs from SEQ ID NO: 3 and the tyrosine shaded in FIG. 2A and the heavy chain variable region includes the 3 CDRs from SEQ ID NO: 6 and/or 86 and the threonine shaded in FIG. 2B.

Nucleic Acids

In some embodiments, the polypeptides of the antigen binding constructs can be encoded by nucleic acids and expressed in vivo or in vitro, or these peptide can be synthesized chemically. Thus, in some embodiments, a nucleic acid encoding an antigen binding construct is provided. In some embodiments, the nucleic acid encodes one part or monomer of a cys-diabody or minibody. In some embodiments, the nucleic acid encodes two or more monomers, for example, at least 2 monomers. Nucleic acids encoding multiple monomers can include nucleic acid cleavage sites between at least two monomers, can encode transcription or translation start site between two or more monomers, and/or can encode proteolytic target sites between two or more monomers.

In some embodiments, an expression vector contains a nucleic acid encoding an antigen binding construct as disclosed herein. In some embodiments, the expression vector includes pcDNA3.1™/myc-His (−) Version A vector for mammalian expression (Invitrogen, Inc.) or a variant thereof. The pcDNA3.1 expression vector features a CMV promoter for mammalian expression and both mammalian (Neomycin) and bacterial (Ampicillin) selection markers. In some embodiments, the expression vector includes a plasmid. In some embodiments, the vector includes a viral vector, for example a retroviral or adenoviral vector. In embodiments, the vector includes a cosmid, YAC, or BAC.

In some embodiments, the nucleotide sequence encoding at least one of the minibody monomers comprises at least one of SEQ ID NO: 8, 10, 12, 16, 26, 36, 46, 48, 58, or 60, or a sequence having at least about 80% identity, for example about 80%, 85%, 86%, 87%, 88%, 89%, 90%, 91%, 92%, 93, 94, 95%, 96%, 97%, 98%, 99%, or greater identity thereto. In some embodiments, the nucleotide sequence encoding at least one of the minibody monomers comprises at least one of minibody sequences within FIGS. 36A-36I, or a sequence having at least about 80% identity, for example about 80%, 85%, 86%, 87%, 88%, 89%, 90%, 91%, 92%, 93, 94, 95%, 96%, 97%, 98%, 99%, or greater identity thereto.

In some embodiments, the nucleotide sequence encoding at least one of the cys-diabody monomers includes SEQ ID NO: 14, 18, 20, 22, 24, 28, 30, 32, 34, 38, 40, 42, 44, 50, 52, 54, 56, 62, 64, 66, or 68, or a sequence having at least about 80% identity, for example about 80%, 85%, 86%, 87%, 88%, 89%, 90%, 91%, 92%, 93, 94, 95%, 96%, 97%, 98%, 99% or greater identity thereto. In some embodiments, the nucleotide sequence encoding at least one of the cys-diabodies comprises at least one of cys-diabody sequences within FIGS. 36A-36I, or a sequence having at least about 80% identity, for example about 80%, 85%, 86%, 87%, 88%, 89%, 90%, 91%, 92%, 93, 94, 95%, 96%, 97%, 98%, 99%, or greater identity thereto.

In some embodiments, the nucleotide sequence encoding at least one of the scFv includes SEQ ID NO: 14, 18, 20, 22, 24, 28, 30, 32, 34, 38, 40, 42, 44, 50, 52, 54, 56, 62, 64, 66, or 68, or a sequence having at least about 80% identity, for example about 80%, 85%, 86%, 87%, 88%, 89%, 90%, 91%, 92%, 93, 94, 95%, 96%, 97%, 98%, 99% or greater identity thereto. In some embodiments, the nucleotide sequence encoding at least one of the scFv comprises at least one of scFv sequences within FIGS. 36A-36I, or a sequence having at least about 80% identity, for example about 80%, 85%, 86%, 87%, 88%, 89%, 90%, 91%, 92%, 93, 94, 95%, 96%, 97%, 98%, 99%, or greater identity thereto.

Cell Lines

In some embodiments, a cell line is provided that expresses at least one of the antigen binding constructs described herein. In some embodiments, a mammalian cell line (for example, CHO-K1 cell line) is an expression system to produce the minibodies, cys-diabodies, scFv, or other antibodies as described herein. In some embodiments, the minibodies, cys-diabodies, scFv, and other antibodies or antibody fragments described herein are non-glycosylated, and a mammalian expression system is not required, as such post-translational modifications are not needed. Thus, in some embodiments, one or more of a wide variety of mammalian or non-mammalian expression systems are used to produce the antigen binding constructs disclosed herein (for example, anti-CD3 minibodies and cys-diabodies) including, but not limited to mammalian expression systems (for example, CHO-K1 cells), bacterial expression systems (for example, *E. Coli, B. subtilis*) yeast expression systems (for example, *Pichia, S. cerevisiae*) or any other known expression system. Other systems can include insect cells and/or plant cells.

Antigen Binding Construct Modifications

In some embodiments, the antigen binding construct includes at least one modification. Exemplary modifications include, but are not limited to, antigen binding constructs that have been modified by glycosylation, acetylation, pegylation, phosphorylation, amidation, derivatization by known protecting/blocking groups, proteolytic cleavage, and linkage to a cellular ligand or other protein. Any of numerous chemical modifications may be carried out by known techniques, including, but not limited to specific chemical cleavage, acetylation, gormylation and metabolic synthesis of tunicamycin. In some embodiments, the derivative can contain one or more non-natural amino acids.

In some embodiments, the antigen binding construct is conjugated to another substance to form an anti-target conjugate. The conjugates described herein can be prepared by known methods of linking antigen binding constructs with lipids, carbohydrates, protein or other atoms and molecules. In some embodiments, the conjugate is formed by site-specific conjugation using a suitable linkage or bond. Site-specific conjugation is more likely to preserve the binding activity of an antigen binding construct. The substance may be conjugated or attached at the hinge region of a reduced antigen binding construct via disulfide bond formation. For example, introduction of cysteine residues at the C-terminus of a scFv fragment, such as those that can be introduced in the cys-diabodies described herein, allows site-specific thiol-reactive coupling at a site away from the antigen binding site to a wide variety of agents. Other linkages or bonds used to form the conjugate can include, but are not limited to, a covalent bond, a non-covalent bond, a sulfide linkage, a hydrazone linkage, a hydrazine linkage, an ester linkage, an amido linkage, and amino linkage, an imino linkage, a thiosemicabazone linkage, a semicarbazone linkage, an oxime linkage and a carbon-carbon linkage. In some embodiments, no cysteine or other linking aspect or tail, need be included in the antigen binding construct.

Detectable Markers

In some embodiments, a modified antigen binding construct is conjugated to a detectable marker. As used herein, a "detectable marker" includes an atom, molecule, or compound that is useful in diagnosing, detecting or visualizing a location and/or quantity of a target molecule, cell, tissue, organ and the like. Detectable markers that can be used in accordance with the embodiments herein include, but are not limited to, radioactive substances (for example, radioisotopes, radionuclides, radiolabels or radiotracers), dyes, contrast agents, fluorescent compounds or molecules, bioluminescent compounds or molecules, enzymes and enhancing agents (for example, paramagnetic ions). In addition, some nanoparticles, for example quantum dots and metal nanoparticles (described below) can be suitable for use as a detection agent. In some embodiments, the detectable marker is IndoCyanine Green (ICG).

Exemplary radioactive substances that can be used as detectable markers in accordance with the embodiments herein include, but are not limited to, $^{18}$F, $^{18}$F-FAC, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{75}$Sc, $^{77}$As, $^{86}$Y, $^{90}$Y, $^{89}$Sr, $^{89}$Zr, $^{94}$Tc, $^{94}$Tc, $^{99}$mTc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra and $^{225}$Ac. Exemplary Paramagnetic ions substances that can be used as detectable markers include, but are not limited to ions of transition and lanthanide metals (for example metals having atomic numbers of 6 to 9, 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

When the detectable marker is a radioactive metal or paramagnetic ion, in some embodiments, the marker can be reacted with a reagent having a long tail with one or more chelating groups attached to the long tail for binding these ions. The long tail can be a polymer such as a polylysine, polysaccharide, or other derivatized or derivatizable chain having pendant groups to which may be bound to a chelating group for binding the ions. Examples of chelating groups that may be used according to the embodiments herein include, but are not limited to, ethylenediaminetetraacetic acid (EDTA), diethylenetriaminepentaacetic acid (DTPA), DOTA, NOTA, NOGADA, NETA, deferoxamine (DfO), porphyrins, polyamines, crown ethers, bis-thiosemicarbazones, polyoximes, and like groups. The chelate can be linked to the antigen binding construct by a group which allows formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antigen binding constructs and carriers described herein. Macrocyclic chelates such as NOTA, NOGADA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis.

Exemplary contrast agents that can be used as detectable markers in accordance with the embodiments of the disclosure include, but are not limited to, barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations thereof.

Bioluminescent and fluorescent compounds or molecules and dyes that can be used as detectable markers in accordance with the embodiments of the disclosure include, but are not limited to, fluorescein, fluorescein isothiocyanate (FITC), OREGON GREEN™ rhodamine, Texas red, tetrarhodimine isothiocynate (TRITC), Cy3, Cy5, and the like), fluorescent markers (for example, green fluorescent protein (GFP), phycoerythrin, and the like), autoquenched fluorescent compounds that are activated by tumor-associated proteases, enzymes (for example, luciferase, horseradish peroxidase, alkaline phosphatase, and the like), nanoparticles, biotin, digoxigenin or combination thereof.

Enzymes that can be used as detectable markers in accordance with the embodiments of the disclosure include, but are not limited to, horseradish peroxidase, alkaline phosphatase, acid phoshatase, glucose oxidase, β-galactosidase, β-glucoronidase or β-lactamase. Such enzymes may be used in combination with a chromogen, a fluorogenic compound or a luminogenic compound to generate a detectable signal.

In some embodiments, the antigen binding construct is conjugated to a nanoparticle. The term "nanoparticle" refers to a microscopic particle whose size is measured in nanometers, for example, a particle with at least one dimension less than about 100 nm Nanoparticles can be used as detectable substances because they are small enough to scatter visible light rather than absorb it. For example, gold nanoparticles possess significant visible light extinction properties and appear deep red to black in solution. As a result, compositions comprising antigen binding constructs conjugated to nanoparticles can be used for the in vivo imaging of T-cells in a subject. At the small end of the size range, nanoparticles are often referred to as clusters. Metal, dielectric, and semiconductor nanoparticles have been formed, as well as hybrid structures (for example core-shell nanoparticles). Nanospheres, nanorods, and nanocups are just a few of the shapes that have been grown. Semiconductor quantum dots and nanocrystals are examples of additional types of nanoparticles. Such nanoscale particles, when conjugated to an antigen binding construct, can be used as imaging agents for the in vivo detection of T-cells as described herein.

Therapeutic Agents

In some embodiments, an antigen binding construct is conjugated to a therapeutic agent. A "therapeutic agent" as used herein is an atom, molecule, or compound that is useful in the treatment of cancer, inflammation, other disease conditions, or to otherwise suppress an immune response, for example immunosuppression in organ transplants. Examples of therapeutic agents include, but are not limited to, drugs, chemotherapeutic agents, therapeutic antibodies and antibody fragments, toxins, radioisotopes, enzymes (for example, enzymes to cleave prodrugs to a cytotoxic agent at the site of the antigen binding construct binding), nucleases, hormones, immunomodulators, antisense oligonucleotides, chelators, boron compounds, photoactive agents and dyes, and nanoparticles.

Chemotherapeutic agents are often cytotoxic or cytostatic in nature and may include alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as detectable markers in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, aminoglutethimide, asparaginase, azacytidine, *bacillus* calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte-colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolamide, teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Toxins that may be used in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

In some embodiments nanoparticles are used in therapeutic applications as drug carriers that, when conjugated to an antigen binding construct, deliver chemotherapeutic agents, hormonal therapeutic agents, radiotherapeutic agents, toxins, immunosuppressive drugs such as rapamycin or any other cytotoxic or anti-cancer agent known in the art to cancerous cells that overexpress the target on the cell surface.

Any of the antigen binding constructs described herein (for example, mono-valent (scFv) constructs, minibodies, cys-diabodies, and bi-specific constructs), may be further conjugated with one or more additional therapeutic agents, detectable markers, nanoparticles, carriers or a combination thereof. For example, an antigen binding construct may be radiolabeled with 131I and conjugated to a lipid carrier, such that the anti-CD3-lipid conjugate forms a micelle. The micelle can incorporate one or more therapeutic or detectable markers. Alternatively, in addition to the carrier, the antigen binding construct may be conjugated to 131I (for example, at a tyrosine residue) and a drug (for example, at the epsilon amino group of a lysine residue), and the carrier may incorporate an additional therapeutic or detectable marker.

In some embodiments, one or more of the antigen binding constructs provided herein can be combined with other immune cell targeting agents such as antibodies directed to OX40, CD134, CD40, CD154, CD80, CD86, ICOS, CD137 and/or IL-1 receptor antagonists.

Kits

In some embodiments, kits are provided. In some embodiments, the kit includes an antigen binding construct as described herein. In some embodiments, the kit includes a nucleic acid that encodes an antigen binding construct as described herein. In some embodiments, the kit includes a cell line that produces an antigen binding construct as described herein. In some embodiments, the kit includes a detectable marker as described herein. In some embodiments, the kit includes a therapeutic agent as described herein. In some embodiments, the kit includes buffers. In some embodiments, the kit includes positive controls, for example CD3, CD3+ cells, or fragments thereof. In some embodiments, the kit includes negative controls, for example a surface or solution that is substantially free of CD3. In some embodiments, the kit includes packaging. In some embodiments, the kit includes instructions.

Methods of Detecting the Presence or Absence of the Target Molecule

Antigen binding constructs can be used to detect the presence or absence of the target molecule in vivo and/or in vitro. Accordingly, some embodiments include methods of detecting the presence or absence of the target. The method can include applying an antigen binding construct to a sample. The method can include detecting a binding or an absence of binding of the antigen binding construct to the target molecule, CD3.

Figure 1E:
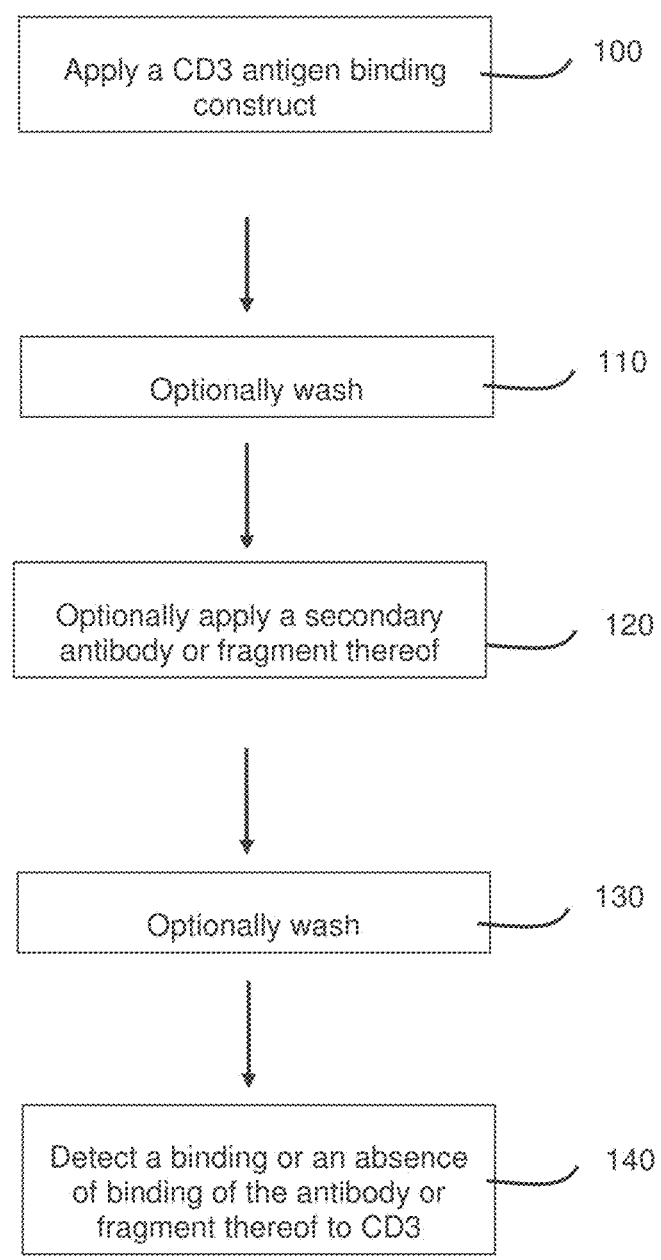

FIG. 1E illustrates some embodiments of methods of detecting the presence or absence of CD3. It will be appreciated that the steps shown in FIG. 1E can be performed in any sequence, and/or can be optionally repeated and/or eliminated, and that additional steps can optionally be added to the method. An antigen binding construct as described herein can be applied to a sample 100. An optional wash 110 can be performed. Optionally, a secondary antigen binding construct can be applied to the sample 120. An optional wash can be performed 130. A binding or absence of binding of the antigen binding construct to the target molecule can be detected 140.

In some embodiments, an antigen binding construct as described herein is applied to a sample in vivo. The antigen binding construct can be administered to a subject. In some embodiments, the subject is a human. In some embodiments, the subject is a non-human mammal, for example a rat, mouse, guinea pig, hamster, rabbit, dog, cat, cow, horse, goat, sheep, donkey, pig, monkey, or ape. In some embodiments, the antigen binding construct is infused into the subject. In some embodiments, the infusion is intravenous. In some embodiments, the infusion is intraperitoneal. In some embodiments, the antigen binding construct is applied topically or locally (as in the case of an interventional or intraoperative application) to the subject. In some embodiments, a capsule containing the antigen binding construct is applied to the subject, for example orally or intraperitoneally. In some embodiments, the antigen binding construct is selected to reduce the risk of an immunogenic response by subject. For example, for a human subject, the antigen binding construct can be humanized as described herein. In some embodiments, following in vivo application of the antigen binding construct, the sample, or a portion of the sample is removed from the host. In some embodiments, the antigen binding construct is applied in vivo, is incubated in vivo for a period of time as described herein, and a sample is removed for analysis in vitro, for example in vitro detection of antigen binding construct bound to the target molecule or the absence thereof as described herein.

In some embodiments, the antigen binding construct is applied to a sample in vitro. In some embodiments, the sample is freshly harvested from a subject, for example a biopsy. In some embodiments, the sample is incubated following harvesting from a subject. In some embodiments, the sample is fixed. In some embodiments the sample includes a whole organ and/or tissue. In some embodiments, the sample includes one or more whole cells. In some embodiments the sample is from cell extracts, for example lysates. In some embodiments, antigen binding construct in solution is added to a solution in the sample. In some embodiments, antigen binding construct in solution is added to a sample that does not contain a solution, for example a lyophilized sample, thus reconstituting the sample. In some embodiments, lyophilized antigen binding construct is added to a sample that contains solution, thus reconstituting the antigen binding construct.

In some embodiments, the antigen binding construct is optionally incubated with the sample. The antigen binding construct can be incubated for a period of no more than about 14 days, for example no more than about 14 days, 9, 8, 7, 6, 5, 4, 3, 2, or 1 day, or no more than about 23 hours, for example no more than about 23 hours, 22, 21, 20, 19, 18, 17, 16, 15, 14, 13, 12, 11, 10, 9, 8, 7, 6, 5, 4, 3, 2, 1, 0.75, 0.5, 0.25, or 0.1 hour, including ranges between any two of the listed values. In some embodiments, the antigen binding construct can be incubated within a subject between 0.1 to three days. In some embodiments, the incubation is within a subject to which the antigen binding construct was administered. In some embodiments, the incubation is within an incubator. In some embodiments, the incubator is maintained at a fixed temperature, for example about 21° C., room temperature, 25° C., 29° C., 34° C., 37° C., or 40° C.

In some embodiments, the antigen binding construct that is not bound to the target is optionally removed from the sample. In some embodiments, the sample is washed. Washing a sample can include removing solution that contains unbound antigen binding construct, and adding solution that does not contain antigen binding construct, for example buffer solution. In some embodiments, an in vitro sample is washed, for example by aspirating, pipetting, pumping, or draining solution that contains unbound antigen binding construct, and adding solution that does not contain antigen binding construct. In some embodiments, an in vivo sample is washed, for example by administering to the subject solution that does not contain antigen binding construct, or by washing a site of topical antigen binding construct administration. In some embodiments, the wash is performed at least two times, for example at least 2, 3, 4, 5, 6, 7, 8, 9, 10, 15, or 20 times. In some embodiments, following the wash or washes, at least about 50% of unbound antibody is removed from the sample, for example at least about 50%, 60%, 70%, 75%, 80%, 85%, 90%, 95%, 97%, 98%, 99% or greater.

In some embodiments, unbound antigen binding construct is eliminated from the sample. Following application of the antigen binding construct to the sample, antigen binding construct bound to the target reaches an equilibrium with antigen binding construct unbound to the target, so that at some time after application of the antigen binding construct, the amount of antigen binding construct bound to the target does not substantially increase. After this time, at least part of the quantity of the antigen binding construct that is unbound to the target can be eliminated. In some embodiments, unbound antigen binding construct is eliminated by metabolic or other bodily processes of the subject to whom the antibody or fragment was delivered. In some embodiments, unbound antigen binding construct is eliminated by the addition of an agent that destroys or destabilized the unbound antigen binding construct, for example a protease or a neutralizing antibody. In some embodiments, 1 day after application of the antigen binding construct, at least about 30% of the antigen binding construct that was applied has been eliminated, for example at least about 30%, 40%, 60%, 70%, 75%, 80%, 85%, 90%, 95%, 97%, 98%, 99%, or 99.9%. In some embodiments, 2 days after application of the antigen binding construct, at least about 40% of the antigen binding construct that was applied has been eliminated, for example at least about 40%, 50%, 60%, 70%, 75%, 80%, 85%, 90%, 95%, 97%, 98%, 99%, or 99.9%.

In some embodiments, the presence or absence of the target, CD3, is detected. The presence or absence of the target can be detected based on the presence or absence of the antigen binding construct in the sample. After removal and/or elimination of the antigen binding construct from the sample, for example by washing and/or metabolic elimination, remaining antigen binding construct in the sample can indicate the presence of the target, while an absence of the antigen binding construct in the sample can indicate the absence of the target.

In some embodiments, the antigen binding construct includes a detectable marker as described herein. Thus, the presence of the antigen binding construct can be inferred by detecting the detectable marker.

In some embodiments, a secondary antigen binding construct is used to detect the antigen binding construct. The secondary antigen binding construct can bind specifically to the antigen binding construct. For example, the secondary antigen binding construct can include a polyclonal or monoclonal antibody, diabody, minibody, etc. against the host type of the antibody, or against the antigen binding construct itself. The secondary antigen binding construct can be conjugated to a detectable marker as described herein. The secondary antigen binding construct can be applied to the sample. In some embodiments, the secondary antigen binding construct is applied to the sample in substantially the same manner as the antigen binding construct. For example, if the antigen binding construct was infused into a subject, the secondary antigen binding construct can also be infused into the subject.

In some embodiments, binding or the absence of binding of the antigen binding construct is detected via at least one of: positron emission tomography (PET), single-photon emission computed tomography (SPECT), magnetic resonance imaging (NMR), or detection of fluorescence emissions. PET can include, but is not limited to microPET imaging. In some embodiments, binding of the absence of binding of the antigen binding construct is detected via two or more forms of imaging. In some embodiments, detection can be via near-infrared (NIR) and/or Cerenkov.

Methods of Targeting a Therapeutic Agent to a Cell

Antigen binding constructs can be used to target a therapeutic molecule, for example a cytotoxin to a target positive cell, such as a cell expressing CD3. Thus, some embodiments include methods of targeting a therapeutic agent to a target positive cell. The method can include administering an antigen binding construct as described herein to a subject. The subject can be a subject in need, for example a subject in need of elimination or neutralization of at least some target positive cells. In some embodiments, the antigen binding construct includes at least on therapeutic agent as described herein. In some embodiments, the therapeutic can be directly conjugated to the antigen binding construct via a covalent bond, such as a disulfide bond. In some embodiments, the subject can benefit from the localization of a CD3 positive cell to another cell or agent.

Optionally, before and/or after administration of the antigen binding construct that includes at least one therapeutic agent, the number and/or localization of the target positive cells of the patient is determined. For example, determining the number and/or localization of target positive cells prior to administration can indicate whether the patient is likely to benefit from neutralization and/or elimination of the target positive cells. Determining the number and/or localization of the target positive cells after administration can indicate whether the target positive cells were eliminated in the patient.

In some embodiments, the CD3 antibody fragments can be used as a therapeutic antigen binding construct to modulate immune system reaction by stimulating and tolerizing T cells via the CD3 epsilon domain of the TCR complex and/or by upregulating T regulatory cells via upregulation of FOXP3 (Saruta M, Yu QT, Fleshner PR, Mantel PY, Schmidt-Weber CB, Banham A H, Papadakis K A. Characterization of FOXP3+CD4+ regulatory T cells in Crohn's disease. Clin Immunol. 2007 December; 125(3):281-90.). Such therapeutics can be useful in treating not only tissue/organ allograft transplants but also autoimmune diseases such as rheumatoid arthritis, multiple sclerosis, type 1 diabetes, lupus erythematosus, etc.

In some embodiments, the antigen binding construct can be used as a therapeutic without linkage to another molecule such as a toxin (see, for example, Chatenoud, L. and Bluestone, J. A. CD3-specific antibodies: a portal to the treatment of autoimmunity Nature Reviews Immunology 2007, 7: 622-632) Such antigen binding constructs can also be useful for modulating the biologic activity associated with CD3 expression on immune cells to treat a variety of diseases including cancer, diabetes, autoimmune and inflammatory conditions. In some embodiments, the antigen binding construct alone can be used as an immunosuppressant and shows activity to inhibit CD3 signaling.

In some embodiments, the scFv, minibody and/or cys-diabody antibody fragments have superior pharmacokinetic properties for diagnostic imaging. Current technology utilizes imaging with the intact antibody which requires significantly longer times (~7-8 days post-injection) to produce high contrast images due to the slow serum clearance of full length antibodies. The minibody and cys-diabody provide the opportunity for same-day or next-day imaging. Each day is vital for patients with an aggressively progressing disease, and the ability to identify the proper therapeutic approach at an earlier time-point has the potential to improve patient survival. Same-day or next-day imaging also provides a logistical solution to the problem facing many patients who travel great distances to receive treatment/diagnosis since the duration of travel stays or the need to return one week later would be eliminated when imaging with minibody or cys-diabody fragments versus full length antibodies.

Additionally, in some embodiments, the cys-diabody fragment component monomers contain c-terminus cysteine residues that form disulfide bonds. These covalently bound cys-diabody cysteine residues can be opened via mild chemical reduction to provide an active thiol group for site specific conjugation. Currently, conjugation of antibodies relies on non-specific targeting of tyrosine or lysine residues which are commonly located in the functionally important complementary determining regions (CDRs) of antibodies whereas cysteine residues are rarely located in the CDRs. The location of the c-terminus cysteine residues on the properly folded cys-diabody are opposite the CDRs which prevents steric blocking of CDR-antigen interaction by the conjugated material.

The ability to image a patient's entire body for the presence of an antibody's target prior to and during treatment provides valuable information for personalized patient management. During the testing of an antibody therapy's safety and efficacy, it is useful to be able to select and test the treatment on patients who express the antibody's target as part of their disease progression.

In some embodiments, scFv, minibody and cys-diabody diagnostic fragments matching available antibody therapies allow matching of the patient's disease state with the appropriate antibody therapy.

In some embodiments, a method of targeting a CD3+ cell to a first antigen is provided. The method can include applying a bispecific antigen binding construct to a sample. The bispecific antigen binding construct can include a CD3 antigen binding construct as described herein. The bispecific antibody can include an antigen binding construct that binds to the first antigen, for example 1, 2, 3, 4, 5, or 6 CDR's, an scFv, or a monomer of a minibody or cys-diabody. In some embodiments, the bispecific antibody includes 1, 2, or 3 HCDR's of an antigen binding construct as described herein, and/or 1, 2, or 3 LCDR's of an antigen binding construct as described herein. In some embodiments, the bispecific antigen binding construct includes a scFv of an antigen binding construct as described herein. In some embodiment, the bispecific antigen binding construct includes a $V_H$ or $V_L$ sequence as described herein. In some embodiments, the bispecific antigen binding construct includes a minibody or cys-diabody monomer as described herein. In some embodiments, the bispecific antigen binding construct is applied to a sample in vivo, for example an organ or tissue of a subject. In some embodiments, the bispecific antigen binding construct is applied to an in vitro sample. Without being limited to any one theory, in some embodiments, the bispecific antigen binding construct binds to the target on the target positive cell, and binds to the first antigen (which can be different from CD3) on the first cell, and thus brings the target positive cell in proximity to the first cell. For example, a CD3+ cell can be brought into proximity of a cancer cell, and can facilitate an immune response against that cancer cell.

EXAMPLE 1

CD3 Antibodies and Antibody Fragments

The variable regions of the murine anti-human CD3 antibody OKT3 were reformatted by protein engineering into a minibody.

The murine variable regions of the OKT3 antibody were humanized by grafting the murine Complimentary Determining Region (CDR) grafting onto a human framework. The murine V genes were run against the human V germ-line database. The human V gene with highest sequence homology was examined for critical residues and similarity to antigen binding loop structures. The $V_L$ and $V_H$ CDRs of the murine OKT3 were then incorporated into the human acceptor variable region framework, replacing the human CDRs (FIGS. 2A and 2B). Selected mouse residues were kept in the human framework. As shown by these resulting sequences provided, the humanized OKT3 V sequences are distinct from ABC1.

The minibody format is of approximately 80 kDa in size, with each monomer having a single-chain variable fragment (scFv) linked to the human IgG1 $C_H3$ domain (FIGS. 1A and 1C). The variable heavy ($V_H$) and light ($V_L$) domains which are responsible for the antigen recognition and binding are connected via a GlySer-rich 18 amino acid linker and make up the scFv fragment. The scFv is tethered to the human IgG1 $C_H3$ domain via the human IgG1 upper and core hinge regions (15 residues) followed by a 10 amino acid GlySer linker sequence (for sequence see FIGS. 3A, 3B, 4A, 4B, 5A and 5B).

The minibody (either $V_H$-$V_L$-$C_H3$ or $V_L$-$V_H$-$C_H3$ orientation) exists as a stable dimer due to the association between the $C_H3$ domains as well as the formation of disulfide bonds within the hinge regions. To allow secretion of the minibody, a signal sequence was incorporated to lead the expression construct at the N-terminus (see FIG. 1B, for sequence see FIGS. 3A, and 3B (Murine), 4A, and 4B (ABC1), and 5A, and 5B (humanized)).

The cys-diabody is a bivalent antibody fragment of ~55 kDa in size. It was formed by two identical scFv fragments that open up and cross-pair due to a shorter GlySer-rich linker between the $V_L$ and $V_H$ domains in each scFv (FIGS. 1B and 1D, for sequence see FIG. 6).

A cysteine preceded by two Glycines (GlyGlyCys) is at the C-terminus which allows the diabody to form covalent disulfide bonds.

In some embodiments, the $V_H$ cysteine residue highlighted in the sequences (FIGS. 2A, 2B, 3A, 3B, 4A, 4B, 5A, 5B, and 6) can be a serine. This results in improved expression levels and allows for site specific conjugation of the cys-diabody protein. In some embodiments, HCDR3 includes a serine as follows: YYDDHYSLDY (SEQ ID NO: 69). In some embodiments, any of the heavy chain sequences or fragments provided herein can have the cysteine highlighted converted to the serine. Thus, for example, in some embodiments, the cys-diabody and/or minibody, and/or antibody, and/or antigen binding construct includes HCDR1 from the HCDR1 in SEQ ID NO: 6, HCDR2 from the HCDR2 in SEQ ID NO: 6, HCDR3 of YYDDHYSLDY (SEQ ID NO: 69), LCDR1 of the LCDR1 in SEQ ID NO: 3, LCDR2 of the LCDR2 in SEQ ID NO: 3, and LCDR3 of the LCDR3 in SEQ ID NO: 3.

In some embodiments, the two sulfhydryl groups (following mild reduction) provide a strategy for site-specific conjugation of functional moieties such as radiolabels and a mechanism for reliable labeling that does not interfere with the cys-diabody's binding activity.

EXAMPLE 2

Cloning into pcDNA3.1/myc-His

Figure 7:
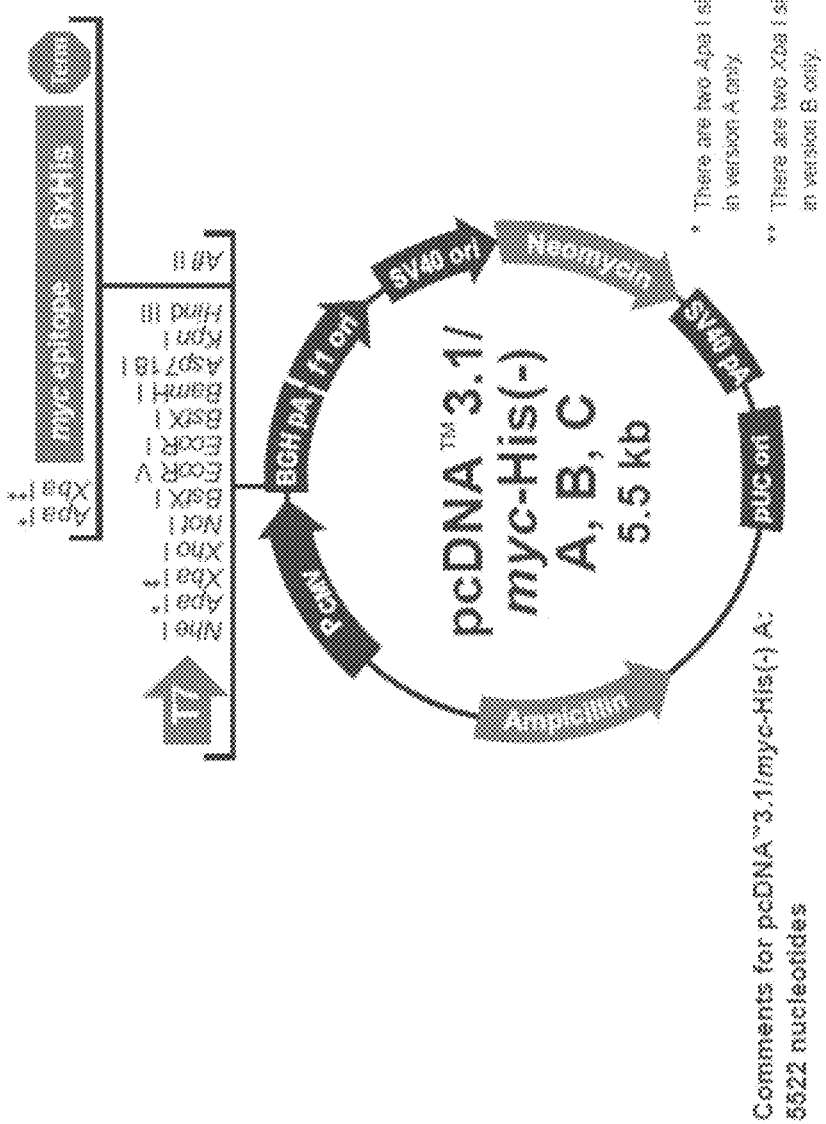
FIG. 7 depicts a vector map for pcDNA 3.1/myc-His (−) Versions A, B, C. This expression vector features the CMV promoter for mammalian expression and Neomycin resistance for selection.

The cDNA for all minibody and cys-diabody sequences were cloned into the pcDNA3.1/myc-His (−) Version A vector for mammalian expression from Invitrogen Corp. The vector map is shown in FIG. 7.

EXAMPLE 3

Expression of OKT Minibodies

The OKT3 minibody constructs were transiently transfected into CHO-K1 cells to validate expression. The transfections were performed using the Lipofectamine reagent in a 6-well plate format. Following a 72 hour transfection, the supernatants were harvested and filtered to remove any cells.

Figure 8:
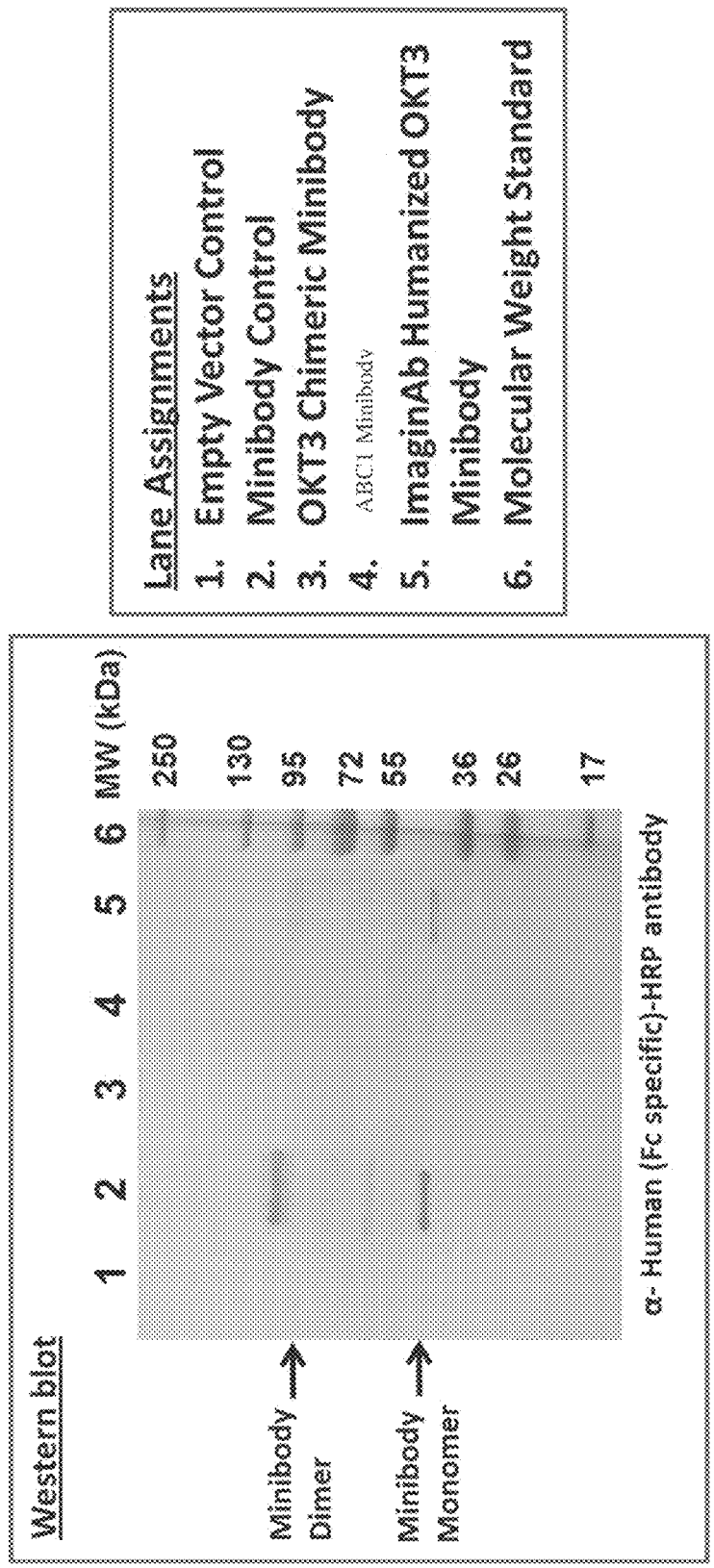
FIG. 8 is an image of a western blot.

Western blot analysis was performed on supernatant from the transient transfections to confirm the expression of the antibody fragments. Supernatant from the transfection of a standard minibody was used as a positive control. Under non-reducing conditions, the OKT3 minibodies ran at the expected molecular weight of 80-90 kDa. Transfection supernatants were run out by SDS-PAGE and transferred to PVDF membrane. The membrane was probed with an anti-human IgG (Fc-specific) antibody conjugated with Horse Radish Peroxidase (HRP) and developed by incubating with the HRP substrate TMB. FIG. 8 displays the results from the western blot).

A band representing the monomeric form is also detected at approximately 40 kDa. Of the three minibody constructs (from FIGS. 3A, 3B, 4A, 4B, 5A, and 5B), the humanized OKT3 (sequence shown in FIGS. 5A and 5B) is the best expressing fragment.

EXAMPLE 4

In Vivo Detection of CD3

A humanized CD3 cys-diabody of SEQ ID NO: 13 is conjugated with a relevant chelator via C-terminal cysteines on the cys-diabody and subsequently radiolabeled with isotopes such as In111, Zr 89, Cu64, etc. Alternatively, the cys-diabody can be radiolabeled after attaching relevant chelators to Lysine residues or directly radiolabeled with Iodine. The cys-diabody is infused intravenously into a healthy human subject. The cys-diabody is incubated in the human subject for 10 minutes post-infusion Immediately after the 10 minute incubation, the localization of the cys-diabody is detected via a PET scan or external scintillation system.

Localization of cys-diabody is used to determine localization of CD3 in the subject.

EXAMPLE 5

In Vivo Detection of CD3

A humanized CD3 minibody that is a homodimer of monomers of SEQ ID NO: 11 Is provided. The minibody is infused intravenously into a healthy human subject. The minibody is incubated in the human subject for 1 hour post-infusion. A secondary antibody, a humanized cys-diabody that binds specifically to the CD3 minibody and is conjugated to 33P is provided Immediately after the one-hour incubation, the secondary antibody is infused into to subject. The secondary antibody is incubated for one hour. Immediately after the one-hour incubation of the secondary antibody, the localization of the minibody is detected via PET imaging.

Localization of cys-diabody is used to determine localization of CD3 in the subject.

EXAMPLE 6

Therapeutic Treatment Using a Cys-Diabody

A humanized CD3 cys-diabody that is a homodimer of monomers of SEQ ID NO: 11 is provided. The cys-diabody is infused intravenously into a subject having rheumatoid arthritis in an amount adequate to bind to sufficient levels of CD3 in the subject to provide a lessening of the symptoms of rheumatoid arthritis in the subject.

EXAMPLE 7

Additional Antigen Binding Constructs

In addition to the OKT3-derived minibody and cys-diabody fragments, additional fragments were reformatted in silico to create a set of minibodies and cys-diabody variants that are initially tested for each set of parental antibody variable regions (FIGS. 9A, 9B, 10-13, 14A, 14B, 15-18, 19A, 19B, and 20-23). Also reformatted were sequences of the minibody and cys-diabody fragments based on the variable regions of two other anti-human CD3 antibodies, ABC2 (FIGS. 24A, 24B, 25A, 25B and 26-29) and ABC3 (FIGS. 30A, 30B, 31A, 31B, and 32-35).

EXAMPLE 8

Additional Antigen Binding Constructs

Additional minibody constructs with VL-VH orientation were engineered using VH genes in which the cysteine at position 105 in CDR3 had been changed to serine (C105S) (see, for example SEQ ID NO: 86). These constructs included a chimeric (mouse/human) OKT3 minibody (muVL-muVH_C105S), and 2 humanized minibodies; huVL_vA-huVH_vA_C105S (variant A), and huVL_vB-huVH_vB_C105S (variant B).

These additional anti-CD3 minibody constructs and their respective minibody constructs without the C105S change were transiently transfected into CHO-K1 cells to validate expression. The transfections were performed using the Lipofectamine reagent in a 6-well plate format. Following a 72 hour transfection, the supernatants were harvested and filtered to remove any cells.

Figure 38:
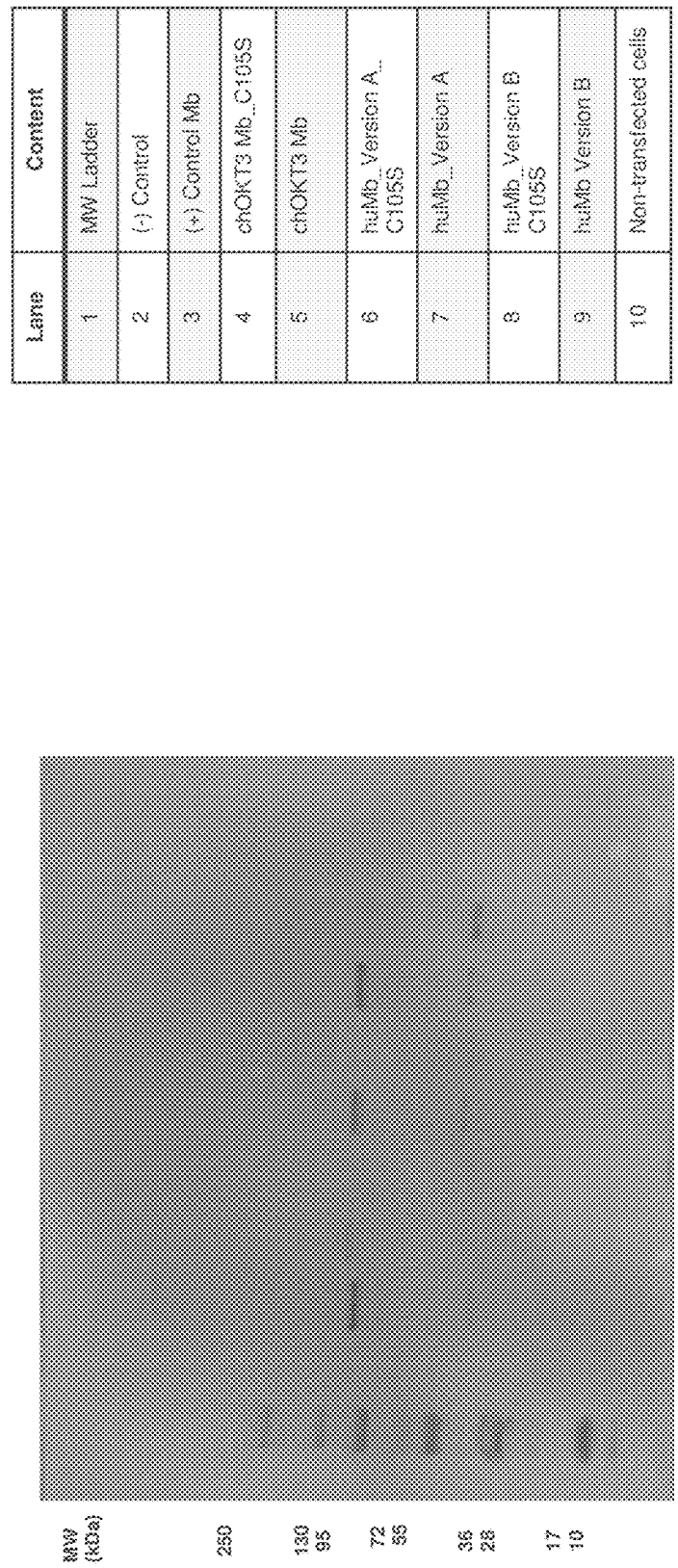
FIG. 38 is an image of a western blot analysis demonstrating rescue of expression of all minibody variants following replacement of the cysteine at position 105 with serine.
Figure 39D:
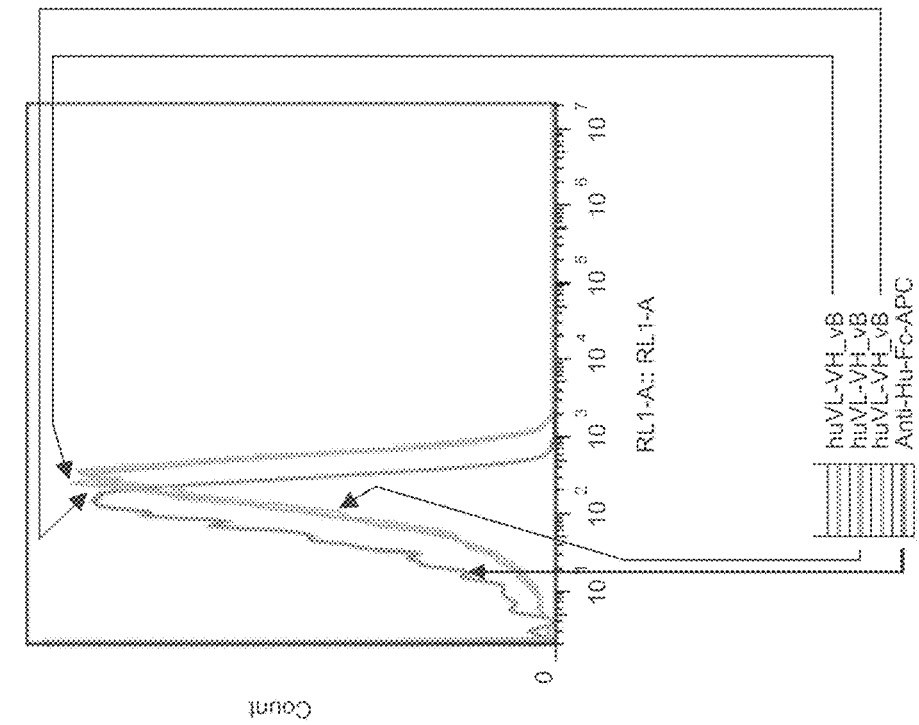
Figure 39C:
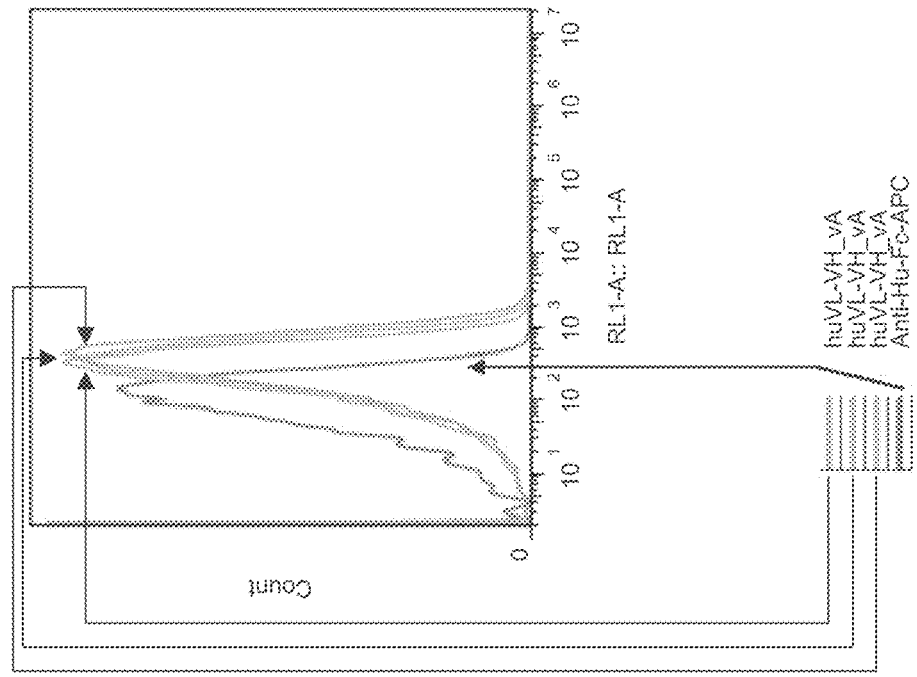

Western blot analysis was performed on the supernatants to evaluate expression of the antibody fragments. Supernatants were run on SDS-PAGE and transferred to PVDF membrane. Minibody variants were detected with anti-human horse radish peroxidase (HRP) conjugated IgG (Fc-specific). A positive isotype control was included (supernatant from transient transfection of an irrelevant minibody). Under non-reducing conditions, the minibodies migrate at the expected molecular weight of 80-90 kDa (FIG. 38). As seen with other previously expressed minibodies, a band representing the monomeric form is also detected at approximately 40 kDa (FIG. 38). Re-engineered fragments containing the amino acid substitution (C105S) rescued expression for all three minibody fragments respectively.

The supernatants were also evaluated for binding to cell surface CD3 on Jurkat cells (T-lymphocytes). All three minibodies showed binding to Jurkat cells (FIGS. 39A-39D). Jurkat cells were incubated (in triplicate) with cell culture supernatants from transient Mb transfections and analysis was performed with 10,000 events/point. All histograms show APC signal (RL1-A) vs. cell number. The binding of minibody variants to Jurkat cells was detected following staining with anti-human Fc-specific-APC antibodies. The OKT antibody, positive control, was detected with anti-mouse Fc-specific-APC antibodies. Staining with the secondary APC-conjugated antibodies alone was used as a negative control.

All embodiments and configurations discussed in regard to the sequences in FIGS. 2A and/or 2B are also contemplated for the sequences within FIGS. 36A-36I. In some embodiments, any construct employing SEQ ID NO: 6 disclosed herein can alternatively employ SEQ ID NO: 86. In some embodiments, any construct employing HCDR3 of SEQ ID NO: 6 disclosed herein can alternatively employ HCDR3 of SEQ ID NO: 86, for example, SEQ ID NO: 69 with the cysteine option.

In this application, the use of the singular can include the plural unless specifically stated otherwise or unless, as will be understood by one of skill in the art in light of the present disclosure, the singular is the only functional embodiment. Thus, for example, "a" can mean more than one, and "one embodiment" can mean that the description applies to multiple embodiments.

Incorporation By Reference

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

Equivalents

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

We claim:

1. A humanized antigen binding construct that comprises:
a HCDR1 of the HCDR1 in SEQ ID NO: 86;
a HCDR2 of the HCDR2 in SEQ ID NO: 86;
a HCDR3 of the HCDR3 in SEQ ID NO: 86;
a LCDR1 of the LCDR1 in SEQ ID NO: 3;
a LCDR2 of the LCDR2 in SEQ ID NO: 3; and
a LCDR3 of the LCDR3 in SEQ ID NO: 3,
wherein the humanized antigen binding construct binds specifically to CD3, and
wherein the humanized antigen binding construct comprises a humanized minibody or a humanized cys-diabody,
wherein the human antigen binding construct further comprises at least one of:
a LFR3 of the LFR3 in SEQ ID NO: 3; or
a HFR3 of the HFR3 in SEQ ID NO: 6 or 86.

2. The antigen binding construct of claim 1, further comprising a detectable marker selected from the group consisting of at least one of a radioactive substance, a dye, a contrast agent, a fluorescent compound, a bioluminescent compound, an enzyme, an enhancing agent, or a nanoparticle.

3. A humanized OKT3 minibody that binds to CD3, the humanized minibody comprising a polypeptide that comprises:
a single-chain variable fragment (scFv) that binds to CD3, the scFv comprising a variable heavy (VH) domain linked a variable light (VL) domain,
wherein the scFv comprises a LFR3 of the LFR3 in SEQ ID NO: 3, or a HFR3 of the HFR3 in SEQ ID NO: 6 or 86, or both;
a hinge; and
a human IgG $C_H3$ sequence,
a HCDR1 of the HCDR1 in SEQ ID NO: 6 or 86;
a HCDR2 of the HCDR2 in SEQ ID NO: 6 or 86;
a HCDR3 of the HCDR3 in SEQ ID NO: 6 or 86;
a LCDR1 of the LCDR1 in SEQ ID NO: 3;
a LCDR2 of the LCDR2 in SEQ ID NO: 3; and
a LCDR3 of the LCDR3 in SEQ ID NO: 3.

4. The humanized minibody of claim 3, further comprising a detectable marker selected from the group consisting of a radioactive substance, a dye, a contrast agent, a fluorescent compound, a bioluminescent compound, an enzyme, an enhancing agent, or a nanoparticle.

5. The antigen binding construct of claim 1, wherein the antigen binding construct comprises the humanized minibody.

6. The antigen binding construct of claim 1, wherein the antigen binding construct comprises a heavy chain variable domain that is a heavy chain variable domain in SEQ ID NO: 86, and a light chain variable domain that is a light chain variable domain in SEQ ID NO: 3.

7. The antigen binding construct of claim 1, wherein the antigen binding construct comprises a heavy chain variable domain that is a heavy chain variable domain in SEQ ID NO: 6, and a light chain variable domain that is a light chain variable domain in SEQ ID NO: 3.

8. A humanized minibody that binds to CD3, wherein the humanized minibody comprises:
a polypeptide that comprises:
a single-chain variable fragment (scFv) that binds to CD3, the scFv comprising a variable heavy (VH) domain linked to a variable light (VL) domain,
wherein the scFv comprises a LFR3 of the LFR3 in SEQ ID NO: 3, or a HFR3 of the HFR3 in SEQ ID NO: 6 or 86, or both;
a hinge;
a human IgG $C_H3$ sequence;
a HCDR1 of the HCDR1 in SEQ ID NO: 6 or 86;
a HCDR2 of the HCDR2 in SEQ ID NO: 6 or 86;
a HCDR3 of the HCDR3 in SEQ ID NO: 6 or 86;
a LCDR1 of the LCDR1 in SEQ ID NO: 3;
a LCDR2 of the LCDR2 in SEQ ID NO: 3; and
a LCDR3 of the LCDR3 in SEQ ID NO: 3.

9. A humanized minibody that binds to CD3, wherein the humanized minibody comprises:
a polypeptide that comprises:
a single-chain variable fragment (scFv) that binds to CD3, the scFv comprising a variable heavy (VH) domain linked to a variable light (VL) domain,
wherein the scFv comprises a LFR3 of the LFR3 in SEQ ID NO: 3, or a HFR3 of the HFR3 in SEQ ID NO: 6 or 86, or both;
a hinge;
a human IgG $C_H3$ sequence;
a HCDR1 of the HCDR1 in SEQ ID NO: 6 or 86;
a HCDR2 of the HCDR2 in SEQ ID NO: 6 or 86;
a HCDR3 of the HCDR3 in SEQID NO: 6 or 86;
a LCDR1 of the LCDR1 in SEQ ID NO: 3;
a LCDR2 of the LCDR2 in SEQ ID NO: 3;
a LCDR3 of the LCDR3 in SEQ ID NO: 3, and
a detectable marker selected from the group consisting of a radioactive substance, a dye, a contrast agent, a fluorescent compound, a bioluminescent compound, an enzyme, an enhancing agent, or a nanoparticle.

* * * * *

SEQUENCE LISTING

```
<160> NUMBER OF SEQ ID NOS: 125

<210> SEQ ID NO 1
<211> LENGTH: 106
<212> TYPE: PRT
<213> ORGANISM: Mus musculus

<400> SEQUENCE: 1

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
                20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
        50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 2
<211> LENGTH: 108
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
 1               5                  10                  15
```

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Gln Gly Thr Lys Val Glu Ile Lys
            100                 105

<210> SEQ ID NO 3
<211> LENGTH: 106
<212> TYPE: PRT
<213> ORGANISM: Artificial Sequence
<220> FEATURE:
<223> OTHER INFORMATION: Antigen binding construct or subpart thereof

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Thr Ser Lys Leu Ala Ser Gly Val Pro Ala His Phe Arg Gly Ser
50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Phe Thr
                85                  90                  95

Phe Gly Gln Gly Thr Lys Val Glu Ile Lys
            100                 105

<210> SEQ ID NO 4
<211> LENGTH: 119
<212> TYPE: PRT
<213> ORGANISM: Mus musculus

<400> SEQUENCE: 4

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 5
<211> LENGTH: 115
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Glu Tyr Phe Gln His Trp Gly Gln Gly Thr Leu Val Thr
            100                 105                 110

Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: Antigen binding construct or subpart thereof

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser
        115

<210> SEQ ID NO 7
<211> LENGTH: 394
<212> TYPE: PRT
<213> ORGANISM: Artificial Sequence
<220> FEATURE:
<223> OTHER INFORMATION: Antigen binding construct or subpart thereof

<400> SEQUENCE: 7

```
Met Glu Thr Asp Thr Leu Leu Leu Trp Val Leu Leu Leu Trp Val Pro
  1               5                  10                  15
Gly Ser Thr Gly Gln Ile Val Leu Thr Gln Ser Pro Ala Ile Met Ser
             20                  25                  30
Ala Ser Pro Gly Glu Lys Val Thr Met Thr Cys Ser Ala Ser Ser Ser
         35                  40                  45
Val Ser Tyr Met Asn Trp Tyr Gln Gln Lys Ser Gly Thr Ser Pro Lys
     50                  55                  60
Arg Trp Ile Tyr Asp Thr Ser Lys Leu Ala Ser Gly Val Pro Ala His
 65                  70                  75                  80
Phe Arg Gly Ser Gly Ser Gly Thr Ser Tyr Ser Leu Thr Ile Ser Gly
                 85                  90                  95
Met Glu Ala Glu Asp Ala Ala Thr Tyr Tyr Cys Gln Gln Trp Ser Ser
            100                 105                 110
Asn Pro Phe Thr Phe Gly Ser Gly Thr Lys Leu Glu Ile Asn Gly Ser
        115                 120                 125
Thr Ser Gly Gly Gly Ser Gly Gly Gly Ser Gly Gly Gly Ser Ser
        130                 135                 140
Gln Val Gln Leu Gln Gln Ser Gly Ala Glu Leu Ala Arg Pro Gly Ala
145                 150                 155                 160
Ser Val Lys Met Ser Cys Lys Ala Ser Gly Tyr Thr Phe Thr Arg Tyr
                165                 170                 175
Thr Met His Trp Val Lys Gln Arg Pro Gly Gln Gly Leu Glu Trp Ile
            180                 185                 190
Gly Tyr Ile Asn Pro Ser Arg Gly Tyr Thr Asn Tyr Asn Gln Lys Phe
        195                 200                 205
Lys Asp Lys Ala Thr Leu Thr Thr Asp Lys Ser Ser Ser Thr Ala Tyr
210                 215                 220
Met Gln Leu Ser Ser Leu Thr Ser Glu Asp Ser Ala Val Tyr Tyr Cys
225                 230                 235                 240
Ala Arg Tyr Tyr Asp Asp His Tyr Cys Leu Asp Tyr Trp Gly Gln Gly
                245                 250                 255
Thr Thr Leu Thr Val Ser Ser Glu Pro Lys Ser Cys Asp Lys Thr His
            260                 265                 270
Thr Cys Pro Pro Cys Gly Gly Gly Ser Ser Gly Gly Ser Gly Gly
        275                 280                 285
Gln Pro Arg Glu Pro Gln Val Tyr Thr Leu Pro Pro Ser Arg Asp Glu
        290                 295                 300
Leu Thr Lys Asn Gln Val Ser Leu Thr Cys Leu Val Lys Gly Phe Tyr
305                 310                 315                 320
Pro Ser Asp Ile Ala Val Glu Trp Glu Ser Asn Gly Gln Pro Glu Asn
                325                 330                 335
Asn Tyr Lys Thr Thr Pro Pro Val Leu Asp Ser Asp Gly Ser Phe Phe
            340                 345                 350
Leu Tyr Ser Lys Leu Thr Val Asp Lys Ser Arg Trp Gln Gln Gly Asn
        355                 360                 365
Val Phe Ser Cys Ser Val Met His Glu Ala Leu His Asn His Tyr Thr
370                 375                 380
Gln Lys Ser Leu Ser Leu Ser Pro Gly Lys
385                 390

<210> SEQ ID NO 8
<211> LENGTH: 1185
<212> TYPE: DNA
```

<213> ORGANISM: Artificial Sequence
<220> FEATURE:
<223> OTHER INFORMATION: Antigen binding construct or subpart thereof

<400> SEQUENCE: 8

```
atggaaaccg acactctgct gctgtgggtc ctgctgctgt gggtgcccgg atcaactgga    60
cagatcgtgc tgactcagtc tcccgctatc atgtctgcct cacctggcga aaaagtgaca   120
atgacctgtt ccgcctcttc ttccgtgtct tacatgaatt ggtaccagca gaaatctggg   180
actagtccta aacggtggat ctacgatact agcaaactgg cttctggcgt gcctgctcat   240
ttccgtggtt ctggctctgg aacctcttac tctctgacca tctctggcat ggaggccgag   300
gatgccgcca cctactactg ccagcagtgg agttcaaacc ctttcacatt cggctccggc   360
acaaaactgg agatcaacgg ctctactagt ggtggaggat ctggtggtgg atctggaggg   420
ggcggatcat ctcaggtcca gctgcagcag tctggtgctg aactggcacg tcctggtgcc   480
tccgtgaaaa tgtcttgtaa ggcctctggt tacacctttc ccggtacac tatgcattgg   540
gtcaaacagc gccctgggca gggactgaa tggattggct acatcaaccc ttctcgtggc   600
tacacaaact acaatcagaa attcaaggac aaggccaccc tgacaaccga caaatcttct   660
tcaaccgcct acatgcagct gtcatccctg acctctgagg atagtgctgt gtactactgt   720
gctcggtact acgacgatca ctactgtctg gactactggg gacagggaac aacactgact   780
gtgtcctccg aacccaaatc ctgtgacaaa acccacacct gtccaccttg tggcggtgga   840
tcatctggcg agggagtgg agggcagcct agggagcctc aggtctacac actgccacct   900
tctcgggacg aactgacaaa aaaccaggtg tccctgacat gtctggtgaa gggcttctac   960
ccttccgata tcgctgtgga gtgggagtca atggccagc cgaaaacaa ctacaaaacc  1020
accccacctg tgctggattc cgatggctct ttcttcctgt actctaaact gaccgtggat  1080
aagagtcgat ggcagcaggg aaacgtgttc tcttgctccg tgatgcacga ggccctgcat  1140
aatcattaca cccagaaatc actgtctctg tcacccggca atga                  1185
```

<210> SEQ ID NO 9
<211> LENGTH: 394
<212> TYPE: PRT
<213> ORGANISM: Artificial Sequence
<220> FEATURE:
<223> OTHER INFORMATION: Antigen binding construct or subpart thereof

<400> SEQUENCE: 9

```
Met Glu Thr Asp Thr Leu Leu Leu Trp Val Leu Leu Leu Trp Val Pro
  1               5                  10                  15

Gly Ser Thr Gly Asp Ile Gln Met Thr Gln Ser Pro Ser Ser Leu Ser
             20                  25                  30

Ala Ser Val Gly Asp Arg Val Thr Ile Thr Cys Ser Ala Ser Ser Ser
         35                  40                  45

Val Ser Tyr Met Asn Trp Tyr Gln Gln Thr Pro Gly Lys Ala Pro Lys
     50                  55                  60

Arg Trp Ile Tyr Asp Thr Ser Lys Leu Ala Ser Gly Val Pro Ser Arg
 65                  70                  75                  80

Phe Ser Gly Ser Gly Ser Gly Thr Asp Tyr Thr Phe Thr Ile Ser Ser
                 85                  90                  95

Leu Gln Pro Glu Asp Ile Ala Thr Tyr Tyr Cys Gln Gln Trp Ser Ser
            100                 105                 110

Asn Pro Phe Thr Phe Gly Gln Gly Thr Lys Leu Gln Ile Thr Gly Ser
        115                 120                 125
```

Thr Ser Gly Gly Gly Ser Gly Gly Gly Ser Ser
    130             135             140

Gln Val Gln Leu Val Gln Ser Gly Gly Val Val Gln Pro Gly Arg
145             150                 155                 160

Ser Leu Arg Leu Ser Cys Lys Ala Ser Gly Tyr Thr Phe Thr Arg Tyr
            165                 170                 175

Thr Met His Trp Val Arg Gln Ala Pro Gly Lys Gly Leu Glu Trp Ile
                180                 185                 190

Gly Tyr Ile Asn Pro Ser Arg Gly Tyr Thr Asn Tyr Asn Gln Lys Val
            195                 200                 205

Lys Asp Arg Phe Thr Ile Ser Arg Asp Asn Ser Lys Asn Thr Ala Phe
210                 215                 220

Leu Gln Met Asp Ser Leu Arg Pro Glu Asp Thr Gly Val Tyr Phe Cys
225                 230                 235                 240

Ala Arg Tyr Tyr Asp Asp His Tyr Cys Leu Asp Tyr Trp Gly Gln Gly
                245                 250                 255

Thr Pro Val Thr Val Ser Ser Glu Pro Lys Ser Cys Asp Lys Thr His
            260                 265                 270

Thr Cys Pro Pro Cys Gly Gly Gly Ser Gly Gly Gly Ser Gly Gly
            275                 280                 285

Gln Pro Arg Glu Pro Gln Val Tyr Thr Leu Pro Pro Ser Arg Asp Glu
290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
            355                 360                 365

Val Phe Ser Cys Ser Val Met His Glu Ala Leu His Asn His Tyr Thr
370                 375                 380

Gln Lys Ser Leu Ser Leu Ser Pro Gly Lys
385                 390

<210> SEQ ID NO 10
<211> LENGTH: 1185
<212> TYPE: DNA
<213> ORGANISM: Artificial Sequence
<220> FEATURE:
<223> OTHER INFORMATION: Antigen binding construct or subpart thereof

<400> SEQUENCE: 10
atggaaaccg cacactctgct gctgtgggtc ctgctgctgt gggtgcccgg atcaactggt      60
gacatccaga tgacacagtc tccctcttct ctgtccgcct ctgtgggcga tcgagtgaca     120
atcacctgta gcgcttcatc ctccgtgtct tacatgaatt ggtaccagca gacccctggc     180
aaagctccta acgatggat ctacgacacc tccaaactgg cttccggcgt gccttcacga     240 tttctggtt ctggttctgg gaccgactac acctttacca tctcatcact gcagcctgag     300
gatatcgcca catactactg tcagcagtgg tctagcaacc ctttcacatt cgggcagggc     360
acaaaactgc agatcaccgg ctcaacctct ggcggtggct ctggcggcgg tagtggtggt     420
ggtggttcta gtcaggtcca gctggtccag tctggtggag gagtggtcca gcccgggaga     480
tcactgaggc tgtcctgtaa ggctagtggc tacacttta cacggtacac catgcattgg     540

```
gtgaggcagg cacctgggaa aggcctggaa tggatcggat acatcaaccc tagtagggga    600
tacacaaact acaatcagaa agtcaaggac cggttcacaa tctctaggga caactctaaa    660
aacaccgctt ttctgcagat ggactcactg aggcctgagg acactggagt gtactttgt     720 gctcggtact acgatgatca ttactgcctg gattactggg gacagggac  acctgtcact    780 gtctcttccg aacccaaatc ttgtgacaaa acccacacat gccctccatg tggtggcgga    840
tcctctggtg gcggttctgg ggggcagcct agggaacctc aggtgtacac actgccacct    900
tctcgtgacg aactgaccaa aaaccaggtg tcactgacct gtctggtcaa gggcttttac    960
ccttccgaca ttgctgtgga gtgggagtca aatggccagc ctgaaaacaa ctacaaaacc   1020 acacccccg tcctggattc cgatggctct ttcttcctgt actctaaact gaccgtcgac    1080
aaatctcgat ggcagcaggg aaacgtgttc tcttgttccg tcatgcacga ggctctgcac   1140
aatcactaca cacagaaatc actgagcctg agccctggaa aatga                   1185
```

<210> SEQ ID NO 11
<211> LENGTH: 394
<212> TYPE: PRT
<213> ORGANISM: Artificial Sequence
<220> FEATURE:
<223> OTHER INFORMATION: Antigen binding construct or subpart thereof

<400> SEQUENCE: 11

```
Met Glu Thr Asp Thr Leu Leu Leu Trp Val Leu Leu Leu Trp Val Pro
  1               5                  10                  15

Gly Ser Thr Gly Asp Ile Gln Met Thr Gln Ser Pro Ser Ser Leu Ser
             20                  25                  30

Ala Ser Val Gly Asp Arg Val Thr Ile Thr Cys Ser Ala Ser Ser Ser
         35                  40                  45

Val Ser Tyr Met Asn Trp Tyr Gln Gln Thr Pro Gly Lys Ala Pro Lys
     50                  55                  60

Arg Trp Ile Tyr Asp Thr Ser Lys Leu Ala Ser Gly Val Pro Ser Arg
 65                  70                  75                  80

Phe Ser Gly Ser Gly Ser Gly Thr Asp Tyr Thr Phe Thr Ile Ser Ser
                 85                  90                  95

Leu Gln Pro Glu Asp Ile Ala Thr Tyr Tyr Cys Gln Gln Trp Ser Ser
            100                 105                 110

Asn Pro Phe Thr Phe Gly Gln Gly Thr Lys Leu Gln Ile Thr Gly Ser
        115                 120                 125

Thr Ser Gly Gly Gly Ser Gly Gly Gly Ser Gly Gly Gly Gly Ser Ser
    130                 135                 140

Gln Val Gln Leu Val Gln Ser Gly Gly Gly Val Val Gln Pro Gly Arg
145                 150                 155                 160

Ser Leu Arg Leu Ser Cys Lys Ala Ser Gly Tyr Thr Phe Thr Arg Tyr
                165                 170                 175

Thr Met His Trp Val Arg Gln Ala Pro Gly Lys Gly Leu Glu Trp Ile
            180                 185                 190

Gly Tyr Ile Asn Pro Ser Arg Gly Tyr Thr Asn Tyr Asn Gln Lys Val
        195                 200                 205

Lys Asp Arg Phe Thr Ile Ser Arg Asp Asn Ser Lys Asn Thr Ala Phe
    210                 215                 220

Leu Gln Met Asp Ser Leu Arg Pro Glu Asp Thr Gly Val Tyr Phe Cys
225                 230                 235                 240

Ala Arg Tyr Tyr Asp Asp His Tyr Cys Leu Asp Tyr Trp Gly Gln Gly
```

```
                245                 250                 255
Thr Pro Val Thr Val Ser Ser Glu Pro Lys Ser Cys Asp Lys Thr His
            260                 265                 270
Thr Cys Pro Pro Cys Gly Gly Gly Ser Ser Gly Gly Ser Gly Gly
        275                 280                 285
Gln Pro Arg Glu Pro Gln Val Tyr Thr Leu Pro Pro Ser Arg Asp Glu
    290                 295                 300
Leu Thr Lys Asn Gln Val Ser Leu Thr Cys Leu Val Lys Gly Phe Tyr
305                 310                 315                 320
Pro Ser Asp Ile Ala Val Glu Trp Glu Ser Asn Gly Gln Pro Glu Asn
                325                 330                 335
Asn Tyr Lys Thr Thr Pro Pro Val Leu Asp Ser Asp Gly Ser Phe Phe
            340                 345                 350
Leu Tyr Ser Lys Leu Thr Val Asp Lys Ser Arg Trp Gln Gln Gly Asn
        355                 360                 365
Val Phe Ser Cys Ser Val Met His Glu Ala Leu His Asn His Tyr Thr
370                 375                 380
Gln Lys Ser Leu Ser Leu Ser Pro Gly Lys
385                 390
```

<210> SEQ ID NO 12
<211> LENGTH: 1185
<212> TYPE: DNA
<213> ORGANISM: Artificial Sequence
<220> FEATURE:
<223> OTHER INFORMATION: Antigen binding construct or subpart thereof

<400> SEQUENCE: 12

```
atggaaaccg acactctgct gctgtgggtc ctgctgctgt gggtgcccgg atcaactggt    60
gacatccaga tgacacagtc tccctcttct ctgtccgcct ctgtgggcga tcgagtgaca   120
atcacctgta gcgcttcatc ctccgtgtct tacatgaatt ggtaccagca gacccctggc   180
aaagctccta acgatggat ctacgacacc tccaaactgg cttccggcgt gccttcacga   240
ttttctggtt ctggttctgg gaccgactac acctttacca tctcatcact gcagcctgag   300
gatatcgcca catactactg tcagcagtgg tctagcaacc ctttcacatt cgggcagggc   360
acaaaactgc agatcaccgg ctcaacctct ggcggtggct ctggcggcgg tagtggtggt   420
ggtggttcta gtcaggtcca gctggtccag tctggtggag agtggtcca gcccgggaga   480
tcactgaggc tgtcctgtaa ggctagtggc tacactttta cacggtacac catgcattgg   540
gtgaggcagg cacctgggaa aggcctggaa tggatcggat acatcaaccc tagtagggga   600
tacacaaaact acaatcagaa agtcaaggac cggttcacaa tctctaggga caactctaaa   660
aacaccgctt ttctgcagat ggactcactg aggcctgagg acactggagt gtactttgt    720
gctcggtact acgatgatca ttactgcctg gattactggg gacagggac acctgtcact   780
gtctcttccg aacccaaatc ttgtgacaaa acccacacat gccctccatg tggtggcgga   840
tcctctggtg gcggttctgg ggggcagcct agggaacctc aggtgtacac actgccacct   900
tctcgtgacg aactgaccaa aaaccaggtg tcactgacct gtctggtcaa gggcttttac   960
ccttccgaca ttgctgtgga gtgggagtca atggccagc tgaaaacaa ctacaaaacc  1020
acaccccccg tcctggattc cgatggctct ttcttcctgt actctaaact gaccgtcgac  1080
aaatctcgat ggcagcaggg aaacgtgttc tcttgttccg tcatgcacga ggctctgcac  1140
aatcactaca cacagaaatc actgagcctg agccctggaa aatga              1185
```

<210> SEQ ID NO 13
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 13

```
Met Glu Thr Asp Thr Leu Leu Leu Trp Val Leu Leu Trp Val Pro
 1               5                  10                  15

Gly Ser Thr Gly Glu Ile Val Leu Thr Gln Ser Pro Ala Thr Leu Ser
                20                  25                  30

Leu Ser Pro Gly Glu Arg Ala Thr Leu Ser Cys Ser Ala Ser Ser Ser
            35                  40                  45

Val Ser Tyr Met Asn Trp Tyr Gln Gln Lys Pro Gly Gln Ala Pro Arg
 50                  55                  60

Leu Leu Ile Tyr Asp Thr Ser Lys Leu Ala Ser Gly Val Pro Ala His
 65                  70                  75                  80

Phe Arg Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Ser Ser
            100                 105                 110

Asn Pro Phe Thr Phe Gly Gln Gly Thr Lys Val Glu Ile Lys Ser Gly
        115                 120                 125

Gly Gly Gly Gln Val Gln Leu Val Gln Ser Gly Ala Glu Val Lys Lys
130                 135                 140

Pro Gly Ala Ser Val Lys Val Ser Cys Lys Ala Ser Gly Tyr Thr Phe
145                 150                 155                 160

Thr Arg Tyr Thr Met His Trp Val Arg Gln Ala Pro Gly Gln Gly Leu
                165                 170                 175

Glu Trp Met Gly Tyr Ile Asn Pro Ser Arg Gly Tyr Thr Asn Tyr Asn
            180                 185                 190

Gln Lys Phe Lys Asp Arg Val Thr Met Thr Thr Asp Thr Ser Ile Ser
        195                 200                 205

Thr Ala Tyr Met Glu Leu Ser Arg Leu Arg Ser Asp Asp Thr Ala Val
    210                 215                 220

Tyr Tyr Cys Ala Arg Tyr Tyr Asp Asp His Tyr Cys Leu Asp Tyr Trp
225                 230                 235                 240

Gly Gln Gly Thr Leu Val Thr Val Ser Ser Gly Gly Cys
                245                 250
```

<210> SEQ ID NO 14
<211> LENGTH: 759
<212> TYPE: DNA
<213> ORGANISM: Artificial Sequence
<220> FEATURE:
<223> OTHER INFORMATION: Antigen binding construct or subpart thereof

<400> SEQUENCE: 14

```
atggaaaccg acactctgct gctgtgggtc ctgctgctgt gggtgcccgg atcaactgga      60
gaaatcgtgc tgactcagtc ccctgctaca ctgtctctgt cacctggcga acgagcaaca     120
ctgtcctgtt ctgcctcttc ttctgtctca tacatgaact ggtaccagca gaaacctgga     180
caggctccta gactgctgat ctacgacacc tctaaactgg catctggcgt gcccgctcat     240
tttcgtggct ctggatctgg aaccgacttt accctgacca tctcttccct ggaacctgag     300
gattttgccg tgtactactg ccagcagtgg tctagtaacc ctttcacttt tggccagggc     360
```

```
actaaagtgg agatcaaatc cggtggtggc ggacaggtcc agctggtcca gagtggagct    420
gaggtgaaaa acccggcgc ttccgtcaaa gtctcctgta aggctagcgg atacacattc     480
acacgctaca ccatgcattg ggtccggcag gctcccggac agggcctgga atggatggga    540
tacatcaacc cttctcgggg ctacacaaac tacaaccaga aattcaagga tcgagtgacc    600
atgacaaccg acactagcat ctctaccgcc tacatggaac tgagccggct gagatccgat    660
gataccgctg tctactactg tgctcggtac tacgatgatc attactgcct ggattactgg    720
gggcagggca cactggtgac tgtgagttcc ggaggatgt                           759
```

<210> SEQ ID NO 15
<211> LENGTH: 435
<212> TYPE: PRT
<213> ORGANISM: Artificial Sequence
<220> FEATURE:
<223> OTHER INFORMATION: Antigen binding construct or subpart thereof

<400> SEQUENCE: 15

```
Met Glu Thr Asp Thr Leu Leu Trp Val Leu Leu Trp Val Pro
 1               5                  10                  15

Gly Ser Thr Gly Met Asp Trp Val Trp Thr Leu Leu Phe Leu Leu Ser
                20                  25                  30

Val Thr Ala Gly Val His Ser Gln Val Gln Leu Gln Gln Ser Gly Ala
         35                  40                  45

Glu Leu Ala Arg Pro Gly Ala Ser Val Lys Met Ser Cys Lys Ala Ser
     50                  55                  60

Gly Tyr Thr Phe Thr Arg Tyr Thr Met His Trp Val Lys Gln Arg Pro
 65                  70                  75                  80

Gly Gln Gly Leu Glu Trp Ile Gly Tyr Ile Asn Pro Ser Arg Gly Tyr
                 85                  90                  95

Thr Asn Tyr Asn Gln Lys Phe Lys Asp Lys Ala Thr Leu Thr Thr Asp
            100                 105                 110

Lys Ser Ser Ser Thr Ala Tyr Met Gln Leu Ser Ser Leu Thr Ser Glu
        115                 120                 125

Asp Ser Ala Val Tyr Tyr Cys Ala Arg Tyr Tyr Asp Asp His Tyr Cys
    130                 135                 140

Leu Asp Tyr Trp Gly Gln Gly Thr Thr Leu Thr Val Ser Ser Gly Ser
145                 150                 155                 160

Thr Ser Gly Gly Gly Ser Gly Gly Ser Gly Gly Gly Ser Ser
                165                 170                 175

Met Asp Phe Gln Val Gln Ile Phe Ser Phe Leu Leu Ile Ser Ala Ser
            180                 185                 190

Val Ile Ile Ser Arg Gly Gln Ile Val Leu Thr Gln Ser Pro Ala Ile
        195                 200                 205

Met Ser Ala Ser Pro Gly Glu Lys Val Thr Met Thr Cys Ser Ala Ser
    210                 215                 220

Ser Ser Val Ser Tyr Met Asn Trp Tyr Gln Gln Lys Ser Gly Thr Ser
225                 230                 235                 240

Pro Lys Arg Trp Ile Tyr Asp Thr Ser Lys Leu Ala Ser Gly Val Pro
                245                 250                 255

Ala His Phe Arg Gly Ser Gly Ser Gly Thr Ser Tyr Ser Leu Thr Ile
            260                 265                 270

Ser Gly Met Glu Ala Glu Asp Ala Ala Thr Tyr Tyr Cys Gln Gln Trp
        275                 280                 285
```

```
Ser Ser Asn Pro Phe Thr Phe Gly Ser Gly Thr Lys Leu Glu Ile Asn
    290                 295                 300

Glu Pro Lys Ser Cys Asp Lys Thr His Thr Cys Pro Pro Cys Gly Gly
305                 310                 315                 320

Gly Ser Ser Gly Gly Gly Ser Gly Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 16
<211> LENGTH: 1308
<212> TYPE: DNA
<213> ORGANISM: Artificial Sequence
<220> FEATURE:
<223> OTHER INFORMATION: Antigen binding construct or subpart thereof

<400> SEQUENCE: 16
atggaaaccg acaccctgct gctgtgggtg ctgctgctct gggtcccagg ctccaccggt    60
atggattggg tgtggacctt gctattcctg ttgtcagtaa ctgcaggtgt ccactcccag   120
gtccagctgc agcagtctgg ggctgaactg gcaagacctg ggcctcagt gaagatgtcc    180 tgcaaggctt ctggctacac ctttactagg tacacgatgc actgggtaaa cagagaggct   240
ggacagggtc tggaatggat tggatacatt aatcctagcc gtggttatac taattacaat   300
cagaagttca aggacaaggc cacattgact acagacaaat cctccagcac agcctacatg   360
caactgagca gcctgacatc tgaggactct gcagtctatt actgtgcaag atattatgat   420
gatcattact gccttgacta ctggggccaa ggcaccactc tcacagtctc ctcaggctcc   480
acatccggcg gaggctctgg cggtggatct ggcggaggcg gctcatccat ggattttcaa   540
gtgcagattt tcagcttcct gctaatcagt gcctcagtca atatatccag aggacaaatt   600
gttctcaccc agtctccagc aatcatgtct gcatctccag gggagaaggt caccatgacc   660
tgcagtgcca gctcaagtgt aagttacatg aactggtacc agcagaagtc aggcacctcc   720
cccaaaagat ggatttatga cacatccaaa ctggcttctg gagtccctgc tcacttcagg   780
ggcagtgggt ctgggacctc ttactctctc acaatcagcg gcatggaggc tgaagatgct   840
gccacttatt actgccagca gtggagtagt aacccattca cgttcggctc ggggacaaag   900
ttggaaataa acgagcctaa gtcctgcgac aagacccaca cctgtccccc ttgcggcgga   960
ggaagcagcg gaggcggatc cggtggccag cctcgggagc ctcaggtgta caccctgcct  1020
ccctcccggg acgagctgac caagaaccag gtgtccctga cctgtctggt caagggcttc  1080
tacccttccg atatcgccgt ggagtgggag tccaacggcc agcctgagaa caactacaag  1140 accaccccctc ctgtgctgga ctccgacggc tccttcttcc tgtactccaa gctcacagtg  1200
```

```
gataagtccc ggtggcagca gggcaacgtg ttctcctgct ccgtgatgca cgaggccctg    1260
cacaaccact atacccagaa gtccctgtcc ctgtctcctg gcaagtga                 1308
```

<210> SEQ ID NO 17
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 17

```
Met Glu Thr Asp Thr Leu Leu Leu Trp Val Leu Leu Leu Trp Val Pro
  1               5                  10                  15

Gly Ser Thr Gly Gln Ile Val Leu Thr Gln Ser Pro Ala Ile Met Ser
             20                  25                  30

Ala Ser Pro Gly Glu Lys Val Thr Met Thr Cys Ser Ala Ser Ser Ser
         35                  40                  45

Val Ser Tyr Met Asn Trp Tyr Gln Gln Lys Ser Gly Thr Ser Pro Lys
     50                  55                  60

Arg Trp Ile Tyr Asp Thr Ser Lys Leu Ala Ser Gly Val Pro Ala His
 65                  70                  75                  80

Phe Arg Gly Ser Gly Ser Gly Thr Ser Tyr Ser Leu Thr Ile Ser Gly
                 85                  90                  95

Met Glu Ala Glu Asp Ala Ala Thr Tyr Tyr Cys Gln Gln Trp Ser Ser
            100                 105                 110

Asn Pro Phe Thr Phe Gly Ser Gly Thr Lys Leu Glu Ile Asn Ser Gly
        115                 120                 125

Gly Gly Gly Gln Val Gln Leu Gln Gln Ser Gly Ala Glu Leu Ala Arg
    130                 135                 140

Pro Gly Ala Ser Val Lys Met Ser Cys Lys Ala Ser Gly Tyr Thr Phe
145                 150                 155                 160

Thr Arg Tyr Thr Met His Trp Val Lys Gln Arg Pro Gly Gln Gly Leu
                165                 170                 175

Glu Trp Ile Gly Tyr Ile Asn Pro Ser Arg Gly Tyr Thr Asn Tyr Asn
            180                 185                 190

Gln Lys Phe Lys Asp Lys Ala Thr Leu Thr Thr Asp Lys Ser Ser Ser
        195                 200                 205

Thr Ala Tyr Met Gln Leu Ser Ser Leu Thr Ser Glu Asp Ser Ala Val
    210                 215                 220

Tyr Tyr Cys Ala Arg Tyr Tyr Asp Asp His Tyr Cys Leu Asp Tyr Trp
225                 230                 235                 240

Gly Gln Gly Thr Thr Leu Thr Val Ser Ser Gly Gly Cys
                245                 250
```

<210> SEQ ID NO 18
<211> LENGTH: 762
<212> TYPE: DNA
<213> ORGANISM: Artificial Sequence
<220> FEATURE:
<223> OTHER INFORMATION: Antigen binding construct or subpart thereof

<400> SEQUENCE: 18

```
atggaaaccg acaccctgct gctgtgggtc ctgctcctct gggtgccagg ctctaccggc    60
caaattgttc tcacccagtc tccagcaatc atgtctgcat ctccagggga gaaggtcacc   120
atgacctgca gtgccagctc aagtgtaagt tacatgaact ggtaccagca gaagtcaggc   180
```

```
acctcccca aaagatggat ttatgacaca tccaaactgg cttctggagt ccctgctcac    240
ttcaggggca gtgggtctgg gacctcttac tctctcacaa tcagcggcat ggaggctgaa    300
gatgctgcca cttattactg ccagcagtgg agtagtaacc cattcacgtt cggctcgggg    360
acaaagttgg aaataaactc tggtggaggc gggcaggtcc agctgcagca gtctggggct    420
gaactggcaa gacctggggc ctcagtgaag atgtcctgca aggcttctgg ctacaccttt    480
actaggtaca cgatgcactg ggtaaaacag aggcctggac agggtctgga atggattgga    540
tacattaatc ctagccgtgg ttatactaat tacaatcaga gttcaagga caaggccaca    600 ttgactacag acaaatcctc cagcacagcc tacatgcaac tgagcagcct gacatctgag    660
gactctgcag tctattactg tgcaagatat tatgatgatc attactgcct tgactactgg    720
ggccaaggca ccactctcac agtctcctca ggcggatgct ga                      762
```

<210> SEQ ID NO 19
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 19

```
Met Glu Thr Asp Thr Leu Leu Leu Trp Val Leu Leu Leu Trp Val Pro
 1               5                  10                  15

Gly Ser Thr Gly Gln Val Gln Leu Gln Gln Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Arg Tyr Thr Met His Trp Val Lys Gln Arg Pro Gly Gln Gly
    50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Thr Leu Thr Val Ser Ser Gly Gly Gly Gly
    130                 135                 140

Gln Ile Val Leu Thr Gln Ser Pro Ala Ile Met Ser Ala Ser Pro Gly
145                 150                 155                 160

Glu Lys Val Thr Met Thr Cys Ser Ala Ser Ser Ser Val Ser Tyr Met
                165                 170                 175

Asn Trp Tyr Gln Gln Lys Ser Gly Thr Ser Pro Lys Arg Trp Ile Tyr
            180                 185                 190

Asp Thr Ser Lys Leu Ala Ser Gly Val Pro Ala His Phe Arg Gly Ser
        195                 200                 205

Gly Ser Gly Thr Ser Tyr Ser Leu Thr Ile Ser Gly Met Glu Ala Glu
    210                 215                 220

Asp Ala Ala Thr Tyr Tyr Cys Gln Gln Trp Ser Ser Asn Pro Phe Thr
225                 230                 235                 240

Phe Gly Ser Gly Thr Lys Leu Glu Ile Asn Gly Gly Cys
                245                 250
```

<210> SEQ ID NO 20
<211> LENGTH: 759
<212> TYPE: DNA
<213> ORGANISM: Artificial Sequence
<220> FEATURE:
<223> OTHER INFORMATION: Antigen binding construct or subpart thereof

<400> SEQUENCE: 20

```
atggaaaccg acaccctgct gctgtgggtg ctgctgctct gggtcccagg ctccaccggt    60
caggtccagc tgcagcagtc tggggctgaa ctggcaagac tgggggcctc agtgaagatg   120
tcctgcaagg cttctggcta cacctttact aggtacacga tgcactgggt aaaacagagg   180
cctggacagg gtctggaatg gattggatac attaatccta gccgtggtta tactaattac   240
aatcagaagt tcaaggacaa ggccacattg actacagaca atcctccag cacagcctac   300
atgcaactga gcagcctgac atctgaggac tctgcagtct attactgtgc aagatattat   360
gatgatcatt actgccttga ctactgggc caaggcacca ctctcacagt ctcctcaagt   420
ggtgaggag gccaaattgt tctcacccag tctccagcaa tcatgtctgc atctccaggg   480
gagaaggtca ccatgacctg cagtgccagc tcaagtgtaa gttacatgaa ctggtaccag   540
cagaagtcag gcacctcccc caaaagatgg atttatgaca catccaaact ggcttctgga   600
gtccctgctc acttcagggg cagtgggtct gggacctctt actctctcac aatcagcggc   660
atggaggctg aagatgctgc cacttattac tgccagcagt ggagtagtaa cccattcacg   720
ttcggctcgg ggacaaagtt ggaaataaac ggcggctgc                           759
```

<210> SEQ ID NO 21
<211> LENGTH: 256
<212> TYPE: PRT
<213> ORGANISM: Artificial Sequence
<220> FEATURE:
<223> OTHER INFORMATION: Antigen binding construct or subpart thereof

<400> SEQUENCE: 21

```
Met Glu Thr Asp Thr Leu Leu Leu Trp Val Leu Leu Leu Trp Val Pro
  1               5                  10                  15

Gly Ser Thr Gly Gln Ile Val Leu Thr Gln Ser Pro Ala Ile Met Ser
             20                  25                  30

Ala Ser Pro Gly Glu Lys Val Thr Met Thr Cys Ser Ala Ser Ser Ser
         35                  40                  45

Val Ser Tyr Met Asn Trp Tyr Gln Gln Lys Ser Gly Thr Ser Pro Lys
     50                  55                  60

Arg Trp Ile Tyr Asp Thr Ser Lys Leu Ala Ser Gly Val Pro Ala His
 65                  70                  75                  80

Phe Arg Gly Ser Gly Ser Gly Thr Ser Tyr Ser Leu Thr Ile Ser Gly
                 85                  90                  95

Met Glu Ala Glu Asp Ala Ala Thr Tyr Tyr Cys Gln Gln Trp Ser Ser
            100                 105                 110

Asn Pro Phe Thr Phe Gly Ser Gly Thr Lys Leu Glu Ile Asn Gly Gly
        115                 120                 125

Gly Ser Gly Gly Gly Gly Gln Val Gln Leu Gln Gln Ser Gly Ala Glu
    130                 135                 140

Leu Ala Arg Pro Gly Ala Ser Val Lys Met Ser Cys Lys Ala Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
```

```
            180                 185                 190
Asn Tyr Asn Gln Lys Phe Lys Asp Lys Ala Thr Leu Thr Thr Asp Lys
        195                 200                 205

Ser Ser Ser Thr Ala Tyr Met Gln Leu Ser Ser Leu Thr Ser Glu Asp
    210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Gly Gly Cys
            245                 250                 255

<210> SEQ ID NO 22
<211> LENGTH: 768
<212> TYPE: DNA
<213> ORGANISM: Artificial Sequence
<220> FEATURE:
<223> OTHER INFORMATION: Antigen binding construct or subpart thereof

<400> SEQUENCE: 22
atggaaaccg acaccctgct gctgtgggtg ctgctgctct gggtcccagg ctccaccggt      60
caaattgttc tcacccagtc tccagcaatc atgtctgcat ctccagggga aaggtcacc     120 atgacctgca gtgccagctc aagtgtaagt tacatgaact ggtaccagca gaagtcaggc     180
acctccccca aaagatggat ttatgacaca tccaaactgg cttctggagt ccctgctcac     240
ttcaggggca gtgggtctgg gacctcttac tctctcacaa tcagcggcat ggaggctgaa     300
gatgctgcca cttattactg ccagcagtgg agtagtaacc cattcacgtt cggctcgggg     360
acaaagttgg aaataaacgg cggagggagt ggcggaggcg ccaggtcca gctgcagcag     420 tctggggctg aactggcaag acctggggcc tcagtgaaga tgtcctgcaa ggcttctggc     480 tacacccttta ctaggtacac gatgcactgg gtaaaacaga ggcctggaca gggtctggaa     540
tggattggat acattaatcc tagccgtggt tatactaatt acaatcagaa gttcaaggac     600
aaggccacat tgactacaga caaatcctcc agcacagcct acatgcaact gagcagcctg     660
acatctgagg actctgcagt ctattactgt gcaagatatt atgatgatca ttactgcctt     720
gactactggg gccaaggcac cactctcaca gtctcctcag gcggctgc                    768

<210> SEQ ID NO 23
<211> LENGTH: 256
<212> TYPE: PRT
<213> ORGANISM: Artificial Sequence
<220> FEATURE:
<223> OTHER INFORMATION: Antigen binding construct or subpart thereof

<400> SEQUENCE: 23

Met Glu Thr Asp Thr Leu Leu Leu Trp Val Leu Leu Leu Trp Val Pro
1               5                  10                  15

Gly Ser Thr Gly Gln Val Gln Leu Gln Gln Ser Gly Ala Glu Leu Ala
            20                  25                  30

Arg Pro Gly Ala Ser Val Lys Met Ser Cys Lys Ala Ser Gly Tyr Thr
        35                  40                  45

Phe Thr Arg Tyr Thr Met His Trp Val Lys Gln Arg Pro Gly Gln Gly
    50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Lys Ala Thr Leu Thr Thr Asp Lys Ser Ser
                85                  90                  95

Ser Thr Ala Tyr Met Gln Leu Ser Ser Leu Thr Ser Glu Asp Ser Ala
```

Val Tyr Tyr Cys Ala Arg Tyr Tyr Asp Asp His Tyr Cys Leu Asp Tyr
            100                 105                 110
                115                 120                 125

Trp Gly Gln Gly Thr Thr Leu Thr Val Ser Ser Gly Gly Gly Ser Gly
    130                 135                 140

Gly Gly Gly Gln Ile Val Leu Thr Gln Ser Pro Ala Ile Met Ser Ala
145                 150                 155                 160

Ser Pro Gly Glu Lys Val Thr Met Thr Cys Ser Ala Ser Ser Ser Val
                165                 170                 175

Ser Tyr Met Asn Trp Tyr Gln Gln Lys Ser Gly Thr Ser Pro Lys Arg
            180                 185                 190

Trp Ile Tyr Asp Thr Ser Lys Leu Ala Ser Gly Val Pro Ala His Phe
        195                 200                 205

Arg Gly Ser Gly Ser Gly Thr Ser Tyr Ser Leu Thr Ile Ser Gly Met
    210                 215                 220

Glu Ala Glu Asp Ala Ala Thr Tyr Tyr Cys Gln Gln Trp Ser Ser Asn
225                 230                 235                 240

Pro Phe Thr Phe Gly Ser Gly Thr Lys Leu Glu Ile Asn Gly Gly Cys
                245                 250                 255

<210> SEQ ID NO 24
<211> LENGTH: 768
<212> TYPE: DNA
<213> ORGANISM: Artificial Sequence
<220> FEATURE:
<223> OTHER INFORMATION: Antigen binding construct or subpart thereof

<400> SEQUENCE: 24
atggaaaccg acaccctgct gctgtgggtg ctgctgctct gggtcccagg ctccaccggt      60
caggtccagc tgcagcagtc tggggctgaa ctggcaagac tggggcctc agtgaagatg     120 tcctgcaagg cttctggcta cacctttact aggtacacga tgcactgggt aaaacagagg     180
cctggacagg gtctggaatg gattggatac attaatccta gccgtggtta tactaattac     240
aatcagaagt tcaaggacaa ggccacattg actacagaca atcctccag cacagcctac     300 atgcaactga gcagcctgac atctgaggac tctgcagtct attactgtgc aagatattat     360
gatgatcatt actgccttga ctactggggc caaggcacca ctctcacagt ctcctcaggc     420
ggagggagtg gcggaggcgg ccaaattgtt ctcacccagt ctccagcaat catgtctgca     480
tctccagggg agaaggtcac catgacctgc agtgccagct caagtgtaag ttacatgaac     540
tggtaccagc agaagtcagg cacctccccc aaaagatgga tttatgacac atccaaactg     600
gcttctggag tccctgctca cttcagggc agtgggtctg ggacctctta ctctctcaca     660
atcagcggca tggaggctga agatgctgcc acttattact gccagcagtg gagtagtaac     720
ccattcacgt tcggctcggg gacaaagttg gaaataaacg gcggctgc                  768

<210> SEQ ID NO 25
<211> LENGTH: 394
<212> TYPE: PRT
<213> ORGANISM: Artificial Sequence
<220> FEATURE:
<223> OTHER INFORMATION: Antigen binding construct or subpart thereof

<400> SEQUENCE: 25

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Gly Gly Val Val

```
            20                  25                  30
Gln Pro Gly Arg Ser Leu Arg Leu Ser Cys Lys Ala Ser Gly Tyr Thr
            35                  40                  45
Phe Thr Arg Tyr Thr Met His Trp Val Arg Gln Ala Pro Gly Lys Gly
            50                  55                  60
Leu Glu Trp Ile Gly Tyr Ile Asn Pro Ser Arg Gly Tyr Thr Asn Tyr
 65                 70                  75                  80
Asn Gln Lys Val Lys Asp Arg Phe Thr Ile Ser Arg Asp Asn Ser Lys
                85                  90                  95
Asn Thr Ala Phe Leu Gln Met Asp Ser Leu Arg Pro Glu Asp Thr Gly
            100                 105                 110
Val Tyr Phe Cys Ala Arg Tyr Tyr Asp Asp His Tyr Cys Leu Asp Tyr
            115                 120                 125
Trp Gly Gln Gly Thr Pro Val Thr Val Ser Ser Gly Ser Thr Ser Gly
            130                 135                 140
Gly Gly Ser Gly Gly Gly Ser Gly Gly Gly Ser Ser Asp Ile Gln
145                 150                 155                 160
Met Thr Gln Ser Pro Ser Ser Leu Ser Ala Ser Val Gly Asp Arg Val
                165                 170                 175
Thr Ile Thr Cys Ser Ala Ser Ser Val Ser Tyr Met Asn Trp Tyr
                180                 185                 190
Gln Gln Thr Pro Gly Lys Ala Pro Lys Arg Trp Ile Tyr Asp Thr Ser
                195                 200                 205
Lys Leu Ala Ser Gly Val Pro Ser Arg Phe Ser Gly Ser Gly Ser Gly
            210                 215                 220
Thr Asp Tyr Thr Phe Thr Ile Ser Ser Leu Gln Pro Glu Asp Ile Ala
225                 230                 235                 240
Thr Tyr Tyr Cys Gln Gln Trp Ser Ser Asn Pro Phe Thr Phe Gly Gln
                245                 250                 255
Gly Thr Lys Leu Gln Ile Thr Glu Pro Lys Ser Cys Asp Lys Thr His
            260                 265                 270
Thr Cys Pro Pro Cys Gly Gly Gly Ser Gly Gly Gly Ser Gly Gly
            275                 280                 285
Gln Pro Arg Glu Pro Gln Val Tyr Thr Leu Pro Pro Ser Arg Asp Glu
            290                 295                 300
Leu Thr Lys Asn Gln Val Ser Leu Thr Cys Leu Val Lys Gly Phe Tyr
305                 310                 315                 320
Pro Ser Asp Ile Ala Val Glu Trp Glu Ser Asn Gly Gln Pro Glu Asn
                325                 330                 335
Asn Tyr Lys Thr Thr Pro Pro Val Leu Asp Ser Asp Gly Ser Phe Phe
            340                 345                 350
Leu Tyr Ser Lys Leu Thr Val Asp Lys Ser Arg Trp Gln Gln Gly Asn
            355                 360                 365
Val Phe Ser Cys Ser Val Met His Glu Ala Leu His Asn His Tyr Thr
            370                 375                 380
Gln Lys Ser Leu Ser Leu Ser Pro Gly Lys
385                 390

<210> SEQ ID NO 26
<211> LENGTH: 1185
<212> TYPE: DNA
<213> ORGANISM: Artificial Sequence
<220> FEATURE:
<223> OTHER INFORMATION: Antigen binding construct or subpart thereof
```

<400> SEQUENCE: 26

```
atggaaaccg acaccctgct gctgtgggtg ctgctgctct gggtcccagg ctccaccggt    60
caggtccagc tggtccagtc tggtggagga gtggtccagc ccgggagatc actgaggctg   120
tcctgtaagg ctagtggcta cacttttaca cggtacacca tgcattgggt gaggcaggca   180
cctgggaaag gcctggaatg gatcggatac atcaaccta gtagggata cacaaactac   240
aatcagaaag tcaaggaccg gttcacaatc tctagggaca actctaaaaa caccgctttt   300
ctgcagatgg actcactgag gcctgaggac actggagtgt acttttgtgc tcggtactac   360
gatgatcatt actgcctgga ttactgggga caggggacac ctgtcactgt ctcttccggc   420
tccacatccg gcggaggctc tggcggtgga tctggcggag gcggctcatc cgacatccag   480
atgacacagt ctccctcttc tctgtccgcc tctgtgggcg atcgagtgac aatcacctgt   540
agcgcttcat cctccgtgtc ttacatgaat tggtaccagc agacccctgg caaagctcct   600
aaacgatgga tctacgacac ctccaaactg gcttccggcg tgccttcacg attttctggt   660
tctggttctg ggaccgacta caccttttacc atctcatcac tgcagcctga ggatatcgcc   720
acatactact gtcagcagtg gtctagcaac ccttttcacat tcgggcaggg cacaaaactg   780
cagatcaccg agcctaagtc ctgcgacaag acccacacct gtcccccttg cggcggagga   840
agcagcggag gcggatccgg tggccagcct cgggagcctc aggtgtacac cctgcctccc   900
tcccgggacg agctgaccaa gaaccaggtg tccctgacct gtctggtcaa gggcttctac   960
ccttccgata tcgccgtgga gtgggagtcc aacggccagc tgagaacaa ctacaagacc  1020
accccctcctg tgctggactc cgacggctcc ttcttcctgt actccaagct cacagtggat  1080
aagtcccggt ggcagcaggg caacgtgttc tcctgctccg tgatgcacga ggccctgcac  1140
aaccactata cccagaagtc cctgtccctg tctcctggca agtga             1185
```

<210> SEQ ID NO 27
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 27

```
Met Glu Thr Asp Thr Leu Leu Leu Trp Val Leu Leu Trp Val Pro
  1               5                  10                  15

Gly Ser Thr Gly Asp Ile Gln Met Thr Gln Ser Pro Ser Ser Leu Ser
             20                  25                  30

Ala Ser Val Gly Asp Arg Val Thr Ile Thr Cys Ser Ala Ser Ser Ser
         35                  40                  45

Val Ser Tyr Met Asn Trp Tyr Gln Gln Thr Pro Gly Lys Ala Pro Lys
     50                  55                  60

Arg Trp Ile Tyr Asp Thr Ser Lys Leu Ala Ser Gly Val Pro Ser Arg
 65                  70                  75                  80

Phe Ser Gly Ser Gly Ser Gly Thr Asp Tyr Thr Phe Thr Ile Ser Ser
                 85                  90                  95

Leu Gln Pro Glu Asp Ile Ala Thr Tyr Tyr Cys Gln Gln Trp Ser Ser
            100                 105                 110

Asn Pro Phe Thr Phe Gly Gln Gly Thr Lys Leu Gln Ile Thr Ser Gly
        115                 120                 125

Gly Gly Gly Gln Val Gln Leu Val Gln Ser Gly Gly Val Val Gln
    130                 135                 140
```

```
Pro Gly Arg Ser Leu Arg Leu Ser Cys Lys Ala Ser Gly Tyr Thr Phe
145                 150                 155                 160

Thr Arg Tyr Thr Met His Trp Val Arg Gln Ala Pro Gly Lys Gly Leu
                165                 170                 175

Glu Trp Ile Gly Tyr Ile Asn Pro Ser Arg Gly Tyr Thr Asn Tyr Asn
            180                 185                 190

Gln Lys Val Lys Asp Arg Phe Thr Ile Ser Arg Asp Asn Ser Lys Asn
        195                 200                 205

Thr Ala Phe Leu Gln Met Asp Ser Leu Arg Pro Glu Asp Thr Gly Val
    210                 215                 220

Tyr Phe Cys Ala Arg Tyr Tyr Asp Asp His Tyr Cys Leu Asp Tyr Trp
225                 230                 235                 240

Gly Gln Gly Thr Pro Val Thr Val Ser Ser Gly Gly Cys
                245                 250
```

<210> SEQ ID NO 28
<211> LENGTH: 759
<212> TYPE: DNA
<213> ORGANISM: Artificial Sequence
<220> FEATURE:
<223> OTHER INFORMATION: Antigen binding construct or subpart thereof

<400> SEQUENCE: 28

```
atggaaaccg acaccctgct gctgtgggtg ctgctgctct gggtcccagg ctccaccggt    60
gacatccaga tgacacagtc tccctcttct ctgtccgcct ctgtgggcga tcgagtgaca   120
atcacctgta gcgcttcatc ctccgtgtct tacatgaatt ggtaccagca gacccctggc   180
aaagctccta acgatggat ctacgacacc tccaaactgg cttccggcgt gccttcacga    240
tttttctggtt ctggttctgg gaccgactac acctttacca tctcatcact gcagcctgag   300
gatatcgcca catactactg tcagcagtgg tctagcaacc ctttcacatt cgggcagggc   360
acaaaactgc agatcaccag tggtggagga ggccaggtcc agctggtcca gtctggtgga   420
ggagtggtcc agcccggag atcactgagg ctgtcctgta aggctagtgg ctacactttt    480
acacggtaca ccatgcattg ggtgaggcag gcacctggga aaggcctgga atggatcgga   540
tacatcaacc ctagtagggg atacacaaac tacaatcaga aagtcaagga ccggttcaca   600
atctctaggg acaactctaa aaacaccgct tttctgcaga tggactcact gaggcctgag   660
gacactggag tgtactttg tgctcggtac tacgatgatc attactgcct ggattactgg   720
ggacagggga cacctgtcac tgtctcttcc ggcggctgc                          759
```

<210> SEQ ID NO 29
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 29

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Gly Gly Val Val
                20                  25                  30

Gln Pro Gly Arg Ser Leu Arg Leu Ser Cys Lys Ala Ser Gly Tyr Thr
            35                  40                  45

Phe Thr Arg Tyr Thr Met His Trp Val Arg Gln Ala Pro Gly Lys Gly
        50                  55                  60
```

```
Leu Glu Trp Ile Gly Tyr Ile Asn Pro Ser Arg Gly Tyr Thr Asn Tyr
 65                  70                  75                  80

Asn Gln Lys Val Lys Asp Arg Phe Thr Ile Ser Arg Asp Asn Ser Lys
                 85                  90                  95

Asn Thr Ala Phe Leu Gln Met Asp Ser Leu Arg Pro Glu Asp Thr Gly
            100                 105                 110

Val Tyr Phe Cys Ala Arg Tyr Tyr Asp Asp His Tyr Cys Leu Asp Tyr
        115                 120                 125

Trp Gly Gln Gly Thr Pro Val Thr Val Ser Ser Gly Gly Gly Gly
    130                 135                 140

Asp Ile Gln Met Thr Gln Ser Pro Ser Ser Leu Ser Ala Ser Val Gly
145                 150                 155                 160

Asp Arg Val Thr Ile Thr Cys Ser Ala Ser Ser Val Ser Tyr Met
            165                 170                 175

Asn Trp Tyr Gln Gln Thr Pro Gly Lys Ala Pro Lys Arg Trp Ile Tyr
                180                 185                 190

Asp Thr Ser Lys Leu Ala Ser Gly Val Pro Ser Arg Phe Ser Gly Ser
            195                 200                 205

Gly Ser Gly Thr Asp Tyr Thr Phe Thr Ile Ser Ser Leu Gln Pro Glu
        210                 215                 220

Asp Ile Ala Thr Tyr Tyr Cys Gln Gln Trp Ser Ser Asn Pro Phe Thr
225                 230                 235                 240

Phe Gly Gln Gly Thr Lys Leu Gln Ile Thr Gly Gly Cys
                245                 250

<210> SEQ ID NO 30
<211> LENGTH: 759
<212> TYPE: DNA
<213> ORGANISM: Artificial Sequence
<220> FEATURE:
<223> OTHER INFORMATION: Antigen binding construct or subpart thereof

<400> SEQUENCE: 30
atggaaaccg acaccctgct gctgtgggtg ctgctgctct gggtcccagg ctccaccggt      60
caggtccagc tggtccagtc tggtggagga gtggtccagc ccgggagatc actgaggctg     120
tcctgtaagg ctagtggcta cacttttaca cggtacacca tgcattgggt gaggcaggca     180
cctgggaaag gcctggaatg gatcggatac atcaacccta gtaggggata cacaaactac     240
aatcagaaag tcaaggaccg gttcacaatc tctagggaca ctctaaaaa caccgctttt     300 ctgcagatgg actcactgag gcctgaggac actggagtgt acttttgtgc tcggtactac     360
gatgatcatt actgcctgga ttactgggga caggggacac ctgtcactgt ctcttccagt     420
ggtggaggag gcgacatcca gatgacacag tctccctctt ctctgtccgc ctctgtgggc     480
gatcgagtga caatcacctg tagcgcttca tcctccgtgt cttacatgaa ttggtaccag     540
cagacccctg gcaaagctcc taaacgatgg atctacgaca cctccaaact ggcttccggc     600
gtgccttcac gattttctgg ttctggttct gggaccgact acacctttac catctcatca     660
ctgcagcctg aggatatcgc cacatactac tgtcagcagt ggtctagcaa ccctttcaca     720
ttcgggcagg gcacaaaact gcagatcacc ggcggctgc                            759

<210> SEQ ID NO 31
<211> LENGTH: 256
<212> TYPE: PRT
<213> ORGANISM: Artificial Sequence
<220> FEATURE:
<223> OTHER INFORMATION: Antigen binding construct or subpart thereof
```

<400> SEQUENCE: 31

```
Met Glu Thr Asp Thr Leu Leu Leu Trp Val Leu Leu Leu Trp Val Pro
 1               5                  10                  15
Gly Ser Thr Gly Asp Ile Gln Met Thr Gln Ser Pro Ser Ser Leu Ser
             20                  25                  30
Ala Ser Val Gly Asp Arg Val Thr Ile Thr Cys Ser Ala Ser Ser Ser
         35                  40                  45
Val Ser Tyr Met Asn Trp Tyr Gln Gln Thr Pro Gly Lys Ala Pro Lys
     50                  55                  60
Arg Trp Ile Tyr Asp Thr Ser Lys Leu Ala Ser Gly Val Pro Ser Arg
 65                  70                  75                  80
Phe Ser Gly Ser Gly Ser Gly Thr Asp Tyr Thr Phe Thr Ile Ser Ser
                 85                  90                  95
Leu Gln Pro Glu Asp Ile Ala Thr Tyr Tyr Cys Gln Gln Trp Ser Ser
            100                 105                 110
Asn Pro Phe Thr Phe Gly Gln Gly Thr Lys Leu Gln Ile Thr Gly Gly
        115                 120                 125
Gly Ser Gly Gly Gly Gly Gln Val Gln Leu Val Gln Ser Gly Gly Gly
    130                 135                 140
Val Val Gln Pro Gly Arg Ser Leu Arg Leu Ser Cys Lys Ala Ser Gly
145                 150                 155                 160
Tyr Thr Phe Thr Arg Tyr Thr Met His Trp Val Arg Gln Ala Pro Gly
                165                 170                 175
Lys Gly Leu Glu Trp Ile Gly Tyr Ile Asn Pro Ser Arg Gly Tyr Thr
            180                 185                 190
Asn Tyr Asn Gln Lys Val Lys Asp Arg Phe Thr Ile Ser Arg Asp Asn
        195                 200                 205
Ser Lys Asn Thr Ala Phe Leu Gln Met Asp Ser Leu Arg Pro Glu Asp
    210                 215                 220
Thr Gly Val Tyr Phe Cys Ala Arg Tyr Tyr Asp Asp His Tyr Cys Leu
225                 230                 235                 240
Asp Tyr Trp Gly Gln Gly Thr Pro Val Thr Val Ser Ser Gly Gly Cys
                245                 250                 255
```

<210> SEQ ID NO 32
<211> LENGTH: 768
<212> TYPE: DNA
<213> ORGANISM: Artificial Sequence
<220> FEATURE:
<223> OTHER INFORMATION: Antigen binding construct or subpart thereof

<400> SEQUENCE: 32

```
atggaaaccg acaccctgct gctgtgggtg ctgctgctct gggtcccagg ctccaccggt    60
gacatccaga tgacacagtc tccctcttct ctgtccgcct ctgtgggcga tcgagtgaca   120
atcacctgta gcgcttcatc ctccgtgtct tacatgaatt ggtaccagca gacccctggc   180
aaagctccta acgatggat ctacgacacc tccaaactgg cttccggcgt gccttcacga   240
tttttctggtt ctggttctgg gaccgactac acctttacca tctcatcact gcagcctgag   300
gatatcgcca catactactg tcagcagtgg tctagcaacc ctttcacatt cgggcagggc   360
acaaaactgc agatcaccgg cggagggagt ggcggaggcg gccaggtcca gctggtccag   420
tctggtggag gagtggtcca gcccgggaga tcactgaggc tgtcctgtaa ggctagtggc   480
tacactttta cacggtacac catgcattgg gtgaggcagg cacctgggaa aggcctggaa   540
```

```
tggatcggat acatcaaccc tagtagggga tacacaaact acaatcagaa agtcaaggac      600
cggttcacaa tctctaggga caactctaaa aacaccgctt ttctgcagat ggactcactg      660
aggcctgagg acactggagt gtactttgt gctcggtact acgatgatca ttactgcctg      720
gattactggg gacaggggac acctgtcact gtctcttccg gcggctgc                  768
```

<210> SEQ ID NO 33
<211> LENGTH: 256
<212> TYPE: PRT
<213> ORGANISM: Artificial Sequence
<220> FEATURE:
<223> OTHER INFORMATION: Antigen binding construct or subpart thereof

<400> SEQUENCE: 33

```
Met Glu Thr Asp Thr Leu Leu Leu Trp Val Leu Leu Leu Trp Val Pro
 1               5                  10                  15

Gly Ser Thr Gly Gln Val Gln Leu Val Gln Ser Gly Gly Gly Val Val
            20                  25                  30

Gln Pro Gly Arg Ser Leu Arg Leu Ser Cys Lys Ala Ser Gly Tyr Thr
        35                  40                  45

Phe Thr Arg Tyr Thr Met His Trp Val Arg Gln Ala Pro Gly Lys Gly
    50                  55                  60

Leu Glu Trp Ile Gly Tyr Ile Asn Pro Ser Arg Gly Tyr Thr Asn Tyr
65                  70                  75                  80

Asn Gln Lys Val Lys Asp Arg Phe Thr Ile Ser Arg Asp Asn Ser Lys
                85                  90                  95

Asn Thr Ala Phe Leu Gln Met Asp Ser Leu Arg Pro Glu Asp Thr Gly
            100                 105                 110

Val Tyr Phe Cys Ala Arg Tyr Tyr Asp Asp His Tyr Cys Leu Asp Tyr
        115                 120                 125

Trp Gly Gln Gly Thr Pro Val Thr Val Ser Ser Gly Gly Gly Ser Gly
    130                 135                 140

Gly Gly Gly Asp Ile Gln Met Thr Gln Ser Pro Ser Ser Leu Ser Ala
145                 150                 155                 160

Ser Val Gly Asp Arg Val Thr Ile Thr Cys Ser Ala Ser Ser Ser Val
                165                 170                 175

Ser Tyr Met Asn Trp Tyr Gln Gln Thr Pro Gly Lys Ala Pro Lys Arg
            180                 185                 190

Trp Ile Tyr Asp Thr Ser Lys Leu Ala Ser Gly Val Pro Ser Arg Phe
        195                 200                 205

Ser Gly Ser Gly Ser Gly Thr Asp Tyr Thr Phe Thr Ile Ser Ser Leu
    210                 215                 220

Gln Pro Glu Asp Ile Ala Thr Tyr Tyr Cys Gln Gln Trp Ser Ser Asn
225                 230                 235                 240

Pro Phe Thr Phe Gly Gln Gly Thr Lys Leu Gln Ile Thr Gly Cys
                245                 250                 255
```

<210> SEQ ID NO 34
<211> LENGTH: 768
<212> TYPE: DNA
<213> ORGANISM: Artificial Sequence
<220> FEATURE:
<223> OTHER INFORMATION: Antigen binding construct or subpart thereof

<400> SEQUENCE: 34

```
atggaaaccg acaccctgct gctgtgggtg ctgctgctct gggtcccagg ctccaccggt       60
caggtccagc tggtccagtc tggtggagga gtggtccagc ccgggagatc actgaggctg      120
```

```
tcctgtaagg ctagtggcta cacttttaca cggtacacca tgcattgggt gaggcaggca    180
cctgggaaag gcctggaatg gatcggatac atcaaccota gtagggata cacaaactac    240 aatcagaaag tcaaggaccg gttcacaatc tctagggaca actctaaaaa caccgctttt    300
ctgcagatgg actcactgag gcctgaggac actggagtgt acttttgtgc tcggtactac    360
gatgatcatt actgcctgga ttactgggga caggggacac ctgtcactgt ctcttccggc    420
ggagggagtg gcggaggcgg cgacatccag atgacacagt ctcctcttc tctgtccgcc    480 tctgtgggcg atcgagtgac aatcacctgt agcgcttcat cctccgtgtc ttacatgaat    540
tggtaccagc agaccoctgg caaagctcct aaacgatgga tctacgacac ctccaaactg    600
gcttccggcg tgccttcacg atttttctggt tctggttctg gaccgacta cacctttacc    660 atctcatcac tgcagcctga ggatatcgcc acatactact gtcagcagtg gtctagcaac    720 ccttcacat tcgggcaggg cacaaaactg cagatcaccg gcggctgc    768
```

<210> SEQ ID NO 35
<211> LENGTH: 394
<212> TYPE: PRT
<213> ORGANISM: Artificial Sequence
<220> FEATURE:
<223> OTHER INFORMATION: Antigen binding construct or subpart thereof

<400> SEQUENCE: 35

```
Met Glu Thr Asp Thr Leu Leu Leu Trp Val Leu Leu Leu Trp Val Pro
 1               5                  10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Arg Tyr Thr Met His Trp Val Arg Gln Ala Pro Gly Gln Gly
    50                  55                  60

Leu Glu Trp Met Gly Tyr Ile Asn Pro Ser Arg Gly Tyr Thr Asn Tyr
65                  70                  75                  80

Asn Gln Lys Phe Lys Asp Arg Val Thr Met Thr Thr Asp Thr Ser Ile
                85                  90                  95

Ser Thr Ala Tyr Met Glu Leu Ser Arg Leu Arg Ser Asp Asp Thr Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Leu Val Thr Val Ser Ser Gly Ser Thr Ser Gly
    130                 135                 140

Gly Gly Ser Gly Gly Gly Ser Gly Gly Gly Ser Ser Glu Ile Val
145                 150                 155                 160

Leu Thr Gln Ser Pro Ala Thr Leu Ser Leu Ser Pro Gly Glu Arg Ala
                165                 170                 175

Thr Leu Ser Cys Ser Ala Ser Ser Val Ser Tyr Met Asn Trp Tyr
            180                 185                 190

Gln Gln Lys Pro Gly Gln Ala Pro Arg Leu Leu Ile Tyr Asp Thr Ser
        195                 200                 205

Lys Leu Ala Ser Gly Val Pro Ala His Phe Arg Gly Ser Gly Ser Gly
    210                 215                 220

Thr Asp Phe Thr Leu Thr Ile Ser Ser Leu Glu Pro Glu Asp Phe Ala
225                 230                 235                 240

Val Tyr Tyr Cys Gln Gln Trp Ser Ser Asn Pro Phe Thr Phe Gly Gln
```

```
            245                 250                 255
Gly Thr Lys Val Glu Ile Lys Glu Pro Lys Ser Cys Asp Lys Thr His
            260                 265                 270

Thr Cys Pro Pro Cys Gly Gly Ser Ser Gly Gly Ser Gly Gly
            275                 280                 285

Gln Pro Arg Glu Pro Gln Val Tyr Thr Leu Pro Pro Ser Arg Asp Glu
            290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
                340                 345                 350

Leu Tyr Ser Lys Leu Thr Val Asp Lys Ser Arg Trp Gln Gln Gly Asn
                355                 360                 365

Val Phe Ser Cys Ser Val Met His Glu Ala Leu His Asn His Tyr Thr
                370                 375                 380

Gln Lys Ser Leu Ser Leu Ser Pro Gly Lys
385                 390

<210> SEQ ID NO 36
<211> LENGTH: 1185
<212> TYPE: DNA
<213> ORGANISM: Artificial Sequence
<220> FEATURE:
<223> OTHER INFORMATION: Antigen binding construct or subpart thereof

<400> SEQUENCE: 36
atggaaaccg acaccctgct gctgtgggtg ctgctgctct gggtcccagg ctccaccggt      60
caggtccagc tggtccagag tggagctgag gtgaaaaaac ccggcgcttc cgtcaaagtc     120
tcctgtaagg ctagcggata caccttttact cgctacacca tgcattgggt ccggcaggct    180
cccggacagg gcctggaatg gatgggatac atcaacccctt ctcggggcta cacaaactac    240
aatcagaaat tcaaggatcg agtgaccatg acaaccgaca cttcaatctc taccgcttac    300
atggaactgt ctcggctgag gagtgacgat accgctgtct actactgtgc tcggtactac    360
gacgaccatt actgcctgga ttactggggg cagggcacac tggtgactgt gtctagcggc    420
tccacatccg gcggaggctc tggcggtgga tctggcggag cggctcatc cgaaatcgtg     480 ctgactcagt cccctgctac actgtctctg tcacctggcg aacgagcaac actgtcctgt    540
tctgcctctt cttctgtctc atacatgaac tggtaccagc agaaacctgg acaggctcct    600
agactgctga tctacgacac ctctaaactg gcatctggcg tgcccgctca ttttcgtggc    660
tctggatctg gaaccgactt taccctgacc atctcttccc tggaacctga ggattttgcc    720
gtgtactact gccagcagtg gtctagtaac ccctttcactt ttggccaggg cactaaagtg    780
gagatcaagg agcctaagtc ctgcgacaag acccacacct gtccccttg cggcggagga    840 agcagcggag gcggatccgg tggccagcct cgggagcctc aggtgtacac cctgcctccc    900
tcccgggacg agctgaccaa gaaccaggtg tccctgacct gtctggtcaa gggcttctac    960
ccttccgata tcgccgtgga gtgggagtcc aacggccagc tgagaacaa ctacaagacc    1020 accccctcctg tgctggactc cgacggctcc ttcttcctgt actccaagct cacagtggat    1080 aagtccggt ggcagcaggg caacgtgttc tcctgctccg tgatgcacga ggccctgcac    1140
aaccactata cccagaagtc cctgtccctg tctcctggca agtga                    1185
```

<210> SEQ ID NO 37
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 37

```
Met Glu Thr Asp Thr Leu Leu Leu Trp Val Leu Leu Leu Trp Val Pro
1               5                   10                  15

Gly Ser Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Val Ser Tyr Met Asn Trp Tyr Gln Gln Lys Pro Gly Gln Ala Pro Arg
    50                  55                  60

Leu Leu Ile Tyr Asp Thr Ser Lys Leu Ala Ser Gly Val Pro Ala His
65                  70                  75                  80

Phe Arg Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Ser Ser
            100                 105                 110

Asn Pro Phe Thr Phe Gly Gln Gly Thr Lys Val Glu Ile Lys Ser Gly
        115                 120                 125

Gly Gly Gly Gln Val Gln Leu Val Gln Ser Gly Ala Glu Val Lys Lys
    130                 135                 140

Pro Gly Ala Ser Val Lys Val Ser Cys Lys Ala Ser Gly Tyr Thr Phe
145                 150                 155                 160

Thr Arg Tyr Thr Met His Trp Val Arg Gln Ala Pro Gly Gln Gly Leu
                165                 170                 175

Glu Trp Met Gly Tyr Ile Asn Pro Ser Arg Gly Tyr Thr Asn Tyr Asn
            180                 185                 190

Gln Lys Phe Lys Asp Arg Val Thr Met Thr Thr Asp Thr Ser Ile Ser
        195                 200                 205

Thr Ala Tyr Met Glu Leu Ser Arg Leu Arg Ser Asp Asp Thr Ala Val
    210                 215                 220

Tyr Tyr Cys Ala Arg Tyr Tyr Asp Asp His Tyr Cys Leu Asp Tyr Trp
225                 230                 235                 240

Gly Gln Gly Thr Leu Val Thr Val Ser Ser Gly Gly Cys
                245                 250
```

<210> SEQ ID NO 38
<211> LENGTH: 759
<212> TYPE: DNA
<213> ORGANISM: Artificial Sequence
<220> FEATURE:
<223> OTHER INFORMATION: Antigen binding construct or subpart thereof

<400> SEQUENCE: 38

```
atggaaaccg acaccctgct gctgtgggtg ctgctgctct gggtcccagg ctccaccggt      60
gaaatcgtgc tgactcagtc ccctgctaca ctgtctctgt cacctggcga acgagcaaca    120
ctgtcctgtt ctgcctcttc ttctgtctca tacatgaact ggtaccagca gaaacctgga    180
caggctccta gactgctgat ctacgacacc tctaaactgg catctggcgt gcccgctcat    240
tttcgtggct ctggatctgg aaccgacttt accctgacca tctcttccct ggaacctgag    300
gattttgccg tgtactactg ccagcagtgg tctagtaacc cttttcactt tggccagggc    360
```

```
actaaagtgg agatcaagag tggtggagga ggccaggtcc agctggtcca gagtggagct    420
gaggtgaaaa acccggcgc ttccgtcaaa gtctcctgta aggctagcgg atacaccttt    480
actcgctaca ccatgcattg ggtccggcag gctcccggac agggcctgga atggatggga    540
tacatcaacc cttctcgggg ctacacaaac tacaatcaga aattcaagga tcgagtgacc    600
atgacaaccg acacttcaat ctctaccgct tacatggaac tgtctcggct gaggagtgac    660
gataccgctg tctactactg tgctcggtac tacgacgacc attactgcct ggattactgg    720
gggcagggca cactggtgac tgtgtctagc ggcggctgc                          759
```

<210> SEQ ID NO 39
<211> LENGTH: 253
<212> TYPE: PRT
<213> ORGANISM: Artificial Sequence
<220> FEATURE:
<223> OTHER INFORMATION: Antigen binding construct or subpart thereof

<400> SEQUENCE: 39

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Arg Tyr Thr Met His Trp Val Arg Gln Ala Pro Gly Gln Gly
    50                  55                  60

Leu Glu Trp Met Gly Tyr Ile Asn Pro Ser Arg Gly Tyr Thr Asn Tyr
65                  70                  75                  80

Asn Gln Lys Phe Lys Asp Arg Val Thr Met Thr Thr Asp Thr Ser Ile
                85                  90                  95

Ser Thr Ala Tyr Met Glu Leu Ser Arg Leu Arg Ser Asp Asp Thr Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Leu Val Thr Val Ser Ser Gly Gly Gly Gly
    130                 135                 140

Glu Ile Val Leu Thr Gln Ser Pro Ala Thr Leu Ser Leu Ser Pro Gly
145                 150                 155                 160

Glu Arg Ala Thr Leu Ser Cys Ser Ala Ser Ser Val Ser Tyr Met
                165                 170                 175

Asn Trp Tyr Gln Gln Lys Pro Gly Gln Ala Pro Arg Leu Leu Ile Tyr
            180                 185                 190

Asp Thr Ser Lys Leu Ala Ser Gly Val Pro Ala His Phe Arg Gly Ser
        195                 200                 205

Gly Ser Gly Thr Asp Phe Thr Leu Thr Ile Ser Ser Leu Glu Pro Glu
    210                 215                 220

Asp Phe Ala Val Tyr Tyr Cys Gln Gln Trp Ser Ser Asn Pro Phe Thr
225                 230                 235                 240

Phe Gly Gln Gly Thr Lys Val Glu Ile Lys Gly Gly Cys
                245                 250
```

<210> SEQ ID NO 40
<211> LENGTH: 759
<212> TYPE: DNA
<213> ORGANISM: Artificial Sequence
<220> FEATURE:

<223> OTHER INFORMATION: Antigen binding construct or subpart thereof

<400> SEQUENCE: 40

```
atggaaaccg acaccctgct gctgtgggtg ctgctgctct gggtcccagg ctccaccggt      60
caggtccagc tggtccagag tggagctgag gtgaaaaaac ccggcgcttc cgtcaaagtc     120
tcctgtaagg ctagcggata caccttcact cgctacacca tgcattgggt ccggcaggct     180
cccggacagg gcctggaatg gatgggatac atcaacccct tctcggggcta cacaaactac    240
aatcagaaat tcaaggatcg agtgaccatg acaaccgaca cttcaatctc taccgcttac    300
atggaactgt ctcggctgag gagtgacgat accgctgtct actactgtgc tcggtactac    360
gacgaccatt actgcctgga ttactggggg cagggcacac tggtgactgt gtctagcagt     420
ggtggaggag cgaaatcgt gctgactcag tcccctgcta cactgtctct gtcacctggc      480
gaacgagcaa cactgtcctg ttctgcctct tcttctgtct catacatgaa ctggtaccag     540
cagaaacctg acaggctcc tagactgctg atctacgaca cctctaaaact ggcatctggc     600
gtgcccgctc atttttcgtgg ctctggatct ggaaccgact ttaccctgac catctcttcc   660
ctggaacctg aggattttgc cgtgtactac tgccagcagt ggtctagtaa ccctttcact    720
tttggccagg gcactaaagt ggagatcaag ggcggctgc                            759
```

<210> SEQ ID NO 41
<211> LENGTH: 236
<212> TYPE: PRT
<213> ORGANISM: Artificial Sequence
<220> FEATURE:
<223> OTHER INFORMATION: Antigen binding construct or subpart thereof

<400> SEQUENCE: 41

```
Met Glu Thr Asp Thr Leu Leu Leu Trp Val Leu Leu Leu Trp Val Pro
  1               5                  10                  15

Gly Ser Thr Gly Glu Ile Val Leu Thr Gln Ser Pro Ala Thr Leu Ser
             20                  25                  30

Leu Ser Pro Gly Glu Arg Ala Thr Gln Ala Pro Arg Leu Leu Ile Tyr
         35                  40                  45

Asp Thr Ser Lys Leu Ala Ser Gly Val Pro Ala His Phe Arg Gly Ser
     50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Asn Pro Phe Thr
                 85                  90                  95

Phe Gly Gln Gly Thr Lys Val Glu Ile Lys Gly Gly Gly Ser Gly Gly
            100                 105                 110

Gly Gly Gln Val Gln Leu Val Gln Ser Gly Ala Glu Val Lys Lys Pro
        115                 120                 125

Gly Ala Ser Val Lys Val Ser Cys Lys Ala Ser Gly Tyr Thr Phe Thr
    130                 135                 140

Arg Tyr Thr Met His Trp Val Arg Gln Ala Pro Gly Gln Gly Leu Glu
145                 150                 155                 160

Trp Met Gly Tyr Ile Asn Pro Ser Arg Gly Tyr Thr Asn Tyr Asn Gln
                165                 170                 175

Lys Phe Lys Asp Arg Val Thr Met Thr Thr Asp Thr Ser Ile Ser Thr
            180                 185                 190

Ala Tyr Met Glu Leu Ser Arg Leu Arg Ser Asp Asp Thr Ala Val Tyr
        195                 200                 205
```

Tyr Cys Ala Arg Tyr Tyr Asp Asp His Tyr Cys Leu Asp Tyr Trp Gly
    210             215                 220

Gln Gly Thr Leu Val Thr Val Ser Ser Gly Gly Cys
225                 230             235

<210> SEQ ID NO 42
<211> LENGTH: 768
<212> TYPE: DNA
<213> ORGANISM: Artificial Sequence
<220> FEATURE:
<223> OTHER INFORMATION: Antigen binding construct or subpart thereof

<400> SEQUENCE: 42
atggaaaccg acaccctgct gctgtgggtg ctgctgctct gggtcccagg ctccaccggt      60
gaaatcgtgc tgactcagtc ccctgctaca ctgtctctgt cacctggcga acgagcaaca     120
ctgtcctgtt ctgcctcttc ttctgtctca tacatgaact ggtaccagca gaaacctgga     180
caggctccta gactgctgat ctacgacacc tctaaactgg catctggcgt gcccgctcat     240
tttcgtggct ctggatctgg aaccgacttt accctgacca tctcttccct ggaacctgag     300
gattttgccg tgtactactg ccagcagtgg tctagtaacc cttttcacttt tggccagggc    360 actaaagtgg agatcaaggg cggagggagt ggcggaggcg ccaggtcca gctggtccag      420 agtggagctg aggtgaaaaa acccggcgct tccgtcaaag tctcctgtaa ggctagcgga     480
tacaccttta ctcgctacac catgcattgg gtccggcagg ctcccggaca gggcctggaa     540
tggatgggat acatcaaccc ttctcggggc tacacaaact acaatcagaa attcaaggat     600
cgagtgacca tgacaaccga cacttcaatc tctaccgctt acatggaact gtctcggctg     660
aggagtgacg ataccgctgt ctactactgt gctcggtact acgacgacca ttactgcctg     720
gattactggg gcagggcac actggtgact gtgtctagcg gcggctgc                   768

<210> SEQ ID NO 43
<211> LENGTH: 256
<212> TYPE: PRT
<213> ORGANISM: Artificial Sequence
<220> FEATURE:
<223> OTHER INFORMATION: Antigen binding construct or subpart thereof

<400> SEQUENCE: 43

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Arg Tyr Thr Met His Trp Val Arg Gln Ala Pro Gly Gln Gly
    50                  55                  60

Leu Glu Trp Met Gly Tyr Ile Asn Pro Ser Arg Gly Tyr Thr Asn Tyr
65                  70                  75                  80

Asn Gln Lys Phe Lys Asp Arg Val Thr Met Thr Asp Thr Ser Ile
                85                  90                  95

Ser Thr Ala Tyr Met Glu Leu Ser Arg Leu Arg Ser Asp Asp Thr Ala
            100                 105                 110

Val Tyr Tyr Cys Ala Arg Tyr Tyr Asp Asp His Tyr Cys Leu Asp Tyr
        115                 120                 125

Trp Gly Gln Gly Thr Leu Val Thr Val Ser Ser Gly Gly Gly Ser Gly
    130                 135                 140

Gly Gly Gly Glu Ile Val Leu Thr Gln Ser Pro Ala Thr Leu Ser Leu
145                 150                 155                 160

Ser Pro Gly Glu Arg Ala Thr Leu Ser Cys Ser Ala Ser Ser Ser Val
                165                 170                 175

Ser Tyr Met Asn Trp Tyr Gln Gln Lys Pro Gly Gln Ala Pro Arg Leu
            180                 185                 190

Leu Ile Tyr Asp Thr Ser Lys Leu Ala Ser Gly Val Pro Ala His Phe
        195                 200                 205

Arg Gly Ser Gly Ser Gly Thr Asp Phe Thr Leu Thr Ile Ser Ser Leu
    210                 215                 220

Glu Pro Glu Asp Phe Ala Val Tyr Tyr Cys Gln Gln Trp Ser Ser Asn
225                 230                 235                 240

Pro Phe Thr Phe Gly Gln Gly Thr Lys Val Glu Ile Lys Gly Gly Cys
                245                 250                 255

<210> SEQ ID NO 44
<211> LENGTH: 768
<212> TYPE: DNA
<213> ORGANISM: Artificial Sequence
<220> FEATURE:
<223> OTHER INFORMATION: Antigen binding construct or subpart thereof

<400> SEQUENCE: 44
atggaaaccg acaccctgct gctgtgggtg ctgctgctct gggtcccagg ctccaccggt    60
caggtccagc tggtccagag tggagctgag gtgaaaaaac ccggcgcttc cgtcaaagtc   120
tcctgtaagg ctagcggata cacctttact cgctacacca tgcattgggt ccggcaggct   180
cccggacagg gcctggaatg gatgggatac atcaaccctt ctcggggcta cacaaactac   240
aatcagaaat tcaaggatcg agtgaccatg acaaccgaca cttcaatctc taccgcttac   300
atggaactgt ctcggctgag gagtgacgat accgctgtct actactgtgc tcggtactac   360
gacgaccatt actgcctgga ttactggggg cagggcacac tggtgactgt gtctagcggc   420
ggagggagtg gcggaggcgg cgaaatcgtg ctgactcagt cccctgctac actgtctctg   480
tcacctggcg aacgagcaac actgtcctgt tctgcctctt cttctgtctc atacatgaac   540
tggtaccagc agaaacctgg acaggctcct agactgctga tctacgacac ctctaaactg   600
gcatctggcg tgcccgctca ttttcgtggc tctggatctg gaaccgactt taccctgacc   660
atctcttccc tggaacctga ggattttgcc gtgtactact gccagcagtg gtctagtaac   720
cctttcactt ttggccaggg cactaaagtg gagatcaagg gcggctgc                 768

<210> SEQ ID NO 45
<211> LENGTH: 389
<212> TYPE: PRT
<213> ORGANISM: Artificial Sequence
<220> FEATURE:
<223> OTHER INFORMATION: Antigen binding construct or subpart thereof

<400> SEQUENCE: 45

Met Glu Thr Asp Thr Leu Leu Leu Trp Val Leu Leu Leu Trp Val Pro
1               5                   10                  15

Gly Ser Thr Gly Asp Ile Gln Leu Thr Gln Pro Asn Ser Val Ser Thr
                20                  25                  30

Ser Leu Gly Ser Thr Val Lys Leu Ser Cys Thr Leu Ser Ser Gly Asn
            35                  40                  45

Ile Glu Asn Asn Tyr Val His Trp Tyr Gln Leu Tyr Glu Gly Arg Ser
        50                  55                  60

```
Pro Thr Thr Met Ile Tyr Asp Asp Asp Lys Arg Pro Asp Gly Val Pro
 65                  70                  75                  80

Asp Arg Phe Ser Gly Ser Ile Asp Arg Ser Ser Asn Ser Ala Phe Leu
                 85                  90                  95

Thr Ile His Asn Val Ala Ile Glu Asp Glu Ala Ile Tyr Phe Cys His
            100                 105                 110

Ser Tyr Val Ser Ser Phe Asn Val Phe Gly Gly Gly Thr Lys Leu Thr
        115                 120                 125

Val Leu Gly Ser Thr Ser Gly Gly Gly Ser Gly Gly Gly Ser Gly Gly
130                 135                 140

Gly Gly Ser Ser Asp Ile Gln Leu Thr Gln Pro Asn Ser Val Ser Thr
145                 150                 155                 160

Ser Leu Gly Ser Thr Val Lys Leu Ser Cys Thr Leu Ser Ser Gly Asn
                165                 170                 175

Ile Glu Asn Asn Tyr Val His Trp Tyr Gln Leu Tyr Glu Gly Arg Ser
            180                 185                 190

Pro Thr Thr Met Ile Tyr Asp Asp Asp Lys Arg Pro Asp Gly Val Pro
        195                 200                 205

Asp Arg Phe Ser Gly Ser Ile Asp Arg Ser Ser Asn Ser Ala Phe Leu
210                 215                 220

Thr Ile His Asn Val Ala Ile Glu Asp Glu Ala Ile Tyr Phe Cys His
225                 230                 235                 240

Ser Tyr Val Ser Ser Phe Asn Val Phe Gly Gly Gly Thr Lys Leu Thr
                245                 250                 255

Val Leu Glu Pro Lys Ser Cys Asp Lys Thr His Thr Cys Pro Pro Cys
            260                 265                 270

Gly Gly Gly Ser Ser Gly Gly Gly Ser Gly Gly Gln Pro Arg Glu Pro
        275                 280                 285

Gln Val Tyr Thr Leu Pro Pro Ser Arg Asp Glu Leu Thr Lys Asn Gln
290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
        355                 360                 365

Val Met His Glu Ala Leu His Asn His Tyr Thr Gln Lys Ser Leu Ser
370                 375                 380

Leu Ser Pro Gly Lys
385

<210> SEQ ID NO 46
<211> LENGTH: 1170
<212> TYPE: DNA
<213> ORGANISM: Artificial Sequence
<220> FEATURE:
<223> OTHER INFORMATION: Antigen binding construct or subpart thereof

<400> SEQUENCE: 46
atggaaaccg acaccctgct gctgtgggtg ctgctgctct gggtcccagg ctccaccggt      60
gacatccagc tgactcagcc caactctgtg tctacgtctc taggaagcac agtcaagctg     120
tcttgcacac tcagctctgg taacatagaa aacaactatg tgcactggta ccagctatat     180
```

```
gagggaagat ctcccaccac tatgatttat gatgatgata agagaccgga tggtgtccct    240
gacaggttct ctggctccat tgacaggtct tccaactcag ccttcctgac aatccataat    300
gtggcaattg aagatgaagc tatctacttc tgtcattctt atgttagtag ttttaatgtt    360
ttcggcggtg gaacaaagct cactgtcctt ggctccacat ccggcggagg ctctggcggt    420
ggatctggcg gaggcggctc atccgacatc cagctgactc agcccaactc tgtgtctacg    480
tctctaggaa gcacagtcaa gctgtcttgc acactcagct ctggtaacat agaaaacaac    540
tatgtgcact ggtaccagct atatgaggga agatctccca ccactatgat ttatgatgat    600
gataagagac cggatggtgt ccctgacagg ttctctggct ccattgacag gtcttccaac    660
tcagccttcc tgacaatcca taatgtggca attgaagatg aagctatcta cttctgtcat    720
tcttatgtta gtagttttaa tgttttcggc ggtggaacaa agctcactgt ccttgagcct    780
aagtcctgcg acaagaccca cacctgtccc ccttgcggcg gaggaagcag cggaggcgga    840
tccggtggcc agcctcggga gcctcaggtg tacaccctgc ctccctcccg ggacgagctg    900
accaagaacc aggtgtccct gacctgtctg gtcaagggct tctacccttc cgatatcgcc    960
gtggagtggg agtccaacgg ccagcctgag aacaactaca agaccacccc tcctgtgctg   1020
gactccgacg gctccttctt cctgtactcc aagctcacag tggataagtc ccggtggcag   1080
cagggcaacg tgttctcctg ctccgtgatg cacgaggccc tgcacaacca ctatacccag   1140
aagtccctgt ccctgtctcc tggcaagtga                                     1170

<210> SEQ ID NO 47
<211> LENGTH: 389
<212> TYPE: PRT
<213> ORGANISM: Artificial Sequence
<220> FEATURE:
<223> OTHER INFORMATION: Antigen binding construct or subpart thereof

<400> SEQUENCE: 47

Met Glu Thr Asp Thr Leu Leu Leu Trp Val Leu Leu Leu Trp Val Pro
  1               5                  10                  15

Gly Ser Thr Gly Asp Ile Gln Leu Thr Gln Pro Asn Ser Val Ser Thr
                 20                  25                  30

Ser Leu Gly Ser Thr Val Lys Leu Ser Cys Thr Leu Ser Ser Gly Asn
             35                  40                  45

Ile Glu Asn Asn Tyr Val His Trp Tyr Gln Leu Tyr Glu Gly Arg Ser
         50                  55                  60

Pro Thr Thr Met Ile Tyr Asp Asp Asp Lys Arg Pro Asp Gly Val Pro
 65                  70                  75                  80

Asp Arg Phe Ser Gly Ser Ile Asp Arg Ser Ser Asn Ser Ala Phe Leu
                 85                  90                  95

Thr Ile His Asn Val Ala Ile Glu Asp Glu Ala Ile Tyr Phe Cys His
                100                 105                 110

Ser Tyr Val Ser Ser Phe Asn Val Phe Gly Gly Gly Thr Lys Leu Thr
                115                 120                 125

Val Leu Gly Ser Thr Ser Gly Gly Gly Ser Gly Gly Gly Ser Gly Gly
            130                 135                 140

Gly Gly Ser Ser Asp Ile Gln Leu Thr Gln Pro Asn Ser Val Ser Thr
145                 150                 155                 160

Ser Leu Gly Ser Thr Val Lys Leu Ser Cys Thr Leu Ser Ser Gly Asn
                165                 170                 175

Ile Glu Asn Asn Tyr Val His Trp Tyr Gln Leu Tyr Glu Gly Arg Ser
                180                 185                 190
```

```
Pro Thr Thr Met Ile Tyr Asp Asp Asp Lys Arg Pro Asp Gly Val Pro
        195                 200                 205

Asp Arg Phe Ser Gly Ser Ile Asp Arg Ser Ser Asn Ser Ala Phe Leu
    210                 215                 220

Thr Ile His Asn Val Ala Ile Glu Asp Glu Ala Ile Tyr Phe Cys His
225                 230                 235                 240

Ser Tyr Val Ser Phe Asn Val Phe Gly Gly Thr Lys Leu Thr
                245                 250                 255

Val Leu Glu Pro Lys Ser Cys Asp Lys Thr His Thr Cys Pro Pro Cys
            260                 265                 270

Gly Gly Gly Ser Ser Gly Gly Gly Ser Gly Gly Gln Pro Arg Glu Pro
                275                 280                 285

Gln Val Tyr Thr Leu Pro Pro Ser Arg Asp Glu Leu Thr Lys Asn Gln
        290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Lys Leu
            340                 345                 350

Thr Val Asp Lys Ser Arg Trp Gln Gln Gly Asn Val Phe Ser Cys Ser
        355                 360                 365

Val Met His Glu Ala Leu His Asn His Tyr Thr Gln Lys Ser Leu Ser
370                 375                 380

Leu Ser Pro Gly Lys
385

<210> SEQ ID NO 48
<211> LENGTH: 1170
<212> TYPE: DNA
<213> ORGANISM: Artificial Sequence
<220> FEATURE:
<223> OTHER INFORMATION: Antigen binding construct or subpart thereof

<400> SEQUENCE: 48
atggaaaccg acaccctgct gctgtgggtg ctgctgctct gggtcccagg ctccaccggt    60
gacatccagc tgactcagcc caactctgtg tctacgtctc taggaagcac agtcaagctg   120
tcttgcacac tcagctctgg taacatagaa aacaactatg tgcactggta ccagctatat   180
gagggaagat ctcccaccac tatgatttat gatgatgata gagaccgga tggtgtccct   240 gacaggttct ctggctccat tgacaggtct tccaactcag ccttcctgac aatccataat   300
gtggcaattg aagatgaagc tatctacttc tgtcattctt atgttagtag tttaatgtt   360 ttcggcggtg gaacaaagct cactgtcctt ggctccacat ccggcggagg ctctggcggt   420
ggatctggcg gaggcggctc atccgacatc cagctgactc agcccaactc tgtgtctacg   480
tctctaggaa gcacagtcaa gctgtcttgc acactcagct ctggtaacat agaaaacaac   540
tatgtgcact ggtaccagct atatgaggga agatctccca ccactatgat ttatgatgat   600
gataagagac cggatggtgt ccctgacagg ttctctggct ccattgacag gtcttccaac   660
tcagccttcc tgacaatcca taatgtggca attgaagatg aagctatcta cttctgtcat   720
tcttatgtta gtagttttaa tgttttcggc ggtggaacaa agctcactgt ccttgagcct   780
aagtcctgcg acaagaccca cacctgtccc cttgcggcg aggaagcag cggaggcgga   840 tccggtggcc agcctcggga gcctcaggtg tacaccctgc tccctcccg ggacgagctg   900
```

```
accaagaacc aggtgtccct gacctgtctg gtcaagggct tctacccttc cgatatcgcc    960
gtggagtggg agtccaacgg ccagcctgag aacaactaca agaccacccc tcctgtgctg   1020
gactccgacg gctccttctt cctgtactcc aagctcacag tggataagtc ccggtggcag   1080
cagggcaacg tgttctcctg ctccgtgatg cacgaggccc tgcacaacca ctatacccag   1140
aagtccctgt ccctgtctcc tggcaagtga                                    1170
```

<210> SEQ ID NO 49
<211> LENGTH: 248
<212> TYPE: PRT
<213> ORGANISM: Artificial Sequence
<220> FEATURE:
<223> OTHER INFORMATION: Antigen binding construct or subpart thereof

<400> SEQUENCE: 49

```
Met Glu Thr Asp Thr Leu Leu Leu Trp Val Leu Leu Leu Trp Val Pro
  1               5                  10                  15

Gly Ser Thr Gly Asp Ile Gln Leu Thr Gln Pro Asn Ser Val Ser Thr
             20                  25                  30

Ser Leu Gly Ser Thr Val Lys Leu Ser Cys Thr Leu Ser Ser Gly Asn
         35                  40                  45

Ile Glu Asn Asn Tyr Val His Trp Tyr Gln Leu Tyr Glu Gly Arg Ser
     50                  55                  60

Pro Thr Thr Met Ile Tyr Asp Asp Asp Lys Arg Pro Asp Gly Val Pro
 65                  70                  75                  80

Asp Arg Phe Ser Gly Ser Ile Asp Arg Ser Ser Asn Ser Ala Phe Leu
                 85                  90                  95

Thr Ile His Asn Val Ala Ile Glu Asp Glu Ala Ile Tyr Phe Cys His
            100                 105                 110

Ser Tyr Val Ser Ser Phe Asn Val Phe Gly Gly Gly Thr Lys Leu Thr
        115                 120                 125

Val Leu Ser Gly Gly Gly Gly Asp Ile Gln Leu Thr Gln Pro Asn Ser
    130                 135                 140

Val Ser Thr Ser Leu Gly Ser Thr Val Lys Leu Ser Cys Thr Leu Ser
145                 150                 155                 160

Ser Gly Asn Ile Glu Asn Asn Tyr Val His Trp Tyr Gln Leu Tyr Glu
                165                 170                 175

Gly Arg Ser Pro Thr Thr Met Ile Tyr Asp Asp Asp Lys Arg Pro Asp
            180                 185                 190

Gly Val Pro Asp Arg Phe Ser Gly Ser Ile Asp Arg Ser Ser Asn Ser
        195                 200                 205

Ala Phe Leu Thr Ile His Asn Val Ala Ile Glu Asp Glu Ala Ile Tyr
    210                 215                 220

Phe Cys His Ser Tyr Val Ser Ser Phe Asn Val Phe Gly Gly Gly Thr
225                 230                 235                 240

Lys Leu Thr Val Leu Gly Gly Cys
                245
```

<210> SEQ ID NO 50
<211> LENGTH: 744
<212> TYPE: DNA
<213> ORGANISM: Artificial Sequence
<220> FEATURE:
<223> OTHER INFORMATION: Antigen binding construct or subpart thereof

<400> SEQUENCE: 50

```
atggaaaccg acaccctgct gctgtgggtg ctgctgctct gggtcccagg ctccaccggt    60
gacatccagc tgactcagcc caactctgtg tctacgtctc taggaagcac agtcaagctg   120
tcttgcacac tcagctctgg taacatagaa aacaactatg tgcactggta ccagctatat   180
gagggaagat ctcccaccac tatgatttat gatgatgata agagaccgga tggtgtccct   240
gacaggttct ctggctccat tgacaggtct tccaactcag ccttcctgac aatccataat   300
gtggcaattg aagatgaagc tatctacttc tgtcattctt atgttagtag tttaatgtt   360
ttcggcggtg aacaaagct cactgtcctt agtggtggag gaggcgacat ccagctgact   420
cagcccaact ctgtgtctac gtctctagga agcacagtca agctgtcttg cacactcagc   480
tctggtaaca tagaaaacaa ctatgtgcac tggtaccagc tatatgaggg aagatctccc   540
accactatga tttatgatga tgataagaga ccggatggtg tccctgacag gttctctggc   600
tccattgaca ggtcttccaa ctcagccttc ctgacaatcc ataatgtggc aattgaagat   660
gaagctatct acttctgtca ttcttatgtt agtagtttta atgttttcgg cggtggaaca   720
aagctcactg tccttggcgg ctgc                                          744
```

<210> SEQ ID NO 51
<211> LENGTH: 248
<212> TYPE: PRT
<213> ORGANISM: Artificial Sequence
<220> FEATURE:
<223> OTHER INFORMATION: Antigen binding construct or subpart thereof

<400> SEQUENCE: 51

```
Met Glu Thr Asp Thr Leu Leu Leu Trp Val Leu Leu Leu Trp Val Pro
 1               5                  10                  15

Gly Ser Thr Gly Asp Ile Gln Leu Thr Gln Pro Asn Ser Val Ser Thr
             20                  25                  30

Ser Leu Gly Ser Thr Val Lys Leu Ser Cys Thr Leu Ser Ser Gly Asn
         35                  40                  45

Ile Glu Asn Asn Tyr Val His Trp Tyr Gln Leu Tyr Glu Gly Arg Ser
     50                  55                  60

Pro Thr Thr Met Ile Tyr Asp Asp Asp Lys Arg Pro Asp Gly Val Pro
 65                  70                  75                  80

Asp Arg Phe Ser Gly Ser Ile Asp Arg Ser Ser Asn Ser Ala Phe Leu
                 85                  90                  95

Thr Ile His Asn Val Ala Ile Glu Asp Glu Ala Ile Tyr Phe Cys His
            100                 105                 110

Ser Tyr Val Ser Ser Phe Asn Val Phe Gly Gly Gly Thr Lys Leu Thr
        115                 120                 125

Val Leu Ser Gly Gly Gly Gly Asp Ile Gln Leu Thr Gln Pro Asn Ser
    130                 135                 140

Val Ser Thr Ser Leu Gly Ser Thr Val Lys Leu Ser Cys Thr Leu Ser
145                 150                 155                 160

Ser Gly Asn Ile Glu Asn Asn Tyr Val His Trp Tyr Gln Leu Tyr Glu
                165                 170                 175

Gly Arg Ser Pro Thr Thr Met Ile Tyr Asp Asp Asp Lys Arg Pro Asp
            180                 185                 190

Gly Val Pro Asp Arg Phe Ser Gly Ser Ile Asp Arg Ser Ser Asn Ser
        195                 200                 205

Ala Phe Leu Thr Ile His Asn Val Ala Ile Glu Asp Glu Ala Ile Tyr
    210                 215                 220

Phe Cys His Ser Tyr Val Ser Ser Phe Asn Val Phe Gly Gly Gly Thr
```

Lys Leu Thr Val Leu Gly Gly Cys
                245

<210> SEQ ID NO 52
<211> LENGTH: 744
<212> TYPE: DNA
<213> ORGANISM: Artificial Sequence
<220> FEATURE:
<223> OTHER INFORMATION: Antigen binding construct or subpart thereof

<400> SEQUENCE: 52

```
atggaaaccg acaccctgct gctgtgggtg ctgctgctct gggtcccagg ctccaccggt      60
gacatccagc tgactcagcc caactctgtg tctacgtctc taggaagcac agtcaagctg     120
tcttgcacac tcagctctgg taacatagaa aacaactatg tgcactggta ccagctatat     180
gagggaagat ctcccaccac tatgatttat gatgatgata agagaccgga tggtgtccct     240
gacaggttct ctggctccat tgacaggtct tccaactcag ccttcctgac aatccataat     300
gtggcaattg aagatgaagc tatctacttc tgtcattctt atgttagtag ttttaatgtt     360
ttcggcggtg gaacaaagct cactgtcctt agtggtggag gaggcgacat ccagctgact     420
cagcccaact ctgtgtctac gtctctagga agcacagtca agctgtcttg cacactcagc     480
tctggtaaca tagaaaacaa ctatgtgcac tggtaccagc tatatgaggg aagatctccc     540
accactatga tttatgatga tgataagaga ccggatggtg tccctgacag gttctctggc     600
tccattgaca ggtcttccaa ctcagccttc ctgacaatcc ataatgtggc aattgaagat     660
gaagctatct acttctgtca ttcttatgtt agtagtttta atgttttcgg cggtggaaca     720
aagctcactg tccttggcgg ctgc                                            744
```

<210> SEQ ID NO 53
<211> LENGTH: 251
<212> TYPE: PRT
<213> ORGANISM: Artificial Sequence
<220> FEATURE:
<223> OTHER INFORMATION: Antigen binding construct or subpart thereof

<400> SEQUENCE: 53

Met Glu Thr Asp Thr Leu Leu Leu Trp Val Leu Leu Leu Trp Val Pro
 1               5                  10                  15

Gly Ser Thr Gly Asp Ile Gln Leu Thr Gln Pro Asn Ser Val Ser Thr
            20                  25                  30

Ser Leu Gly Ser Thr Val Lys Leu Ser Cys Thr Leu Ser Ser Gly Asn
        35                  40                  45

Ile Glu Asn Asn Tyr Val His Trp Tyr Gln Leu Tyr Glu Gly Arg Ser
    50                  55                  60

Pro Thr Thr Met Ile Tyr Asp Asp Asp Lys Arg Pro Asp Gly Val Pro
65                  70                  75                  80

Asp Arg Phe Ser Gly Ser Ile Asp Arg Ser Ser Asn Ser Ala Phe Leu
                85                  90                  95

Thr Ile His Asn Val Ala Ile Glu Asp Glu Ala Ile Tyr Phe Cys His
            100                 105                 110

Ser Tyr Val Ser Ser Phe Asn Val Phe Gly Gly Gly Thr Lys Leu Thr
        115                 120                 125

Val Leu Gly Gly Gly Ser Gly Gly Gly Asp Ile Gln Leu Thr Gln
    130                 135                 140

Pro Asn Ser Val Ser Thr Ser Leu Gly Ser Thr Val Lys Leu Ser Cys

```
145                 150                 155                 160
Thr Leu Ser Ser Gly Asn Ile Glu Asn Asn Tyr Val His Trp Tyr Gln
                165                 170                 175

Leu Tyr Glu Gly Arg Ser Pro Thr Thr Met Ile Tyr Asp Asp Asp Lys
            180                 185                 190

Arg Pro Asp Gly Val Pro Asp Arg Phe Ser Gly Ser Ile Asp Arg Ser
        195                 200                 205

Ser Asn Ser Ala Phe Leu Thr Ile His Asn Val Ala Ile Glu Asp Glu
    210                 215                 220

Ala Ile Tyr Phe Cys His Ser Tyr Val Ser Ser Phe Asn Val Phe Gly
225                 230                 235                 240

Gly Gly Thr Lys Leu Thr Val Leu Gly Gly Cys
                245                 250

<210> SEQ ID NO 54
<211> LENGTH: 753
<212> TYPE: DNA
<213> ORGANISM: Artificial Sequence
<220> FEATURE:
<223> OTHER INFORMATION: Antigen binding construct or subpart thereof

<400> SEQUENCE: 54
atggaaaccg acaccctgct gctgtgggtg ctgctgctct gggtcccagg ctccaccggt    60
gacatccagc tgactcagcc caactctgtg tctacgtctc taggaagcac agtcaagctg   120
tcttgcacac tcagctctgg taacatagaa aacaactatg tgcactggta ccagctatat   180
gagggaagat ctcccaccac tatgatttat gatgatgata agagaccgga tggtgtccct   240
gacaggttct ctggctccat tgacaggtct tccaactcag ccttcctgac aatccataat   300
gtggcaattg aagatgaagc tatctacttc tgtcattctt atgttagtag ttttaatgtt   360
ttcggcggtg gaacaaagct cactgtcctt ggcggaggga gtggcggagg cggcgacatc   420
cagctgactc agcccaactc tgtgtctacg tctctaggaa gcacagtcaa gctgtcttgc   480
acactcagct ctggtaacat agaaaacaac tatgtgcact ggtaccagct atatgaggga   540
agatctccca ccactatgat ttatgatgat gataagagac cggatggtgt ccctgacagg   600
ttctctggct ccattgacag gtcttccaac tcagccttcc tgacaatcca taatgtggca   660
attgaagatg aagctatcta cttctgtcat tcttatgtta gtagttttaa tgttttcggc   720
ggtggaacaa agctcactgt ccttggcggc tgc                                753

<210> SEQ ID NO 55
<211> LENGTH: 251
<212> TYPE: PRT
<213> ORGANISM: Artificial Sequence
<220> FEATURE:
<223> OTHER INFORMATION: Antigen binding construct or subpart thereof

<400> SEQUENCE: 55

Met Glu Thr Asp Thr Leu Leu Leu Trp Val Leu Leu Leu Trp Val Pro
  1               5                  10                  15

Gly Ser Thr Gly Asp Ile Gln Leu Thr Gln Pro Asn Ser Val Ser Thr
            20                  25                  30

Ser Leu Gly Ser Thr Val Lys Leu Ser Cys Thr Leu Ser Ser Gly Asn
        35                  40                  45

Ile Glu Asn Asn Tyr Val His Trp Tyr Gln Leu Tyr Glu Gly Arg Ser
    50                  55                  60

Pro Thr Thr Met Ile Tyr Asp Asp Asp Lys Arg Pro Asp Gly Val Pro
```

```
                65                  70                  75                  80
Asp Arg Phe Ser Gly Ser Ile Asp Arg Ser Ser Asn Ser Ala Phe Leu
                    85                  90                  95

Thr Ile His Asn Val Ala Ile Glu Asp Glu Ala Ile Tyr Phe Cys His
                100                 105                 110

Ser Tyr Val Ser Ser Phe Asn Val Phe Gly Gly Gly Thr Lys Leu Thr
                115                 120                 125

Val Leu Gly Gly Gly Ser Gly Gly Gly Asp Ile Gln Leu Thr Gln
130                 135                 140

Pro Asn Ser Val Ser Thr Ser Leu Gly Ser Thr Val Lys Leu Ser Cys
145                 150                 155                 160

Thr Leu Ser Ser Gly Asn Ile Glu Asn Asn Tyr Val His Trp Tyr Gln
                165                 170                 175

Leu Tyr Glu Gly Arg Ser Pro Thr Thr Met Ile Tyr Asp Asp Asp Lys
                180                 185                 190

Arg Pro Asp Gly Val Pro Asp Arg Phe Ser Gly Ser Ile Asp Arg Ser
                195                 200                 205

Ser Asn Ser Ala Phe Leu Thr Ile His Asn Val Ala Ile Glu Asp Glu
210                 215                 220

Ala Ile Tyr Phe Cys His Ser Tyr Val Ser Ser Phe Asn Val Phe Gly
225                 230                 235                 240

Gly Gly Thr Lys Leu Thr Val Leu Gly Gly Cys
                245                 250

<210> SEQ ID NO 56
<211> LENGTH: 753
<212> TYPE: DNA
<213> ORGANISM: Artificial Sequence
<220> FEATURE:
<223> OTHER INFORMATION: Antigen binding construct or subpart thereof

<400> SEQUENCE: 56
atggaaaccg acaccctgct gctgtgggtg ctgctgctct gggtcccagg ctccaccggt     60
gacatccagc tgactcagcc caactctgtg tctacgtctc taggaagcac agtcaagctg    120
tcttgcacac tcagctctgg taacatagaa aacaactatg tgcactggta ccagctatat    180
gagggaagat ctcccaccac tatgatttat gatgatgata agagaccgga tggtgtccct    240
gacaggttct ctggctccat tgacaggtct tccaactcag ccttcctgac aatccataat    300
gtggcaattg aagatgaagc tatctacttc tgtcattctt atgttagtag ttttaatgtt    360
ttcggcggtg gaacaaagct cactgtcctt ggcggaggga gtggcggagg cggcgacatc    420
cagctgactc agcccaactc tgtgtctacg tctctaggaa gcacagtcaa gctgtcttgc    480
acactcagct ctggtaacat agaaaacaac tatgtgcact ggtaccagct atatgaggga    540
agatctccca ccactatgat ttatgatgat gataagagac cggatggtgt ccctgacagg    600
ttctctggct ccattgacag gtcttccaac tcagccttcc tgacaatcca taatgtggca    660
attgaagatg aagctatcta cttctgtcat tcttatgtta gtagttttaa tgttttcggc    720
ggtggaacaa agctcactgt ccttggcggc tgc                                 753

<210> SEQ ID NO 57
<211> LENGTH: 395
<212> TYPE: PRT
<213> ORGANISM: Artificial Sequence
<220> FEATURE:
<223> OTHER INFORMATION: Antigen binding construct or subpart thereof
```

<400> SEQUENCE: 57

```
Met Glu Thr Asp Thr Leu Leu Leu Trp Val Leu Leu Leu Trp Val Pro
1               5                   10                  15

Gly Ser Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
        115                 120                 125

Gly Ser Thr Ser Gly Gly Gly Ser Gly Gly Ser Gly Gly Gly Gly
    130                 135                 140

Ser Ser Gln Val Gln Leu Val Glu Ser Gly Gly Gly Val Val Gln Pro
145                 150                 155                 160

Gly Arg Ser Leu Arg Leu Ser Cys Ala Ala Ser Gly Phe Lys Phe Ser
                165                 170                 175

Gly Tyr Gly Met His Trp Val Arg Gln Ala Pro Gly Lys Gly Leu Glu
            180                 185                 190

Trp Val Ala Val Ile Trp Tyr Asp Gly Ser Lys Lys Tyr Tyr Val Asp
        195                 200                 205

Ser Val Lys Gly Arg Phe Thr Ile Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Arg Gln Met Gly Tyr Trp His Phe Asp Leu Trp Gly Arg
                245                 250                 255

Gly Thr Leu Val Thr Val Ser Ser Glu Pro Lys Ser Cys Asp Lys Thr
            260                 265                 270

His Thr Cys Pro Pro Cys Gly Gly Gly Ser Ser Gly Gly Gly Ser Gly
        275                 280                 285

Gly Gln Pro Arg Glu Pro Gln Val Tyr Thr Leu Pro Pro Ser Arg Asp
    290                 295                 300

Glu Leu Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
    370                 375                 380

Thr Gln Lys Ser Leu Ser Leu Ser Pro Gly Lys
385                 390                 395
```

<210> SEQ ID NO 58

<211> LENGTH: 1188
<212> TYPE: DNA
<213> ORGANISM: Artificial Sequence
<220> FEATURE:
<223> OTHER INFORMATION: Antigen binding construct or subpart thereof

<400> SEQUENCE: 58

```
atggaaaccg acaccctgct gctgtgggtg ctgctgctct gggtcccagg ctccaccggt    60
gaaattgtgc tgacccagag cccggcgacc ctgagcctga gccgggcga acgcgcgacc   120
ctgagctgcc gcgcgagcca gagcgtgagc agctatctgg cgtggtatca gcagaaaccg   180
ggccaggcgc cgcgcctgct gatttatgat gcgagcaacc gcgcgaccgg cattccggcg   240
cgctttagcg gcagcggcag cggcaccgat tttaccctga ccattagcag cctggaaccg   300
gaagattttg cggtgtatta ttgccagcag cgcagcaact ggccgccgct gacctttggc   360
ggcggcacca aagtggaaat taaaggctcc acatccggcg gaggctctgg cggtggatct   420
ggcggaggcg gctcatccca ggtgcagctg gtggaaagcg gcggcggcgt ggtgcagccg   480
ggccgcagcc tgcgcctgag ctgcgcggcg agcggcttta aatttagcgg ctatggcatg   540
cattgggtgc gccaggcgcc gggcaaaggc ctgaatgggt ggcggtgat ttggtatgat   600
ggcagcaaaa aatattatgt ggatagcgtg aaaggccgct ttaccattag ccgcgataac   660
agcaaaaaca ccctgtatct gcagatgaac agcctgcgcg cggaagatac cgcggtgtat   720
tattgcgcgc gccagatggg ctattggcat tttgatctgt ggggccgcgg caccctggtg   780
accgtgagca gcgagcctaa gtcctgcgac aagacccaca cctgtccccc ttgcggcgga   840
ggaagcagcg gaggcggatc cggtggccag cctcggagc ctcaggtgta caccctgcct   900
ccctcccggg acgagctgac caagaaccag gtgtccctga cctgtctggt caagggcttc   960
taccttccg atatcgccgt ggagtgggag tccaacggcc agcctgagaa caactacaag  1020
accaccctc ctgtgctgga ctccgacggc tccttcttcc tgtactccaa gctcacagtg  1080
gataagtccc ggtggcagca gggcaacgtg ttctcctgct ccgtgatgca cgaggccctg  1140
cacaaccact ataccagaa gtccctgtcc ctgtctcctg gcaagtga                1188
```

<210> SEQ ID NO 59
<211> LENGTH: 395
<212> TYPE: PRT
<213> ORGANISM: Artificial Sequence
<220> FEATURE:
<223> OTHER INFORMATION: Antigen binding construct or subpart thereof

<400> SEQUENCE: 59

```
Met Glu Thr Asp Thr Leu Leu Leu Trp Val Leu Leu Leu Trp Val Pro
  1               5                  10                  15

Gly Ser Thr Gly Gln Val Gln Leu Val Glu Ser Gly Gly Gly Val Val
             20                  25                  30

Gln Pro Gly Arg Ser Leu Arg Leu Ser Cys Ala Ala Ser Gly Phe Lys
         35                  40                  45

Phe Ser Gly Tyr Gly Met His Trp Val Arg Gln Ala Pro Gly Lys Gly
     50                  55                  60

Leu Glu Trp Val Ala Val Ile Trp Tyr Asp Gly Ser Lys Lys Tyr Tyr
 65                  70                  75                  80

Val Asp Ser Val Lys Gly Arg Phe Thr Ile Ser Arg Asp Asn Ser Lys
                 85                  90                  95

Asn Thr Leu Tyr Leu Gln Met Asn Ser Leu Arg Ala Glu Asp Thr Ala
            100                 105                 110
```

Val Tyr Tyr Cys Ala Arg Gln Met Gly Tyr Trp His Phe Asp Leu Trp
            115                 120                 125

Gly Arg Gly Thr Leu Val Thr Val Ser Ser Gly Ser Thr Ser Gly Gly
130                 135                 140

Gly Ser Gly Gly Gly Ser Gly Gly Gly Ser Ser Glu Ile Val Leu
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Ser Val Ser Ser Tyr Leu Ala Trp Tyr
            180                 185                 190

Gln Gln Lys Pro Gly Gln Ala Pro Arg Leu Leu Ile Tyr Asp Ala Ser
        195                 200                 205

Asn Arg Ala Thr Gly Ile Pro Ala Arg Phe Ser Gly Ser Gly Ser Gly
210                 215                 220

Thr Asp Phe Thr Leu Thr Ile Ser Ser Leu Glu Pro Glu Asp Phe Ala
225                 230                 235                 240

Val Tyr Tyr Cys Gln Gln Arg Ser Asn Trp Pro Pro Leu Thr Phe Gly
                245                 250                 255

Gly Gly Thr Lys Val Glu Ile Lys Glu Pro Lys Ser Cys Asp Lys Thr
            260                 265                 270

His Thr Cys Pro Pro Cys Gly Gly Gly Ser Gly Gly Gly Ser Gly
        275                 280                 285

Gly Gln Pro Arg Glu Pro Gln Val Tyr Thr Leu Pro Pro Ser Arg Asp
        290                 295                 300

Glu Leu Thr Lys Asn Gln Val Ser Leu Thr Cys Leu Val Lys Gly Phe
305                 310                 315                 320

Tyr Pro Ser Asp Ile Ala Val Glu Trp Glu Ser Asn Gly Gln Pro Glu
                325                 330                 335

Asn Asn Tyr Lys Thr Thr Pro Pro Val Leu Asp Ser Asp Gly Ser Phe
            340                 345                 350

Phe Leu Tyr Ser Lys Leu Thr Val Asp Lys Ser Arg Trp Gln Gln Gly
        355                 360                 365

Asn Val Phe Ser Cys Ser Val Met His Glu Ala Leu His Asn His Tyr
370                 375                 380

Thr Gln Lys Ser Leu Ser Leu Ser Pro Gly Lys
385                 390                 395

<210> SEQ ID NO 60
<211> LENGTH: 1188
<212> TYPE: DNA
<213> ORGANISM: Artificial Sequence
<220> FEATURE:
<223> OTHER INFORMATION: Antigen binding construct or subpart thereof

<400> SEQUENCE: 60
atggaaaccg acaccctgct gctgtgggtg ctgctgctct gggtcccagg ctccaccggt      60
caggtgcagc tggtggaaag cggcggcggc gtggtgcagc cgggccgcag cctgcgcctg     120
agctgcgcgg cgagcggctt taaatttagc ggctatggca tgcattgggt cgcccaggcg     180
ccgggcaaag gcctggaatg ggtggcggtg atttggtatg atggcagcaa aaaatattat     240
gtggatagcg tgaaaggccg ctttaccatt agccgcgata cagcaaaaa caccctgtat     300 ctgcagatga acagcctgcg cgcggaagat accgcggtgt attattgcgc gcgccagatg     360
ggctattggc attttgatct gtggggccgc ggcaccctgg tgaccgtgag cagcggctcc     420
acatccggcg gaggctctgg cggtggatct ggcggaggcg gctcatccga aattgtgctg     480

```
acccagagcc cggcgaccct gagcctgagc ccgggcgaac gcgcgaccct gagctgccgc    540
gcgagccaga gcgtgagcag ctatctggcg tggtatcagc agaaaccggg ccaggcgccg    600
cgcctgctga tttatgatgc gagcaaccgc gcgaccggca ttccggcgcg ctttagcggc    660
agcggcagcg gcaccgattt taccctgacc attagcagcc tggaaccgga agattttgcg    720
gtgtattatt gccagcagcg cagcaactgg ccgccgctga cctttggcgg cggcaccaaa    780
gtggaaatta aagagcctaa gtcctgcgac aagacccaca cctgtccccc ttgcggcgga    840
ggaagcagcg gaggcggatc cggtggccag cctcgggagc tcaggtgta cccctgcct     900 ccctcccggg acgagctgac caagaaccag gtgtccctga cctgtctggt caagggcttc    960 taccttccg atatcgccgt ggagtgggag tccaacggcc agcctgagaa caactacaag   1020
accacccctc ctgtgctgga ctccgacggc tccttcttcc tgtactccaa gctcacagtg   1080
gataagtccc ggtggcagca gggcaacgtg ttctcctgct ccgtgatgca cgaggccctg   1140
cacaaccact atacccagaa gtccctgtcc ctgtctcctg gcaagtga               1188
```

<210> SEQ ID NO 61
<211> LENGTH: 254
<212> TYPE: PRT
<213> ORGANISM: Artificial Sequence
<220> FEATURE:
<223> OTHER INFORMATION: Antigen binding construct or subpart thereof

<400> SEQUENCE: 61

```
Met Glu Thr Asp Thr Leu Leu Leu Trp Val Leu Leu Leu Trp Val Pro
 1               5                  10                  15

Gly Ser Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
        115                 120                 125

Ser Gly Gly Gly Gly Gln Val Gln Leu Val Glu Ser Gly Gly Gly Val
    130                 135                 140

Val Gln Pro Gly Arg Ser Leu Arg Leu Ser Cys Ala Ala Ser Gly Phe
145                 150                 155                 160

Lys Phe Ser Gly Tyr Gly Met His Trp Val Arg Gln Ala Pro Gly Lys
                165                 170                 175

Gly Leu Glu Trp Val Ala Val Ile Trp Tyr Asp Gly Ser Lys Lys Tyr
            180                 185                 190

Tyr Val Asp Ser Val Lys Gly Arg Phe Thr Ile Ser Arg Asp Asn Ser
        195                 200                 205

Lys Asn Thr Leu Tyr Leu Gln Met Asn Ser Leu Arg Ala Glu Asp Thr
    210                 215                 220

Ala Val Tyr Tyr Cys Ala Arg Gln Met Gly Tyr Trp His Phe Asp Leu
225                 230                 235                 240
```

Trp Gly Arg Gly Thr Leu Val Thr Val Ser Ser Gly Gly Cys
           245                 250

<210> SEQ ID NO 62
<211> LENGTH: 762
<212> TYPE: DNA
<213> ORGANISM: Artificial Sequence
<220> FEATURE:
<223> OTHER INFORMATION: Antigen binding construct or subpart thereof

<400> SEQUENCE: 62

```
atggaaaccg acaccctgct gctgtgggtg ctgctgctct gggtcccagg ctccaccggt      60
gaaattgtgc tgacccagag cccggcgacc ctgagcctga gcccgggcga acgcgcgacc     120
ctgagctgcc gcgcgagcca gagcgtgagc agctatctgg cgtggtatca gcagaaaccg     180
ggccaggcgc cgcgcctgct gatttatgat gcgagcaacc gcgcgaccgg cattccggcg     240
cgctttagcg gcagcggcag cggcaccgat tttaccctga ccattagcag cctggaaccg     300
gaagattttg cggtgtatta ttgccagcag cgcagcaact ggccgccgct gacctttggc     360
ggcggcacca agtggaaaat taaaagtggt ggaggaggcc aggtgcagct ggtggaaagc     420
ggcggcggcg tggtgcagcc gggccgcagc ctgcgcctga gctgcgcggc gagcggcttt     480
aaatttagcg gctatggcat gcattgggtg cgccaggcgc cgggcaaagg cctggaatgg     540
gtggcggtga tttggtatga tggcagcaaa aaatattatg tggatagcgt gaaaggccgc     600
tttaccatta gccgcgataa cagcaaaaac accctgtatc tgcagatgaa cagcctgcgc     660
gcggaagata ccgcggtgta ttattgcgcg cgccagatgg gctattggca ttttgatctg     720
tggggccgcg gcaccctggt gaccgtgagc agcggcggct gc                         762
```

<210> SEQ ID NO 63
<211> LENGTH: 254
<212> TYPE: PRT
<213> ORGANISM: Artificial Sequence
<220> FEATURE:
<223> OTHER INFORMATION: Antigen binding construct or subpart thereof

<400> SEQUENCE: 63

Met Glu Thr Asp Thr Leu Leu Leu Trp Val Leu Leu Trp Val Pro
 1               5                  10                  15

Gly Ser Thr Gly Gln Val Gln Leu Val Glu Ser Gly Gly Val Val
            20                  25                  30

Gln Pro Gly Arg Ser Leu Arg Leu Ser Cys Ala Ala Ser Gly Phe Lys
        35                  40                  45

Phe Ser Gly Tyr Gly Met His Trp Val Arg Gln Ala Pro Gly Lys Gly
    50                  55                  60

Leu Glu Trp Val Ala Val Ile Trp Tyr Asp Gly Ser Lys Lys Tyr Tyr
65                  70                  75                  80

Val Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Gln Met Gly Tyr Trp His Phe Asp Leu Trp
        115                 120                 125

Gly Arg Gly Thr Leu Val Thr Val Ser Ser Gly Gly Gly Gly Glu
    130                 135                 140

Ile Val Leu Thr Gln Ser Pro Ala Thr Leu Ser Leu Ser Pro Gly Glu
145                 150                 155                 160

```
Arg Ala Thr Leu Ser Cys Arg Ala Ser Gln Ser Val Ser Ser Tyr Leu
                165                 170                 175

Ala Trp Tyr Gln Gln Lys Pro Gly Gln Ala Pro Arg Leu Leu Ile Tyr
            180                 185                 190

Asp Ala Ser Asn Arg Ala Thr Gly Ile Pro Ala Arg Phe Ser Gly Ser
        195                 200                 205

Gly Ser Gly Thr Asp Phe Thr Leu Thr Ile Ser Ser Leu Glu Pro Glu
    210                 215                 220

Asp Phe Ala Val Tyr Tyr Cys Gln Gln Arg Ser Asn Trp Pro Pro Leu
225                 230                 235                 240

Thr Phe Gly Gly Gly Thr Lys Val Glu Ile Lys Gly Gly Cys
                245                 250
```

<210> SEQ ID NO 64
<211> LENGTH: 762
<212> TYPE: DNA
<213> ORGANISM: Artificial Sequence
<220> FEATURE:
<223> OTHER INFORMATION: Antigen binding construct or subpart thereof

<400> SEQUENCE: 64

```
atggaaaccg acaccctgct gctgtgggtg ctgctgctct gggtcccagg ctccaccggt    60
caggtgcagc tggtggaaag cggcggcggc gtggtgcagc cgggccgcag cctgcgcctg   120
agctgcgcgg cgagcggctt taaatttagc ggctatggca tgcattgggt gcgccaggcg   180
ccgggcaaag gcctggaatg ggtggcggtg atttggtatg atggcagcaa aaaatattat   240
gtggatagcg tgaaaggccg ctttaccatt agccgcgata acagcaaaaa caccctgtat   300
ctgcagatga acagcctgcg cgcggaagat accgcggtgt attattgcgc gcgccagatg   360
ggctattggc attttgatct gtggggccgc ggcaccctgg tgaccgtgag cagcagtggt   420
ggaggaggcg aaattgtgct gacccagagc ccggcgaccc tgagcctgag cccgggcgaa   480
cgcgcgaccc tgagctgccg cgcgagccag agcgtgagca gctatctggc gtggtatcag   540
cagaaaccgg gccaggcgcc cgcgcctgctg atttatgatg cgagcaaccg cgcgaccggc   600
attccggcgc gctttagcgg cagcggcagc ggcaccgatt ttaccctgac cattagcagc   660
ctggaaccgg aagattttgc ggtgtattat tgccagcagc gcagcaactg gccgccgctg   720
acctttggcg gcggcaccaa agtggaaatt aaaggcggct gc                      762
```

<210> SEQ ID NO 65
<211> LENGTH: 257
<212> TYPE: PRT
<213> ORGANISM: Artificial Sequence
<220> FEATURE:
<223> OTHER INFORMATION: Antigen binding construct or subpart thereof

<400> SEQUENCE: 65

```
Met Glu Thr Asp Thr Leu Leu Leu Trp Val Leu Leu Leu Trp Val Pro
  1               5                  10                  15

Gly Ser Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
         35                  40                  45

Val Ser Ser Tyr Leu Ala Trp Tyr Gln Gln Lys Pro Gly Gln Ala Pro
     50                  55                  60

Arg Leu Leu Ile Tyr Asp Ala Ser Asn Arg Ala Thr Gly Ile Pro Ala
 65                  70                  75                  80
```

```
Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
        115                 120                 125

Gly Gly Gly Ser Gly Gly Gly Gly Gln Val Gln Leu Val Glu Ser Gly
    130                 135                 140

Gly Gly Val Val Gln Pro Gly Arg Ser Leu Arg Leu Ser Cys Ala Ala
145                 150                 155                 160

Ser Gly Phe Lys Phe Ser Gly Tyr Gly Met His Trp Val Arg Gln Ala
                165                 170                 175

Pro Gly Lys Gly Leu Glu Trp Val Ala Val Ile Trp Tyr Asp Gly Ser
            180                 185                 190

Lys Lys Tyr Tyr Val Asp Ser Val Lys Gly Arg Phe Thr Ile Ser Arg
        195                 200                 205

Asp Asn Ser Lys Asn Thr Leu Tyr Leu Gln Met Asn Ser Leu Arg Ala
    210                 215                 220

Glu Asp Thr Ala Val Tyr Tyr Cys Ala Arg Gln Met Gly Tyr Trp His
225                 230                 235                 240

Phe Asp Leu Trp Gly Arg Gly Thr Leu Val Thr Val Ser Ser Gly Gly
                245                 250                 255

Cys

<210> SEQ ID NO 66
<211> LENGTH: 771
<212> TYPE: DNA
<213> ORGANISM: Artificial Sequence
<220> FEATURE:
<223> OTHER INFORMATION: Antigen binding construct or subpart thereof

<400> SEQUENCE: 66
atggaaaccg acaccctgct gctgtgggtg ctgctgctct gggtcccagg ctccaccggt    60
gaaattgtgc tgacccagag cccggcgacc ctgagcctga gccgggcga acgcgcgacc   120 ctgagctgcc gcgcgagcca gagcgtgagc agctatctgg cgtggtatca gcagaaaccg   180
ggccaggcgc cgcgcctgct gatttatgat gcgagcaacc gcgcgaccgg cattccggcg   240
cgctttagcg gcagcggcag cggcaccgat tttaccctga ccattagcag cctggaaccg   300
gaagattttg cggtgtatta ttgccagcag cgcagcaact ggccgccgct gacctttggc   360
ggcggcacca aagtggaaat taaaggcgga gggagtggcg gaggcggcca ggtgcagctg   420
gtggaaagcg gcggcggcgt ggtgcagccg ggccgcagcc tgcgcctgag ctgcgcggcg   480
agcggcttta aatttagcgg ctatggcatg cattgggtgc gccaggcgcc gggcaaaggc   540
ctggaatggg tggcggtgat ttggtatgat ggcagcaaaa aatattatgt ggatagcgtg   600
aaaggccgct ttaccattag ccgcgataac agcaaaaaca ccctgtatct gcagatgaac   660
agcctgcgcg cggaagatac cgcggtgtat tattgcgcgc gccagatggg ctattggcat   720
tttgatctgt ggggccgcgg caccctggtg accgtgagca gcggcggctg c             771

<210> SEQ ID NO 67
<211> LENGTH: 257
<212> TYPE: PRT
<213> ORGANISM: Artificial Sequence
<220> FEATURE:
<223> OTHER INFORMATION: Antigen binding construct or subpart thereof
```

<400> SEQUENCE: 67

| | | | | | | | | | | | | | | |
|---|---|---|---|---|---|---|---|---|---|---|---|---|---|---|
|Met|Glu|Thr|Asp|Thr|Leu|Leu|Leu|Trp|Val|Leu|Leu|Leu|Trp|Val|Pro
|1| | | |5| | | | |10| | | | |15|

Gly Ser Thr Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Lys
        35                  40                  45

Phe Ser Gly Tyr Gly Met His Trp Val Arg Gln Ala Pro Gly Lys Gly
    50                  55                  60

Leu Glu Trp Val Ala Val Ile Trp Tyr Asp Gly Ser Lys Lys Tyr Tyr
65                  70                  75                  80

Val Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Gln Met Gly Tyr Trp His Phe Asp Leu Trp
        115                 120                 125

Gly Arg Gly Thr Leu Val Thr Val Ser Ser Gly Gly Gly Ser Gly Gly
    130                 135                 140

Gly Gly Glu Ile Val Leu Thr Gln Ser Pro Ala Thr Leu Ser Leu Ser
145                 150                 155                 160

Pro Gly Glu Arg Ala Thr Leu Ser Cys Arg Ala Ser Gln Ser Val Ser
                165                 170                 175

Ser Tyr Leu Ala Trp Tyr Gln Gln Lys Pro Gly Gln Ala Pro Arg Leu
            180                 185                 190

Leu Ile Tyr Asp Ala Ser Asn Arg Ala Thr Gly Ile Pro Ala Arg Phe
        195                 200                 205

Ser Gly Ser Gly Ser Gly Thr Asp Phe Thr Leu Thr Ile Ser Ser Leu
    210                 215                 220

Glu Pro Glu Asp Phe Ala Val Tyr Tyr Cys Gln Gln Arg Ser Asn Trp
225                 230                 235                 240

Pro Pro Leu Thr Phe Gly Gly Gly Thr Lys Val Glu Ile Lys Gly Gly
                245                 250                 255

Cys

<210> SEQ ID NO 68
<211> LENGTH: 771
<212> TYPE: DNA
<213> ORGANISM: Artificial Sequence
<220> FEATURE:
<223> OTHER INFORMATION: Antigen binding construct or subpart thereof

<400> SEQUENCE: 68

```
atggaaaccg acaccctgct gctgtgggtg ctgctgctct gggtcccagg ctccaccggt    60
caggtgcagc tggtggaaag cggcggcggc gtggtgcagc cggccgcag cctgcgcctg   120 agctgcgcgg cgagcggctt taaatttagc ggctatggca tgcattgggt gcgccaggcg   180
ccgggcaaag gcctggaatg ggtggcggtg atttggtatg atggcagcaa aaaatattat   240
gtggatagcg tgaaaggccg ctttaccatt agccgcgata caagcaaaaa caccctgtat   300
ctgcagatga acagcctgcg cgcggaagat accgcggtgt attattgcgc gcgccagatg   360
ggctattggc atttgatct gtgggccgc ggcaccctgg tgaccgtgag cagcggcgga   420
gggagtggcg gaggcggcga aattgtgctg acccagagcc cggcgaccct gagcctgagc   480
```

```
ccgggcgaac gcgcgaccct gagctgccgc gcgagccaga gcgtgagcag ctatctggcg      540
tggtatcagc agaaaccggg ccaggcgccg cgcctgctga tttatgatgc gagcaaccgc      600
gcgaccggca ttccggcgcg ctttagcggc agcggcagcg gcaccgattt taccctgacc      660
attagcagcc tggaaccgga agattttgcg gtgtattatt gccagcagcg cagcaactgg      720
ccgccgctga cctttggcgg cggcaccaaa gtggaaatta aaggcggctg c              771
```

<210> SEQ ID NO 69
<211> LENGTH: 10
<212> TYPE: PRT
<213> ORGANISM: Artificial Sequence
<220> FEATURE:
<223> OTHER INFORMATION: Antigen binding construct or subpart thereof
<220> FEATURE:
<221> NAME/KEY: VARIANT
<222> LOCATION: 7
<223> OTHER INFORMATION: Xaa = C or S

<400> SEQUENCE: 69

Tyr Tyr Asp Asp His Tyr Xaa Leu Asp Tyr
 1               5                  10

<210> SEQ ID NO 70
<211> LENGTH: 106
<212> TYPE: PRT
<213> ORGANISM: Mus musculus

<400> SEQUENCE: 70

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
             20                  25                  30

Asn Trp Tyr Gln Gln Lys Ser Gly Thr Ser Pro Lys Arg Trp Ile Tyr
         35                  40                  45

Asp Thr Ser Lys Leu Ala Ser Gly Val Pro Ala His Phe Arg Gly Ser
 50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                 85                  90                  95

Phe Gly Ser Gly Thr Lys Leu Glu Ile Asn
            100                 105

<210> SEQ ID NO 71
<211> LENGTH: 318
<212> TYPE: DNA
<213> ORGANISM: Homo sapiens

<400> SEQUENCE: 71

```
gacatccaga tgacccagtc tccttcttct ctgtctgctt ctgtcggaga cagagtcaca       60
atcacatgtt ctgcttctag ctctgtctct tacatgaact ggtaccagca gacacctgga      120
aaggctccta agcggtggat ctacgacaca tctaagctcg cttctggagt cccttctaga      180
ttctctggtt ctggctctgg aacagactac acattcacaa tctcttctct ccaacctgag      240
gacatcgcta catactactg ccaacagtgg tctagcaatc ctttcacatt cggacaggga      300
acaaagctgc agatcaca                                                    318
```

<210> SEQ ID NO 72
<211> LENGTH: 106

```
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Asn Pro Phe Thr
                85                  90                  95

Phe Gly Gln Gly Thr Lys Leu Gln Ile Thr
            100                 105

<210> SEQ ID NO 73
<211> LENGTH: 318
<212> TYPE: DNA
<213> ORGANISM: Artificial Sequence
<220> FEATURE:
<223> OTHER INFORMATION: Antigen binding construct or subpart thereof

<400> SEQUENCE: 73
gaaattgtgt tgacacagtc tccagccacc ctgtctttgt ctccagggga aagagccacc      60
ctctcctgca gtgccagctc aagtgtaagt tacatgaact ggtaccaaca gaaacctggc     120
caggctccca ggctcctcat ctatgacaca tccaaactgg cttctggagt ccctgctcac     180
ttcaggggca gtgggtctgg gacagacttc actctcacca tcagcagcct agagcctgaa     240
gattttgcag tttattactg tcagcagtgg agtagtaacc cattcacgtt cggccaaggg     300
accaaggtgg aaatcaaa                                                    318

<210> SEQ ID NO 74
<211> LENGTH: 106
<212> TYPE: PRT
<213> ORGANISM: Artificial Sequence
<220> FEATURE:
<223> OTHER INFORMATION: Antigen binding construct or subpart thereof

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Leu Ile Tyr
            35                  40                  45

Asp Thr Ser Lys Leu Ala Ser Gly Val Pro Ala His Phe Arg Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Phe Thr
                85                  90                  95

Phe Gly Gln Gly Thr Lys Val Glu Ile Lys
            100                 105
```

<210> SEQ ID NO 75
<211> LENGTH: 357
<212> TYPE: DNA
<213> ORGANISM: Mus musculus

<400> SEQUENCE: 75
caggtccagc tgcagcagtc tggggctgaa ctggcaagac ctggggcctc agtgaagatg        60
tcctgcaagg cttctggcta cacctttact aggtacacga tgcactgggt aaaacagagg       120
cctggacagg gtctggaatg gattggatac attaatccta gccgtggtta tactaattac       180
aatcagaagt tcaaggacaa ggccacattg actacagaca atcctccag cacagcctac       240 atgcaactga gcagcctgac atctgaggac tctgcagtct attactgtgc aagatattat       300
gatgatcatt actgccttga ctactggggc caaggcacca ctctcacagt ctcctca         357

<210> SEQ ID NO 76
<211> LENGTH: 119
<212> TYPE: PRT
<213> ORGANISM: Mus musculus

<400> SEQUENCE: 76

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 77
<211> LENGTH: 357
<212> TYPE: DNA
<213> ORGANISM: Artificial Sequence
<220> FEATURE:
<223> OTHER INFORMATION: Antigen binding construct or subpart thereof

<400> SEQUENCE: 77
caggtccagc tgcagcagtc tggggctgaa ctggcaagac ctggggcctc agtgaagatg        60
tcctgcaagg cttctggcta cacctttact aggtacacga tgcactgggt aaaacagagg       120
cctggacagg gtctggaatg gattggatac attaatccta gccgtggtta tactaattac       180
aaatgcaact gagcagcctg acatctgagg actctgcagt ctattactgt gcaagatatt       240
attcagaagt tcaaggacaa ggccacattg actacagaca atcctccag cacagcctac       300 gatgatcatt actgcacttga ctactggggc caaggcacca ctctcacagt ctcctca         357

<210> SEQ ID NO 78
<211> LENGTH: 119
<212> TYPE: PRT
<213> ORGANISM: Artificial Sequence
<220> FEATURE:
<223> OTHER INFORMATION: Antigen binding construct or subpart thereof

<400> SEQUENCE: 78

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser
        115
```

<210> SEQ ID NO 79
<211> LENGTH: 357
<212> TYPE: DNA
<213> ORGANISM: Homo sapiens

<400> SEQUENCE: 79

```
caggttcagc tggtgcagtc tggaggagga gtcgtccagc ctggaaggtc cctgagactg      60
tcttgtaagg cttctggata caccttcact agatacacaa tgcactgggt cagacaggct     120
cctggaaagg gactcgagtg gattggatac attaatccta gcagaggtta ctactaactac    180
aatcagactg cagatggact cactcagacc tgaggatacc ggagtctatt tttgtgctag     240
atattacagg tgaaggacag attcacaatt tctagagaca attctaagaa tacagccttc     300
gatgaccact actgtctgga ctactggggc caaggtaccc cggtcaccgt gagctca        357
```

<210> SEQ ID NO 80
<211> LENGTH: 119
<212> TYPE: PRT
<213> ORGANISM: Homo sapiens

<400> SEQUENCE: 80

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Val
        50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
```

<210> SEQ ID NO 81
<211> LENGTH: 357
<212> TYPE: DNA
<213> ORGANISM: Artificial Sequence
<220> FEATURE:
<223> OTHER INFORMATION: Antigen binding construct or subpart thereof

<400> SEQUENCE: 81

```
caggttcagc tggtgcagtc tggaggagga gtcgtccagc ctggaaggtc cctgagactg      60
tcttgtaagg cttctggata caccttcact agatacacaa tgcactgggt cagacaggct     120
cctggaaagg gactcgagtg gattggatac attaatccta gcagaggtta tactaactac     180
aatcagaagg tgaaggacag attcacaatt tctagagaca attctaagaa tacagccttc     240
ctgcagatgg actcactcag acctgaggat accggagtct attttgtgc tagatattac      300
gatgaccact actcactgga ctactggggc caaggtaccc cggtcaccgt gagctca         357
```

<210> SEQ ID NO 82
<211> LENGTH: 119
<212> TYPE: PRT
<213> ORGANISM: Artificial Sequence
<220> FEATURE:
<223> OTHER INFORMATION: Antigen binding construct or subpart thereof

<400> SEQUENCE: 82

```
Gln Val Gln Leu Val Gln Ser Gly Gly Gly Val Val Gln Pro Gly Arg
  1               5                  10                  15
Ser Leu Arg Leu Ser Cys Lys Ala Ser Gly Tyr Thr Phe Thr Arg Tyr
             20                  25                  30
Thr Met His Trp Val Arg Gln Ala Pro Gly Lys Gly Leu Glu Trp Ile
         35                  40                  45
Gly Tyr Ile Asn Pro Ser Arg Gly Tyr Thr Asn Tyr Asn Gln Lys Val
     50                  55                  60
Lys Asp Arg Phe Thr Ile Ser Arg Asp Asn Ser Lys Asn Thr Ala Phe
 65                  70                  75                  80
Leu Gln Met Asp Ser Leu Arg Pro Glu Asp Thr Gly Val Tyr Phe Cys
                 85                  90                  95
Ala Arg Tyr Tyr Asp Asp His Tyr Ser Leu Asp Tyr Trp Gly Gln Gly
            100                 105                 110
Thr Pro Val Thr Val Ser Ser
        115
```

<210> SEQ ID NO 83
<211> LENGTH: 357
<212> TYPE: DNA
<213> ORGANISM: Artificial Sequence
<220> FEATURE:
<223> OTHER INFORMATION: Antigen binding construct or subpart thereof

<400> SEQUENCE: 83

```
caggtgcagc tggtgcagtc tggggctgag gtgaagaagc ctggggcctc agtgaaggtc      60
tcctgcaagg cttctggata caccttcacc aggtacacga tgcactgggt gcgacaggcc     120
cctggacaag ggcttgagtg gatgggatac attaatccta gccgtggtta ctaattac       180
aatcagaagt tcaaggacag ggtcaccatg accacagaca cgtccatcag cacagcctac     240
atggagctga gcaggctgag atctgacgac acggccgtgt attactgtgc gagatattat     300
gatgatcatt actgccttga ctactggggc cagggcaccc tggtcaccgt ctcctca         357
```

<210> SEQ ID NO 84
<211> LENGTH: 119
<212> TYPE: PRT
<213> ORGANISM: Artificial Sequence
<220> FEATURE:
<223> OTHER INFORMATION: Antigen binding construct or subpart thereof

<400> SEQUENCE: 84

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Arg Tyr
                 20                  25                  30
Thr Met His Trp Val Arg Gln Ala Pro Gly Gln Gly Leu Glu Trp Met
             35                  40                  45
Gly Tyr Ile Asn Pro Ser Arg Gly Tyr Thr Asn Tyr Asn Gln Lys Phe
         50                  55                  60
Lys Asp Arg Val Thr Met Thr Thr Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Tyr Tyr Asp Asp His Tyr Cys Leu Asp Tyr Trp Gly Gln Gly
                100                 105                 110
Thr Leu Val Thr Val Ser Ser
            115
```

<210> SEQ ID NO 85
<211> LENGTH: 357
<212> TYPE: DNA
<213> ORGANISM: Artificial Sequence
<220> FEATURE:
<223> OTHER INFORMATION: Antigen binding construct or subpart thereof

<400> SEQUENCE: 85

```
caggtgcagc tggtgcagtc tggggctgag gtgaagaagc ctggggcctc agtgaaggtc      60
tcctgcaagg cttctggata caccttcacc aggtacacga tgcactgggt gcgacaggcc     120
cctggacaag gcttgagtg gatgggatac attaatccta gccgtggtta tactaattac     180
aatcagaagt tcaaggacag ggtcaccatg accacagaca cgtccatcag cacagcctac     240
atggagctga gcaggctgag atctgacgac acggccgtgt attactgtgc gagatattat     300
gatgatcatt actcacttga ctactggggc cagggcaccc tggtcaccgt ctcctca       357
```

<210> SEQ ID NO 86
<211> LENGTH: 119
<212> TYPE: PRT
<213> ORGANISM: Artificial Sequence
<220> FEATURE:
<223> OTHER INFORMATION: Antigen binding construct or subpart thereof

<400> SEQUENCE: 86

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Thr Arg Tyr
                 20                  25                  30
Thr Met His Trp Val Arg Gln Ala Pro Gly Gln Gly Leu Glu Trp Met
             35                  40                  45
Gly Tyr Ile Asn Pro Ser Arg Gly Tyr Thr Asn Tyr Asn Gln Lys Phe
         50                  55                  60
```

```
Lys Asp Arg Val Thr Met Thr Thr Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115
```

<210> SEQ ID NO 87
<211> LENGTH: 60
<212> TYPE: DNA
<213> ORGANISM: Artificial Sequence
<220> FEATURE:
<223> OTHER INFORMATION: Antigen binding construct or subpart thereof

<400> SEQUENCE: 87
atggaaaccg acaccctgct gctgtgggtg ctgctgctct gggtcccagg ctccaccggt    60

<210> SEQ ID NO 88
<211> LENGTH: 20
<212> TYPE: PRT
<213> ORGANISM: Artificial Sequence
<220> FEATURE:
<223> OTHER INFORMATION: Antigen binding construct or subpart thereof

<400> SEQUENCE: 88

```
Met Glu Thr Asp Thr Leu Leu Leu Trp Val Leu Leu Leu Trp Val Pro
  1               5                  10                  15

Gly Ser Thr Gly
            20
```

<210> SEQ ID NO 89
<211> LENGTH: 15
<212> TYPE: DNA
<213> ORGANISM: Artificial Sequence
<220> FEATURE:
<223> OTHER INFORMATION: Antigen binding construct or subpart thereof

<400> SEQUENCE: 89
agtggtggag gaggc                                                     15

<210> SEQ ID NO 90
<211> LENGTH: 5
<212> TYPE: PRT
<213> ORGANISM: Artificial Sequence
<220> FEATURE:
<223> OTHER INFORMATION: Antigen binding construct or subpart thereof

<400> SEQUENCE: 90

```
Ser Gly Gly Gly Gly
  1               5
```

<210> SEQ ID NO 91
<211> LENGTH: 24
<212> TYPE: DNA
<213> ORGANISM: Artificial Sequence
<220> FEATURE:
<223> OTHER INFORMATION: Antigen binding construct or subpart thereof

<400> SEQUENCE: 91
ggcggaggga gtggcggagg cggc                                           24

<210> SEQ ID NO 92

```
<211> LENGTH: 8
<212> TYPE: PRT
<213> ORGANISM: Artificial Sequence
<220> FEATURE:
<223> OTHER INFORMATION: Antigen binding construct or subpart thereof

<400> SEQUENCE: 92

Gly Gly Gly Ser Gly Gly Gly Gly
 1               5

<210> SEQ ID NO 93
<211> LENGTH: 9
<212> TYPE: DNA
<213> ORGANISM: Artificial Sequence
<220> FEATURE:
<223> OTHER INFORMATION: Antigen binding construct or subpart thereof

<400> SEQUENCE: 93 ggcggctgc                                                            9

<210> SEQ ID NO 94
<211> LENGTH: 3
<212> TYPE: PRT
<213> ORGANISM: Artificial Sequence
<220> FEATURE:
<223> OTHER INFORMATION: Antigen binding construct or subpart thereof

<400> SEQUENCE: 94

Gly Gly Cys
 1

<210> SEQ ID NO 95
<211> LENGTH: 60
<212> TYPE: DNA
<213> ORGANISM: Artificial Sequence
<220> FEATURE:
<223> OTHER INFORMATION: Antigen binding construct or subpart thereof

<400> SEQUENCE: 95
atggaaaccg acaccctgct gctgtgggtg ctgctgctct gggtcccagg ctccaccggt    60

<210> SEQ ID NO 96
<211> LENGTH: 20
<212> TYPE: PRT
<213> ORGANISM: Artificial Sequence
<220> FEATURE:
<223> OTHER INFORMATION: Antigen binding construct or subpart thereof

<400> SEQUENCE: 96

Met Glu Thr Asp Thr Leu Leu Leu Trp Val Leu Leu Leu Trp Val Pro
 1               5                  10                  15

Gly Ser Thr Gly
            20

<210> SEQ ID NO 97
<211> LENGTH: 54
<212> TYPE: DNA
<213> ORGANISM: Artificial Sequence
<220> FEATURE:
<223> OTHER INFORMATION: Antigen binding construct or subpart thereof

<400> SEQUENCE: 97
ggctccacat ccggcggagg ctctggcggt ggatctggcg gaggcggctc atcc          54

<210> SEQ ID NO 98
<211> LENGTH: 18
```

```
<212> TYPE: PRT
<213> ORGANISM: Artificial Sequence
<220> FEATURE:
<223> OTHER INFORMATION: Antigen binding construct or subpart thereof

<400> SEQUENCE: 98

Gly Ser Thr Ser Gly Gly Gly Ser Gly Gly Gly Ser Gly Gly Gly Gly
 1               5                  10                  15

Ser Ser

<210> SEQ ID NO 99
<211> LENGTH: 393
<212> TYPE: DNA
<213> ORGANISM: Artificial Sequence
<220> FEATURE:
<223> OTHER INFORMATION: Antigen binding construct or subpart thereof

<400> SEQUENCE: 99
gagcctaagt cctgcgacaa gacccacacc tgtcccccct tgcggcggagg aagcagcgga    60 ggcggatccg gtggccagcc tcgggagcct caggtgtaca ccctgcctcc ctcccgggac   120
gagctgacca agaaccaggt gtccctgacc tgtctggtca agggcttcta cccttccgat   180
atcgccgtgg agtgggagtc caacggccag cctgagaaca actacaagac cacccctcct   240
gtgctggact ccgacggctc cttcttcctg tactccaagc tcacagtgga taagtcccgg   300
tggcagcagg gcaacgtgtt ctcctgctcc gtgatgcacg aggccctgca caaccactat   360
acccagaagt ccctgtccct gtctcctggc aag                                393

<210> SEQ ID NO 100
<211> LENGTH: 131
<212> TYPE: PRT
<213> ORGANISM: Artificial Sequence
<220> FEATURE:
<223> OTHER INFORMATION: Antigen binding construct or subpart thereof

<400> SEQUENCE: 100

Glu Pro Lys Ser Cys Asp Lys Thr His Thr Cys Pro Pro Cys Gly Gly
 1               5                  10                  15

Gly Ser Ser Gly Gly Gly Ser Gly Gly Gln Pro Arg Glu Pro Gln Val
                20                  25                  30

Tyr Thr Leu Pro Pro Ser Arg Asp Glu Leu Thr Lys Asn Gln Val Ser
            35                  40                  45

Leu Thr Cys Leu Val Lys Gly Phe Tyr Pro Ser Asp Ile Ala Val Glu
        50                  55                  60

Trp Glu Ser Asn Gly Gln Pro Glu Asn Asn Tyr Lys Thr Thr Pro Pro
65                  70                  75                  80

Val Leu Asp Ser Asp Gly Ser Phe Phe Leu Tyr Ser Lys Leu Thr Val
                85                  90                  95

Asp Lys Ser Arg Trp Gln Gln Gly Asn Val Phe Ser Cys Ser Val Met
            100                 105                 110

His Glu Ala Leu His Asn His Tyr Thr Gln Lys Ser Leu Ser Leu Ser
        115                 120                 125

Pro Gly Lys
    130

<210> SEQ ID NO 101
<211> LENGTH: 23
<212> TYPE: PRT
<213> ORGANISM: Artificial Sequence
<220> FEATURE:
```

<223> OTHER INFORMATION: Antigen binding construct or subpart thereof

<400> SEQUENCE: 101

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 102
<211> LENGTH: 25
<212> TYPE: PRT
<213> ORGANISM: Artificial Sequence
<220> FEATURE:
<223> OTHER INFORMATION: Antigen binding construct or subpart thereof

<400> SEQUENCE: 102

Glu Pro Lys Ser Cys Asp Lys Thr His Thr Cys Pro Pro Cys Pro Gly
1               5                   10                  15

Gly Gly Ser Ser Gly Gly Gly Ser Gly
            20                  25

<210> SEQ ID NO 103
<211> LENGTH: 19
<212> TYPE: PRT
<213> ORGANISM: Artificial Sequence
<220> FEATURE:
<223> OTHER INFORMATION: Antigen binding construct or subpart thereof

<400> SEQUENCE: 103

Glu Arg Lys Cys Cys Val Glu Cys Pro Pro Cys Pro Ala Pro Pro Val
1               5                   10                  15

Ala Gly Pro

<210> SEQ ID NO 104
<211> LENGTH: 70
<212> TYPE: PRT
<213> ORGANISM: Artificial Sequence
<220> FEATURE:
<223> OTHER INFORMATION: Antigen binding construct or subpart thereof

<400> SEQUENCE: 104

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro Ala Pro
    50                  55                  60

Glu Leu Leu Gly Gly Pro
65                  70

<210> SEQ ID NO 105
<211> LENGTH: 25
<212> TYPE: PRT
<213> ORGANISM: Artificial Sequence
<220> FEATURE:
<223> OTHER INFORMATION: Antigen binding construct or subpart thereof

<400> SEQUENCE: 105

Glu Leu Lys Thr Pro Leu Gly Asp Thr Thr His Thr Cys Pro Arg Cys
1               5                   10                  15

Pro Ala Pro Glu Leu Leu Gly Gly Pro
            20                  25

<210> SEQ ID NO 106
<211> LENGTH: 23
<212> TYPE: PRT
<213> ORGANISM: Artificial Sequence
<220> FEATURE:
<223> OTHER INFORMATION: Antigen binding construct or subpart thereof

<400> SEQUENCE: 106

Glu Pro Lys Ser Cys Asp Thr Pro Pro Cys Pro Arg Cys Pro Ala
1               5                   10                  15

Pro Glu Leu Leu Gly Gly Pro
            20

<210> SEQ ID NO 107
<211> LENGTH: 20
<212> TYPE: PRT
<213> ORGANISM: Artificial Sequence
<220> FEATURE:
<223> OTHER INFORMATION: Antigen binding construct or subpart thereof

<400> SEQUENCE: 107

Glu Ser Lys Tyr Gly Pro Pro Cys Pro Ser Cys Pro Ala Pro Glu Phe
1               5                   10                  15

Leu Gly Gly Pro
            20

<210> SEQ ID NO 108
<211> LENGTH: 20
<212> TYPE: PRT
<213> ORGANISM: Artificial Sequence
<220> FEATURE:
<223> OTHER INFORMATION: Antigen binding construct or subpart thereof

<400> SEQUENCE: 108

Glu Ser Lys Tyr Gly Pro Pro Cys Pro Pro Cys Pro Ala Pro Glu Phe
1               5                   10                  15

Leu Gly Gly Pro
            20

<210> SEQ ID NO 109
<211> LENGTH: 22
<212> TYPE: PRT
<213> ORGANISM: Artificial Sequence
<220> FEATURE:
<223> OTHER INFORMATION: Antigen binding construct or subpart thereof

<400> SEQUENCE: 109

Met Gln Ser Gly Thr His Trp Arg Val Leu Gly Leu Cys Leu Leu Ser
1               5                   10                  15

Val Gly Val Trp Gly Gln
            20

<210> SEQ ID NO 110
<211> LENGTH: 185
<212> TYPE: PRT
<213> ORGANISM: Homo sapiens

<400> SEQUENCE: 110

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly

```
                    20                  25                  30
Ser Glu Ile Leu Trp Gln His Asn Asp Lys Asn Ile Gly Gly Asp Glu
                35                  40                  45

Asp Asp Lys Asn Ile Gly Ser Asp Glu Asp His Leu Ser Leu Lys Glu
            50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp Val Met Ser Val Ala Thr Ile Val
                100                 105                 110

Ile Val Asp Ile Cys Ile Thr Gly Gly Leu Leu Leu Leu Val Tyr Tyr
            115                 120                 125

Trp Ser Lys Asn Arg Lys Ala Lys Ala Lys Pro Val Thr Arg Gly Ala
            130                 135                 140

Gly Ala Gly Gly Arg Gln Arg Gly Gln Asn Lys Glu Arg Pro Pro Pro
145                 150                 155                 160

Val Pro Asn Pro Asp Tyr Glu Pro Ile Arg Lys Gly Gln Arg Asp Leu
                165                 170                 175

Tyr Ser Gly Leu Asn Gln Arg Arg Ile
                180                 185

<210> SEQ ID NO 111
<211> LENGTH: 17
<212> TYPE: PRT
<213> ORGANISM: Artificial Sequence
<220> FEATURE:
<223> OTHER INFORMATION: Antigen binding construct or subpart thereof

<400> SEQUENCE: 111

Gly Ser Thr Ser Gly Gly Gly Ser Gly Gly Gly Ser Gly Gly Gly Gly
1               5                   10                  15

Ser

<210> SEQ ID NO 112
<211> LENGTH: 18
<212> TYPE: PRT
<213> ORGANISM: Artificial Sequence
<220> FEATURE:
<223> OTHER INFORMATION: Antigen binding construct or subpart thereof

<400> SEQUENCE: 112

Gly Ser Thr Ser Gly Ser Gly Lys Pro Gly Ser Ser Glu Gly Ser Thr
1               5                   10                  15

Lys Gly

<210> SEQ ID NO 113
<211> LENGTH: 15
<212> TYPE: PRT
<213> ORGANISM: Artificial Sequence
<220> FEATURE:
<223> OTHER INFORMATION: Antigen binding construct or subpart thereof

<400> SEQUENCE: 113

Gly Gly Gly Gly Ser Gly Gly Gly Ser Gly Gly Gly Gly Ser
1               5                   10                  15

<210> SEQ ID NO 114
<211> LENGTH: 318
<212> TYPE: DNA
```

<213> ORGANISM: Artificial Sequence
<220> FEATURE:
<223> OTHER INFORMATION: Antigen binding construct or subpart thereof

<400> SEQUENCE: 114

```
caaattgttc tcacccagtc tccagcaatc atgtctgcat ctccagggga gaaggtcacc      60
atgacctgca gtgccagctc aagtgtaagt tacatgaact ggtaccagca gaagtcaggc     120
acctccccca aaagatggat ttatgacaca tccaaactgg cttctggagt ccctgctcac     180 ttcagggca gtgggtctgg gacctcttac tctctcacaa tcagcggcat ggaggctgaa     240
gatgctgcca cttattactg ccagcagtgg agtagtaacc cattcacgtt cggctcgggg     300
acaaagttgg aaataaac                                                  318
```

<210> SEQ ID NO 115
<211> LENGTH: 6
<212> TYPE: PRT
<213> ORGANISM: Artificial Sequence
<220> FEATURE:
<223> OTHER INFORMATION: Antigen binding construct or subpart thereof

<400> SEQUENCE: 115

Gly Gly Cys Gly Gly Cys
 1               5

<210> SEQ ID NO 116
<211> LENGTH: 5
<212> TYPE: PRT
<213> ORGANISM: Artificial Sequence
<220> FEATURE:
<223> OTHER INFORMATION: Antigen binding construct or subpart thereof

<400> SEQUENCE: 116

Gly Gly Cys Gly Cys
 1               5

<210> SEQ ID NO 117
<211> LENGTH: 4
<212> TYPE: PRT
<213> ORGANISM: Artificial Sequence
<220> FEATURE:
<223> OTHER INFORMATION: Antigen binding construct or subpart thereof

<400> SEQUENCE: 117

Gly Gly Cys Cys
 1

<210> SEQ ID NO 118
<211> LENGTH: 15
<212> TYPE: DNA
<213> ORGANISM: Artificial Sequence
<220> FEATURE:
<223> OTHER INFORMATION: Restriction site

<400> SEQUENCE: 118

```
tctagagccg ccacc                                                      15
```

<210> SEQ ID NO 119
<211> LENGTH: 6
<212> TYPE: DNA
<213> ORGANISM: Artificial Sequence
<220> FEATURE:
<223> OTHER INFORMATION: Restriction site

<400> SEQUENCE: 119

| aagctt | 6 |

<210> SEQ ID NO 120
<211> LENGTH: 15
<212> TYPE: DNA
<213> ORGANISM: Artificial Sequence
<220> FEATURE:
<223> OTHER INFORMATION: Restriction site

<400> SEQUENCE: 120

| tctagagccg ccacc | 15 |

<210> SEQ ID NO 121
<211> LENGTH: 6
<212> TYPE: DNA
<213> ORGANISM: Artificial Sequence
<220> FEATURE:
<223> OTHER INFORMATION: Restriction site

<400> SEQUENCE: 121

| aagctt | 6 |

<210> SEQ ID NO 122
<211> LENGTH: 15
<212> TYPE: DNA
<213> ORGANISM: Artificial Sequence
<220> FEATURE:
<223> OTHER INFORMATION: Restriction site

<400> SEQUENCE: 122

| tctagagccg ccacc | 15 |

<210> SEQ ID NO 123
<211> LENGTH: 6
<212> TYPE: DNA
<213> ORGANISM: Artificial Sequence
<220> FEATURE:
<223> OTHER INFORMATION: Restriction site

<400> SEQUENCE: 123

| aagctt | 6 |

<210> SEQ ID NO 124
<211> LENGTH: 15
<212> TYPE: DNA
<213> ORGANISM: Artificial Sequence
<220> FEATURE:
<223> OTHER INFORMATION: Restriction site

<400> SEQUENCE: 124

| tctagagccg ccacc | 15 |

<210> SEQ ID NO 125
<211> LENGTH: 6
<212> TYPE: DNA
<213> ORGANISM: Artificial Sequence
<220> FEATURE:
<223> OTHER INFORMATION: Restriction site

<400> SEQUENCE: 125

| aagctt | 6 |